US012473433B2

(12) United States Patent
Sherif

(10) Patent No.: US 12,473,433 B2
(45) Date of Patent: *Nov. 18, 2025

(54) SPACING LINKER GROUP DESIGN FOR BRIGHTNESS ENHANCEMENT IN DIMERIC OR POLYMERIC DYES

(71) Applicant: SONY GROUP CORPORATION, Tokyo (JP)

(72) Inventor: Hesham Sherif, New York, NY (US)

(73) Assignee: Sony Group Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/438,105

(22) Filed: Feb. 9, 2024

(65) Prior Publication Data

US 2024/0287313 A1 Aug. 29, 2024

Related U.S. Application Data

(63) Continuation of application No. 18/256,125, filed as application No. PCT/US2021/062235 on Dec. 7, 2021.

(60) Provisional application No. 63/219,706, filed on Jul. 8, 2021, provisional application No. 63/122,285, filed on Dec. 7, 2020.

(51) Int. Cl.

| | |
|---|---|
| ***C09B 69/10*** | (2006.01) |
| ***C09B 69/00*** | (2006.01) |
| ***G01N 1/30*** | (2006.01) |
| ***G01N 33/58*** | (2006.01) |

(52) U.S. Cl.

CPC ............ *C09B 69/101* (2013.01); *C09B 69/00* (2013.01); *G01N 1/30* (2013.01); *G01N 33/582* (2013.01)

(58) Field of Classification Search

CPC ....... C07H 21/00; C09B 69/00; C09B 69/101; C09B 69/103; C12Q 1/6806; C12Q 1/6818; C12Q 2563/107; G01N 1/30; G01N 33/582

See application file for complete search history.

(56) References Cited

U.S. PATENT DOCUMENTS 4,450,305 A 5/1984 Kamhi
4,476,229 A 10/1984 Fino et al.
(Continued)

FOREIGN PATENT DOCUMENTS

CA 2263671 A1 2/1998
CN 102174078 A 9/2011
(Continued)

OTHER PUBLICATIONS

"What is an Analyte?," Google Search, dated Mar. 22, 2018, retrieved from https://www.google.com/search?q=what+is+an+analyte&rlz=1C1GCEB_enUS775US775&oq=what+is+an+analyte&aqs=chrome..69i57j0I5.3231j0j7&s . . . 2 pages.
(Continued)

*Primary Examiner* — Galina M. Yakovleva
(74) *Attorney, Agent, or Firm* — Seed Intellectual Property Law Group LLP

(57) ABSTRACT

Compounds useful as fluorescent or colored dyes are disclosed. The compounds have the following structure (A):

(A)

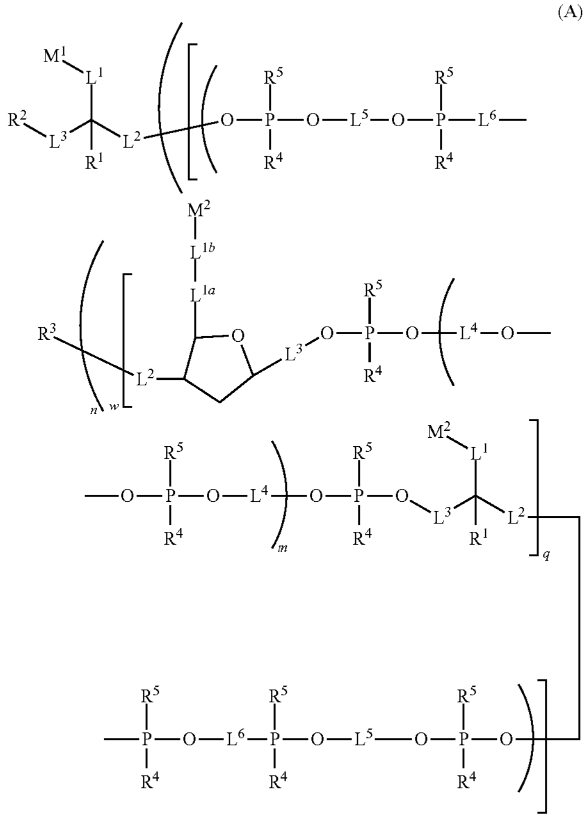

or a stereoisomer, tautomer or salt thereof, wherein $R^1$, $R^2$, $R^3$, $R^4$, $R^5$, $L^1$, $L^{1a}$, $L^{1b}$, $L^2$, $L^3$, $L^4$, $L^5$, $L^6$, $M^1$, $M^2$, m, n, q, and w are as defined herein. Methods associated with preparation and use of such compounds are also provided.

15 Claims, 4 Drawing Sheets

(56) References Cited

U.S. PATENT DOCUMENTS 4,778,753 A 10/1988 Yamanishi et al.
5,053,054 A 10/1991 Kirchanski
5,268,486 A 12/1993 Waggoner et al.
5,318,894 A 6/1994 Pugia
5,582,977 A 12/1996 Yue et al.
5,696,157 A 12/1997 Wang et al.
5,698,391 A 12/1997 Cook et al.
5,886,177 A 3/1999 Cook et al.
5,994,143 A 11/1999 Bieniarz et al.
6,005,093 A 12/1999 Wood et al.
6,140,480 A 10/2000 Kool
6,171,859 B1 1/2001 Herrnstadt et al.
6,218,108 B1 4/2001 Kool
6,365,730 B1 4/2002 Jennings et al.
6,380,431 B1 4/2002 Whipple et al.
6,479,650 B1 11/2002 Kool
6,514,700 B1 2/2003 Singh
6,534,041 B1 3/2003 Licha et al.
6,627,400 B1 9/2003 Singh et al.
6,670,193 B2 12/2003 Kool
6,716,452 B1 4/2004 Piccariello et al.
6,852,709 B2 2/2005 Leong et al.
7,038,063 B2 5/2006 Lee et al.
7,060,708 B2 6/2006 Piccariello et al.
7,172,907 B2 2/2007 Chen et al.
7,423,133 B2 9/2008 Kool et al.
7,667,024 B2 2/2010 Mao et al.
7,897,684 B2 3/2011 Bazan et al.
8,008,522 B2 8/2011 Lukhtanov et al.
8,101,776 B2 1/2012 Berens et al.
8,153,706 B2 4/2012 Vasudevan
8,217,389 B2 7/2012 Nakano et al.
8,293,700 B2 10/2012 Arranz
8,349,308 B2 1/2013 Yurkovetskiy et al.
8,354,515 B2 1/2013 Ueno et al.
8,431,545 B2 4/2013 Kataoka et al.
8,491,993 B2 7/2013 Nguyen et al.
8,546,590 B2 10/2013 Gall
8,632,947 B2 1/2014 Bentley et al.
8,802,738 B2 8/2014 Emrick
8,895,023 B2 11/2014 Rademacher et al.
8,906,603 B2 12/2014 Castro et al.
8,946,394 B2 2/2015 Na et al.
9,029,537 B2 5/2015 Koch
9,085,799 B2 7/2015 Bazan et al.
9,150,782 B2 10/2015 Lee et al.
9,400,273 B1 7/2016 Liu et al.
9,545,447 B2 1/2017 Wooley et al.
9,649,389 B2 5/2017 Groves et al.
9,687,291 B2 6/2017 Shimizu et al.
9,689,877 B2 6/2017 Matray et al.
9,696,310 B2 7/2017 Margulies et al.
9,714,946 B2 7/2017 Bradner et al.
9,765,220 B2 9/2017 Matray et al.
9,822,134 B2 11/2017 Segev
9,851,359 B2 12/2017 Matray et al.
9,884,070 B2 2/2018 Denardo et al.
9,910,051 B2 3/2018 Beacham et al.
9,913,992 B2 3/2018 Demarest et al.
9,932,578 B2 4/2018 Feinstein et al.
9,939,454 B2 4/2018 Dzubay et al.
10,036,754 B2 7/2018 Matray et al.
10,191,060 B2 1/2019 Chiu et al.
10,435,563 B2 10/2019 Matray et al.
10,617,670 B2 4/2020 Sapra et al.
10,709,791 B2 7/2020 Stayton et al.
10,834,091 B2 11/2020 Deninno et al.
10,865,310 B2 12/2020 Matray et al.
10,866,244 B2 12/2020 Matray et al.
10,954,391 B2 3/2021 Matray et al.
10,989,715 B2 4/2021 Matray et al.
11,013,756 B2 5/2021 Haruta et al.
11,084,932 B2 8/2021 Battrell et al.
11,142,647 B2 10/2021 Matray et al.
11,312,736 B1 4/2022 Matray et al.
11,352,502 B2 6/2022 Matray et al.
11,370,922 B2 6/2022 Matray et al.
11,377,563 B2 7/2022 Matray et al.
11,390,754 B2 7/2022 Singh et al.
11,434,374 B2 9/2022 Matray et al.
11,434,377 B2 9/2022 Matray et al.
11,453,783 B2 9/2022 Matray et al.
11,618,906 B2 4/2023 Steele et al.
11,685,835 B2 6/2023 Matray
11,827,661 B2 11/2023 Battrell et al.
11,874,280 B2 1/2024 Jackson et al.
11,931,419 B2 3/2024 Matray
11,945,955 B2 4/2024 Matray et al.
12,006,438 B2 6/2024 Singh et al.
12,018,159 B2 6/2024 Matray et al.
12,145,956 B2 11/2024 Matray et al.
2001/0018503 A1 8/2001 Whipple et al.
2002/0012947 A1 1/2002 Bevers et al.
2002/0099013 A1 7/2002 Piccariello et al.
2002/0142329 A1 10/2002 Matray et al.
2003/0054361 A1 3/2003 Heller
2003/0207208 A1 11/2003 Uenishi
2003/0207264 A1 11/2003 Packard et al.
2004/0014981 A1 1/2004 Lugade et al.
2004/0067498 A1 4/2004 Chenna et al.
2004/0096825 A1 5/2004 Chenna et al.
2004/0138467 A1 7/2004 French et al.
2004/0224372 A1 11/2004 Li et al.
2004/0241768 A1 12/2004 Whitten et al.
2005/0054024 A1 3/2005 Lawrence
2005/0123935 A1 6/2005 Haugland et al.
2006/0008822 A1 1/2006 Manoharan et al.
2006/0035302 A1 2/2006 Lee
2006/0063186 A1 3/2006 Benson et al.
2007/0042398 A1 2/2007 Peng et al.
2007/0077549 A1 4/2007 Buller et al.
2007/0148094 A1 6/2007 Uzgiris
2007/0269902 A1 11/2007 Beechem et al.
2008/0227939 A1 9/2008 Mizoshita et al.
2009/0253792 A1 10/2009 Mickle et al.
2009/0299070 A1 12/2009 Berens et al.
2010/0021901 A1 1/2010 Yin et al.
2010/0039684 A1 2/2010 Kolb et al.
2010/0092386 A1 4/2010 Segev
2010/0129800 A1 5/2010 Aymami Bofarull et al.
2010/0192312 A1 8/2010 Cremer et al.
2010/0248385 A1 9/2010 Tan et al.
2011/0014599 A1 1/2011 Akhavan-Tafti et al.
2011/0144065 A1 6/2011 Denardo et al.
2011/0224516 A1 9/2011 Romey et al.
2012/0021454 A1 1/2012 Bikker et al.
2012/0116079 A1 5/2012 Lukhtanov et al.
2012/0126175 A1 5/2012 Ueno et al.
2013/0059343 A1 3/2013 Cheung
2013/0119363 A1 5/2013 Sasaki et al.
2013/0137755 A1 5/2013 Segev
2013/0202536 A1 8/2013 Mustaev et al.
2013/0244891 A1 9/2013 Waggoner et al.
2014/0023590 A1 1/2014 Gao et al.
2014/0193504 A1 7/2014 Wooley et al.
2014/0275508 A1 9/2014 Scarr et al.
2015/0030541 A1 1/2015 Rogers
2015/0110715 A1 4/2015 Eder et al.
2015/0159198 A1 6/2015 McGall et al.
2015/0232615 A1 8/2015 Kwiatkowski
2015/0258217 A1 9/2015 Caravan
2016/0039850 A1 2/2016 Segev
2016/0176903 A1 6/2016 Segev
2016/0264737 A1 9/2016 Bartholomew et al.
2016/0327859 A1 11/2016 Idei et al.
2016/0347907 A1 12/2016 Dose
2017/0292957 A1* 10/2017 Matray .................. C07F 9/572
2017/0326233 A1 11/2017 Demeule et al.
2018/0065998 A1 3/2018 Battrell et al.
2018/0092993 A1 4/2018 Desai et al.
2018/0141935 A1 5/2018 Josel et al.
2018/0312468 A1 11/2018 Zhang et al.
2019/0136065 A1 5/2019 Singh et al.
2019/0144678 A1 5/2019 Matray et al.

(56) References Cited

U.S. PATENT DOCUMENTS

| | | | |
|---|---|---|---|
| 2019/0153232 | A1 | 5/2019 | Matray et al. |
| 2019/0177549 | A1 | 6/2019 | Matray et al. |
| 2019/0300716 | A1 | 10/2019 | Matray et al. |
| 2019/0378568 | A1 | 12/2019 | Robustelli |
| 2020/0032139 | A1 | 1/2020 | Behrendt et al. |
| 2020/0164085 | A1 | 5/2020 | Brandish et al. |
| 2020/0222554 | A1 | 7/2020 | Matray et al. |
| 2020/0330610 | A1 | 10/2020 | Desai et al. |
| 2020/0353089 | A1 | 11/2020 | Matray |
| 2020/0353094 | A1 | 11/2020 | Matray |
| 2020/0360526 | A1 | 11/2020 | Matray |
| 2021/0032277 | A1 | 2/2021 | Matray et al. |
| 2021/0032474 | A1 | 2/2021 | Matray et al. |
| 2021/0095130 | A1 | 4/2021 | Matray et al. |
| 2021/0096135 | A1 | 4/2021 | Matray et al. |
| 2021/0128591 | A1 | 5/2021 | Matray |
| 2021/0128739 | A1 | 5/2021 | Matray |
| 2021/0139440 | A1 | 5/2021 | Ramsden et al. |
| 2021/0285953 | A1 | 9/2021 | Matray et al. |
| 2021/0395530 | A1 | 12/2021 | Matray et al. |
| 2022/0160887 | A1 | 5/2022 | Matray et al. |
| 2022/0168433 | A1 | 6/2022 | Matray et al. |
| 2022/0168435 | A1 | 6/2022 | Matray et al. |
| 2022/0175951 | A1 | 6/2022 | Boitano et al. |
| 2022/0220314 | A1 | 7/2022 | Singh et al. |
| 2022/0227794 | A1 | 7/2022 | Matray et al. |
| 2022/0305127 | A1 | 9/2022 | Thomas et al. |
| 2022/0372297 | A1 | 11/2022 | Matray et al. |
| 2022/0380603 | A1 | 12/2022 | Matray et al. |
| 2022/0402963 | A1 | 12/2022 | Matray et al. |
| 2023/0012304 | A1 | 1/2023 | Matray et al. |
| 2023/0129481 | A1 | 4/2023 | Matray et al. |
| 2024/0043455 | A1 | 2/2024 | Battrell et al. |
| 2024/0092820 | A1 | 3/2024 | Matray et al. |
| 2024/0132725 | A1 | 4/2024 | Sherif |
| 2024/0207423 | A1 | 6/2024 | Matray |
| 2024/0210408 | A1 | 6/2024 | Jackson et al. |
| 2024/0248094 | A1 | 7/2024 | Matray et al. |
| 2024/0255514 | A1 | 8/2024 | Matray et al. |
| 2024/0287313 | A1 | 8/2024 | Sherif |
| 2024/0287314 | A1 | 8/2024 | Matray et al. |
| 2024/0327440 | A1 | 10/2024 | Jackson et al. |

FOREIGN PATENT DOCUMENTS

| | | | |
|---|---|---|---|
| CN | 103319378 | A | 9/2013 |
| CN | 104072727 | A | 10/2014 |
| CN | 105377994 | A | 3/2016 |
| CN | 106589005 | A | 4/2017 |
| CN | 107106685 | A | 8/2017 |
| CN | 107454903 | A | 12/2017 |
| CN | 107709470 | A | 2/2018 |
| CN | 109153860 | A | 1/2019 |
| EP | 0708837 | B1 | 3/2006 |
| GB | 2 372 256 | A | 8/2002 |
| GB | 2 554 666 | A | 4/2018 |
| JP | S61207395 | A | 9/1986 |
| JP | H04282391 | A | 10/1992 |
| JP | 2000017183 | A | 1/2000 |
| JP | 2003532092 | A | 10/2003 |
| JP | 2011135823 | A | 7/2011 |
| JP | 2014527071 | A | 10/2014 |
| JP | 2016534107 | A | 11/2016 |
| JP | 2017504659 | A | 2/2017 |
| JP | 2017124994 | A | 7/2017 |
| JP | 2018507863 | A | 3/2018 |
| JP | 2018512167 | A | 5/2018 |
| JP | 2018515628 | A | 6/2018 |
| JP | 2019516807 | A | 6/2019 |
| JP | 2019516821 | A | 6/2019 |
| JP | 2021518410 | A | 8/2021 |
| JP | 2021527911 | A | 10/2021 |
| JP | 7069033 | B2 | 5/2022 |
| JP | 7239904 | B2 | 3/2023 |
| KR | 20030032939 | A | 4/2003 |
| KR | 20100138910 | A | 12/2010 |
| KR | 101041446 | B1 | 6/2011 |
| KR | 10-2015-0007795 | A | 1/2015 |
| KR | 20160022358 | A | 2/2016 |
| KR | 20180005650 | A | 1/2018 |
| KR | 10-2020-0133374 | A | 11/2020 |
| KR | 20210032434 | A | 3/2021 |
| KR | 102530707 | B1 | 5/2023 |
| SU | 1121931 | A1 | 4/1988 |
| WO | 9502700 | A1 | 1/1995 |
| WO | 9506731 | A2 | 3/1995 |
| WO | 9832463 | A2 | 7/1998 |
| WO | 0173123 | A2 | 10/2001 |
| WO | 0183502 | A1 | 11/2001 |
| WO | 0222883 | A1 | 3/2002 |
| WO | 02083954 | A1 | 10/2002 |
| WO | 2004007751 | A2 | 1/2004 |
| WO | 2007094135 | A1 | 8/2007 |
| WO | WO 2009113645 | A1 | 9/2009 |
| WO | 2010026957 | A1 | 3/2010 |
| WO | WO 2011088193 | A2 | 7/2011 |
| WO | 2013012687 | A2 | 1/2013 |
| WO | WO 2014102803 | A1 | 7/2014 |
| WO | 2014147642 | A1 | 9/2014 |
| WO | WO-2015027176 | A1 | 2/2015 |
| WO | WO 2015091953 | A1 | 6/2015 |
| WO | 2015155753 | A2 | 10/2015 |
| WO | 2016168750 | A1 | 10/2016 |
| WO | WO 2016183185 | A1 | 11/2016 |
| WO | 2017003639 | A2 | 1/2017 |
| WO | WO 2017062271 | A2 | 4/2017 |
| WO | 2017089890 | A1 | 6/2017 |
| WO | 2017094897 | A1 | 6/2017 |
| WO | WO 2017173355 | A1 | 10/2017 |
| WO | WO 2017177065 | A2 | 10/2017 |
| WO | WO 2017197144 | A1 | 11/2017 |
| WO | 2018045278 | A1 | 3/2018 |
| WO | WO 2019071208 | A1 | 4/2019 |
| WO | 2019126691 | A1 | 6/2019 |
| WO | WO 2019140227 | A1 | 7/2019 |
| WO | WO 2019182765 | A1 | 9/2019 |
| WO | WO 2019182766 | A1 | 9/2019 |
| WO | 2020014634 | A1 | 1/2020 |
| WO | 2020219959 | A1 | 10/2020 |
| WO | WO 2021062176 | A2 | 4/2021 |
| WO | WO-2021067483 | A1 | 4/2021 |
| WO | 2022125564 | A1 | 6/2022 |
| WO | WO-2022115388 | A1 | 6/2022 |

OTHER PUBLICATIONS

Arian et al., "1,9-Dialkoxyanthracene as a 1O2-Sensitive Linker," *J. Am. Chem. Soc. 133*:3972-3980, 2011.

Avirah et al., "Infrared Absorbing Croconaine Dyes: Synthesis and Metal Ion Binding Properties," *J. Org. Chem. 73*(1):274-279, 2008.

Aviñó et al., "Solid-phase synthesis of oligomers carrying several chromophore units linked by phosphodiester backbones," *Bioorganic & Medicinal Chemistry Letters 18*:2306-2310, 2008.

Babitskaya et al., "Bromoacyl Analogues of Phosphatidycholine with Intramolecular Fluorescence Quenching and Their Use as Substrates for Continuous Monitoring of Phospholipase A2 Activity," *Applied Biochemistry and Microbiology 40*(4):351-356, 2004.

Bag et al., "Triazolyl-donor-acceptor chromophore-decorated unnatural amino acids and peptides: FRET events in a β-turn conformation," *Chem. Commun. 50*:433-435, 2014.

Beaucage et al., "The Functionalization of Oligonucleotides Via Phosphoramidite Derivatives," *Tetrahedron 49*(10):1925-1963, 1993.

Becker et al., "New Thermotropic Dyes Based on Amino-Substituted Perylendicarboximides," *Chem. Eur. J. 6*(21):3984-3990, 2000.

Bergstrom et al., "A NaPi2b Antibody-Drug Conjugate Induces Durable Complete Tumor Regressions in Patient-Derived Xenograft Models of NSCLC," *IASLC 17th World Conference on Lung Cancer*, Vienna, Austria, Dec. 4-7, 2016 (8 pages).

Bergstrom et al., "A novel, highly potent HER2-targeted antibody-drug conjugate (ADC) for the treatment of low HER2-expressing

(56) References Cited

OTHER PUBLICATIONS tumors and combination with trastuzumab-based regimens in HER2-driven tumors," Mersana Therapeutics, Abstract LBA-231, 2015.
Bergstrom et al., "Potent Promise," *Innovations in Pharmaceutical Technology 49*:16-20, 2014.
Bergstrom et al., "XMT-1522 induces tumor regressions in pre-clinical models representing HER2-positive and HER2 low-expressing breast cancer," Mersana Therapeutics, Abstract P4-14-28, 2015, 1 page.
Boldyrev et al., "Synthesis and Characteristics of New Fluorescent Probes Based on Cardiolipin," *Russian Journal of Bioorganic Chemistry 35*(2):219-224, 2009.
Braeckmans et al., "Three-dimensional fluorescence recovery after photobleaching with the confocal scanning laser microscope," *Biophysical Journal 85*:2240-2252, 2003.
Braga et al., "Intracellular macromolecular mobility measured by fluorescence recovery after photobleaching with confocal laser scanning microscopes," *Molecular Biology of the Cell 15*:4749-4760, 2004.
Breul et al., "Fluorescent monomers as building blocks for dye labeled polymers: synthesis and application in energy conversion, biolabeling and sensors," Chem. Soc. Rev. 42(12):5366-5407, 2013.
Brinkley, "A brief survey of methods for preparing protein conjugates with dyes, haptens, and cross-linking reagents," *Bioconjugate Chem 3*:2-13, 1992.
Buckhout-White et al., "Assembling programmable FRET-based photonic networks using designer DNA scaffolds," *Nature Communications 5*:5615, Dec. 11, 2014. (16 pages).
CAPLUS Accession No. 1975: 171341, Holy, "Nucleic acid components and their analogs. CLXXII. Aliphatic analogs of nucleosides, nucleotides, and oligonucleotides," *Collection of Czechoslovak Chemical Communications 40*(1):187-214, 1975. (1 page).
CAS Registry No. 862288-26-4, American Chemical Society, 2021. (1 page).
Chang et al., "A General Approach for Generating Fluorescent Probes to Visualize Piconewton Forces at the Cell Surface," *J. Am. Chem. Soc. 138*:2901-2904, 2016. (4 pages).
Chattopadhyay et al., "Brilliant Violet Fluorophores: A New Class of Ultrabright Fluorescent Compounds for Immunofluorescence Experiments," *Cytometry Part A 81A*:456-466, 2012.
Chen et al., "Synthesis and properties of new segmented block poly(urethane-urea)s containing phosphatidylcholine analogues and polybutadienes," *Macro-Molecular Chemistry and Physics 197*(5):1587-1597, May 1996. (11 pages).
Chen et al., "Synthesis of Novel Phosphoramidite Reagents for the Attachment of Antisense Oligonucleotides to Various Regions of the Benzophenanthridine Ring System," *Bioconjugate Chemistry 6*(4):473-482, Jul. 1, 1995. (10 pages).
Chong et al., "Oxygen Quenching of Pyrene-Lipid Fluorescence in Phosphatidylcholine Vesicles—A Probe for Membrane Organization," *Biophys. J. 47*:613-621, 1985.
Ciccotelli et al., "Polyguanine-conjugated antigens for scavenger receptor targeting and self-adjuvanting vaccines (VAC13P.1125)," *The Journal of Immunology 194*(Suppl. 1):214.5, May 1, 2015 [Abstract]. (1 page).
Cuppoletti et al., "Oligomeric fluorescent labels for DNA," *Bioconjug. Chem. 16*(3):528-534, 2005.
Dai et al., "DNA-polyfluorophore excimers as sensitive reporters for esterases and lipases," *Chem. Commun. 46*:1221-1223, 2010.
Damian et al., "Synthesis and DNA Interaction of Platinum Complex/Peptide Chimera as Potential Drug Candidates," *Eur. J. Org. Chem.* 6161-6170, 2010.
De Vos et al., "New Non Nucleosidic Phosphoramidites for the Solid Phase Multi-Labelling of Oligonucleotides: Comb- and Multifork-Like Structures," *Nucleosides & Nucleotides 13*(10):2245-2265, 1994.
Dioubankova et al., "Oligonucleotides containing new fluorescent 1-phenylethynylpyrene and 9,10-bis(phenylethynyl)anthracene uridine-2'-carbamates: synthesis and properties," *Tetrahedron 60*:4617-4626, 2004.
DiVittorio et al., "Synthetic peptides with selective affinity for apoptotic cells," *Org. Biomol. Chem. 4*:1966-1976, 2006.
Doi et al., "Hetero-Selective DNA-Like Duplex Stabilized by Donor-Acceptor Interactions," *Chem. Eur. J. 21*:15974-15980, 2015.
Drescher et al., "General Synthesis and Aggregation Behaviour of New Single-Chain Bolaphospholipids: Variations in Chain and Headgroup Structures," *Chemistry—A European Journal 14*(22):6796-6804, 2008.
Dropulic et al., "Update on New Antivirals Under Development for the Treatment of Double-Stranded DNA Virus Infections," Clinical Pharmacology & Therapeutics 88(5):610-619, Nov. 2010.
Dubrovsky, "Semiconductor nanoparticles as reporters in multiplexed immunoassay and cell analysis," *International Journal of Nanoscience 8*(1 & 2):163-167, 2009.
Finniss et al., "A versatile acid-labile linker for antibody-drug conjugates," Med. Chem, Commun; 5; Apr. 1, 2014, 4 pages.
Franceschin et al., "Synthesis of a Dibromoperylene Phosphoramidite Building Block and Its Incorporation at the 5' End of a G-Quadruplex Forming Oligonucleotide: Spectroscopic Properties and Structural Studies of the Resulting Dibromoperylene Conjugate," *Bioconjugate Chem 22*:1309-1319, 2011.
Franzini et al., "Identification of Structure-Activity Relationships from Screening a Structurally Compact DNA-Encoded Chemical Library," *Angewandte Chemie International Edition 54*:3927-3931, Feb. 3, 2015 [with supporting information]. (41 pages).
Gao et al., "Libraries of Composite Polyfluors Built from Fluorescent Deoxyribosides," *Journal of the American Chemical Society 124*:11590-11591, 2002.
Gao et al., "Modified DNA Analogues That Sense Light Exposure with Color Changes," *Journal of the American Chemical Society 126*:12748-12749, 2004.
Gordon et al., "Analysis of simulated and experimental fluorescence recovery after photobleaching. Data for two diffusing components," *Biophysical Journal 68*:766-778, 1995.
Griesang et al., "Four-Color, Enzyme-Free Interrogation of DNA Sequences with Chemically Activated, 3'-Fluorphore-Labeled Nucleotides," *Angew. Chem. Int. Ed. 45*:6144-6148, 2006.
Gupta et al., "Dendrimers: Novel Polymeric Nanoarchitectures for Solubility Enhancement," *Biomacromolecules 7*(3):649-658, Mar. 2006 [Published online Feb. 15, 2006]. (10 pages).
Guryev et al., "Control of the Fluorescence of Dye-Antibody Conjugates by (2-Hydroxypropyl)-β-cyclodextrin in Fluorescence Microscopy and Flow Cytometry," *Analytical Chemistry 83*:7109-7114, Aug. 16, 2011.
Hanhela et al., "Synthesis and Evaluation of Fluorescent Materials for Colour Control of Peroxyoxalate Chemiluminescence. III. Yellow and Red Fluorescent Emitters," *Australian Journal of Chemistry 34*:1701-1717, 1981.
Haraguchi, "Live Cell Imaging: Approaches for Studying Protein Dynamics in Living Cells," *Cell Structure And Function 27*:333-334, 2002.
Hasegawa et al., "Cysteine, histidine and glycine exhibit anti-inflammatory effects in human coronary arterial endothelial cells," *Clinical and Experimental Immunology 167*:269-274, Jan. 11, 2012. (6 pages).
Irani et al., "Molecular properties of human IgG subclasses and their implications for designing therapeutic monoclonal antibodies against infectious diseases," *Molecular Immunology 67*:171-182, 2015.
Jain et al. "Current ADC Linker Chemistry," *Pharm. Res. 32*:3526-3540, 2015.
Johansson, "Choosing Reporter-Quencher Pairs for Efficient Quenching Through Formation of Intramolecular Dimers," *Methods in Molecular Biology 335*:17-29, 2006.
Kashida et al., "A Cationic Dye Triplet as a Unique "Glue" That Can Connect Fully Matched Termini of DNA Duplexes," *Chem. Eur. J. 17*:2614-2622, 2011.
Khandare et al., "Polymer-drug conjugates: Progress in polymeric prodrugs," *Progress in Polymer Science 31*(4):359-397, Apr. 2006. (39 pages).
Koo et al., "Fluorescent DNA chemosensors: identification of bacterial species by their volatile metabolites," *Chemical Communications 47*:11435-11437, 2011.

(56) References Cited

OTHER PUBLICATIONS

Kozma et al., "Fluorescent Ligands for Adenosine Receptors," *Bioorganic & Medicinal Chemistry Letters 23*: 26-36, 2013.
Krueger at al., "Fluorescent Amino Acids: Modular Building Blocks for the Assembly of New Tools for Chemical Biology," *ChemBioChem 14*:788-799, 2013.
Lapeyre et al., "Aryldithioethyloxycarbonyl (Ardec): A New Family of Amine Protecting Groups Removable under Mild Reducing Conditions and Their Applications to Peptide Synthesis," *Chem. Eur. J. 12*:3655-3671, 2006.
Lee et al., "Monitoring the Hydrophobic Interactions of Internally Pyrene-Labeled Poly(ethylene oxide)s in Water by Fluorescence Spectroscopy," *Macromolecules 31*:9193-9200, 1998.
Leung et al., "7-Amino-4-Methyl-6-Sulfocoumarin-3-Acetic Acid: A Novel Blue Fluorescent Dye for Protein Labeling," *Bioorganic & Medicinal Chemistry Letters 9*: 2229-2232, 1999.
Lewis et al., "Orientation Control of Fluorescence Resonance Energy Transfer Using DNA as a Helical Scaffold," *J. Am. Chem. Soc. 127*(28):10002-10003, 2005.
Li et al., "Polymeric Drugs: Advances in the development of pharmacologically active polymers," *Journal of Controlled Release 219*:369-382, 2015.
Li et al., "Responsive nanogel-based dual fluorescent sensors for temperature and Hg2+ ions with enhanced detection sensitivity," *J. Mater. Chem. 20*:10716-10723, 2010.
Liu et al., "Detection of prostate-specific membrane antigen on HUVECs in response to breast tumor-conditioned medium," *International Journal of Oncology 38*:1349-1355, 2011.
Liu et al., "DNA-Based Micelles: Synthesis, Micellar Properties and Size-Dependent Cell Permeability," *Chem. Eur. J. 16*:3791-3797, 2010 (14 Pages).
Liu et al., "Increased Cytotoxicity and Decreased In Vivo Toxicity of FdUMP[10] Relative to 5-FU," *Nucleosides & Nucleotides 18*(8):1789-1802, Aug. 1999. (14 pages).
Liu et al., "Structure-based programming of lymph-node targeting in molecular vaccines," *Nature 507*:519-522, Mar. 27, 2014 [Published online Feb. 16, 2014]. (15 pages).
Luo et al., "Sensitive and rapid quantification of C-reactive protein using quantum dot-labeled microplate immunoassay," *Journal of Translational Medicine 10*(24):1-9, 2012.
Malakhov et al., "1-(Phenylethynyl)pyrene and 9,10-Bis(phenylethynyl)anthracene, Useful Fluorescent Dyes for DNA Labeling: Excimer Formation and Energy Transfer," *Eur. J. Org. Chem*: 1298-1307, 2004.
Masuko et al., "Fluorescence resonance energy transfer from pyrene to perylene labels for nucleic acid hybridization assays under homogenous solution conditions," *Nucleic Acids Research 28*(8):e34, 2000 (8 pages).
McKinlay et al., "Cell-Penetrating, Guanidinium-Rich Oligophosphoesters: Effective and Versatile Molecular Transporters for Drug and Probe Delivery," *J. Am. Chem. Soc. 138*:3510-3517, Feb. 22, 2016.
Mersana Therapeutics, URL= http://www.mersana.com, download date Jan. 3, 2019, 9 pages.
Midoux et al., "Chemical vectors for gene delivery: a current review on polymers, peptides and lipids containing histidine or imidazole as nucleic acids carriers," *British Journal of Pharmacology 157*:166-178, May 2009. (13 pages).
Mielewczyk et al., "5' end fluorescent labelling of oligonucleotides with riboflavin-derived phosphitylating reagent," *Acta Biochimica Polonica 36*(3-4):225-233, 1989. (9 pages).
Molotkovsky et al., "Perylenoyl- and Anthrylvinyl-Labeled Lipids as Membrane Probes," *Biochimica et Biophysica Acta 778*:281-288, 1984.
Moss, "Nomenclature of Fused and Bridged Fused Ring Systems," *Pure & Appl. Chem. 70*(1):143-216, 1998.
Mthembu et al., "Breaking a Couple: Disulfide Reducing Agents," *ChemBioChem 21*, 2020. (10 pages).
Nolting, "Linker Technology for Antibody-Drug Conjugates," in Ducry (ed.), *Antibody-Drug Conjugates*, Humana Press, Totowa, NJ, 2013, Ch. 5, pp. 71-100.
Nussbaumer et al., "Amplification of Chirality by Supramolecular Polymerization of Pyrene Oligomers," *Angewandte Chemie International Edition 50*:5490-5494, 2011.
Oh et al., "Low-dose guanidine and pyridostigmine: relatively safe and effective long-term symptomatic therapy in Lambert-Eaton myasthenic syndrome," *Muscle & Nerve 20*:1146-1152, Sep. 1997. (7 pages).
Paris et al., "Probing DNA sequences in solution with a monomer-excimer fluorescence color change," *Nucleic Acids Research 26*(16):3789-3793, 1998.
Pelegrin et al., "Antiviral Monoclonal Antibodies: Can They Be More Than Simple Neutralizing Agents?" *Trends in Microbiology 23*(10):653-665, Oct. 2015.
Petersen et al., "Acyclic, achiral enamide nucleoside analogues. The importance of the C=C bond in the analogue for its ability to mimic natural nucleosides," *Organic & Biomolecular Chemistry 1*:3293-3296, Sep. 4, 2003. (4 pages).
Petreus et al., "Polyester imides containing main-chain phosphorus," *Revue Roumaine de Chimie 34*(8):971-978, 1994 (with English Abstract).
Phares et al., "Improving the Stability and Sensing of Electrochemical Biosensors by Employing Trithiol-Anchoring Groups in a Six-Carbon Self-Assembled Monolayer," *Anal. Chem. 81*(3):1095-1100, Feb. 1, 2009.
Poupart et al., "Aminopropargyl derivative of terpyridine-bis(methyl-enamine) tetraacetic acid chelate of europium (Eu (TMT)-AP3): a new reagent for fluorescent labelling of proteins and peptides," Org. Biomol. Chem. 4:4165-4177, Oct. 2006.
Pownall et al., "Kinetics of Spontaneous and Plasma-Stimulated Sphingomyelin Transfer," *Biochimica et Biophysica Acta 712*:169-176, 1982.
PubChem, "US20100012929A1-20100121-C00010_4," SID No. 140452858, retrieved Mar. 29, 2016 from URL https://pubchem.ncbi.nlm.nih.gov/substance/140452858#sectio . . . , 6 pages.
Puri et al., "Synthesis of 5'-polyarene-tethered oligo-DNAs and the thermal stability and spectroscopic properties of their duplexes and triplexes," *Tetrahedron 53*(30):10409-10432, Jul. 28, 1997. (24 pages).
Reed et al., "Structure-activity relationships of cytotoxic cholesterol-modified DNA duplexes," *Journal of Medicinal Chemistry 38*(22):4587-4596, Oct. 27, 1995. (10 pages).
Ren et al., "An Antisense Oligodeoxynucleotide-Doxorubicin Conjugate: Preparation and Its Reversal Multidrug Resistance of Human Carcinoma Cell Line In Vitro," Nucleosides, Nucleotides & Nucleic Acids 23(10):1595-1607, 2004.
RN 230952-79-1, Registry Database Compound, 1999.
Rochat et al., "Water-Soluble Cationic Conjugated Polymers: Response to Electron-Rich Bioanalytes," *J. Am. Chem. Soc. 135*:17703-17706, 2013.
Rupcich et al., "Quenching of Fluorophore-Labeled DNA Oligonucleotides by Divalent Metal Ions: Implications for Selection, Design, and Applications of Signaling Aptamers and Signaling Deoxyribozymes," J. Am. Chem. Soc. 126(3):780-790, 2006.
Saito et al., "Dual-labeled oligonucleotide probe for sensing adenosine via FRET: A novel alternative to SNPs genotyping," Chem. Commun.:2133-2135, 2007.
Samal et al., "Cationic polymers and their therapeutic potential," *Chemical Society Reviews 41*:7147-7194, Aug. 2012. (48 pages).
Shuey et al., "Cyclohexanediol Bisphosphates as Models for Phospholipid-Metal Ion Binding Sites," *Bioorganic Chemistry 21*:95-108, Mar. 1993. (14 pages).
Shuman et al., "Bacterial DNA repair by non-homologous end joining," *Nature Reviews Microbiology 5*:852-861, Nov. 2007.
Singh et al., "Multiplexed measurement of membrane protein populations," *Caplus 2003*:769075, 2003. (2 pages).
Stewart et al., "The Fluorescence of a Chelating Two-Photon-Absorbing Dye is Enhanced with the Addition of Transition Metal Ions but Quenched in the Presence of Acid," *Proc. of SPIE 9939*:993904, 2016 (10 pages).

(56) References Cited

OTHER PUBLICATIONS

STIC Search Report from American Chemical Society, for U.S. Appl. No. 17/255,353, dated Sep. 7, 2023. (143 pages).
Striebel et al., "Enhancing sensitivity of human herpes virus diagnosis with DNA microarrays using dendrimers," *Experimental and Molecular Pathology 77*:89-97, Oct. 2004 [Published online Jul. 15, 2004]. (9 pages).
Stuart et al., "Site-Specific DNA-Doxorubicin Conjugates Display Enhanced Cytotoxicity to Breast Cancer Cells," *Bioconjugate Chemistry 25*:406-413, 2014.
Sun et al., "Dual-Color Fluorescence Imaging of Magnetic Nanoparticles in Live Cancer Cells Using Conjugated Polymer Probes," *Scientific Reports 6*:22368, 2016. (12 pages).
Sun et al., "High yield production of high molecular weight poly-(ethylene glycol)/ α-cyclodextrin polyrotaxanes by aqueous one-pot approach," *Polymer 53*:2884-2889, 2012.
Sun et al., "Self-assembled biodegradable micellar nanoparticles of amphiphilic and cationic block copolymer for siRNA delivery," *Biomaterials 29*:4348-4355, available online Aug. 2008. (8 pages).
Sun et al., "Ultrabright and Multicolorful Fluorescence of Amphiphilic Polyethyleneimine Polymer Dots for Efficiently Combined Imaging and Therapy," *Scientific Reports 3*:3036, 2013. (6 pages).
Tabujew et al., "Chapter One: Functionalization of Cationic Polymers for Drug Delivery Applications," *RSC Polymer Chemistry Series 13*, 2015. (29 pages).
Takakusa et al., "Design and Synthesis of an Enzyme-Cleavable Sensor Molecule for Phosphodiesterase Activity Based on Fluorescence Resonance Energy Transfer," *J. Am. Chem. Soc. 124*(8):1653-1657, 2002.
Teo et al., "Polyfluorophores on a DNA Backbone: A Multicolor Set of Labels Excited at One Wavelength," *J. Am. Chem. Soc. 131*(11):3923-3933, 2009. (NIH Public Access Author Manuscript, available in PMC Mar. 2, 20105, 23 pages).
Teyssot et al., "Aromatic Nitrogen Donors for Efficient Copper(1)-NHC CuAAC under Reductant-Free Conditions," *Eur. J. Org. Chem*. 3507-3515, 2010.
Tram et al., "Oligonucleotide Labeling Using BODIPY Phosphoramidite," *Nucleosides, Nucleotides & Nucleic Acids 30*(1):1-11, 2011.
Vinogradov et al., "Total synthesis and biochemical characterization of mirror image barnase," *Chem Sci. 6*: 2997-3002, 2015.
Vybornyi et al., "Formation of Two-Dimensional Supramolecular Polymers by Amphiphilic Pyrene Oligomers," *Angew. Chem. Int. Ed. 52*:114488-11493, 2013.
Wang et al., "Cruciforms: Assembling Single Crystal Micro- and Nanostructures from Oneto Three Dimensions and Their Applications in Organic Field-Effect Transistors," *Chem. Mater. 21*:2840-2845, 2009.
Wang et al., "DNA Polyfluorophores for Real-Time Multicolor Tracking of Dynamic Biological Systems," *Angew. Chem. Int. Ed. 51*:7176-7180, 2012.
Wang et al., "Fluorescence-Based Evaluation of the Partitioning of Lipids and LipidatedPeptides into Liquid-Ordered Lipid Microdomains: A Model for Molecular Partitioning into Lipid Rafts," *Biophysical Journal 79*:919-933, Aug. 2000.
Wilson et al., "Efficient Quenching of Oligomeric Fluorophores on a DNA Backbone," *Journal of the American Chemical Society 129*(50):15426-15427, 2007.
Wilson et al., "Oligodeoxyfluorosides: Strong Sequence of Dependence of Fluorescence Emission," *Tetrahedron 63*(17):3427-3433, 2007 (18 Pages).
Winiger et al., "Long-Distance Electronic Energy Transfer in Light-Harvesting Supramolecular Polymers," *Angew. Chem. Int. Ed. 53*:13609-13613, 2014.
Wu Yi et al., "$^{Py}$A-Modified Oligodeoxyadenylates: Expanded Fluorescence Phenomena and Structural Formation," *Chemistry—An Asian Journal 7*:60-63, Nov. 2011. (4 pages).
Yu et al., "Targeted Delivery of an Anti-Inflammatory PDE4 Inhibitor to Immune Cells via an Antibody-drug Conjugate," Molecular Therapy 24(12):2078-2089, Dec. 2016.
Yurkovetskiy et al., "Advantages of Polyacetal Polymer-based Antibody Drug Conjugates: Application to Low Expression Targets," Mersana Therapeutics, technical paper #2645, 2014, 1 page.
Zhang et al., "FRET Imaging of Enzyme-Responsive HPMA Copolymer Conjugate," *Macromol. Biosci. 17*:1600125, 2017 (8 pages).
Zhao et al., "Mussel-Inspired One-Pot Synthesis of a Fluorescent and Water-SolublePolydopamine-Polyethyleneimine Copolymer," Macromol. Rapid Commun. 36:909-915, 2015.
Bargh et al., "Cleavable linkers in antibody-drug conjugates," *Chemical Society Reviews 48*(16):4361-4374, Aug. 21, 2019. (15 pages).
CAPLUS Accession No. 1991:467753, Mielewczyk et al., "5' end fluorescent labelling of oligonucleotides with riboflavin-derived phosphitylating reagent," *Acta Biochimica Polonica 36*(3-4):225-233, 1989. (1 page).
CAPLUS Accession No. 1995:665426, Chen et al., "Synthesis of Novel Phosphoramidite Reagents for the Attachment of Antisense Oligonucleotides to Various Regions of the Benzophenanthridine Ring System," *Bioconjugate Chemistry 6*(4):473-482, Jul. 1, 1995. (1 page).
CAPLUS Accession No. 1995:733249, WO9506731A2, filed Mar. 9, 1995. (1 page).
CAPLUS Accession No. 1995:849926, Reed et al., "Structure-Activity Relationships of Cytotoxic Cholesterol-Modified DNA Duplexes," *Journal of Medicinal Chemistry 38*(22):4587-4596, Oct. 27, 1995. (1 page).
CAPLUS Accession No. 1997:497709, Puri et al., "Synthesis of 5'-polyarene-tethered oligo-DNAs and the thermal stability and spectroscopic properties of their duplexes and triplexes," *Tetrahedron 53*(30):10409-10432, Jul. 28, 1997. (1 page).
Kolpashchikov, "Binary Probes for Nucleic Acid Analysis," *Chemical Reviews 110*(8):4709-4723, Jun. 28, 2010. (15 pages).
Kozytska et al., "Discovery of the novel, homogenous payload platform Dolasynthen for Antibody-Drug Conjugates," Mersana Therapeutics, Abstract #272, 2018. (1 page).
Lee et al., "The spectroscopic analysis for binding of amphipathic and antimicrobial model peptides containing pyrenylalanine and tryptophan to lipid bilayer," *Biochimica et Biophysica Acta 984*:174-182, Sep. 4, 1989. (9 pages).
Liso et al., "Polymeric drugs derived from Ibuprofen with improved antiinflammatory profile," *Journal of Biomedical Materials Research 32*:553-560, Dec. 1996. (8 pages).
Liu et al., "Imidazole inhibits autophagy flux by blocking autophagic degradation and triggers apoptosis via increasing FoxO3a-Bim expression," *International Journal of Oncology 46*:721-731, Feb. 2015. (11 pages).
Lvnitski et al., "Introducing charge transfer functionality into prebiotically relevant β-sheet peptide fibrils," *Chemical Communications 50*:6733-6736, May 12, 2014. (4 pages).
Marras et al., "Efficiencies of fluorescence resonance energy transfer and contact-mediated quenching in oligonucleotide probes," *Nucleic Acids Research 30*(21):e122, Nov. 1, 2002. (8 pages).
Pawelczyk et al., "Molecular Consortia-Various Structural and Synthetic Concepts for More Effective Therapeutics Synthesis," *International Journal of Molecular Sciences 19*:1104, Apr. 6, 2018. (19 pages).
Wang et al., "Novel dexamethasone-HPMA copolymer conjugate and its potential application in treatment of rheumatoid arthritis," *Arthritis Research & Therapy 9*(1):R2, Jan. 18, 2007. (9 pages).
Wang, "Modern Synthetic Methods and Technologies of Polymers," Common Knowledge Evidence, Tongji University Press, 1st Edition, Jul. 2013, pp. 210-211. (includes portion of Chinese Office Action with English Summary of relevance) (20 pages).
Xu et al., "Synthesis of [D-Pyrenylalanine4,4']gramicidin S by Solid-Phase-Synthesis and Cyclization-Cleavage Method with Oxime Resin," *Chemistry Letters 21*:191-194, Feb. 1992. (4 pages).
Antos et al., "Site-Specific Protein Labeling via Sortase-Mediated Transpeptidation," Current Protocols in Protein Science, Chapter 15:15.3.1-15.3.9, Apr. 2009 (HHS Public Access Author Manuscript, available in PMC Aug. 10, 2017). (23 pages).
Doronina et al., "Development of potent monoclonal antibody auristatin conjugates for cancer therapy," Nature Biotechnology

(56) References Cited

OTHER PUBLICATIONS

21(7):778-784, Jul. 2003 [Published online Jun. 1, 2003] (with Erratum as published Nature Biotechnology 21(8):941, Aug. 2003). (8 pages).
Lee et al., "Targeted multimodal imaging modalities," Advanced Drug Delivery Reviews 76:60-78, Jul. 24, 2014. (19 pages).
Neidle et al. (Eds.), "Chapter 7: Acridine-based Anticancer Drugs," Molecular Aspects of Anticancer Drug-DNA Interactions, Topics in Molecule in Structural Biology, vol. 2, pp. 270-311, 1994. (52 pages).
Sousa et al., "Phenazines: Natural products for microbial growth control," hLife 2(3):100-112, Mar. 2024. (13 pages).
Wagenknecht, "Fluorescent DNA Base Modifications and Substitutes: Multiple Fluorophore Labeling and the DETEQ Concept," Annals of the New York Academy of Sciences 1130(1):122-130, May 2008. (9 pages).

* cited by examiner

SPACING LINKER GROUP DESIGN FOR BRIGHTNESS ENHANCEMENT IN DIMERIC OR POLYMERIC DYES

BACKGROUND

Technical Field

The present disclosure is generally directed to dimeric and polymeric fluorescent or colored dyes having spacing groups for brightness enhancement, and methods for their preparation and use in various analytical methods.

Description of the Related Art

Fluorescent and/or colored dyes are known to be particularly suitable for applications in which a highly sensitive detection reagent is desirable. Dyes that are able to preferentially label a specific ingredient or component in a sample enable the researcher to determine the presence, quantity and/or location of that specific ingredient or component. In addition, specific systems can be monitored with respect to their spatial and temporal distribution in diverse environments.

Fluorescence and colorimetric methods are extremely widespread in chemistry and biology. These methods give useful information on the presence, structure, distance, orientation, complexation and/or location for biomolecules. In addition, time-resolved methods are increasingly used in measurements of dynamics and kinetics. As a result, many strategies for fluorescence or color labeling of biomolecules, such as nucleic acids and protein, have been developed. Since analysis of biomolecules typically occurs in an aqueous environment, the focus has been on development and use of water soluble dyes.

Highly fluorescent or colored dyes are desirable since use of such dyes increases the signal to noise ratio and provides other related benefits. Accordingly, attempts have been made to increase the signal from known fluorescent and/or colored moieties. For example, dimeric and polymeric compounds comprising two or more fluorescent and/or colored moieties have been prepared in anticipation that such compounds would result in brighter dyes. However, as a result of intramolecular fluorescence quenching, the known dimeric and polymeric dyes have not achieved the desired increase in brightness.

There is thus a need in the art for water soluble dyes having an increased molar brightness. Ideally, such dyes and biomarkers should be intensely colored or fluorescent and should be available in a variety of colors and fluorescent wavelengths. The present disclosure fulfills this need and provides further related advantages.

BRIEF SUMMARY

In brief, embodiments of the present disclosure are generally directed to compounds useful as water soluble, fluorescent and/or colored dyes and/or probes that enable visual detection of analyte molecules, such as biomolecules, as well as reagents for their preparation. Methods for visually detecting analyte molecules using the dyes are also described.

Embodiments of the presently disclosed dyes include two or more fluorescent and/or colored moieties covalently linked by a linker having the structure of:

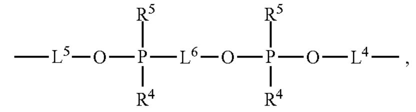

wherein $L^4$ and $L^5$ are linker groups that are different from $L^6$ group. In contrast to previous reports of dimeric and/or polymeric dyes with only a $L^6$ linker group, introducing additional linker groups $L^4$ and $L^5$ to surround $L^6$ helps to increase the rigidity of the linker as well as the spacing between adjacent fluorescent and/or colored moieties. The present dye compounds are significantly brighter than the corresponding dye compounds containing only $L^6$ linker groups. The brightnesses of the present dye compounds also increase over time. While, not wishing to be bound by theory, it is believed that adding additional linker groups around $L^6$ provides more spatial separation and spatial separation stability between the fluorescent and/or colored moieties such that intramolecular fluorescence quenching is reduced and/or eliminated.

In some embodiments, the compounds of this disclosure are useful because they enable FRET fluorescence emission associated with the same. Methods for visually detecting analyte molecules using the dyes are also described.

Embodiments of the presently disclosed dyes include two or more fluorescent and/or colored moieties (i.e., chromophores or FRET donors/acceptors) covalently linked by a linker (e.g., "$L^1$" or "$L^{1c}$" and "$L^{1d}$"). In contrast to previous reports of protein-based, dimeric, and/or polymeric dyes, the present dyes are significantly brighter, enable FRET absorbance and emission as a result of intramolecular interactions, and are robustly reproducible using facile methods known in the art (i.e., automated DNA synthesis methods).

The water soluble, fluorescent or colored dyes of embodiments of the disclosure are intensely colored and/or fluorescent, enable FRET processes (e.g., absorbance, emission, Stokes shifts), and can be readily observed by visual inspection or other means. In some embodiments the compounds may be observed without prior illumination or chemical or enzymatic activation. By appropriate selection of the dye, as described herein, visually detectable analyte molecules of a variety of colors may be obtained.

In some embodiments, compounds having the following structure (I) are provided:

(I)

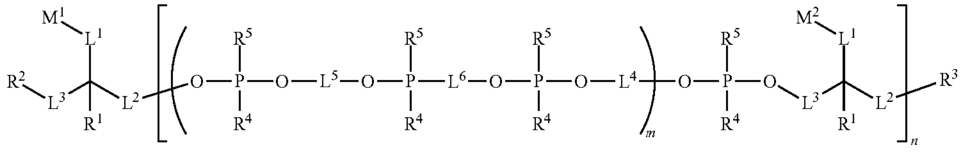

or a stereoisomer, tautomer or salt thereof, wherein $R^1$, $R^2$, $R^3$, $R^4$, $R^5$, $L^1$, $L^2$, $L^3$, $L^4$, $L^5$, $L^6$, $M^1$, $M^2$, m and n are as defined herein.

In some other embodiments, compounds having the following structure (A) are provided:

(A)

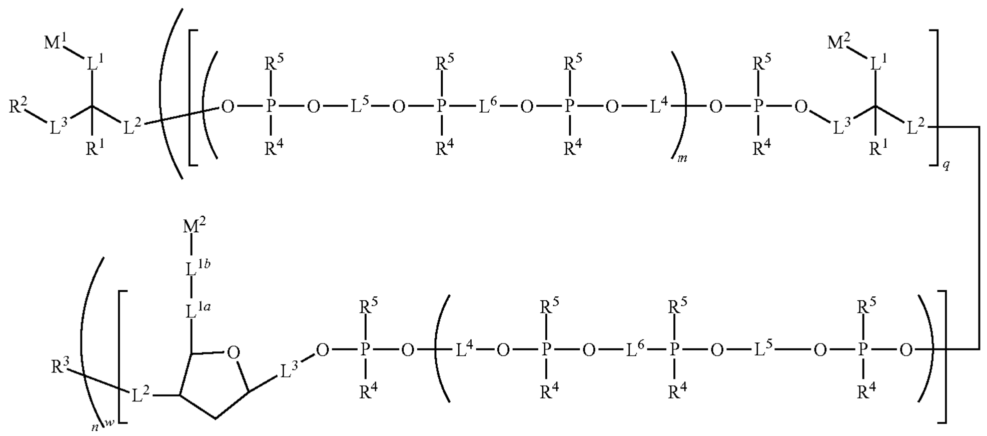

or a stereoisomer, tautomer or salt thereof, wherein $R^1$, $R^2$, $R^3$, $R^4$, $R^5$, $L^{1a}$, $L^{1b}$, $L^2$, $L^3$, $L^4$, $L^5$, $L^6$, $M^1$, $M^2$, m, n, and q are as defined herein.

In other embodiments, compounds having the following structure (II) are provided:

(II)

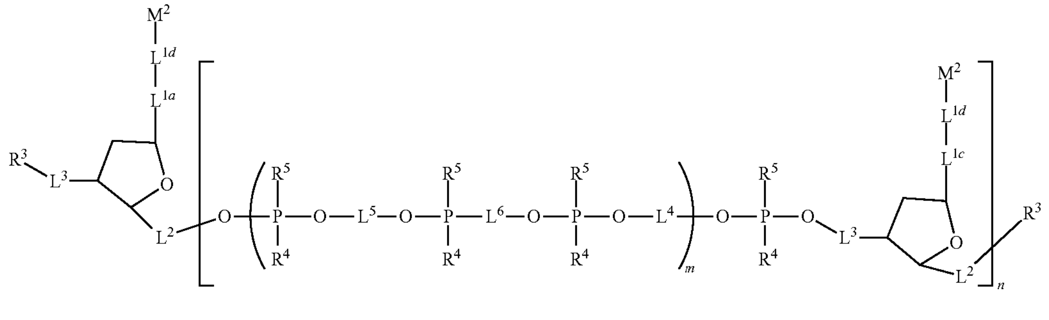

or a stereoisomer, tautomer or salt thereof, wherein $R^1$, $R^2$, $R^3$, $R^4$, $R^5$, $L^{1a}$, $L^{1d}$, $L^2$, $L^3$, $L^4$, $L^5$, $L^6$, $M^1$, $M^2$, m and n are as defined herein.

Compounds of structure (I), (A), or (II) find utility in a number of applications, including use as fluorescent and/or colored dyes in various analytical methods.

In yet other embodiments, a method for staining a sample is provided, the method comprises adding to said sample a compound of structure (I), (A), or (II) in an amount sufficient to produce an optical response when said sample is illuminated at an appropriate wavelength.

In still other embodiments, the present disclosure provides a method for visually detecting an analyte molecule, comprising:

(a) providing a compound as disclosed herein; and (b) detecting the compound by its visible properties.

Other disclosed methods include a method for visually detecting a biomolecule, the method comprising:

(a) admixing a compound as disclosed herein with one or more biomolecules; and (b) detecting the compound by its visible properties.

Other embodiments provide a method for visually detecting an analyte, the method comprising:

(a) providing a compound as disclosed herein, wherein $R^2$ or $R^3$ comprises a linker comprising a covalent bond to a targeting moiety having specificity for the analyte;

(b) admixing the compound and the analyte, thereby associating the targeting moiety and the analyte; and (c) detecting the compound by its visible properties In still other embodiments, the present disclosure provides a method for increasing the brightness of a dye, comprising:

(a) providing a dye solution comprising a compound as disclosed herein; and (b) aging the dye solution for a period of time.

Other embodiments are directed to a composition comprising a compound as disclosed herein and one or more analyte molecules, such as one or more biomolecules. Use of such compositions in analytical methods for detection of the one or more biomolecules is also provided.

In some other different embodiments a compound of structure (III) is provided:

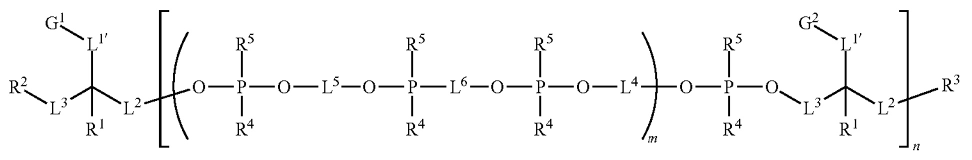

(III)

or a stereoisomer, salt or tautomer thereof, wherein $R^1$, $R^2$, $R^3$, $R^4$, $R^5$, $L^{1'}$, $L^2$, $L^3$, $L^4$, $L^5$, $L^6$, $G^1$, $G^2$, m and n are as defined herein. Compounds of structure (III) find utility in a number of applications, including use as intermediates for preparation of fluorescent and/or colored dyes of structure (I).

In some other different embodiments a compound of structure (IV) is provided:

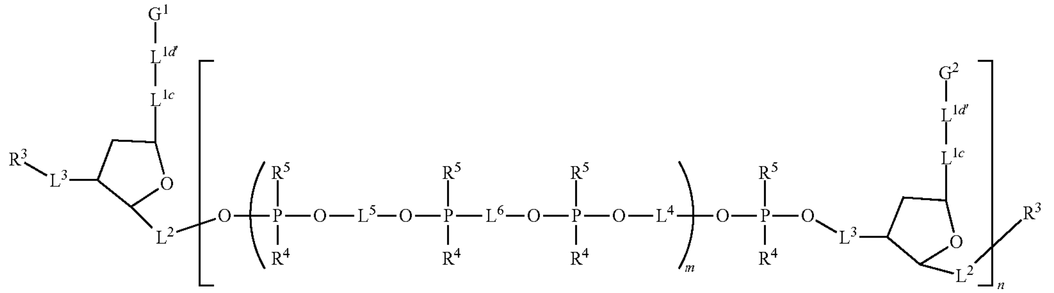

(IV)

or a stereoisomer, salt or tautomer thereof, wherein $R^1$, $R^2$, $R^3$, $R^4$, $R^5$, $L^{1c}$, $L^{1d'}$, $L^2$, $L^3$, $L^4$, $L^5$, $L^6$, $G^1$, $G^2$, m and n are as defined herein. Compounds of structure (III) find utility in a number of applications, including use as intermediates for preparation of fluorescent and/or colored dyes of structure (II).

In yet other embodiments a method for labeling an analyte molecule is provided, the method comprising:

(a) admixing a compound of structure (III) or (IV), wherein $R^2$ or $R^3$ is Q or a linker comprising a covalent bond to Q, with the analyte molecule;

(b) forming a conjugate of the compound and the analyte molecule; and (c) reacting the conjugate with a compound of formula M-$L^{1b}$-G', thereby forming at least one covalent bond by reaction of G and G', wherein $R^2$, $R^3$, Q, G and M-$L^{1b}$-G' are as defined herein.

In some different embodiments another method for labeling an analyte molecule is provided, the method comprising:

(a) admixing a compound of structure (III) or (IV), wherein $R^2$ or $R^3$ is Q or a linker comprising a covalent bond to Q, with a compound of formula M-$L^{1b}$-G', thereby forming at least one covalent bond by reaction of G and G'; and (b) reacting the product of step (A) with the analyte molecule, thereby forming a conjugate of the product of step (A) and the analyte molecule wherein $R^2$, $R^3$, Q, G and M-$L^{1b}$-G' are as defined herein.

In more different embodiments, a method for preparing a compound of structure (I) is provided, the method comprising admixing a compound of structure (III) with a compound of formula M-$L^{1b}$-G', thereby forming at least one covalent bond by reaction of G and G', wherein G and M-$L^{1b}$-G' are as defined herein.

In more different embodiments, a method for preparing a compound of structure (II) is provided, the method comprising admixing a compound of structure (IV) with a compound of formula M-$L^{1b}$-G', thereby forming at least one covalent bond by reaction of G and G', wherein G and M-$L^{1b}$-G' are as defined herein.

These and other aspects of the present disclosure will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1:
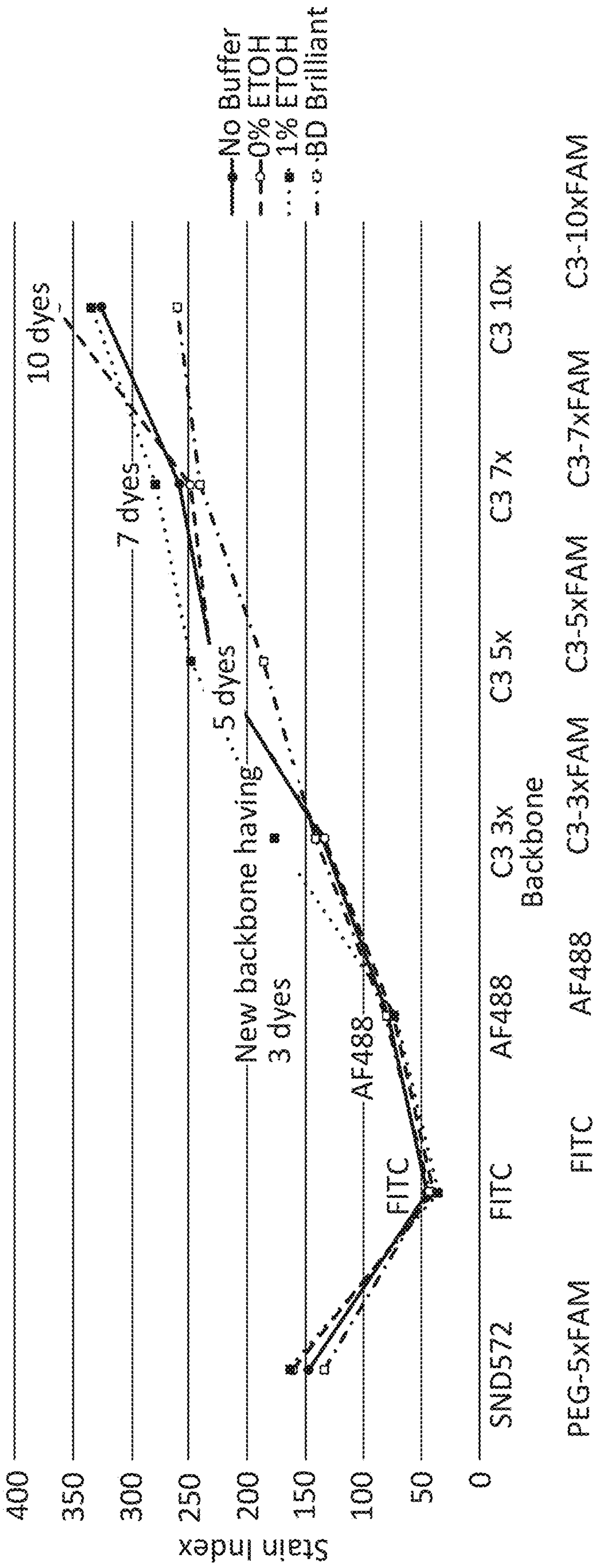
FIG. 1 shows stain index for representative compounds with various M moieties compared to control compounds.

In the following description, certain specific details are set forth in order to provide a thorough understanding of various embodiments of the disclosure. However, one skilled in the art will understand that the disclosure may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ group.

"Carboxy" refers to the —$CO_2H$ group.

"Cyano" refers to the —CN group.

"Formyl" refers to the —C(=O)H group.

"Hydroxy" or "hydroxyl" refers to the —OH group.

"Imino" refers to the =NH group.

"Nitro" refers to the —$NO_2$ group.

"Oxo" refers to the =O substituent group.

"Sulfhydryl" refers to the —SH group.

"Thioxo" refers to the =S group.

"Alkyl" refers to a straight or branched hydrocarbon chain group consisting solely of carbon and hydrogen atoms, containing no unsaturation, having from one to twelve carbon atoms ($C_1$-$C_{12}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, alkyl groups are optionally substituted.

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Alkenylene" or "alkenylene chain" refers to a straight or branched divalent hydrocarbon chain linking the rest of the molecule to a radical group, consisting solely of carbon and hydrogen, containing at least one carbon-carbon double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, alkenylene is optionally substituted.

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms, e.g., ethenylene, propenylene, n-butenylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, alkynylene is optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group is optionally substituted. For example, in some embodiments an alkylether is substituted with an alcohol or —OP(=$R_a$)($R_b$)$R_c$, wherein each of $R_a$, $R_b$ and $R_c$ is as defined for compounds of structure (I).

"Alkoxy" refers to a group of the formula —$OR_a$ where $R_a$ is an alkyl group as defined above containing one to twelve carbon atoms. Unless stated otherwise specifically in the specification, an alkoxy group is optionally substituted.

"Alkoxyalkylether" refers to a group of the formula —$OR_aR_b$ where $R_a$ is an alkylene group as defined above containing one to twelve carbon atoms, and $R_b$ is an alkylether group as defined herein. Unless stated otherwise specifically in the specification, an alkoxyalkylether group is optionally substituted, for example substituted with an alcohol or —OP(=$R_a$)($R_b$)$R_c$, wherein each of $R_a$, $R_b$ and $R_c$ is as defined for compounds of structure (I).

"Heteroalkyl" refers to an alkyl group, as defined above, comprising at least one heteroatom (e.g., N, O, P or S) within the alkyl group or at a terminus of the alkyl group. In some embodiments, the heteroatom is within the alkyl group (i.e., the heteroalkyl comprises at least one carbon-[heteroatom]$_x$ -carbon bond, where x is 1, 2 or 3). In other embodiments, the heteroatom is at a terminus of the alkyl group and thus serves to join the alkyl group to the remainder of the molecule (e.g., M1-H-A), where M1 is a portion of the molecule, H is a heteroatom and A is an alkyl group). Unless stated otherwise specifically in the specification, a heteroalkyl group is optionally substituted. Exemplary heteroalkyl groups include ethylene oxide (e.g., polyethylene oxide), optionally including phosphorous-oxygen bonds, such as phosphodiester bonds.

"Heteroalkoxy" refers to a group of the formula —$OR_a$ where $R_a$ is a heteroalkyl group as defined above containing one to twelve carbon atoms. Unless stated otherwise specifically in the specification, a heteroalkoxy group is optionally substituted.

"Heteroalkylene" refers to an alkylene group, as defined above, comprising at least one heteroatom (e.g., N, O, P or S) within the alkylene chain or at a terminus of the alkylene chain. In some embodiments, the heteroatom is within the alkylene chain (i.e., the heteroalkylene comprises at least one carbon-[heteroatom]-carbon bond, where x is 1, 2 or 3).

In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). Unless stated otherwise specifically in the specification, a heteroalkylene group is optionally substituted. Exemplary heteroalkylene groups include ethylene oxide (e.g., polyethylene oxide) and the "C," "HEG," "TEG," "PEG 1K" and variations thereof, linking groups illustrated below:

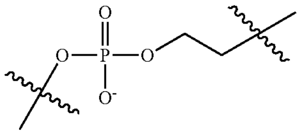

"C linker"

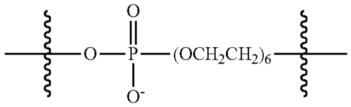

"HEG linker"

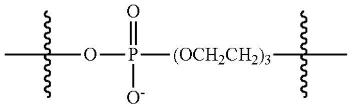

"TEG linker"

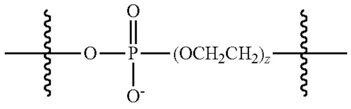

z > 0; e.g., z = 3-10

"EG linker"

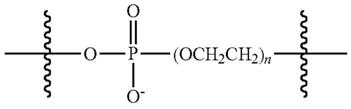

n = 22-26

"PEG 1K linker"

Multimers of the above C-linker, HEG linker and/or PEG 1K linker are included in various embodiments of heteroalkylene linkers.

In some embodiments of the PEG 1K linker, n is 25. Multimers may comprise, for example, the following structure:

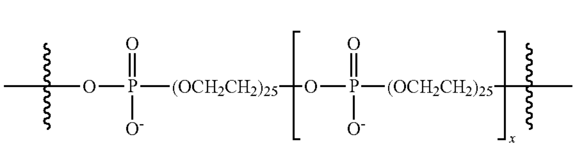

wherein x is 0 or an integer greater than 0, for example, x ranges from 0-100 (e.g., 1, 2, 3, 4, 5, 6, 7, 8, 9, or 10).

"Heteroalkenylene" is a heteroalkylene, as defined above, comprising at least one carbon-carbon double bond. Unless stated otherwise specifically in the specification, a heteroalkenylene group is optionally substituted.

"Heteroalkynylene" is a heteroalkylene comprising at least one carbon-carbon triple bond. Unless stated otherwise specifically in the specification, a heteroalkynylene group is optionally substituted.

"Heteroatomic" in reference to a "heteroatomic linker" refers to a linker group consisting of one or more heteroatoms. Exemplary heteroatomic linkers include single atoms selected from the group consisting of O, N, P and S, and multiple heteroatoms for example a linker having the formula $—P(O^-)(=O)O—$ or $—OP(O^-)(=O)O—$ and multimers and combinations thereof.

"Phosphate" refers to the $—OP(=O)(R_a)R_b$ group, wherein $R_a$ is OH, $O^-$ or $OR_c$; and $R_b$ is OH, $O^-$, $OR_c$, a thiophosphate group or a further phosphate group, wherein $R_c$ is a counter ion (e.g., Na+ and the like).

"Phosphoalkyl" refers to the $—OP(=O)(R_a)R_b$ group, wherein $R_a$ is OH, $O^-$ or $OR_c$; and $R_b$ is —Oalkyl, wherein $R_c$ is a counter ion (e.g., Na+ and the like). Unless stated otherwise specifically in the specification, a phosphoalkyl group is optionally substituted. For example, in certain embodiments, the —Oalkyl moiety in a phosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or $—OP(=R_a)(R_b)R_c$, wherein each of $R_a$, $R_b$ and $R_c$ is as defined for compounds of structure (I).

"Phosphoalkylether" refers to the $—OP(=O)(R_a)R_b$ group, wherein $R_a$ is OH, $O^-$ or $OR_c$; and $R_b$ is —Oalkylether, wherein $R_c$ is a counter ion (e.g., Na+ and the like). Unless stated otherwise specifically in the specification, a phosphoalkylether group is optionally substituted. For example, in certain embodiments, the —Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether, thiophosphoalkylether or $—OP(=R_a)(R_b)R_c$, wherein each of $R_a$, $R_b$ and $R_c$ is as defined for compounds of structure (I).

"Thiophosphate" refers to the $—OP(=R_a)(R_b)R_c$ group, wherein $R_a$ is O or S, $R_b$ is OH, $O^-$, $S^-$, $OR_d$ or $SR_d$; and $R_c$ is OH, SH, $O^-$, $S^-$, $OR_d$, $SR_d$, a phosphate group or a further thiophosphate group, wherein $R_d$ is a counter ion (e.g., Na+ and the like) and provided that: i) $R_a$ is S; ii) $R_b$ is $S^-$ or $SR_d$; iii)$R_c$ is SH, $S^-$ or $SR_d$; or iv) a combination of i), ii) and/or iii).

"Thiophosphoalkyl" refers to the $—OP(=R_a)(R_b)R_c$ group, wherein $R_a$ is O or S, $R_b$ is OH, $O^-$, $S^-$, $OR_d$ or $SR_d$; and $R_c$ is —Oalkyl, wherein $R_d$ is a counter ion (e.g., Na+ and the like) and provided that: i) $R_a$ is S; ii) $R_b$ is $S^-$ or $SR_d$; or iii)$R_a$ is S and $R_b$ is $S^-$ or $SR_d$. Unless stated otherwise specifically in the specification, a thiophosphoalkyl group is optionally substituted. For example, in certain embodiments, the —Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or $—OP(=R_a)(R_b)R_c$, wherein each of $R_a$, $R_b$ and $R_c$ is as defined for compounds of structure (I).

"Thiophosphoalkylether" refers to the $—OP(=R_a)(R_b)R_c$ group, wherein $R_a$ is O or S, $R_b$ is OH, $O^-$, $S^-$, $OR_d$ or $SR_d$; and $R_c$ is —Oalkylether, wherein $R_d$ is a counter ion (e.g., Na+ and the like) and provided that: i) $R_a$ is S; ii) $R_b$ is $S^-$ or $SR_d$; or iii)$R_a$ is S and $R_b$ is $S^-$ or $SR_d$. Unless stated otherwise specifically in the specification, a thiophosphoalkylether group is optionally substituted. For example, in certain embodiments, the —Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or $—OP(=R_a)(R_b)R_c$, wherein each of $R_a$, $R_b$ and $R_c$ is as defined for compounds of structure (I).

"Carbocyclic" refers to a stable 3- to 18-membered aromatic or non-aromatic ring comprising 3 to 18 carbon atoms. Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocycyl radicals include cycloalkyl, while aromatic carbocycyl radicals include aryl. Unless stated otherwise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cyclocalkyls include, for example, cyclopropyl, cyclobutyl, cyclopentyl, cyclohexyl, cycloheptly, and cyclooctyl. Polycyclic cycloalkyls include, for example, adamantyl, norbornyl, decalinyl, 7,7-dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl comprises from 6 to 18 carbon atoms. The aryl ring may be a monocyclic, bicyclic, tricyclic or tetracyclic ring system, which may include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3- to 18-membered aromatic or non-aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclic group is optionally substituted.

"Heteroaryl" refers to a 5- to 14-membered ring system comprising one to thirteen carbon atoms, one to six heteroatoms selected from the group consisting of nitrogen, oxygen and sulfur, and at least one aromatic ring. For purposes of certain embodiments of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group is optionally substituted.

The suffix "-ene" refers to a particular structural feature (e.g., alkyl, aryl, heteroalkyl, heteroaryl) attached to the rest of the molecule through a single bond and attached to a radical group through a single bond. In other words, the suffix "-ene" refers to a linker having the structural features of the moiety to which it is attached. The points of attachment of the "-ene" chain to the rest of the molecule and to the radical group can be through one atom of or any two atoms within the chain. For example, a heteroarylene refers to a linker comprising a heteroaryl moiety as defined herein.

"Fused" refers to a ring system comprising at least two rings, wherein the two rings share at least one common ring atom, for example two common ring atoms. When the fused ring is a heterocyclyl ring or a heteroaryl ring, the common ring atom may be carbon or nitrogen. Fused rings include bicyclic, tricyclic, tertracyclic, and the like.

The term "substituted" used herein means any of the above groups (e.g., alkyl, alkylene, alkenylene, alkynylene, heteroalkylene, heteroalkenylene, heteroalkynylene, alkoxy, alkylether, alkoxyalkylether, heteroalkyl, heteroalkoxy, phosphoalkyl, phosphoalkylether, thiophosphoalkyl, thiophosphoalkylether, carbocyclic, cycloalkyl, aryl, heterocyclic and/or heteroaryl) wherein at least one hydrogen atom (e.g., 1, 2, 3 or all hydrogen atoms) is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $—NR_gR_h$, $—NR_gC(=O)R_h$, $—NR_gC(=O)NR_gR_h$, $—NR_gC(=O)OR_h$, $—NR_gSO_2R_h$, $—OC(=O)NR_gR_h$, $—OR_g$, $—SR_g$, $—SOR_g$, $—SO_2R_g$, $—OSO_2R_g$, $—SO_2OR_g$, $=NSO_2R_g$, and $—SO_2NR_gR_h$. "Substituted" also means any of the above groups in which one or more hydrogen atoms are replaced with $—C(=O)R_g$, $—C(=O)OR_g$, $—C(=O)NR_gR_h$, $—CH_2SO_2R_g$, $—CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In some embodiments, the optional substituent is $—OP(=R_a)(R_b)R_c$, wherein each of $R_a$, $R_b$ and $R_c$ is as defined for compounds of structure (I). In addition, each of the foregoing substituents may also be optionally substituted with one or more of the above substituents.

"Electron withdrawing group" refers to a functional group that draws electrons to itself more than a hydrogen atom would if it occupied the same position in a molecule. These terms are well understood by one skilled in the art and are discussed in Advanced Organic Chemistry, by J. March, John Wiley & Sons, New York, N.Y., pp. 16-18 (1985) and the discussion therein is incorporated herein by reference. Examples of electron withdrawing groups include, but are not limited to, halo, halo (e.g., F, Cl, Br, I), $NO_2$, CN, $SO_3H$, $—SO_2\ R_a$, $—SO_3\ R_a$, —COOH, $—CO\ R_a$, $COOR_a$, $CONH\ R_a$, $CON(R_a)_2$, haloalkyl groups, and 5-14 membered electron-poor heteroaryl groups, wherein $R_a$ is an alkyl, alkenyl group, or alkynyl group.

"Conjugation" refers to the overlap of one p-orbital with another p-orbital across an intervening sigma bond. Conjugation may occur in cyclic or acyclic compounds. A "degree of conjugation" refers to the overlap of at least one p-orbital with another p-orbital across an intervening sigma bond. For example, 1, 3-butadine has one degree of conjugation, while benzene and other aromatic compounds typically have multiple degrees of conjugation. Fluorescent and colored compounds typically comprise at least one degree of conjugation.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

"FRET" refers to Förster resonance energy transfer refers to a physical interaction whereby energy from the excitation of one moiety (e.g., a first chromophore or "donor") is transferred to an adjacent moiety (e.g., a second chromophore or "acceptor"). "FRET" is sometimes also used interchangeably with fluorescence resonance energy transfer (i.e., when each chromophore is a fluorescent moiety). Generally, FRET requires that (1) the excitation or absorption spectrum of the acceptor chromophore overlaps with the emission spectrum of the donor chromophore; (2) the transition dipole moments of the acceptor and donor chromophores are substantially parallel (i.e., at about 0° or 180°); and (3) the acceptor and donor chromophores share a spatial proximity (i.e., close to each other). The transfer of energy from the donor to the acceptor occurs through non-radiative dipole-dipole coupling and the distance between the donor chromophore and acceptor chromophore is generally much less than the wavelength of light.

"Donor" or "donor chromophore" refers to a chromophore (e.g., a fluorophore) that is or can be induced into an excited electronic state and may transfer its excitation or absorbance energy to a nearby acceptor chromophore in a non-radiative fashion through long-range dipole-dipole interactions. Without wishing to be bound by theory, it is thought that the energy transfer occurs because the oscillating dipoles of the respective chromophores have similar resonance frequencies. A donor and acceptor that have these similar resonance frequencies are referred to as a "donor-acceptor pair," which is used interchangeably with "FRET moieties," "FRET pairs," "FRET dyes," or similar.

"Acceptor" or "acceptor chromophore" refers to a chromophore (e.g., a fluorophore) to which excitation or absorbance energy from a donor chromophore is transferred via a non-radiative transfer through long-range dipole-dipole interaction.

"Stoke's shift" refers to a difference between positions (e.g., wavelengths) of the band maxima of excitation or absorbance and emission spectra of an electronic transition (e.g., from excited state to non-excited state, or vice versa). In some embodiments, the compounds have a Stoke's shift greater than 25 nm, greater than 30 nm, greater than 35 nm, greater than 40 nm, greater than 45 nm, greater than 50 nm, greater than 55 nm, greater than 60 nm, greater than 65 nm, greater than 70 nm, greater than 75 nm, greater than 80 nm, greater than 85 nm, greater than 90 nm, greater than 95 nm, greater than 100 nm, greater than 110 nm, greater than 120 nm, greater than 130 nm, greater than 140 nm, greater than 150 nm, greater than 160 nm, greater than 170 nm, greater than 180 nm, greater than 190 nm, or greater than 200 nm.

"J-value" is calculated as an integral value of spectral overlap between the emission spectrum of a donor chromophore and the excitation or absorbance spectrum of an acceptor chromophore. The emission spectrum of the donor chromophore is that which is generated when the donor chromophore is excited with a preferred excitation or absorbance wavelength. Preferred excitation or absorbance wavelengths for donor chromophores are at or near their respective excitation or absorbance maximum well known to a person of ordinary skill in the art (e.g., Pacific Blue has an excitation or absorbance maximum at about 401 nm, FITC has an excitation or absorbance maximum at about 495 nm).

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

The term "biomolecule" refers to any of a variety of biological materials, including nucleic acids, carbohydrates, amino acids, polypeptides, glycoproteins, hormones, aptamers and mixtures thereof. More specifically, the term is intended to include, without limitation, RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. The visually detectable biomolecules of the disclosure (e.g., compounds of structure (I) having a biomolecule linked thereto) are prepared, as further described herein, by contacting a biomolecule with a compound having a reactive group that enables attachment of the biomolecule to the compound via any available atom or functional group, such as an amino, hydroxy, carboxyl, or sulfhydryl group on the biomolecule.

A "reactive group" is a moiety capable of reacting with a second reactive groups (e.g., a "complementary reactive group") to form one or more covalent bonds, for example by a displacement, oxidation, reduction, addition or cycloaddition reaction. Exemplary reactive groups are provided in Table 1, and include for example, nucleophiles, electrophiles, dienes, dienophiles, aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, $\alpha,\beta$-unsaturated carbonyl, alkene, maleimide, $\alpha$-haloimide, epoxide, aziridine, tetrazine, tetrazole, phosphine, biotin, thiirane and the like.

The terms "visible" and "visually detectable" are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000 $M^{-1}$ $cm^{-1}$. The compounds of the disclosure may be detected by observation with the naked eye, or with the aid of an optically based detection device, including, without limitation, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of embodiments of the disclosure, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Nonlimiting examples of photostable visible dyes suitable for use in the compounds and methods of the disclosure include azo dyes, thioindigo dyes, quinacridone pigments, dioxazine, phthalocyanine, perinone, diketopyrrolopyrrole, quinophthalone, and truarycarbonium.

As used herein, the term "perylene derivative" is intended to include any substituted perylene that is visually detectable. However, the term is not intended to include perylene itself. The terms "anthracene derivative", "naphthalene derivative", and "pyrene derivative" are used analogously. In some preferred embodiments, a derivative (e.g., perylene, pyrene, anthracene or naphthalene derivative) is an imide, bisimide or hydrazamimide derivative of perylene, anthracene, naphthalene, or pyrene.

The visually detectable molecules of various embodiments of the disclosure are useful for a wide variety of analytical applications, such as biochemical and biomedical applications, in which there is a need to determine the presence, location, or quantity of a particular analyte (e.g., biomolecule). In another aspect, therefore, the disclosure provides a method for visually detecting a biomolecule, comprising: (a) providing a biological system with a visually detectable biomolecule comprising the compound of structure (I) linked to a biomolecule; and (b) detecting the biomolecule by its visible properties. For purposes of the disclosure, the phrase "detecting the biomolecule by its visible properties" means that the biomolecule, without illumination or chemical or enzymatic activation, is observed with the naked eye, or with the aid of a optically based detection device, including, without limitation, absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Nonlimiting examples of such biological systems include cells, cell extracts, tissue samples, electrophoretic gels, assay mixtures, and hybridization reaction mixtures.

"Solid support" refers to any solid substrate known in the art for solid-phase support of molecules, for example a "microparticle" refers to any of a number of small particles useful for attachment to compounds of the disclosure, including, but not limited to, glass beads, magnetic beads, polymeric beads, nonpolymeric beads, and the like. In certain embodiments, a microparticle comprises polystyrene beads.

A "solid support reside" refers to the functional group remaining attached to a molecule when the molecule is cleaved from the solid support. Solid support residues are known in the art and can be easily derived based on the structure of the solid support and the group linking the molecule thereto.

A "targeting moiety" is a moiety that selectively binds or associates with a particular target, such as an analyte molecule. "Selectively" binding or associating means a targeting moiety preferentially associates or binds with the desired target relative to other targets. In some embodiments the compounds disclosed herein include linkages to targeting moieties for the purpose of selectively binding or associating the compound with an analyte of interest (i.e., the target of the targeting moiety), thus allowing detection of the analyte. Exemplary targeting moieties include, but are not limited to, antibodies, antigens, nucleic acid sequences, enzymes, proteins, cell surface receptor antagonists, and the like. In some embodiments, the targeting moiety is a moiety, such as an antibody, that selectively binds or associates with a target feature on or in a cell, for example a target feature on a cell membrane or other cellular structure, thus allowing for detection of cells of interest. Small molecules that selectively bind or associate with a desired analyte are also contemplated as targeting moieties in certain embodiments. One of skill in the art will understand other analytes, and the corresponding targeting moiety, that will be useful in various embodiments.

"Base pairing moiety" refers to a heterocyclic moiety capable of hybridizing with a complementary heterocyclic moiety via hydrogen bonds (e.g., Watson-Crick base pairing). Base pairing moieties include natural and unnatural bases. Non-limiting examples of base pairing moieties are RNA and DNA bases such adenosine, guanosine, thymidine, cytosine and uridine and analogues thereof.

Embodiments of the disclosure disclosed herein are also meant to encompass all compounds of structure (I) or (II) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$ respectively.

Isotopically-labeled compounds of structure (I) or (II) can generally be prepared by conventional techniques known to those skilled in the art or by processes analogous to those described below and in the following Examples using an appropriate isotopically-labeled reagent in place of the non-labeled reagent previously employed.

“Stable compound” and “stable structure” are meant to indicate a compound that is sufficiently robust to survive isolation to a useful degree of purity from a reaction mixture, and formulation into an efficacious therapeutic agent.

“Optional” or “optionally” means that the subsequently described event or circumstances may or may not occur, and that the description includes instances where said event or circumstance occurs and instances in which it does not. For example, “optionally substituted alkyl” means that the alkyl group may or may not be substituted and that the description includes both substituted alkyl groups and alkyl groups having no substitution.

“Salt” includes both acid and base addition salts.

“Acid addition salt” refers to those salts which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

“Base addition salt” refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Crystallizations may produce a solvate of the compounds described herein. Embodiments of the present disclosure include all solvates of the described compounds. As used herein, the term “solvate” refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compounds of the disclosure may be true solvates, while in other cases the compounds of the disclosure may merely retain adventitious water or another solvent or be a mixture of water plus some adventitious solvent.

Embodiments of the compounds of the disclosure (e.g., compounds of structure I or II), or their salts, tautomers or solvates may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. Embodiments of the present disclosure are meant to include all such possible isomers, as well as their racemic and optically pure forms. Optically active (+) and (−), (R)- and (S)-, or (D)- and (L)- isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A “stereoisomer” refers to a compound made up of the same atoms bonded by the same bonds but having different three-dimensional structures, which are not interchangeable. The present disclosure contemplates various stereoisomers and mixtures thereof and includes “enantiomers”, which refers to two stereoisomers whose molecules are nonsuperimposeable mirror images of one another.

A “tautomer” refers to a proton shift from one atom of a molecule to another atom of the same molecule. The present disclosure includes tautomers of any said compounds. Various tautomeric forms of the compounds are easily derivable by those of ordinary skill in the art.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

As noted above, in one embodiment of the present disclosure, compounds useful as fluorescent and/or colored dyes in various analytical methods are provided. In other embodiments, compounds useful as synthetic intermediates for preparation of compounds useful as fluorescent and/or colored dyes are provided. In general terms, embodiments of the present disclosure are directed to dimers and higher polymers of fluorescent and/or colored moieties. The fluorescent and or colored moieties are linked by a linker. Without wishing to be bound by theory, it is believed the linker helps to maintain sufficient spatial distance between the fluorescent and/or colored moieties such that intramolecular quenching is reduced or eliminated, thus resulting in a dye compound having a high molar “brightness” (e.g., high fluorescence emission).

Accordingly, in some embodiments, compounds of the present disclosure have the following structure (A):

(A)

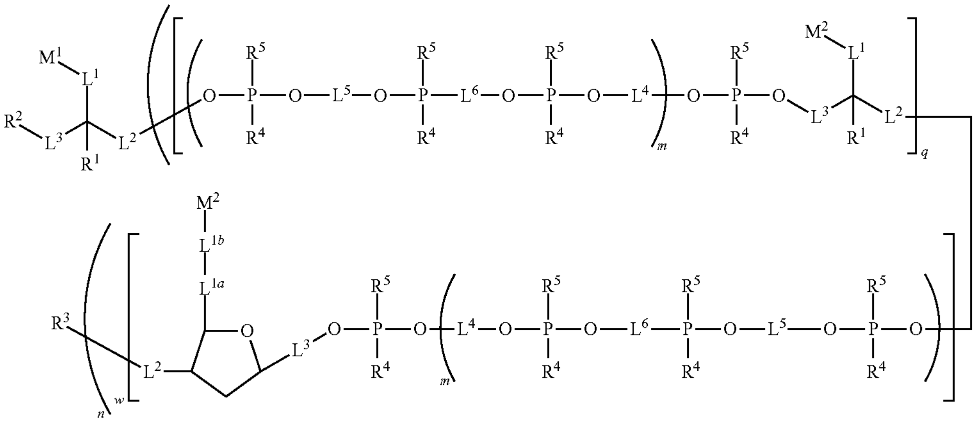

or a stereoisomer, salt or tautomer thereof, wherein:

$M^1$ and $M^2$ are, at each occurrence, independently a chromophore, provided that at least one of $M^1$ and $M^2$ is a FRET donor, and another one of $M^1$ and $M^2$ is a corresponding FRET acceptor;

$L^{1a}$ is, at each occurrence, independently a heteroarylene linker;

$L^1$, $L^{1b}$, $L^2$ and $L^3$ are, at each occurrence, independently optional alkylene, alkenylene, alkynylene, heteroalkylene, heteroalkenylene, heteroalkynylene, heteroarylene or heteroatomic linkers;

$L^4$ and $L^5$ are, at each occurrence, independently alkylene, alkenylene, alkynylene, heteroalkylene, heteroalkenylene, heteroalkynylene or heteroatomic linkers;

$L^6$ is, at each occurrence, independently a heteroalkylene, heteroalkenylene or heteroalkynylene linker, provided that at least one occurrence, $L^6$ is different from each of $L^4$ and $L^5$;

$R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q or a protected form thereof, or L';

$R^4$ is, at each occurrence, independently OH, SH, $O^-$, $S^-$, $OR_d$ or $SR_d$;

$R_5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (A);

m is, at each occurrence, independently an integer of zero or greater, provided that at least one occurrence of m is an integer of one or greater;

n is an integer of one or greater; and q and w are, at each occurrence, independently an integer from 0 to 3, provided at least one occurrence of either q or w is 1.

In some embodiments, w is 0.

In some related embodiments, compounds of the present disclosure have the following structure (I):

(I)

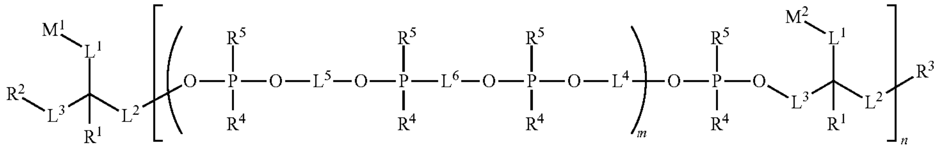

or a stereoisomer, salt or tautomer thereof, wherein:

$M^1$ and $M^2$ are, at each occurrence, independently a moiety comprising two or more carbon-carbon double bonds and at least one degree of conjugation;

$L^1$, $L^2$ and $L^3$ are, at each occurrence, independently optional alkylene, alkenylene, alkynylene, heteroalkylene, heteroalkenylene, heteroalkynylene, heteroarylene or heteroatomic linkers;

$L^4$ and $L^5$ are, at each occurrence, independently alkylene, alkenylene, alkynylene, heteroalkylene, heteroalkenylene or heteroalkynylene;

$L^6$ is, at each occurrence, independently a heteroalkylene, heteroalkenylene or heteroalkynylene linker, provided at least one occurrence, $L^6$ is different from each of $L^4$ and $L^5$;

$R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q or a protected form thereof, or L';

$R^4$ is, at each occurrence, independently OH, SH, $O^-$, $S^-$, $OR_d$ or $SR_d$;

$R^5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, independently an integer of zero or greater, provided at least one occurrence of m is an integer of one or greater; and n is an integer of one or greater.

In some related embodiments, compounds of the present disclosure have the following structure (I):

(I)

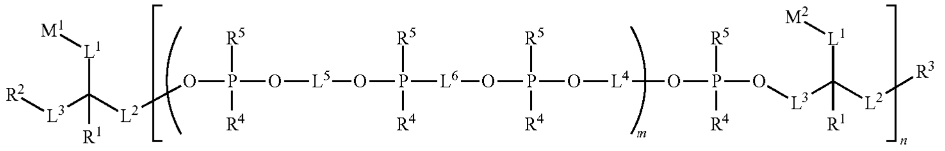

or a stereoisomer, salt or tautomer thereof, wherein:

$M^1$ and $M^2$ are, at each occurrence, independently a chromophore, provided that at least one of $M^1$ and $M^2$ is a FRET donor, and another one of $M^1$ and $M^2$ is a corresponding FRET acceptor;

$L^1$, $L^2$ and $L^3$ are, at each occurrence, independently optional alkylene, alkenylene, alkynylene, heteroalkylene, heteroalkenylene, heteroalkynylene, heteroarylene or heteroatomic linkers;

$L^4$ and $L^5$ are, at each occurrence, independently alkylene, alkenylene, alkynylene, heteroalkylene, heteroalkenylene or heteroalkynylene;

$L^6$ is, at each occurrence, independently a heteroalkylene, heteroalkenylene or heteroalkynylene linker, provided at least one occurrence, $L^6$ is different from each of $L^4$ and L;

$R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q or a protected form thereof, or L';

$R^4$ is, at each occurrence, independently OH, SH, $O^-$, $S^-$, $OR_d$ or $SR_d$;

$R_5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, independently an integer of zero or greater, provided at least one occurrence of m is an integer of one or greater; and n is an integer of one or greater.

The various linkers and substituents (e.g., M, Q, $R^1$, $R^2$, $R^3$, $R^4$, $R^5$, $R_c$, $L^1$, $L^2$, $L^3$ $L^4$ $L^5$ and $L^6$) in the compound of structure (I) are optionally substituted with one more substituent. For example, in some embodiments the optional substituent is selected to optimize the water solubility or other property of the compound of structure (I). In certain embodiments, each alkyl, alkoxy, alkylether, alkoxyalkylether, phosphoalkyl, thiophosphoalkyl, phosphoalkylether and thiophosphoalkylether in the compound of structure (I) is optionally substituted with one more substituent selected from the group consisting of hydroxyl, alkoxy, alkylether, alkoxyalkylether, sulfhydryl, amino, alkylamino, carboxyl, phosphate, thiophosphate, phosphoalkyl, thiophosphoalkyl, phosphoalkylether and thiophosphoalkylether. In certain embodiments the optional substituent is —OP(=$R_a$)($R_b$)$R_c$, where $R_a$, $R_b$ and $R_c$ are as defined for the compound of structure (I).

The optional linker $L^1$ can be used as a point of attachment of the M moiety to the remainder of the compound. For example, in some embodiments a synthetic precursor to the compound of structure (I) is prepared, and the M moiety is attached to the synthetic precursor using any number of facile methods known in the art, for example methods referred to as "click chemistry." For this purpose any reaction which is rapid and substantially irreversible can be used to attach M to the synthetic precursor to form a compound of structure (I). Exemplary reactions include the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse-demand Diels-Alder, alkene and tetrazole photoreaction and various displacement reactions, such as displacement of a leaving group by nucleophilic attack on an electrophilic atom. Exemplary displacement reactions include reaction of an amine with: an activated ester; an N-hydroxysuccinimide ester; an isocyanate; an isothioscyanate or the like. In some embodiments the reaction to form $L^1$ may be performed in an aqueous environment.

Accordingly, in some embodiments $L^1$ is, at each occurrence, a linker comprising a functional group capable of formation by reaction of two complementary reactive groups, for example a functional group which is the product of one of the foregoing "click" reactions. In various embodiments, for at least one occurrence of $L^1$, the functional group can be formed by reaction of an aldehyde, oxime, hydrazone, alkyne, amine, azide, acylazide, acylhalide, nitrile, nitrone, sulfhydryl, disulfide, sulfonyl halide, isothiocyanate, imidoester, activated ester (e.g., N-hydroxysuccinimide ester), ketone, α,β-unsaturated carbonyl, alkene, maleimide, α-haloimide, epoxide, aziridine, tetrazine, tetrazole, phosphine, biotin or thiirane functional group with a complementary reactive group. For example, reaction of an amine with an N-hydroxysuccinimide ester or isothiocyanate.

In other embodiments, for at least one occurrence of $L^1$, the functional group can be formed by reaction of an alkyne and an azide. In other embodiments, for at least one occurrence of $L^1$, the functional group can be formed by reaction of an amine (e.g., primary amine) and an N-hydroxysuccinimide ester or isothiocyanate.

In more embodiments, for at least one occurrence of $L^1$, the functional group comprises an alkene, ester, amide, thioester, disulfide, carbocyclic, heterocyclic or heteroaryl group. In more embodiments, for at least one occurrence of $L^1$, the functional group comprises an alkene, ester, amide, thioester, thiourea, disulfide, carbocyclic, heterocyclic or heteroaryl group. In other embodiments, the functional group comprises an amide or thiourea. In some more specific embodiments, for at least one occurrence of $L^1$, $L^1$ is a linker comprising a triazolyl functional group. While in other embodiments, for at least one occurrence of $L^1$, $L^1$ is a linker comprising an amide or thiourea functional group.

In still other different embodiments of structure (I), $L^1$ is, at each occurrence, independently an alkylene or heteroalkylene linker. In some embodiments, at least one occurrence of $L^1$ heteroalkylene.

In some embodiments, at least one occurrence of $L^1$ has the following structure:

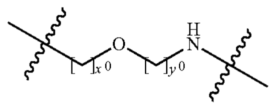

wherein:

$x^0$ and $y^0$ are each independently an integer of one or greater.

In some embodiments, $x^0$ is 1, 2, 3, or 4. In certain embodiments, $y^0$ is 2, 3, 4, or 5. In some specific embodiments, $x^0$ is 1 or 2 and $y^{00}$ is 2, 3, or 4.

In some other embodiments, $L^1$ has one of the following structures:

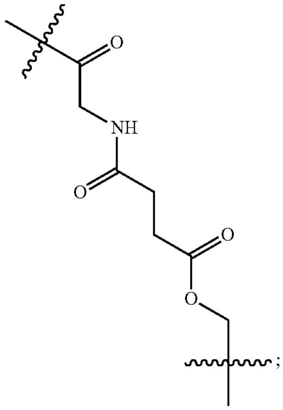
;
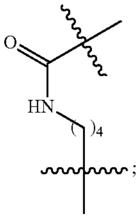
;
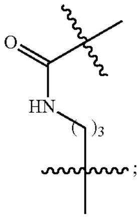
;
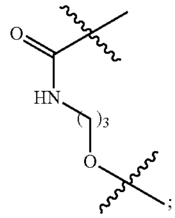
;
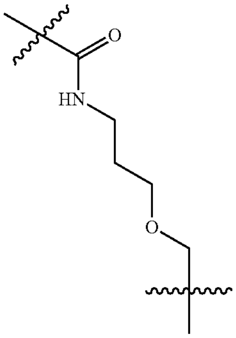
;
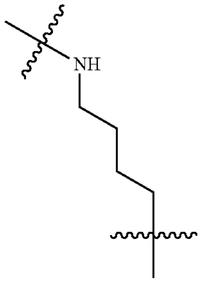
;
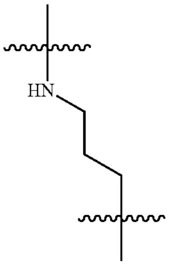
or -continued

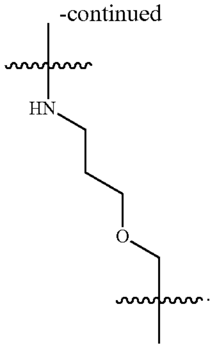

In still other embodiments, for at least one occurrence of $L^1$, $L^1$-$M^1$, or $L^1$-$M^2$ has one of the following structures:

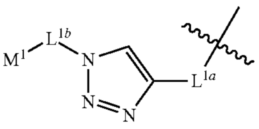
or
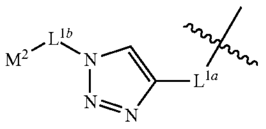

wherein $L^{1a}$ and $L^{1b}$ are each independently optional linkers.

In different embodiments, for at least one occurrence of $L^1$, $L^1$-$M^1$, or $L^1$-$M^2$ has one of the following structures:

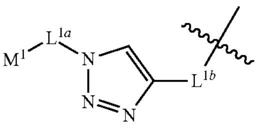
or
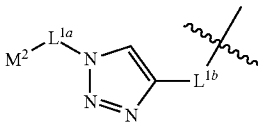

wherein $L^{1a}$ and $L^{1b}$ are each independently optional linkers.

In various embodiments of the foregoing, $L^{1a}$ or $L^{1b}$, or both, is absent. In other embodiments, $L^{1a}$ or $L^{1b}$, or both, is present.

In some embodiments $L^{1a}$ and $L^{1b}$, when present, are each independently alkylene or heteroalkylene. For example, in some embodiments $L^{1a}$ and $L^{1b}$, when present, independently have one of the following structures:

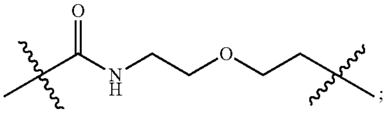
;
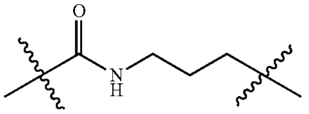
or
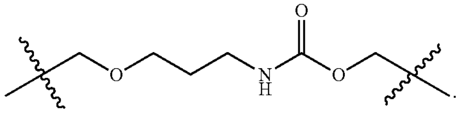

In some embodiments, $M^2$-$L^{1b}$ of structure (A) has the following structure:

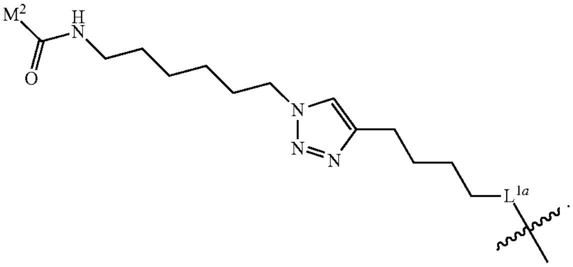

In some embodiments, at least one occurrence $L^4$ and $L^5$ are the same. In some embodiments, at each occurrence $L^4$ and $L^5$ are the same.

In some embodiments, $L^6$ is at each occurrence, independently a heteroalkylene linker. In other more specific embodiments, $L^6$ is at each occurrence, independently an alkylene oxide linker. In some embodiments, $L^6$ is polyethylene oxide. In some related embodiments, the compounds have the following structure (Ia):

(Ia)

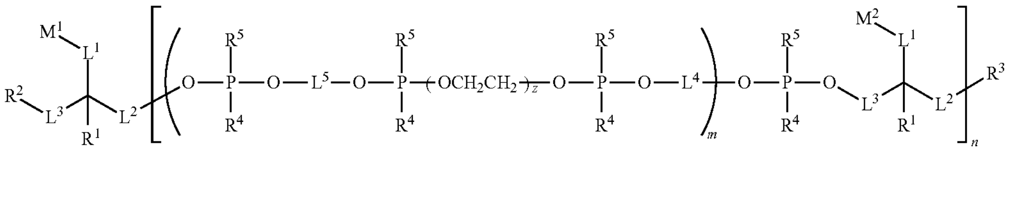

wherein:

$L^4$ and $L^5$ are, at each occurrence, independently an alkylene, alkenylene, alkynylene, heteroalkylene, heteroalkenylene, heteroalkynylene or heteroatomic linker, provided $L^4$ and $L^5$ are not polyethylene oxide;

z is an integer from 1 to 100.

In some embodiments, z is an integer from 1 to 30, for example from 15 to 30 or from 22 to 25. In some embodiments, z is 23. In some embodiments, z is 21, 22, 23, 24 or 25. In some embodiments, z is an integer from 1 to 10, for example from 3 to 6. In some embodiments, z is 3, 4, 5, or 6.

In some embodiments, $L^4$ and $L^5$ are, at each occurrence, independently an alkylene linker. In other more specific embodiments, $L^4$ and $L^5$ are, at each occurrence, independently $C_3$-$C_6$ alkylene. In some embodiments, at least one occurrence $L^4$ and $L^5$ are the same. In other embodiments, at each occurrence, $L^4$ and $L^5$ are the same.

In some more specific embodiments, $L^4$ and $L^5$ are, at each occurrence, independently $C_3$-$C_6$ alkylene. In some embodiments, $L^4$ and $L^5$ are, at each occurrence, independently $C_3$ alkylene, $C_4$ alkylene, or $C_6$ alkylene. In some related embodiments, the compounds have the following structure (Ib):

(Ib)

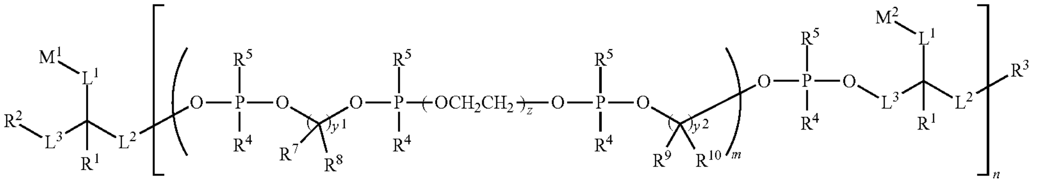

wherein:

$R^7$, $R^8$, $R^9$ and $R^{10}$ are, at each occurrence, independently H or alkyl; and $y^1$ and $y^2$ are, at each occurrence, independently an integer from 1 to 6.

In some embodiments, $L^2$ and $L^3$ are, at each occurrence, independently $C_1$-$C_6$ alkylene, $C_2$-$C_6$ alkenylene or $C_2$-$C_6$ alkynylene. For example, in some embodiments $L^2$ and $L^3$ are, at each occurrence, independently $C_1$-$C_6$ alkylene, and $R^7$, $R^8$, $R^9$ and $R^{10}$ are, at each occurrence, independently H. In some related embodiments, the compounds have the following structure (Ic):

(Ic)

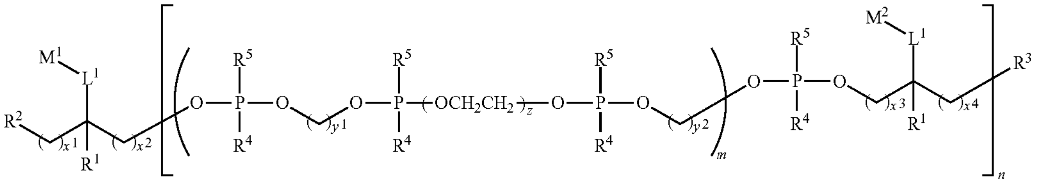

wherein:

$x^1$, $x^2$, $x^3$ and $x^4$ are, at each occurrence, independently an integer from 0 to 6;

$y^1$ and $y^2$ are, at each occurrence, independently an integer from 1 to 6; and z is an integer from 1 to 100.

In some embodiments, $x^1$ and $x^3$ are each 0 at each occurrence, and $x^2$ and $x^4$ are each 1 at each occurrence. In other embodiments, $x^1$, $x^2$, $x^3$ and $x^4$ are each 1 at each occurrence.

In some embodiments, $y^1$ and $y^2$ are each 3 at each occurrence. In other embodiments, $y^1$ and $y^2$ are each 4 at each occurrence. In still other embodiments, $y^1$ and $y^2$ are each 6 at each occurrence.

In some embodiments, z is an integer from 1 to 6. In other embodiments, z is an integer from 15 to 30. In still other embodiments, z is an integer from 22 to 25.

In some embodiments of any of the foregoing compounds of structure (I), at least one occurrence of $R^1$ is H. In more specific embodiments, $R^1$ is H at each occurrence.

In some embodiments, q is 0. In some related embodiments, compounds of the disclosure have the following structure (II):

(II)

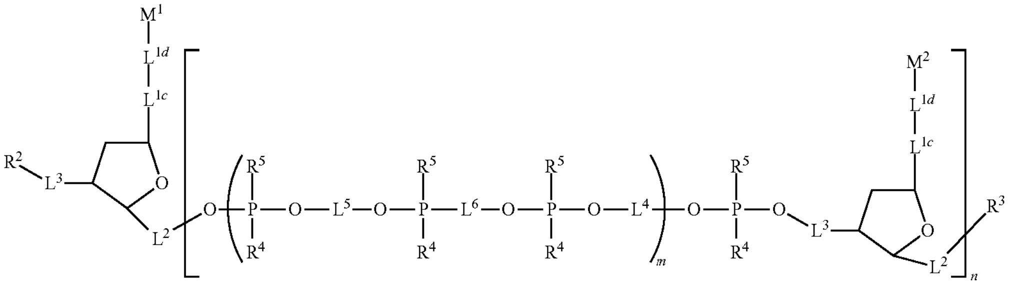

or a stereoisomer, salt or tautomer thereof, wherein:

$M^1$ and $M^2$ are, at each occurrence, independently a moiety comprising two or more carbon-carbon double bonds and at least one degree of conjugation;

$L^{1c}$ is, at each occurrence, independently a heteroarylene linker;

$L^{1d}$, $L^2$ and $L^3$ are, at each occurrence, independently optional alkylene, alkenylene, alkynylene, heteroalkylene, heteroalkenylene or heteroalkynylene linkers;

$L^4$ and $L^5$ are, at each occurrence, independently alkylene, alkenylene, alkynylene, heteroalkylene, heteroalkenylene or heteroalkynylene linkers;

$L^6$ is, at each occurrence, independently a heteroalkylene, heteroalkenylene or heteroalkynylene linker, provided at least one occurrence, $L^6$ is different from each of $L^4$ and L;

$R^2$ and $R^3$ are each independently H, OH, SH, alkyl, alkoxy, alkylether, heteroalkyl, —OP(=$R_a$)($R_b$)$R_c$, Q or a protected form thereof, or L';

$R^4$ is, at each occurrence, independently OH, SH, $O^-$, $S^-$, $OR_d$ or $SR_d$;

$R_5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (II);

m is, at each occurrence, independently an integer of zero or greater, provided at least one occurrence of m is an integer of one or greater; and n is an integer of one or greater.

In some embodiments, compounds of the disclosure have the following structure (II):

(II)

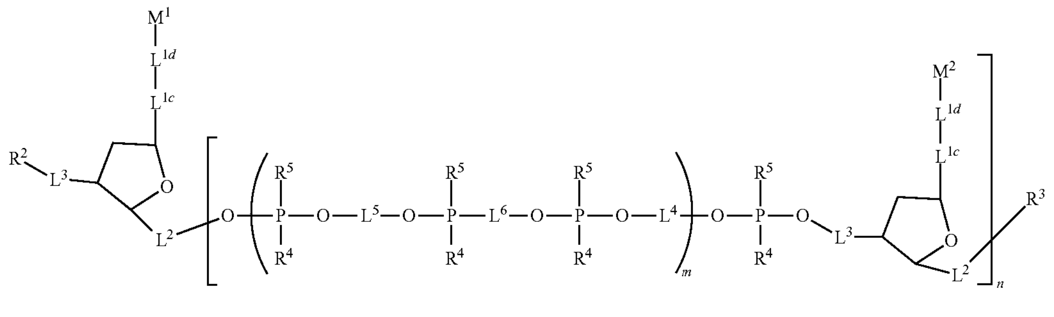

or a stereoisomer, salt or tautomer thereof, wherein:

$M^1$ and $M^2$ are, at each occurrence, independently a chromophore, provided that at least one of $M^1$ and $M^2$ is a FRET donor, and another one of $M^1$ and $M^2$ is a corresponding FRET acceptor;

$L^{1c}$ is, at each occurrence, independently a heteroarylene linker;

$L^{1d}$, $L^2$ and $L^3$ are, at each occurrence, independently optional alkylene, alkenylene, alkynylene, heteroalkylene, heteroalkenylene or heteroalkynylene linkers;

$L^4$ and $L^5$ are, at each occurrence, independently alkylene, alkenylene, alkynylene, heteroalkylene, heteroalkenylene or heteroalkynylene linkers;

$L^6$ is, at each occurrence, independently a heteroalkylene, heteroalkenylene or heteroalkynylene linker, provided at least one occurrence, $L^6$ is different from each of $L^4$ and $L^5$;

$R^2$ and $R^3$ are each independently H, OH, SH, alkyl, alkoxy, alkylether, heteroalkyl, —OP(=$R_a$)($R_b$)$R_c$, Q or a protected form thereof, or L';

$R^4$ is, at each occurrence, independently OH, SH, $O^-$, $S^-$, $OR_d$ or $SR_d$;

$R^5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (II);

m is, at each occurrence, independently an integer of zero or greater, provided at least one occurrence of m is an integer of one or greater; and n is an integer of one or greater.

The various linkers and substituents (e.g., M, Q, $R^2$, $R^3$, $R_c$, $L^{1c}$, $L^{1d}$, $L^2$, $L^3$, $L^4$, $L^5$ and $L^6$ in the compound of structure (II) are optionally substituted with one more substituent. For example, in some embodiments the optional substituent is selected to optimize the water solubility or other property of the compound of structure (II). In certain embodiments, each chromophore, alkyl, alkoxy, alkylether, heteroarylene, heteroalkyl, alkylene, alkenylene, alkynylene, heteroalkylene, heteroalkenylene, heteroalkynylene, alkoxyalkylether, phosphoalkyl, thiophosphoalkyl, phosphoalkylether and thiophosphoalkylether in the compound of structure (II) is optionally substituted with one more substituent selected from the group consisting of hydroxyl, alkoxy, alkylether, alkoxyalkylether, sulfhydryl, amino, alkylamino, carboxyl, phosphate, thiophosphate, phosphoalkyl, thiophosphoalkyl, phosphoalkylether and thiophosphoalkylether. In certain embodiments the optional substituent is —OP(=$R_a$)($R_b$)$R_c$, where $R_a$, $R_b$ and $R_c$ are as defined for the compound of structure (II).

In some embodiments, at least one occurrence of $L^{1c}$ is an optionally substituted 5-7 membered heteroarylene linker. In some more specific embodiments, $L^{1c}$ is, at each occurrence independently an optionally substituted 5-7 membered heteroarylene linker. In some embodiments, $L^{1c}$ is a 6-membered heteroarylene. In some embodiments, $L^{1c}$ comprises two N atoms and two O atoms. In certain embodiments, $L^{1c}$ is, at each occurrence, substituted. In some related embodiments, $L^{1c}$ is substituted, for example, with oxo, alkyl (e.g., methyl, ethyl, etc.) or combinations thereof. In more specific embodiments, $L^{1c}$ is, at each occurrence, substituted with at least one oxo. In some embodiments, $L^{1c}$ has one of the following structures:

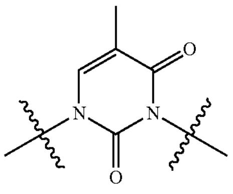

or

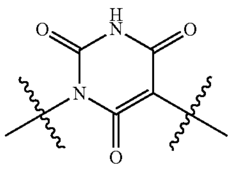

.

In some embodiments, $L^{1d}$ is, at each occurrence, independently an optional alkylene, alkenylene, alkynylene, heteroalkylene, heteroalkenylene, heteroalkynylene, alkyleneheteroarylenealkylene, alkyleneheterocyclylenealkylene, alkylenecarbocyclylenealkylene, heteroalkyleneheteroarylenealkylene, heteroalkyleneheterocyclylenealkylene, heteroalkylenecarbocyclylenealkylene, heteroalkyleneheteroaryleneheteroalkylene, heteroalkyleneheterocyclyleneheteroalkylene, heteroalkylenecarbocyclyleneheteroalkylene, alkyleneheteroaryleneheteroalkylene, alkyleneheterocyclyleneheteroalkylene, alkylenecarbocyclyleneheteroalkylene, heteroarylene, heterocyclylene, carbocyclylene, alkyleneheteroarylene, alkyleneheterocyclylene, heteroarylenealkylene, alkylenecarbocyclylene, carbocyclylenealkylene, heteroalkyleneheteroarylene, heteroalkyleneheterocyclylene, heteroaryleneheteroalkylene, heteroalkylenecarbocyclylene, carbocyclyleneheteroalkylene or heteroatomic linker. In some embodiments, $L^{1d}$ is an optionally substituted heteroalkenylene linker.

In some embodiments, at least one occurrence of $L^{1d}$ is substituted. In certain embodiments, $L^{1d}$ is substituted at each occurrence. In some more specific embodiments, $L^{1d}$ is substituted with oxo.

In other embodiments, $L^{1d}$ is at each occurrence, independently a linker comprising a functional group capable of formation by reaction of two complementary reactive groups (e.g., triazolyl, amide, etc.), for example a Q group.

The optional linker $L^{1d}$ can be used as a point of attachment of the M moiety to the remainder of the compound. For example, in some embodiments a synthetic precursor to the compound of structure (II) is prepared, and the M moiety is attached to the synthetic precursor using any number of facile methods known in the art, for example methods referred to as "click chemistry." For this purpose any reaction which is rapid and substantially irreversible can be used to attach M moiety to the synthetic precursor to form a compound of structure (II). Exemplary reactions include the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, strain-promoted cycloalkyne-azide cycloaddition (Cu-free click), reaction of a strained alkene with an azide, tetrazine or tetrazole, alkene and azide [3+2] cycloaddition, alkene and tetrazine inverse-demand Diels-Alder, alkene and tetrazole photoreaction and various displacement reactions, such as displacement of a leaving group by nucleophilic attack on an electrophilic atom. Exemplary displacement reactions include reaction of an amine with: an activated ester; an N-hydroxysuccinimide ester; an isocyanate; an isothioscyanate or the like. In some embodiments the reaction to form $L^{1d}$ may be performed in an aqueous environment.

Accordingly, in some embodiments $L^{1d}$ is at each occurrence, independently a linker comprising a functional group capable of formation by reaction of two complementary reactive groups, for example a functional group which is the product of one of the foregoing "click" reactions. In various embodiments, for at least one occurrence of $L^{1d}$, the functional group can be formed by reaction of an aldehyde, oxime, hydrazone, alkyne, amine, azide, acylazide, acylhalide, nitrile, nitrone, sulfhydryl, disulfide, sulfonyl halide, isothiocyanate, imidoester, activated ester (e.g., N-hydroxysuccinimide ester), ketone, α,β-unsaturated carbonyl, alkene, maleimide, α-haloimide, epoxide, aziridine, tetrazine, tetrazole, phosphine, biotin or thiirane functional group with a complementary reactive group, for example, via a reaction of an amine with an N-hydroxysuccinimide ester or isothiocyanate.

In other embodiments, for at least one occurrence of $L^{1d}$, the functional group can be formed by reaction of an alkyne and an azide. In other embodiments, for at least one occurrence of $L^{1d}$, the functional group can be formed by reaction of an amine (e.g., primary amine) and an N-hydroxysuccinimide ester or isothiocyanate.

In more embodiments, for at least one occurrence of $L^{1d}$, the functional group comprises an alkene, ester, amide, thioester, disulfide, carbocyclic, heterocyclic or heteroaryl group. In more embodiments, for at least one occurrence of $L^{1d}$, the functional group comprises an alkene, ester, amide, thioester, thiourea, disulfide, carbocyclic, heterocyclic or heteroaryl group. In other embodiments, the functional group comprises an amide or thiourea. In some more specific embodiments, for at least one occurrence of $L^{1d}$, $L^{1b}$ is a linker comprising a triazolyl functional group. In some related embodiments, $L^{1d}$, at each occurrence, independently comprises a triazolyl functional group. While in other embodiments, for at least one occurrence of $L^{1d}$ is a linker comprising an amide or thiourea functional group.

In still other embodiments, for at least one occurrence of $L^{1d}$, $L^{1d}$-$M^1$ or $L^{1d}$-$M^2$ has one of the following structures:

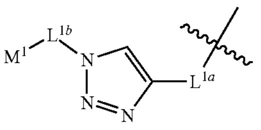
or
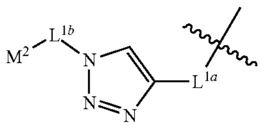

wherein $L^{1a}$ and $L^{1b}$ are each independently optional linkers.

In different embodiments, for at least one occurrence of $L^{1d}$, $L^{1d}$-$M^1$ or $L^{1d}$-$M^2$ has one of the following structures:

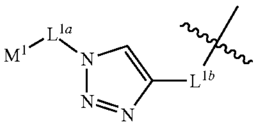
or
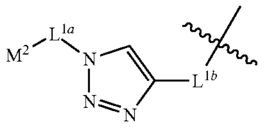

wherein $L^{1a}$ and $L^{1b}$ are each independently optional linkers.

In various embodiments of the foregoing, $L^{1a}$ or $L^{1b}$, or both, is absent. In other embodiments, $L^{1a}$ or $L^{1b}$, or both, is present.

In some embodiments $L^{1a}$ and $L^{1b}$, when present, are each independently alkylene or heteroalkylene. For example, in some embodiments $L^{1a}$ and $L^{1b}$, when present, independently have one of the following structures:

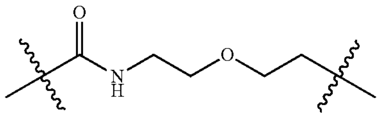
;
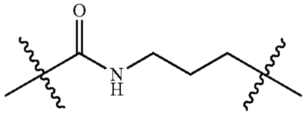
or
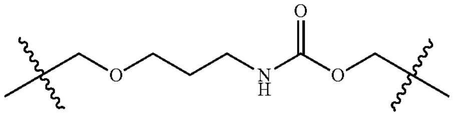
.

In still other different embodiments of structure (I), $L^{1d}$ is at each occurrence, independently an optional alkylene or heteroalkylene linker. In certain embodiments, $L^{1d}$ has one of the following structures:

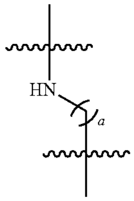 ;

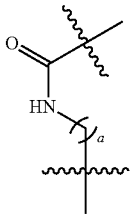 ;

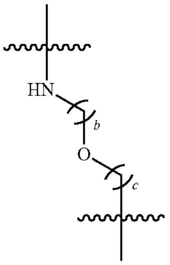 ;

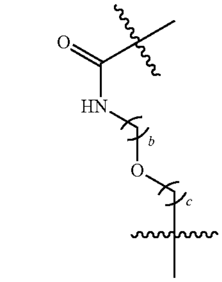 ;

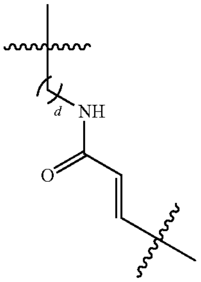 ;

wherein a, b, c, and d are each independently an integer ranging from 1-6.

In some embodiments, at least one occurrence of $L^2$ is an alkylene linker. In more specific embodiments, $L^2$ is an alkylene linker at each occurrence. In certain embodiments, the alkylene linker is a methylene linker.

In some embodiments, at least one occurrence of $L^3$ is absent. In more specific embodiments, $L^3$ is absent at each occurrence.

In some embodiments, at least one occurrence $L^4$ and $L^5$ are the same. In some embodiments, at each occurrence $L^4$ and $L^5$ are the same.

In some embodiments, at least one occurrence of $L^6$ comprises alkylene oxide. In some of the foregoing embodiments, the alkylene oxide is ethylene oxide, for example, polyethylene oxide. In some related embodiments, the compounds have the following structure (IIa):

(IIa)

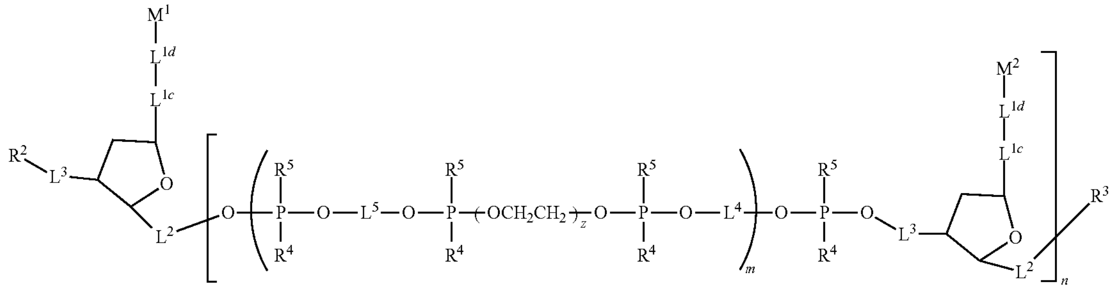

-continued

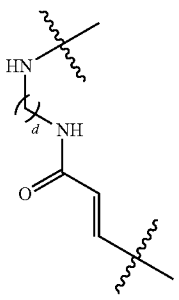 ; or 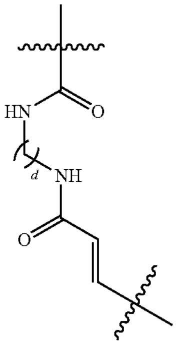 ;

wherein:

$L^4$ and $L^5$ are, at each occurrence, independently an alkylene, alkenylene, alkynylene, heteroalkylene, heteroalkenylene, heteroalkynylene or heteroatomic linker, provided $L^4$ and $L^5$ are not polyethylene oxide; and z is an integer from 1 to 100.

In some embodiments, z is an integer from 1-30, for example from 15 to 30 or from 22 to 25. In some embodiments, z is 23. In some embodiments, z is 21, 22, 23, 24 or 25. In some embodiments, z is an integer from 1 to 10, for example from 3 to 6. In some embodiments, z is 3, 4, 5, or 6.

In some embodiments, $L^4$ and $L^5$ are, at each occurrence, independently an alkylene linker. In some more specific embodiments, $L^4$ and $L^5$ are, at each occurrence, independently $C_3$-$C_6$ alkylene. In some embodiments, $L^4$ and $L^5$ are, at each occurrence, independently $C_3$ alkylene, $C_4$ alkylene, or $C_6$ alkylene. In some related embodiments, the compounds have the following structure (IIb):

(IIb)

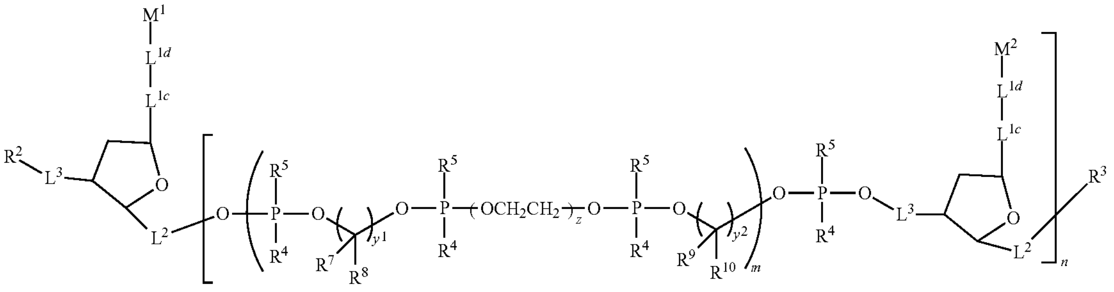

wherein:

$R^7$, $R^8$, $R^9$ and $R^{10}$ are, at each occurrence, independently H or alkyl; and $y^1$ and $y^2$ are, at each occurrence, independently an integer from 1 to 6.

In some embodiments, $R^7$, $R^8$, $R^9$ and $R^{10}$ are, at each occurrence, independently H, and $L^{1c}$ has one of the following structures:

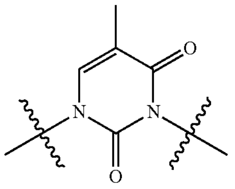

or

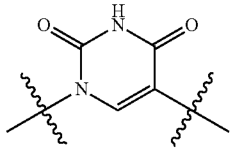

.

In some related embodiments, the compounds have the following structure (IIc), (IId), (IIe), or (IIf):

(IIc)

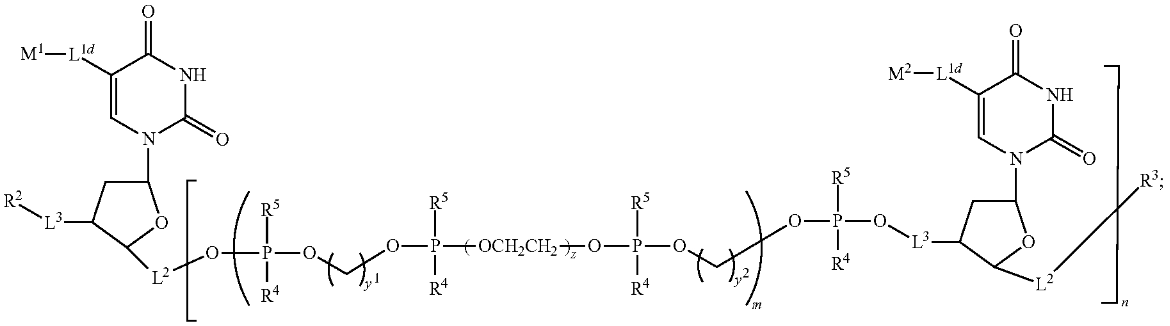

(IId)

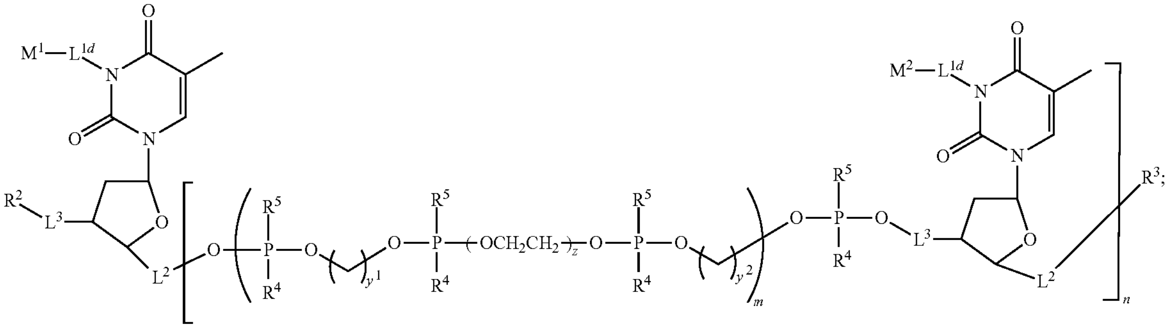

-continued (IIe)

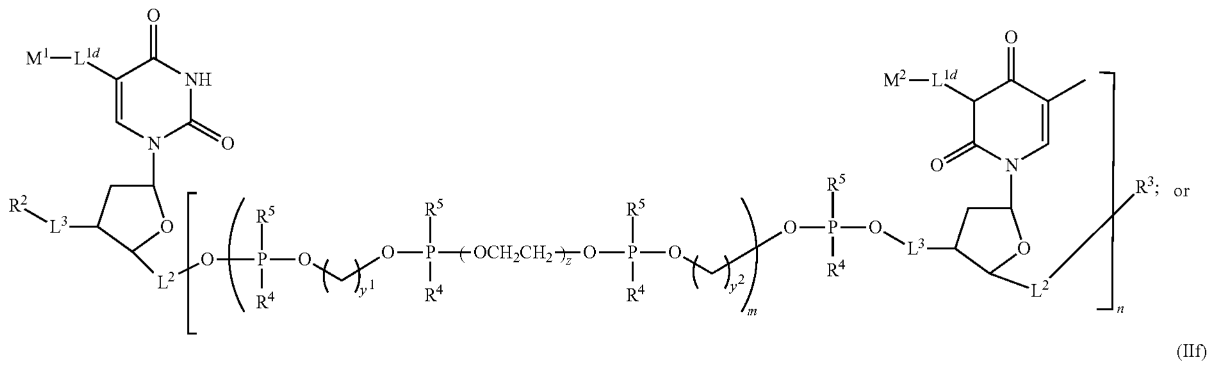

(IIf)

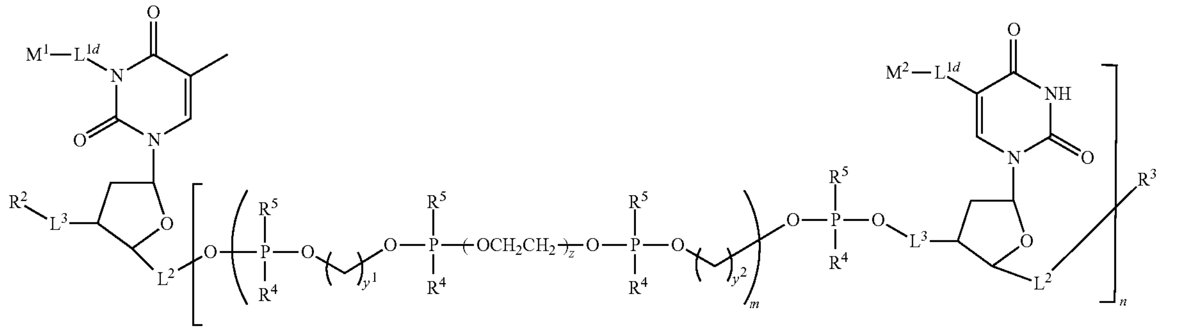

wherein:

$L^{1d}$ is, at each occurrence, independently an optionally substituted alkylene or an optionally substituted heteroalkylene linker.

In some embodiments, $L^{1d}$ is, at each occurrence, independently comprises an amide functional group or a triazolyl functional group.

In still other embodiments of any of the compounds of structure (A), (I), or (II), $R^4$ is, at each occurrence, independently OH, $O^-$ or $OR_d$. It is understood that "$OR_d$" and "$SR_d$" are intended to refer to $O^-$ and $S^-$ associated with a cation. For example, the disodium salt of a phosphate group may be represented as:

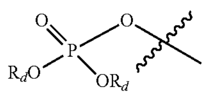

, where $R_d$ is sodium (Na+).

In other embodiments of any of the compounds of structure (A), (I), or (II), at least one occurrence of $R^5$ is oxo. In other embodiments of any of the compounds of structure (A), (I), or (II), $R^5$ is, at each occurrence, oxo.

In other various embodiments, $R^2$ and $R^3$ are each independently OH or $—OP(=R_a)(R_b)R_c$. In some different embodiments, $R^2$ or $R^3$ is OH or $—OP(=R_a)(R_b)R_c$, and the other of $R^2$ or $R^3$ is Q or a linker comprising a covalent bond to Q.

In still more different embodiments of any of the foregoing compounds of structure (A), (I), or (II), $R^2$ and $R^3$ are each independently $—OP(=R_a)(R_b)R_c$. In some of these embodiments, $R_c$ is OL'.

In other embodiments, $R^2$ and $R^3$ are each independently $—OP(=R_a)(R_b)OL'$, and L' is an alkylene or heteroalkylene linker to: Q, a targeting moiety, an analyte (e.g., analyte molecule), a solid support, a solid support residue, a nucleoside or a further compound of structure (A), (I), or (II).

The linker L' can be any linker suitable for attaching Q, a targeting moiety, an analyte (e.g., analyte molecule), a solid support, a solid support residue, a nucleoside or a further compound of structure (A), (I), or (II) to the compound of structure (A), (I), or (II). Advantageously certain embodiments include use of L' moieties selected to increase or optimize water solubility of the compound. In certain embodiments, L' is a heteroalkylene moiety. In some other certain embodiments, L' comprises an alkylene oxide or phosphodiester moiety, or combinations thereof.

In certain embodiments, L' has the following structure:

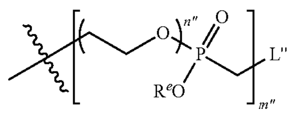

, wherein:

m“and n” are independently an integer from 1 to 10;

$R^e$ is H, an electron pair or a counter ion;

L" is $R^e$ or a direct bond or linkage to: Q, a targeting moiety, an analyte (e.g., analyte molecule), a solid support, a solid support residue, a nucleoside or a further compound of structure (A), (I), or (II).

In some embodiments, m" is an integer from 4 to 10, for example 4, 6 or 10. In other embodiments n" is an integer from 3 to 6, for example 3, 4, 5 or 6. In some embodiments, n" is an integer from 18-28, for example, from 21-23.

In some other embodiments, L" is an alkylene, alkyleneheterocyclylene, alkyleneheterocyclylenealkylene, alkylenecyclylene, alkylenecyclylenealkylene, heteroalkylene, heteroalkyleneheterocyclylene, heteroalkyleneheterocyclyleneheteroalkylene, heteroalkylenecyclylene, or heteroalkylenecycleneheteroalkylene moiety. In some other certain embodiments, L" comprises an alkylene oxide, phosphodiester moiety, sulfhydryl, disulfide or maleimide moiety or combinations thereof.

In certain of the foregoing embodiments, the targeting moiety is an antibody or cell surface receptor antagonist.

In some embodiments, the antibody includes CD3, CD4, FoxP3, TNF-α, IFN-γ, clone 4S.B3, clone 206D, CD8a (D8A8Y) Rabbit mAb, Vimentin (D21H3) XP® Rabbit mAb, phospho-RB-Ser608, phospho-RB-Ser612, phospho-RB-Ser780, phospho-RB-Ser795, phospho-RB-Ser807, or phospho-RB-Ser811, anti-human IL17A, integrin alpha E/CD103, CCR9, or MOPC-21.

In other more specific embodiments of any of the foregoing compounds of structure (A), (I), or (II), $R^2$ or $R^3$ has one of the following structures:

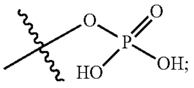

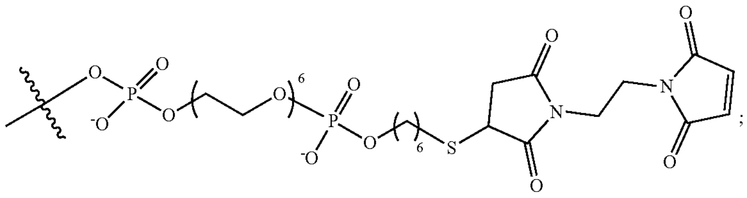

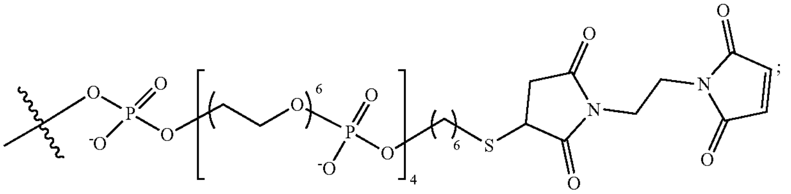

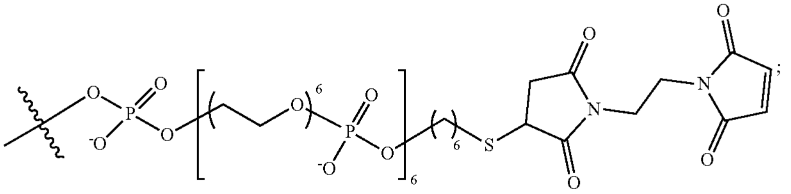

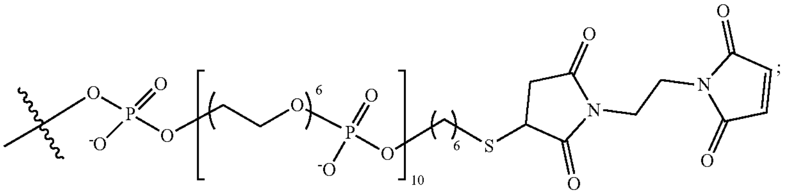

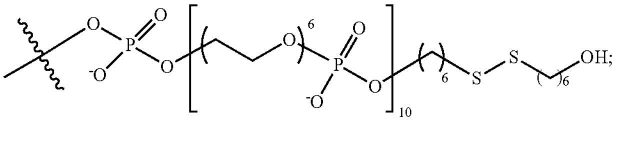

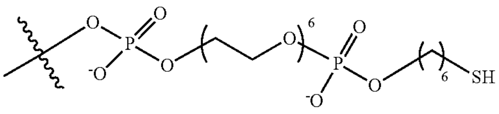

or

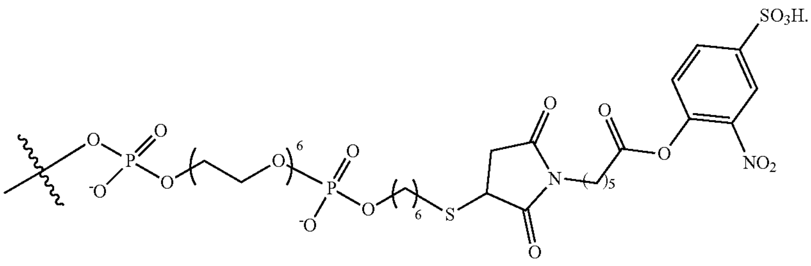

In other more specific embodiments of any of the foregoing compounds of structure (A), (I), or (II), $R^1$ or $R^2$ has one of the following structures:

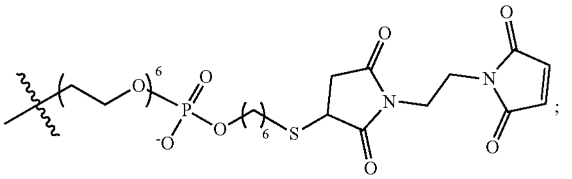

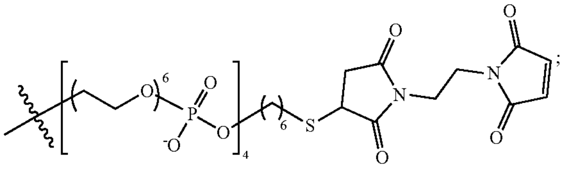

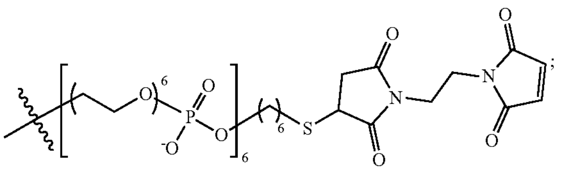

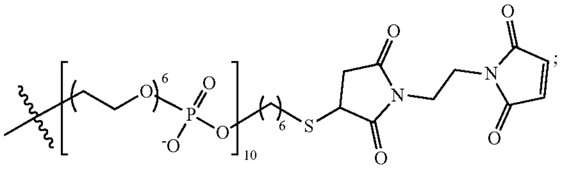

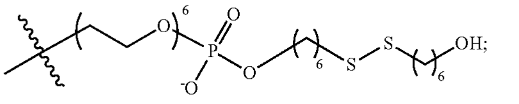

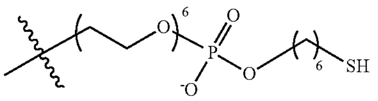

or

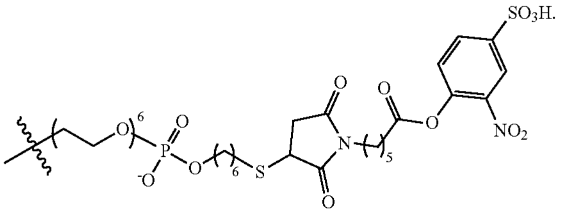

Certain embodiments of compounds of structure (A), (I), or (II) can be prepared according to solid-phase synthetic methods analogous to those known in the art for preparation of oligonucleotides. Accordingly, in some embodiments, L' is a linkage to a solid support, a solid support residue or a nucleoside. Solid supports comprising an activated deoxythymidine (dT) group are readily available, and in some embodiments can be employed as starting material for preparation of compounds of structure (A), (I), or (II). Accordingly, in some embodiments $R^2$ or $R^3$ has the following structure:

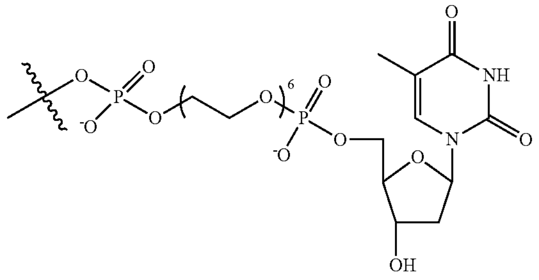

One of skill in the art will understand that the dT group depicted above is included for ease of synthesis and economic efficiencies only, and is not required. Other solid supports can be used and would result in a different nucleoside or solid support residue being present on L', or the nucleoside or solid support residue can be removed or modified post synthesis.

In still other embodiments, Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'. For example, in some embodiments, Q' is present on a further compound of structure (A), (I), or (II) (e.g., in the $R^2$ or $R^3$ position), and Q and Q' comprise complementary reactive groups such that reaction of the compound of structure (I) and the further compound of structure (A), (I), or (II) results in covalently bound dimer of the compound of structure (A), (I), or (II). Multimer compounds of structure (A), (I), or (II) can also be prepared in an analogous manner and are included within the scope of embodiments of the disclosure.

The type of Q group and connectivity of the Q group to the remainder of the compound of structure (A), (I), or (II) is not limited, provided that Q comprises a moiety having appropriate reactivity for forming the desired bond.

In certain embodiments, Q is a moiety which is not susceptible to hydrolysis under aqueous conditions, but is sufficiently reactive to form a bond with a corresponding group on an analyte molecule or solid support (e.g., an amine, azide or alkyne).

Certain embodiments of compounds of structure (A), (I), or (II) comprise Q groups commonly employed in the field of bioconjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group. In some embodiments, the activated ester is an N-succinimide ester, imidoester or polyflourophenyl ester. In other embodiments, the alkyne is an alkyl azide or acyl azide.

The Q groups can be conveniently provided in protected form to increase storage stability or other desired properties, and then the protecting group removed at the appropriate time for conjugation with, for example, a targeting moiety or analyte. Accordingly, Q groups include "protected forms" of a reactive group, including any of the reactive groups described above and in the Table 1 below. A "protected form" of Q refers to a moiety having lower reactivity under predetermined reaction conditions relative to Q, but which can be converted to Q under conditions, which preferably do not degrade or react with other portions of the compound of structure (A), (I), or (II). One of skill in the art can derive appropriate protected forms of Q based on the particular Q and desired end use and storage conditions. For example, when Q is SH, a protected form of Q includes a disulfide, which can be reduce to reveal the SH moiety using commonly known techniques and reagents.

Exemplary Q moieties are provided in Table I below.

TABLE 1

| Exemplary Q Moieties | |
|---|---|
| Structure | Class |
| 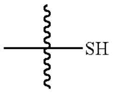 [SMILES: *S] | Sulfhydryl |
| 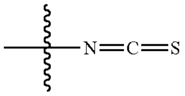 [SMILES: *N=C=S] | Isothio-cyanate |
| 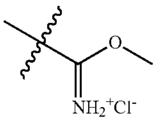 | Imidoester |
| 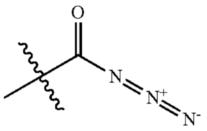 [SMILES: *C(=O)N=[N+]=[N-]] | Acyl Azide |
| 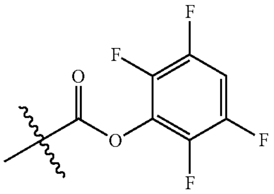 [SMILES: *C(=O)Oc1c(F)c(F)cc(F)c1F] | Activated Ester |
| 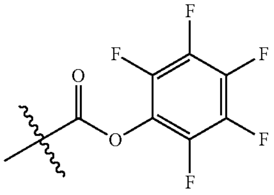 [SMILES: *C(=O)Oc1c(F)c(F)c(F)c(F)c1F] | Activated Ester |
| 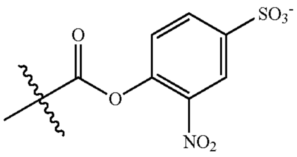 | Activated Ester |
| 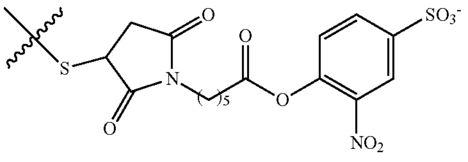 | Activated Ester |

TABLE 1-continued

| Exemplary Q Moieties | |
|---|---|
| Structure | Class |
| 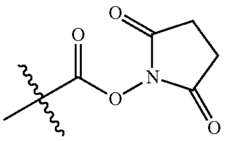 [SMILES: *C(=O)ON1C(=O)CCC1=O] | Activated Ester |
| 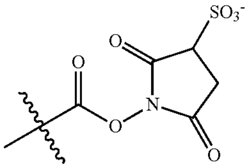 | Activated Ester |
| 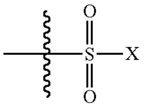 X = halo | Sulfonyl halide |
| 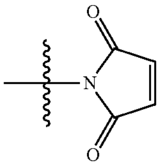 [SMILES: *N1C(=O)C=CC1=O] | Maleimide |
| 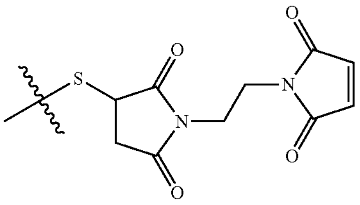 [SMILES: *SC1CC(=O)N(CCN2C(=O)C=CC2=O)C1=O] | Maleimide |
| 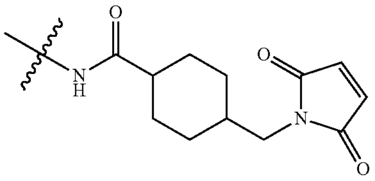 [SMILES: *NC(=O)C1CCC(CN2C(=O)C=CC2=O)CC1] | Maleimide |
| 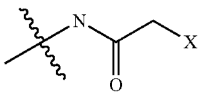 X = halo | α-haloimide |
| 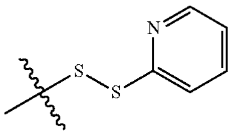 [SMILES: *SSc1ccccn1] | Disulfide |
| 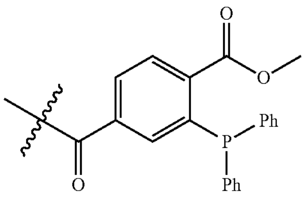 [SMILES: *C(=O)c1ccc(C(=O)OC)c(P(c2ccccc2)c2ccccc2)c1] | Phosphine |

TABLE 1-continued

| Exemplary Q Moieties | |
|---|---|
| Structure | Class |
| 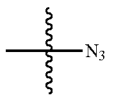 | Azide |
| 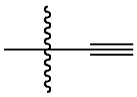 [SMILES: *C#C] | Alkyne |
| 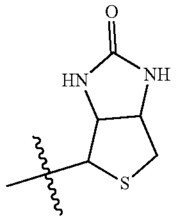 [SMILES: *C1SCC2NC(=O)NC21] | Biotin |
| 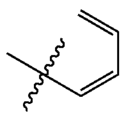 [SMILES: */C=C\C=C] | Diene |
| 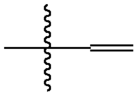 [SMILES: *C=C] | Alkene/ dienophile |
| 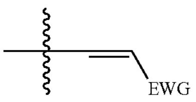 EWG = eletron withdrawing group | Alkene/ dienophile |
| —$NH_2$ | Amino |

It should be noted that in some embodiments, wherein Q is SH, the SH moiety will tend to form disulfide bonds with another sulfhydryl group, for example on another compound of structure (A), (I), or (II). Accordingly, some embodiments include compounds of structure (A), (I), or (II), which are in the form of disulfide dimers, the disulfide bond being derived from SH Q groups.

Also included within the scope of certain embodiments are compounds of structure (I), wherein one, or both, of $R^2$ and $R^3$ comprises a linkage to a further compound of structure (I). For example, wherein one or both of $R^2$ and $R^3$ are —OP(=$R_a$)($R_b$)$R_c$, and $R_c$ is OL', and L' is a linker comprising a covalent bond to a further compound of structure (I). Such compounds can be prepared by preparing a first compound of structure (I) having for example about 10 "M" moieties (i.e., n=9) and having an appropriate "Q" for reaction with a complementary Q' group on a second compound of structure (I). In this manner, compounds of structure (I), having any number of "M" moieties, for example 100 or more, can be prepared without the need for sequentially coupling each monomer. Exemplary embodiments of such compounds of structure (I) have the following structure (I')

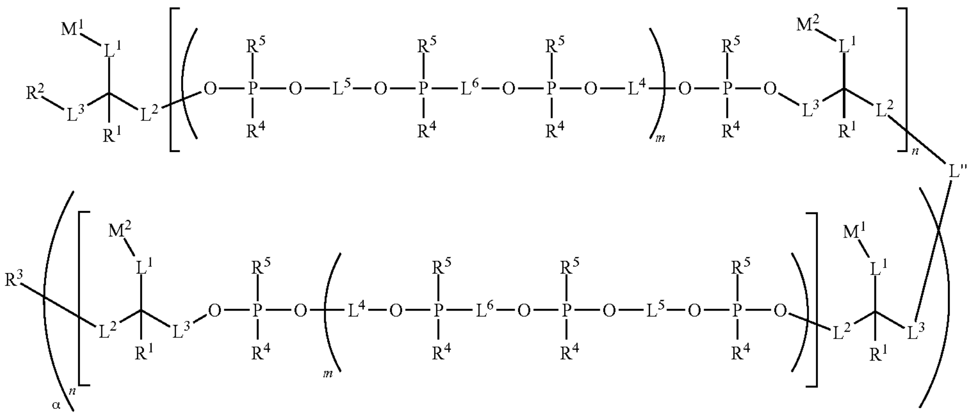

(I')

wherein:

each occurrence of $R^1$, $R^2$, $R^3$, $R^4$, $R^5$, $L^1$, $L^2$, $L^3$, $L^4$, $L^5$, $L^6$, $M^1$, $M^2$, m and n are independently as defined for a compound of structure (I);

L" is a linker comprising a functional group resulting from reaction of a Q moiety with a corresponding Q moiety; and α is an integer greater than 1, for example from 1 to 100, or 1 to 10.

Compounds of structure (I') are derivable by those of ordinary skill in the art, for example by dimerizing or polymerizing compounds of structure (I) provided herein.

Also included within the scope of certain embodiments are compounds of structure (II), wherein one, or both, of $R^2$ and $R^3$ comprises a linkage to a further compound of structure (II). For example, wherein one or both of $R^2$ and $R^3$ are $—OP(=R_a)(R_b)R_c$, and $R_c$ is OL', and L' is a linker comprising a covalent bond to a further compound of structure (II). Such compounds can be prepared by preparing a first compound of structure (II) having for example about 10 "M" moieties (i.e., n=9) and having an appropriate "Q" for reaction with a complementary Q' group on a second compound of structure (I). In this manner, compounds of structure (II), having any number of "M" moieties, for example 100 or more, can be prepared without the need for sequentially coupling each monomer. Exemplary embodiments of such compounds of structure (II) have the following structure (II')

(II')

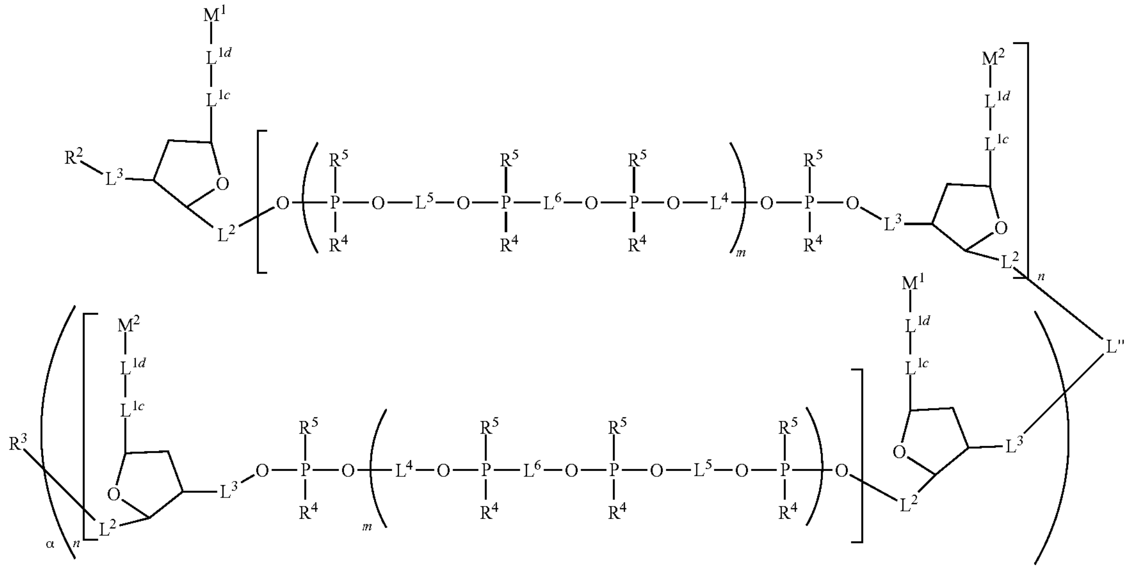

wherein:

each occurrence of $R^1$, $R^2$, $R^3$, $R^4$, $R^5$, $L^1$, $L^{1d}$, $L^2$, $L^3$, $L^4$, $L^5$, $L^6$, $M^1$, $M^2$, m and n are independently as defined for a compound of structure (II);

L" is a linker comprising a functional group resulting from reaction of a Q moiety with a corresponding Q' moiety; and α is an integer greater than 1, for example from 1 to 100, or 1 to 10.

Compounds of structure (II') are derivable by those of ordinary skill in the art, for example by dimerizing or polymerizing compounds of structure (II) provided herein.

In other embodiments, the Q moiety is conveniently masked (e.g., protected) as a disulfide moiety, which can later be reduced to provide an activated Q moiety for binding to a desired analyte molecule or targeting moiety. For example, the Q moiety may be masked as a disulfide having the following structure:

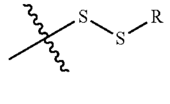

wherein R is an optionally substituted alkyl group. For example, in some embodiments, Q is provided as a disulfide moiety having the following structure:

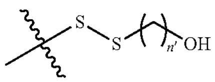

where n is an integer from 1 to 10, for example 6.

In some other embodiments, one of $R^2$ or $R^3$ is OH or $-OP(=R_a)(R_b)R_c$, and the other of $R^2$ or $R^3$ is a linker comprising a covalent bond to an analyte molecule or a linker comprising a covalent bond to a solid support. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In still different embodiments, the solid support is a polymeric bead or nonpolymeric bead.

The value for m is another variable that can be selected based on the desired fluorescence and/or color intensity. In some embodiments, m is, at each occurrence, independently an integer from 1 to 10. In other embodiments, m is, at each occurrence, independently an integer from 1 to 5, for example 1, 2, 3, 4 or 5.

In other embodiments, m is, at each occurrence, independently an integer greater than 2, and z is an integer from 15 to 30, for example in some embodiment m is, at each occurrence, independently an integer greater than 2, such as 3, 4, 5 or 6, and z is an integer from 22 to 25.

The fluorescence intensity can also be tuned by selection of different values of n. In certain embodiments, n is an integer from 1 to 100. In other embodiments, n is an integer from 1 to 10. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

The value for q is another variable that ban be selected based on the desired fluorescence and/or color intensity. In some embodiments, q is at each occurrence, independently and integer from 0 to 3. For example, in some embodiments, q is 0. In some embodiments, q is 1. In some embodiments, q is 2. In some embodiments, q is 3.

The value for w is another variable that ban be selected based on the desired fluorescence and/or color intensity. In some embodiments, w is at each occurrence, independently and integer from 0 to 3. For example, in some embodiments, w is 0. In some embodiments, w is 1. In some embodiments, w is 2. In some embodiments, w is 3.

$M^1$ and $M^2$ are selected based on the desired optical properties, for example based on a desired color and/or fluorescence emission wavelength. In some embodiments, $M^1$ and $M^2$ are the same at each occurrence; however, it is important to note that each occurrence of $M^1$ or $M^2$ need not be an identical $M^1$ or $M^2$, and certain embodiments include compounds wherein $M^1$ and $M^2$ are not the same at each occurrence. For example, in some embodiments each $M^1$ and $M^2$ are not the same and the different $M^1$ and $M^2$ moieties are selected to have absorbance and/or emissions for use in fluorescence resonance energy transfer (FRET) methods. For example, in such embodiments the different M moieties are selected to form FRET donor-acceptor pairs such that absorbance of radiation at one wavelength causes emission of radiation at a different wavelength by a FRET mechanism. Exemplary $M^1$ and $M^2$ moieties can be appropriately selected by one of ordinary skill in the art based on the desired end use. Exemplary $M^1$ and $M^2$ moieties for FRET methods include fluorescein and 5-TAMRA (5-carboxytetramethylrhodamine, succinimidyl ester) dyes.

$M^1$ and $M^2$ may be attached to the remainder of the molecule from any position (i.e., atom) on $M^1$ and $M^2$. One of skill in the art will recognize means for attaching $M^1$ and $M^2$ to the remainder of molecule. Exemplary methods include the "click" reactions described herein.

In some embodiments, $M^1$ and $M^2$ is a fluorescent or colored moiety. Any fluorescent and/or colored moiety may be used, for examples those known in the art and typically employed in colorimetric, UV, and/or fluorescent assays may be used. Examples of M moieties which are useful in various embodiments of the disclosure include, but are not limited to: Xanthene derivatives (e.g., fluorescein, rhodamine, Oregon green, eosin or Texas red); Cyanine derivatives (e.g., cyanine, indocarbocyanine, oxacarboLlcyanine, thiacarbocyanine or merocyanine); Squaraine derivatives and ring-substituted squaraines, including Seta, SeTau, and Square dyes; Naphthalene derivatives (e.g., dansyl and prodan derivatives); Coumarin derivatives; oxadiazole derivatives (e.g., pyridyloxazole, nitrobenzoxadiazole or benzoxadiazole); Anthracene derivatives (e.g., anthraquinones, including DRAQ5, DRAQ7 and CyTRAK Orange); Pyrene derivatives such as cascade blue; Oxazine derivatives (e.g., Nile red, Nile blue, cresyl violet, oxazine 170); Acridine derivatives (e.g., proflavin, acridine orange, acridine yellow); Arylmethine derivatives: auramine, crystal violet, malachite green; and Tetrapyrrole derivatives (e.g., porphin, phthalocyanine or bilirubin). Other exemplary M moieties include: Cyanine dyes, xanthate dyes (e.g., Hex, Vic, Nedd, Joe or Tet); Yakima yellow; Redmond red; tamra; texas red and Alexa Fluor® dyes such as Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, or Alexa Fluor® 680.

Compounds of the present disclosure find utility as fluorescent and/or colored dyes with high quantum efficiencies. This is due, in part, to the overlap of the emission spectrum of a donor moiety (e.g., $M^1$) with the absorbance or excitation spectrum of an acceptor moiety (e.g., $M^2$). Accordingly, some embodiments provide a FRET donor having excitation maximum value between 300 and 900 nm and emission maximum value between 350 and 900 nm. For example, in some embodiments the FRET donor includes 2,5-diphenyloxazole having 311 nm excitation maximum value and 375 nm emission maximum value. In another example, in some embodiments the FRET donor includes dansyl fluorophore having 333 nm excitation maximum value and 518 nm emission maximum value. In yet another example, in some embodiments the FRET donor Alexa Fluor® 350 having 346 nm excitation maximum value and 442 nm emission maximum value. In yet further example, in some embodiments the FRET donor includes pyrene having 340 nm excitation maximum value and 376 nm emission maximum value. In yet further example, in some embodiments the FRET donor includes coumarin 343 having 437 nm excitation maximum value and 477 nm emission maximum value. In yet another example, in some embodiments the FRET donor Alexa Fluor® 430 having 430 nm excitation maximum value and 539 nm emission maximum value. In yet another example, in some embodiments the FRET donor 5-carboxyfluorescein (FAM) having 495 nm excitation maximum value and 519 nm emission maximum value. In yet another example, in some embodiments the FRET donor cyanide dye (CY3®) having 550 nm excitation maximum value and 615 nm emission maximum value emission maximum value. In yet another example, in some embodiments the FRET donor Alexa Fluor® 555 having 555 nm excitation maximum value and 572 nm emission maximum value. In yet another example, in some embodiments the FRET donor Alexa Fluor® 568 having 578 nm excitation maximum value and 603 nm emission maximum value. In yet another example, in some embodiments the FRET donor Alexa Fluor® 633 having 630 nm excitation maximum value and 650 nm emission maximum value. In yet another example, in some embodiments the FRET donor Alexa Fluor® 647 having 650 nm excitation maximum value and 668 nm emission maximum value. In yet another example, in some embodiments the FRET donor MB800 having 774 nm excitation maximum value and 798 nm emission maximum value. In yet another example, in some embodiments the FRET donor Alexa Fluor® 800 having 801 nm excitation maximum value and 814 nm emission maximum value. In yet another example, in some embodiments the FRET donor Alexa Fluor® 810 having 812 nm excitation maximum value and 826 nm emission maximum value. In yet another example, in some embodiments the FRET donor CF820 having 820 nm excitation maximum value and 830 nm emission maximum value. In yet another example, in some embodiments the FRET donor iFluor® 820 having 820 nm excitation maximum value and 849 nm emission maximum value. In yet another example, in some embodiments the FRET donor PromoFluor 840/iFluor® 840 having 838 nm excitation maximum value and 880 nm emission maximum value. In yet another example, in some embodiments the FRET donor iFluor® 860 having 852 nm excitation maximum value and 877 nm emission maximum value.

In some embodiments provide a FRET acceptor having excitation maximum value between 400 and 800 nm and emission maximum value between 500 and 500 nm. For example, in some embodiments the FRET acceptor 5-carboxyfluorescein (FAM) having 495 nm excitation maximum value and 519 nm emission maximum value. In another example, in some embodiments the FRET acceptor includes Alexa Fluor® 543 having 548 nm excitation maximum value and 566 nm emission maximum value. In yet another example, in some embodiments the FRET acceptor includes Alexa Fluor® 532 having 532 nm excitation maximum value and 554 nm emission maximum value. In yet another example, in some embodiments the FRET acceptor includes Alexa Fluor® 546 having 554 nm excitation maximum value and 570 nm emission maximum value. In yet another example, in some embodiments the FRET acceptor includes Alexa Fluor® 555 having 555 nm excitation maximum value and 572 nm emission maximum value. In yet another example, in some embodiments the FRET acceptor includes Alexa Fluor® 568 having 578 nm excitation maximum value and 603 nm emission maximum value. In yet another example, in some embodiments the FRET acceptor includes Alexa Fluor® 594 having 590 nm excitation maximum value and 617 nm emission maximum value. In yet another example, in some embodiments the FRET acceptor includes Alexa Fluor® 633 having 630 nm excitation maximum value and 650 nm emission maximum value. In yet another example, in some embodiments the FRET acceptor includes Alexa Fluor® 660 having 663 nm excitation maximum value and 690 nm emission maximum value. In yet another example, in some embodiments the FRET acceptor includes Alexa Fluor® 647 having 650 nm excitation maximum value and 668 nm emission maximum value. In yet another example, in some embodiments the FRET acceptor includes Alexa Fluor® 680 having 679 nm excitation maximum value and 702 nm emission maximum value. In yet another example, in some embodiments the FRET acceptor includes Alexa Fluor® 750 having 756 nm excitation maximum value and 776 nm emission maximum value.

Embodiments of the present disclosure allow for various combinations of FRET donor/acceptor pairs to enhance the brightness as a sensor. For example, in some embodiments, the FRET donor/acceptor pair is 2,5-diphenyloxazole as a FRET donor and Alexa Fluor® 430 as a FRET acceptor. In another example, in some embodiments, the FRET donor/acceptor pair is Dansyl fluorophore as a FRET donor and Alexa Fluor® 543 or Alexa Fluor® 532 as a FRET acceptor. In yet another example, in some embodiments, the FRET donor/acceptor pair is Alexa Fluor® 350 as a FRET donor and Alexa Fluor® 430 as a FRET acceptor. In yet another example, in some embodiments, the FRET donor/acceptor pair is pyrene as a FRET donor and Alexa Fluor® 430 as a donor/acceptor pair is Coumarin 343 as a FRET donor and FAM as a FRET acceptor. In yet another example, in some embodiments, the FRET donor/acceptor pair is Alexa Fluor® 430 as a FRET donor and Alexa Fluor® 543, Alexa Fluor® 532, Alexa Fluor® 546, Alexa Fluor® 555, Alexa Fluor® 568, or Alexa Fluor® 594 as a FRET acceptor. In yet another example, in some embodiments, the FRET donor/acceptor pair is FAM as a FRET donor and Alexa Fluor® 532, Alexa Fluor® 555, Alexa Fluor® 546, Alexa Fluor® 568, or Alexa Fluor® 594 as a FRET acceptor. In yet another example, in some embodiments, the FRET donor/acceptor pair is CY3® as a FRET donor and Alexa Fluor® 532, Alexa Fluor® 633 as a FRET acceptor. Fluor® 532, Alexa Fluor® 633 as a FRET acceptor. In yet another example, in some embodiments, the FRET donor/acceptor pair is Alexa Fluor® 555 as a FRET donor and Alexa Fluor® 633 or Alexa Fluor® 660 as a FRET acceptor. In yet another example, in some embodiments, the FRET donor/acceptor pair is Alexa Fluor® 568 as a FRET donor and Alexa Fluor® 633, Alexa Fluor® 647, Alexa Fluor® 660, or Alexa Fluor® 680 as a FRET acceptor. In yet another example, in some embodiments, the FRET donor/acceptor pair is Alexa Fluor® 633 as a FRET donor and Alexa Fluor® 680 as a FRET acceptor. In yet another example, in some embodiments, the FRET donor/acceptor pair is Alexa Fluor® 647 as a FRET donor and Alexa Fluor® 680 or Alexa Fluor® 750 as a FRET acceptor.

In still other embodiments of any of the foregoing, $M^1$ and $M^2$ comprise three or more aryl or heteroaryl rings, or combinations thereof, for example four or more aryl or heteroaryl rings, or combinations thereof, or even five or more aryl or heteroaryl rings, or combinations thereof. In some embodiments, $M^1$ and $M^2$ comprise six aryl or heteroaryl rings, or combinations thereof. In further embodiments, the rings are fused. For example in some embodiments, $M^1$ and $M^2$ comprise three or more fused rings, four or more fused rings, five or more fused rings, or even six or more fused rings.

In some embodiments, $M^1$ or $M^2$ is cyclic. For example, in some embodiments $M^1$ or $M^2$ is carbocyclic. In other embodiments, $M^1$ or $M^2$ is heterocyclic. In still other embodiments of the foregoing, $M^1$ or $M^2$, at each occurrence, independently comprises an aryl moiety. In some of these embodiments, the aryl moiety is multicyclic. In other more specific examples, the aryl moiety is a fused-multicyclic aryl moiety, for example which may comprise at least 3, at least 4, or even more than 4 aryl rings.

In other embodiments of any of the foregoing compounds of structure (A), (I), (II), (I') or (I"), $M^1$ or $M^2$, at each occurrence, independently comprises at least one heteroatom. For example, in some embodiments, the heteroatom is nitrogen, oxygen or sulfur.

In still more embodiments of any of the foregoing, $M^1$ or $M^2$, at each occurrence, independently comprises at least one substituent. For example, in some embodiments the substituent is a fluoro, chloro, bromo, iodo, amino, alkylamino, arylamino, hydroxy, sulfhydryl, alkoxy, aryloxy, phenyl, aryl, methyl, ethyl, propyl, butyl, isopropyl, t-butyl, carboxy, sulfonate, amide, or formyl group.

In some even more specific embodiments of the foregoing, $M^1$ or $M^2$, at each occurrence, independently is a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9, 10-ethynylanthracene or ter-naphthyl moiety. In other embodiments, $M^1$ or $M^2$ is, at each occurrence, independently p-terphenyl, perylene, azobenzene, phenazine, phenanthroline, acridine, thioxanthrene, chrysene, rubrene, coronene, cyanine, perylene imide, or perylene amide or a derivative thereof. In still more embodiments, $M^1$ or $M^2$ is, at each occurrence, independently a coumarin dye, resorufin dye, dipyrrometheneboron difluoride dye, ruthenium bipyridyl dye, energy transfer dye, thiazole orange dye, polymethine, or N-aryl-1,8-naphthalimide dye.

In still more embodiments of any of the foregoing, $M^1$ or $M^2$ at each occurrence is the same. In other embodiments, each $M^1$ or $M^2$ is different. In still more embodiments, one or more $M^1$ or $M^2$ is the same and one or more $M^1$ or $M^2$ is different.

In some embodiments, $M^1$ or $M^2$ is pyrene, perylene, perylene monoimide, 5-carboxyfluorescein (FAM), 6-FAM. 6-FITC, 5-FITC, or a derivative thereof.

In some embodiments, $M^1$ or $M^2$ has one of the following structures:

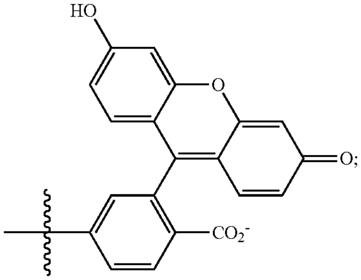

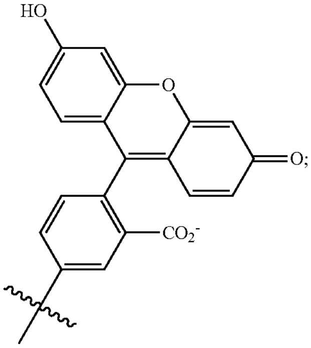

-continued

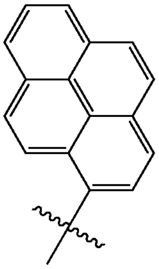
;
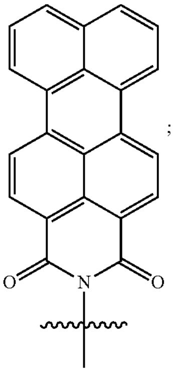
;

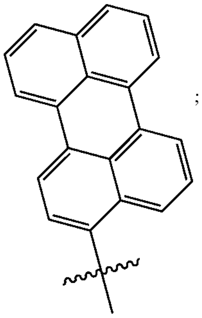
;

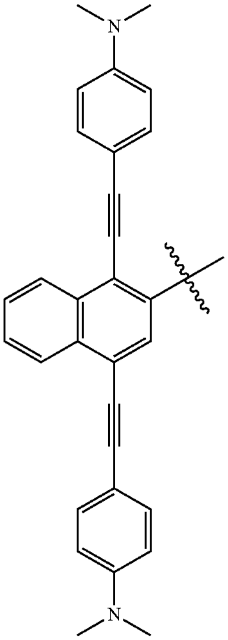
;

-continued
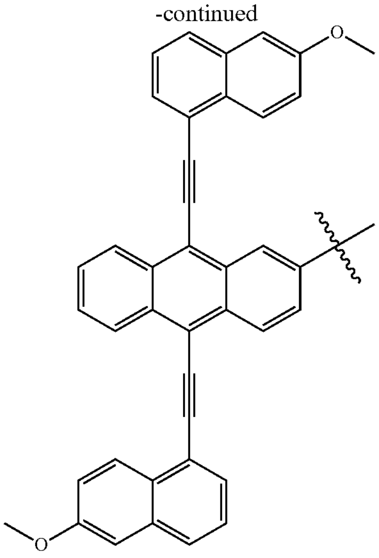
or
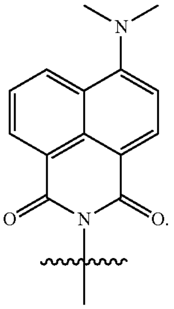
Although $M^1$ or $M^2$ moieties comprising carboxylic acid groups are depicted in the anionic form ($CO_2^-$) above, one of skill in the art will understand that this will vary depending on pH, and the protonated form ($CO_2H$) is included in various embodiments.
In some embodiments, $M^1$ or $M^2$ has one of the following structures:
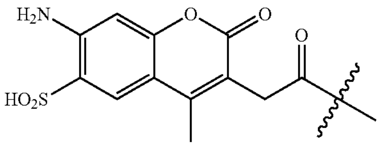
;
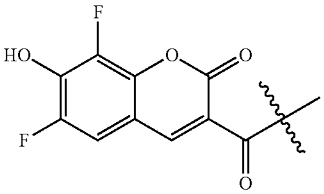
;
-continued
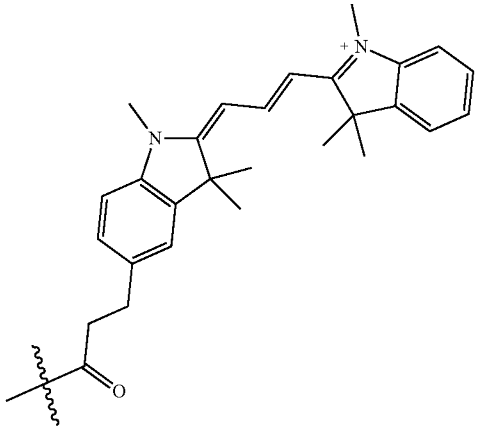
;
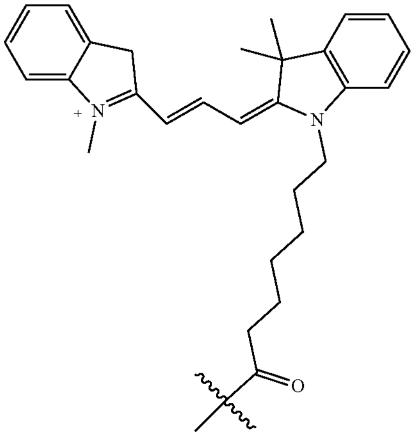
;
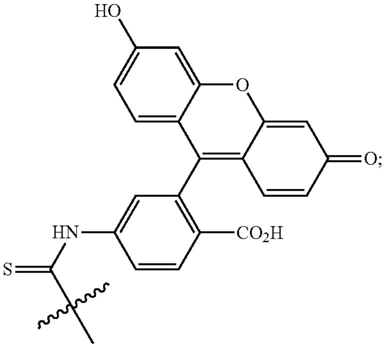
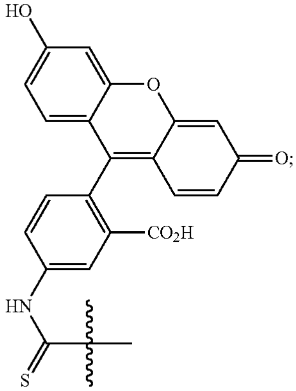

-continued
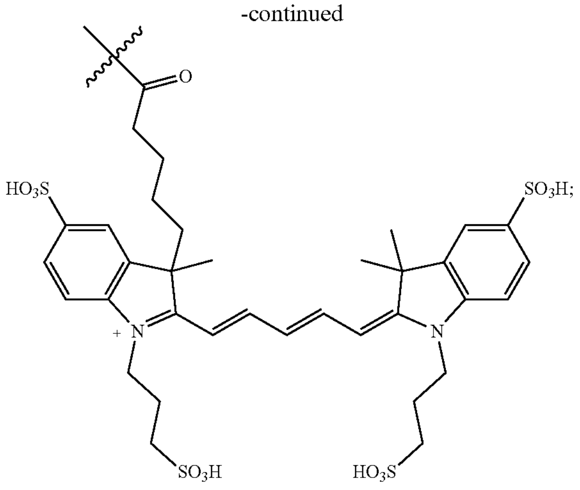
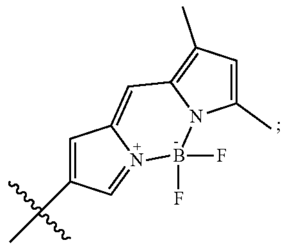
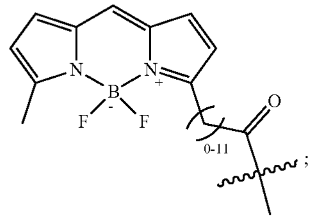
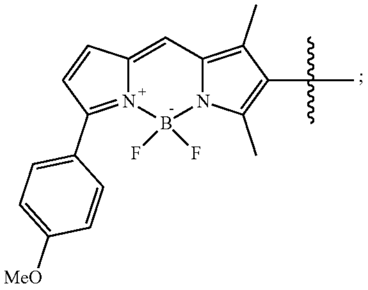
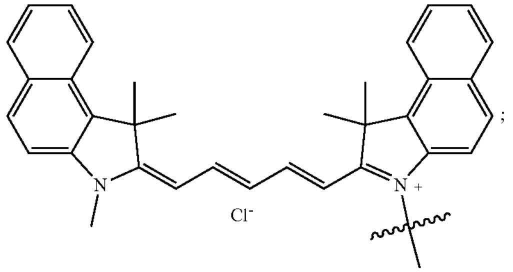
-continued
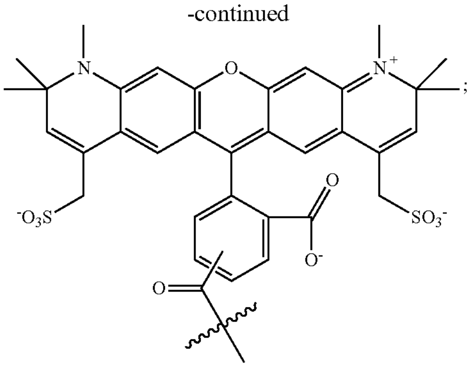
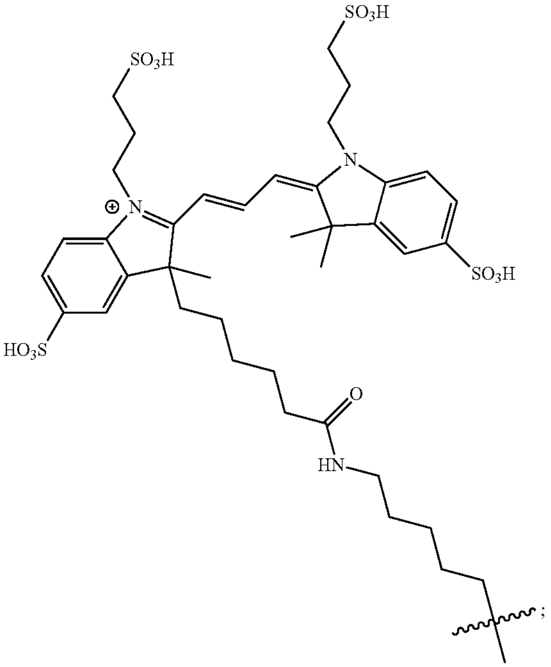
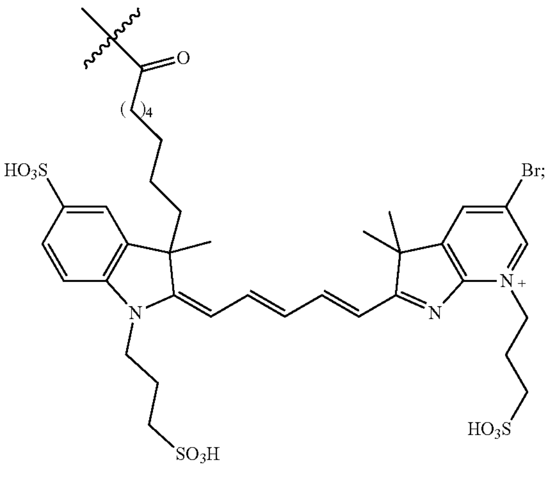

-continued
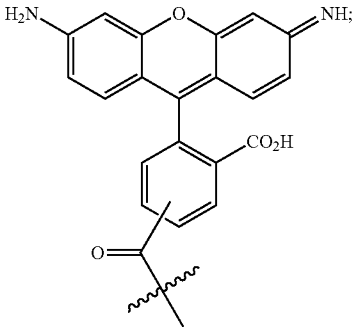
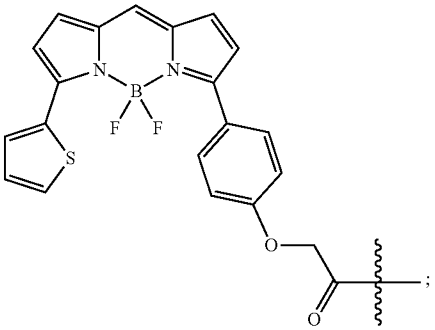
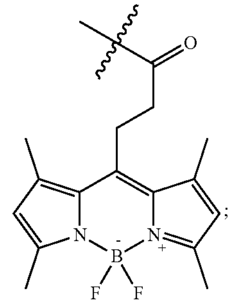
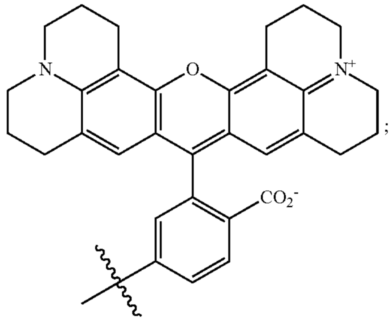
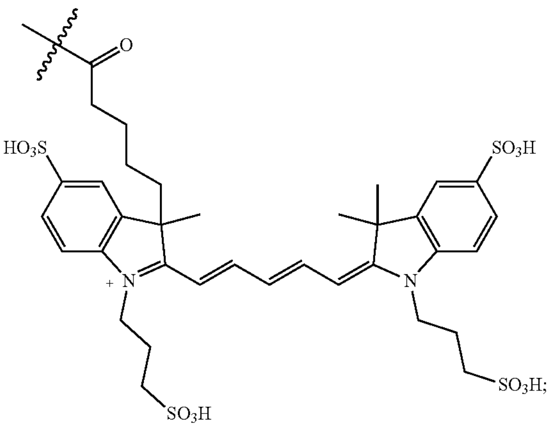
-continued
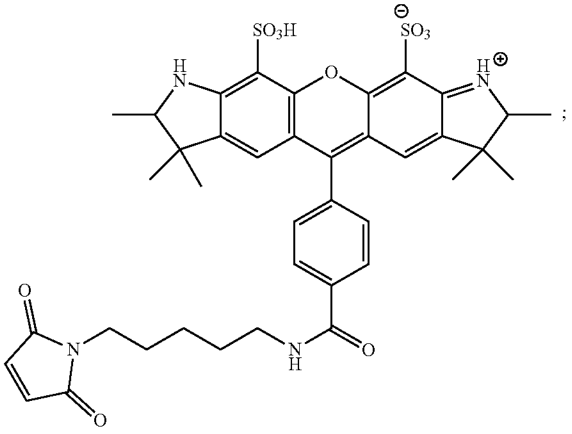
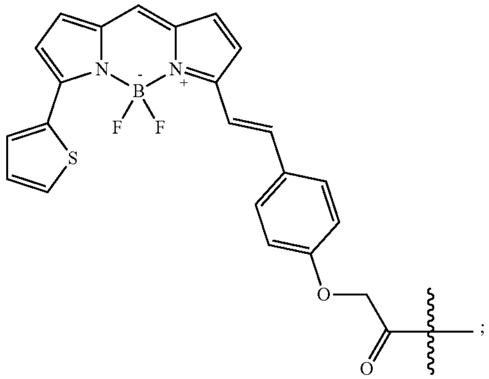
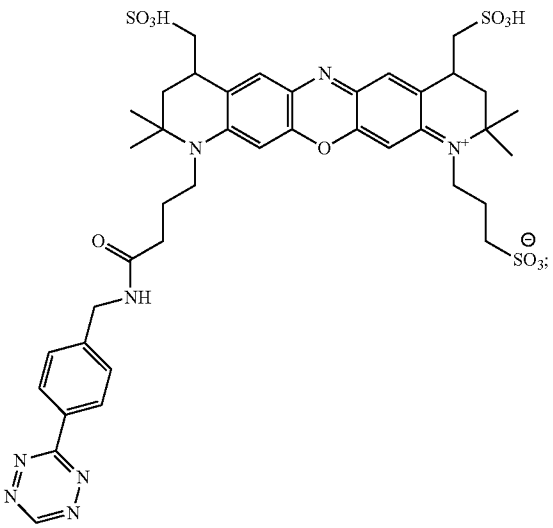
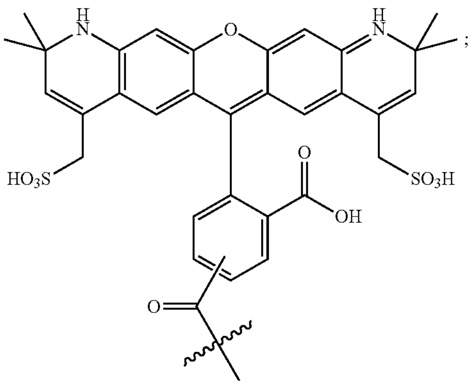

-continued
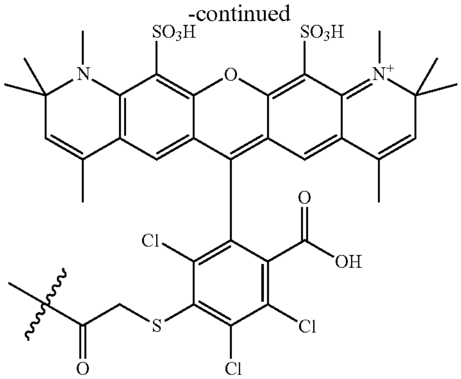
;
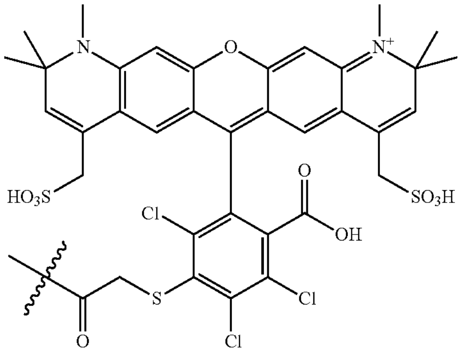
;
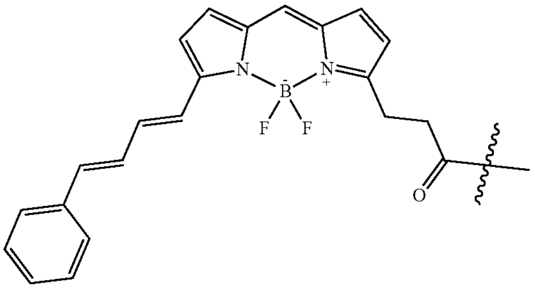
;
-continued
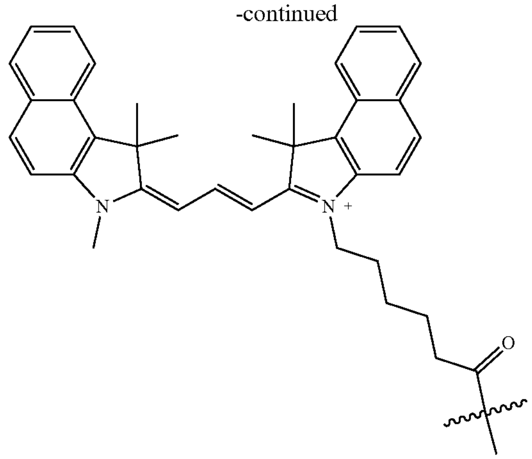
or
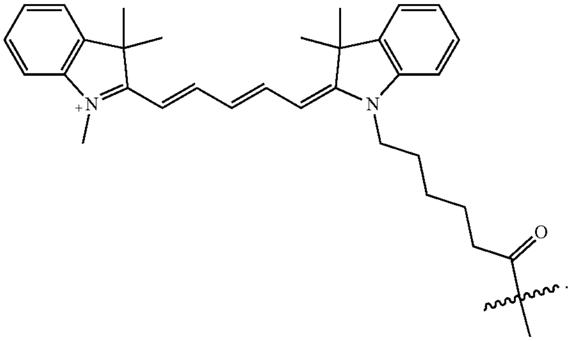
In some specific embodiments, the compound of structure (A), (I), or (II) is a compound selected from Table 2. The compounds in Table 2 were prepared according to the procedures set forth in the Examples and their identity confirmed by mass spectrometry.

TABLE 2
| Exemplary Compounds of Structure (A), (I), or (II) | |
|---|---|
| No. | Structure |
| I-1 | 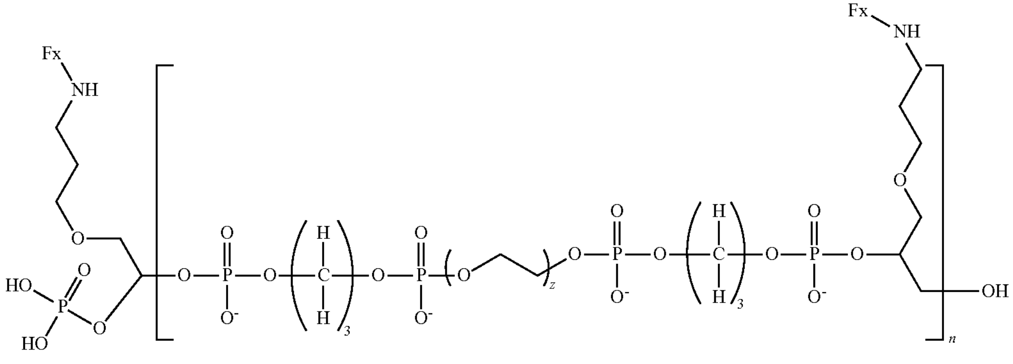<br>z =22-25 and PEG MW = about 1,000<br>n = 1-10 |
| I-2 | 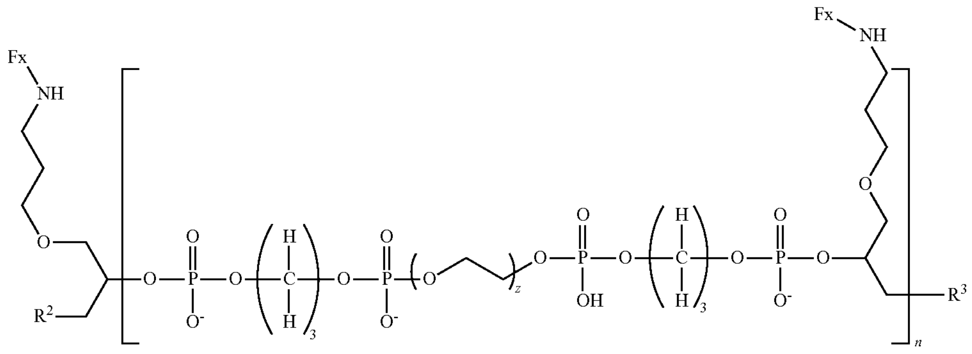<br>$R^2$ = 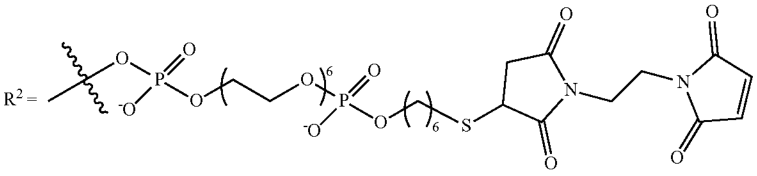 |

TABLE 2-continued
| Exemplary Compounds of Structure (A), (I), or (II) | |
|---|---|
| No. | Structure |
| | 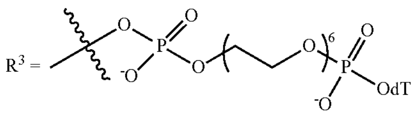 z = 22-25 and PEG MW = about 1,000 |
| I-3 | 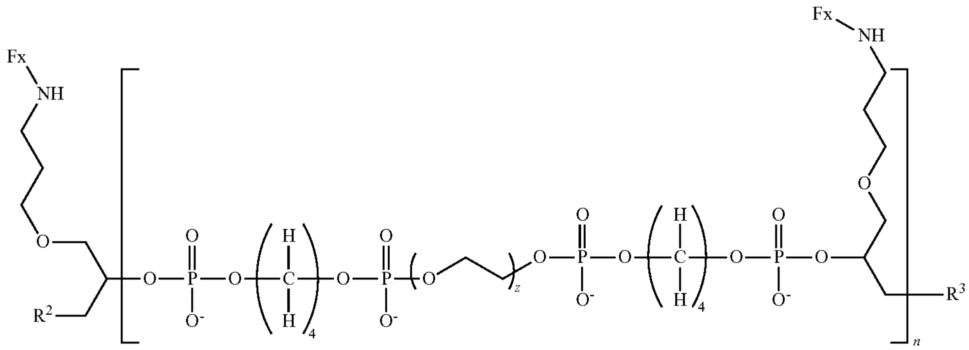 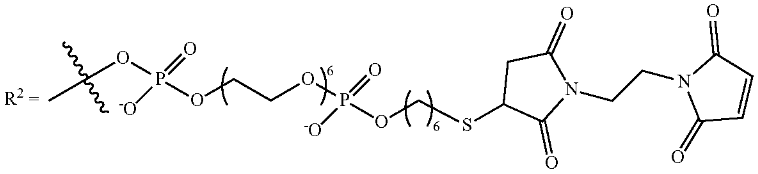 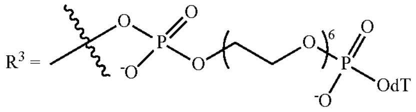 z = 22-25 and PEG MW = about 1,000<br>n = 1-10 |

TABLE 2-continued
| Exemplary Compounds of Structure (A), (I), or (II) | |
|---|---|
| No. | Structure |
| I-4 | 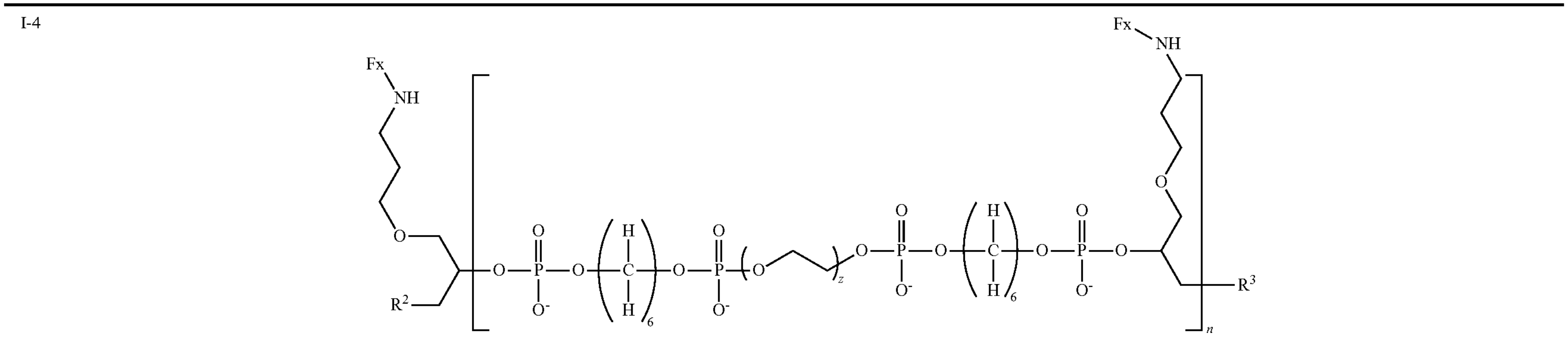<br>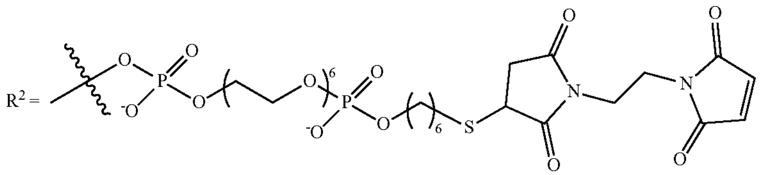<br>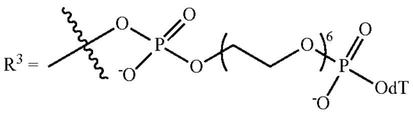<br>z = 22-25 and PEG MW = about 1,000<br>n = 1-10 |
| I-5 | 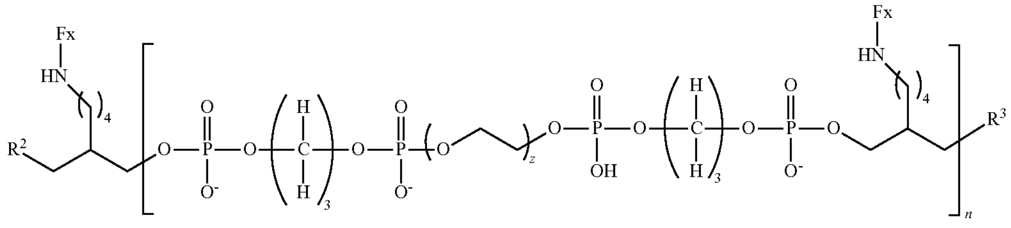 |

TABLE 2-continued
| Exemplary Compounds of Structure (A), (I), or (II) | |
|---|---|
| No. | Structure |
| | 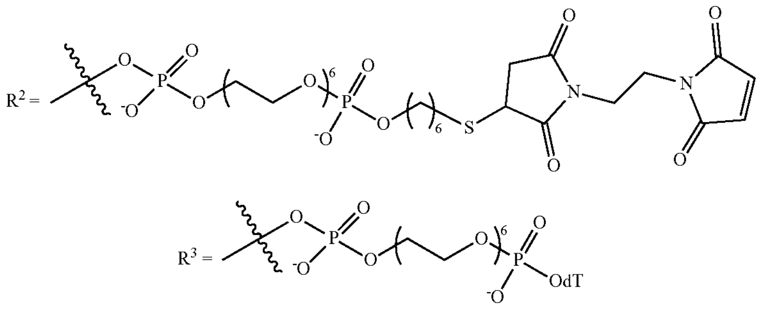 z = 22-25 and PEG MW = about 1,000<br>n = 1-10 |
| I-6 | 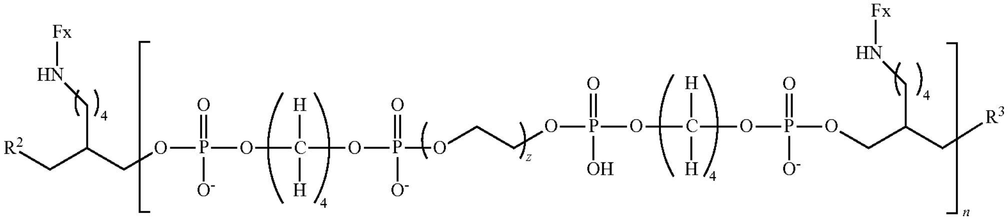 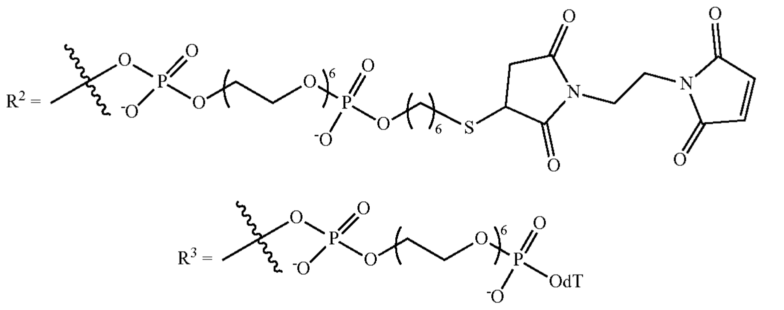 z = 22-25 and PEG MW = about 1,000<br>n = 1-10 |

TABLE 2-continued
| Exemplary Compounds of Structure (A), (I), or (II) | |
|---|---|
| No. | Structure |
| I-7 | 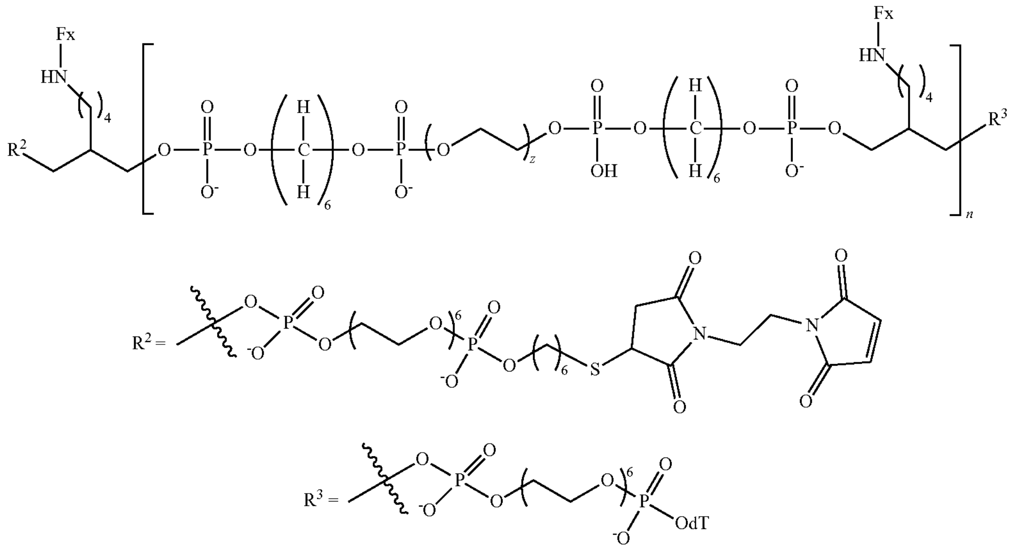 z = 22-25 and PEG MW = about 1,000<br>n = 1-10 |
| I-8 | 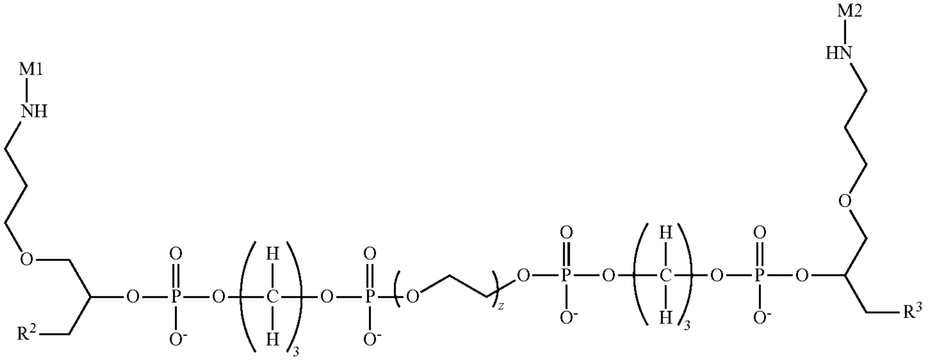 |

TABLE 2-continued
| Exemplary Compounds of Structure (A), (I), or (II) | |
|---|---|
| No. | Structure |
| | $R^2$ = 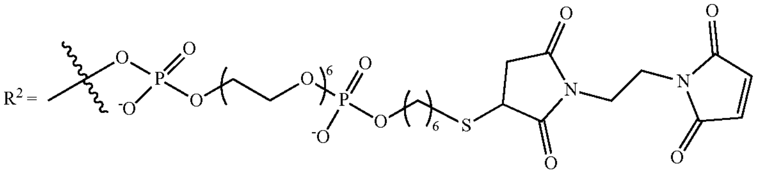<br>$R^3$ = 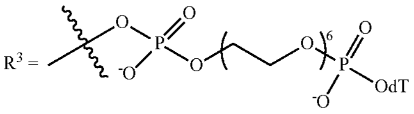<br>z = 6 or 22-25 and PEG MW = about 1,000 |

TABLE 2-continued
Exemplary Compounds of Structure (A), (I), or (II)
| No. | Structure |
| --- | --- |
| I-9 | 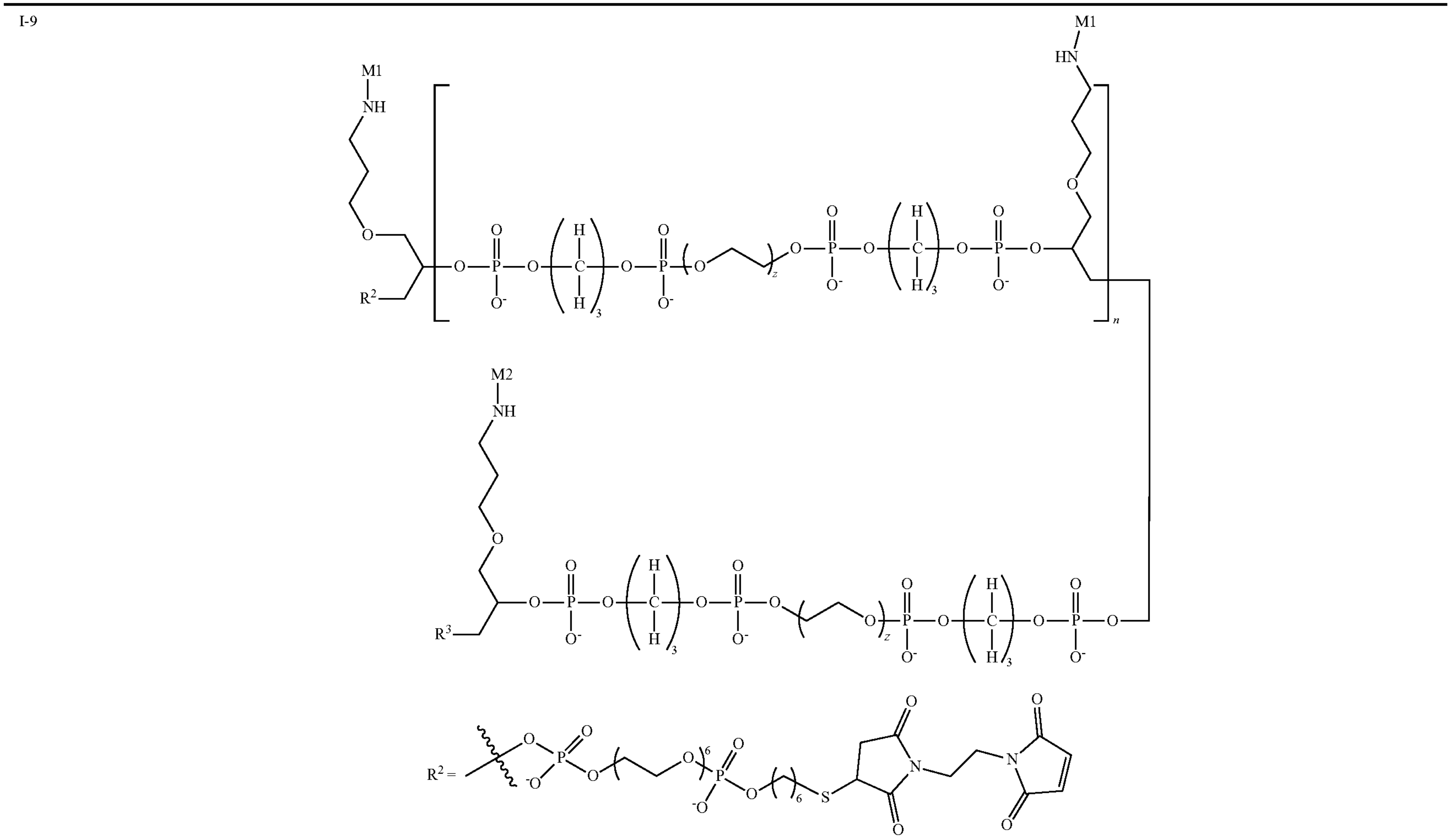 |

TABLE 2-continued
| Exemplary Compounds of Structure (A), (I), or (II) | |
|---|---|
| No. | Structure |
| | 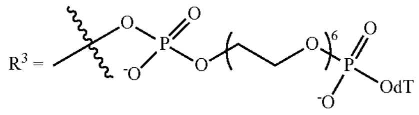<br>z = 6 or 22-25 and PEG MW = about 1,000<br>n = 1-4 |
| II-1 | 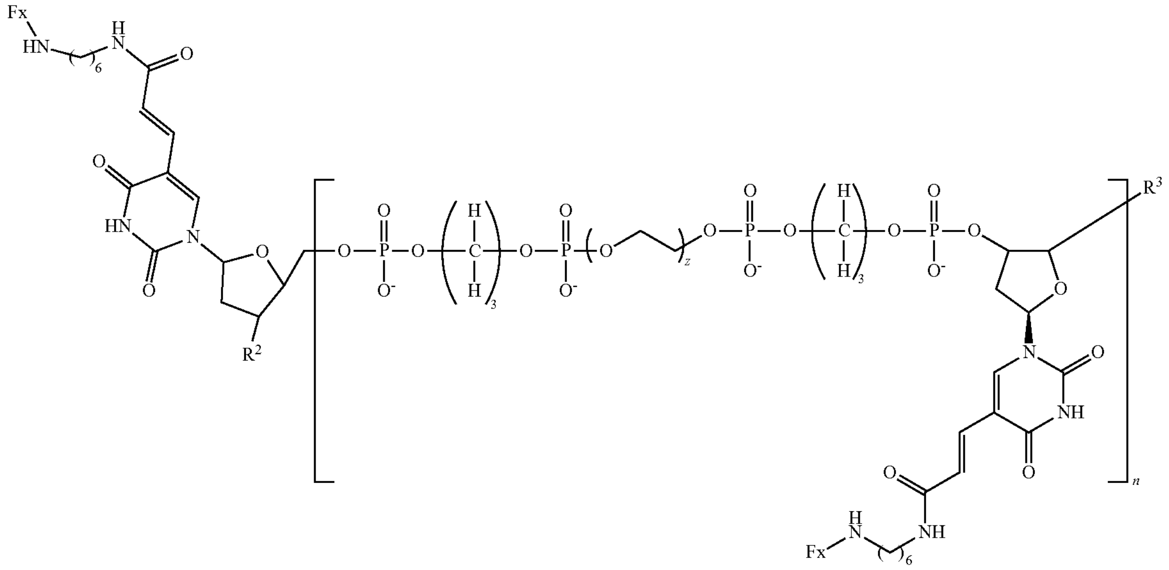<br>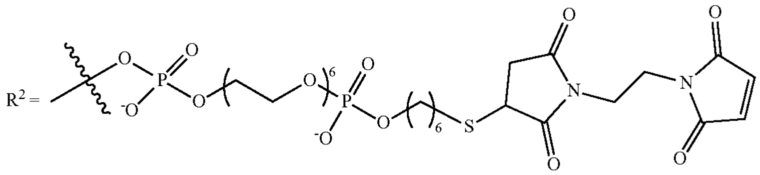 |

TABLE 2-continued
| Exemplary Compounds of Structure (A), (I), or (II) | |
|---|---|
| No. | Structure |
| | $R^3$ = 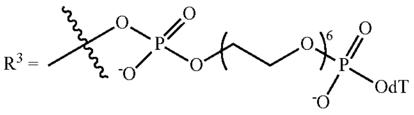<br>z = 22-25 and PEG MW = about 1,000<br>n = 1-10 |
| II-2 | 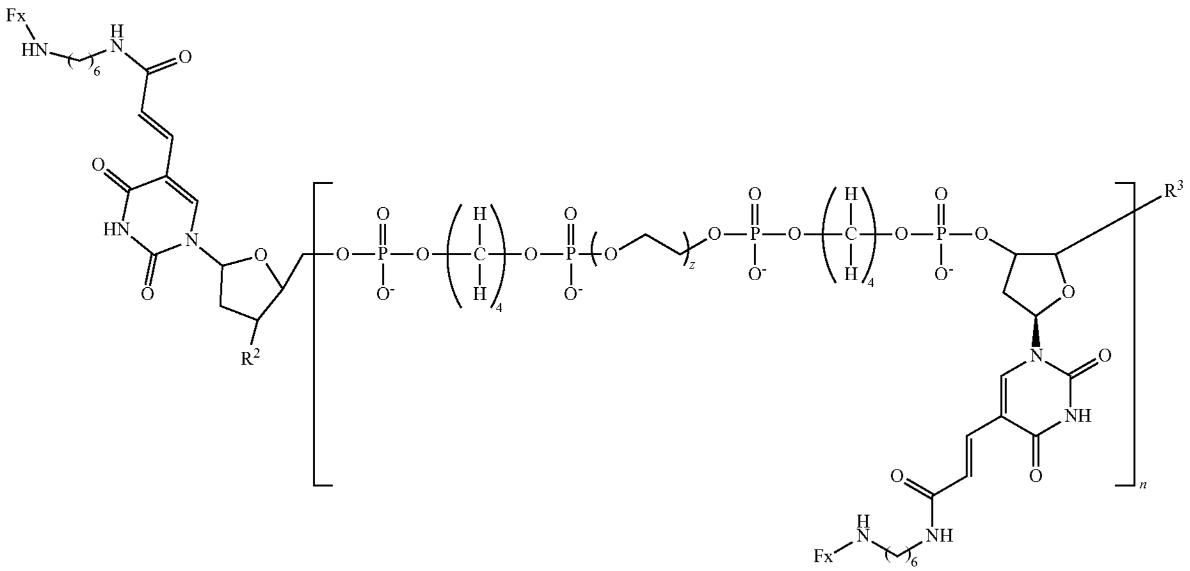<br>$R^2$ = 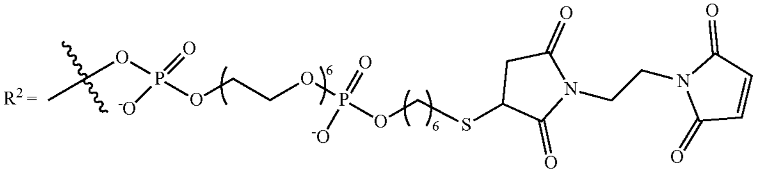 |

TABLE 2-continued
| Exemplary Compounds of Structure (A), (I), or (II) | |
|---|---|
| No. | Structure |
| | 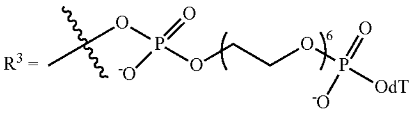<br>z = 22-25 and PEG MW = about 1,000<br>n = 1-10 |
| II-3 | 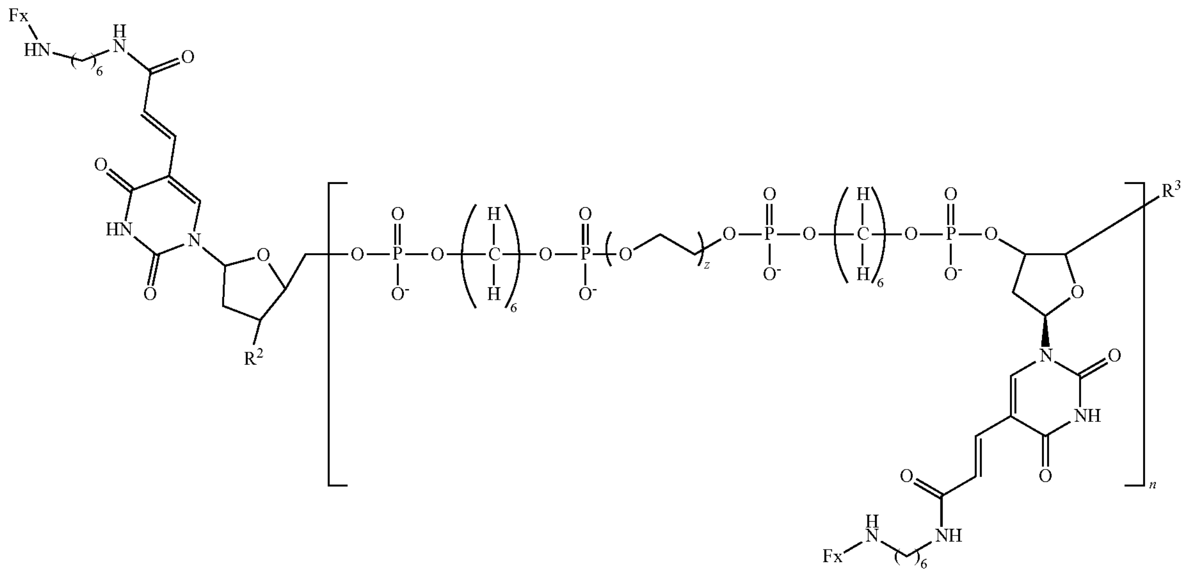<br>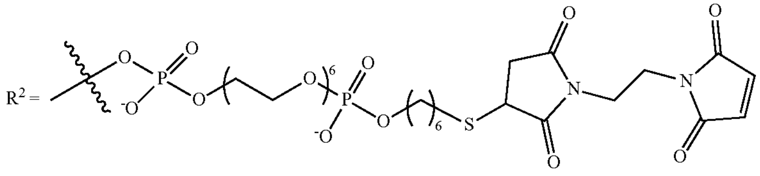 |

TABLE 2-continued
| Exemplary Compounds of Structure (A), (I), or (II) | |
|---|---|
| No. | Structure |
| | 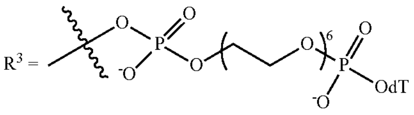<br>z = 22-25 and PEG MW = about 1,000<br>n = 1-10 |
| II-4 | 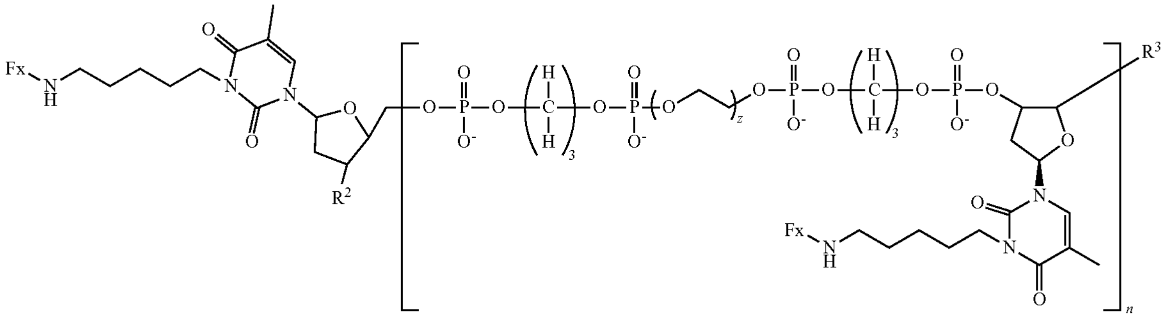<br>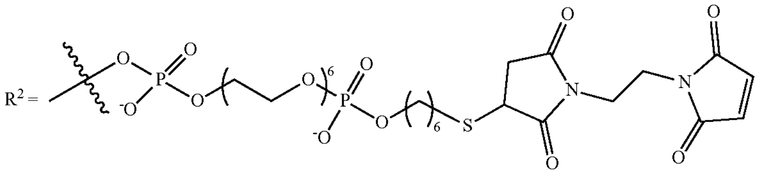<br>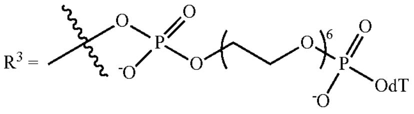<br>z = 22-25 and PEG MW = about 1,000<br>n = 1-10 |

TABLE 2-continued
| Exemplary Compounds of Structure (A), (I), or (II) | |
|---|---|
| No. | Structure |
| II-5 | 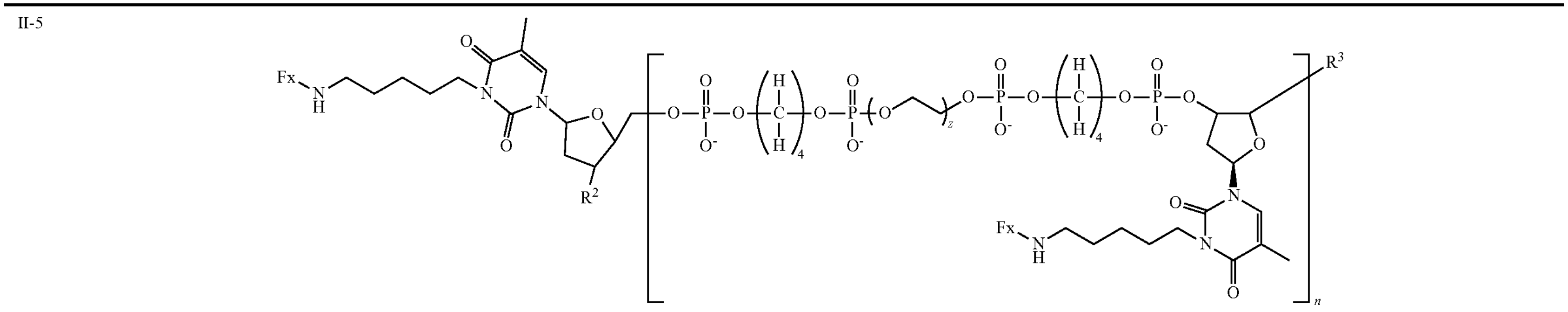<br>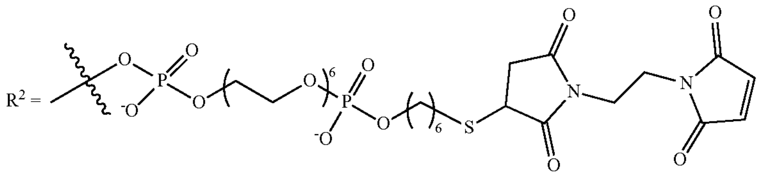<br>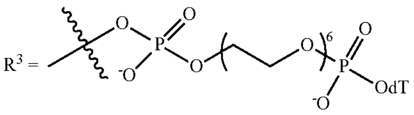<br>z = 22-25 and PEG MW = about 1,000<br>n = 1-10 |
| II-6 | 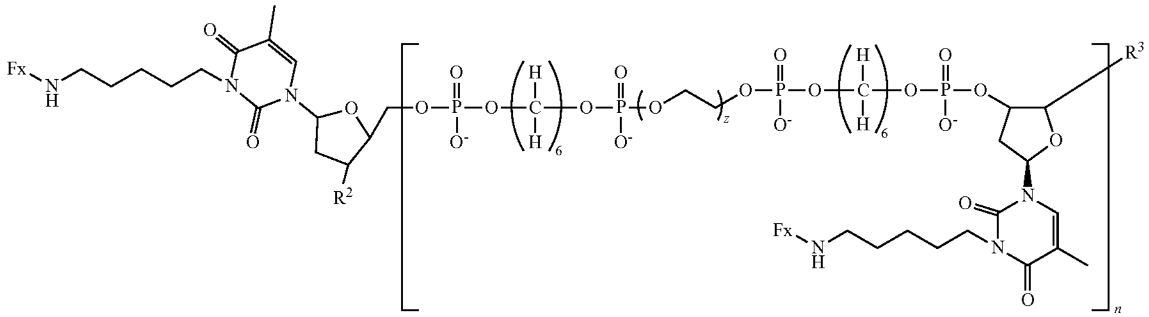 |

TABLE 2-continued
| Exemplary Compounds of Structure (A), (I), or (II) | |
|---|---|
| No. | Structure |
| | $R^2$ = 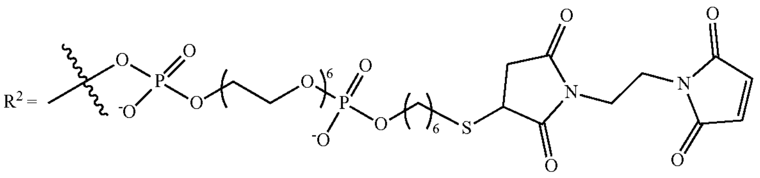 $R^3$ = 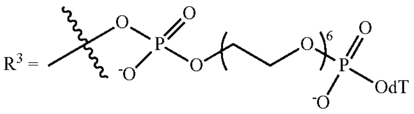 z = 22-25 and PEG MW = about 1,000 n = 1-10 |
| A-1 | 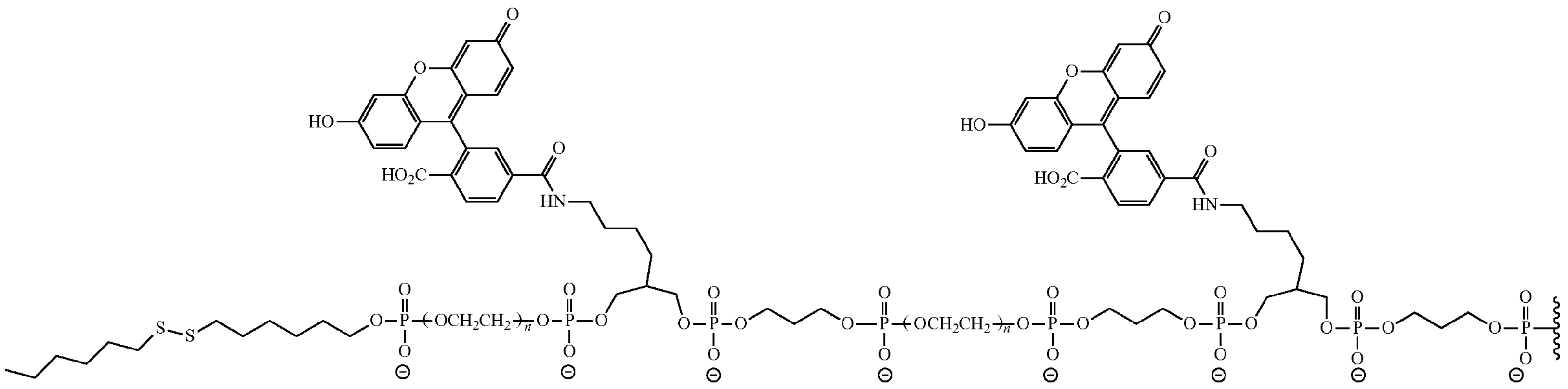 |

TABLE 2-continued
| Exemplary Compounds of Structure (A), (I), or (II) | |
|---|---|
| No. | Structure |
| A-2 | 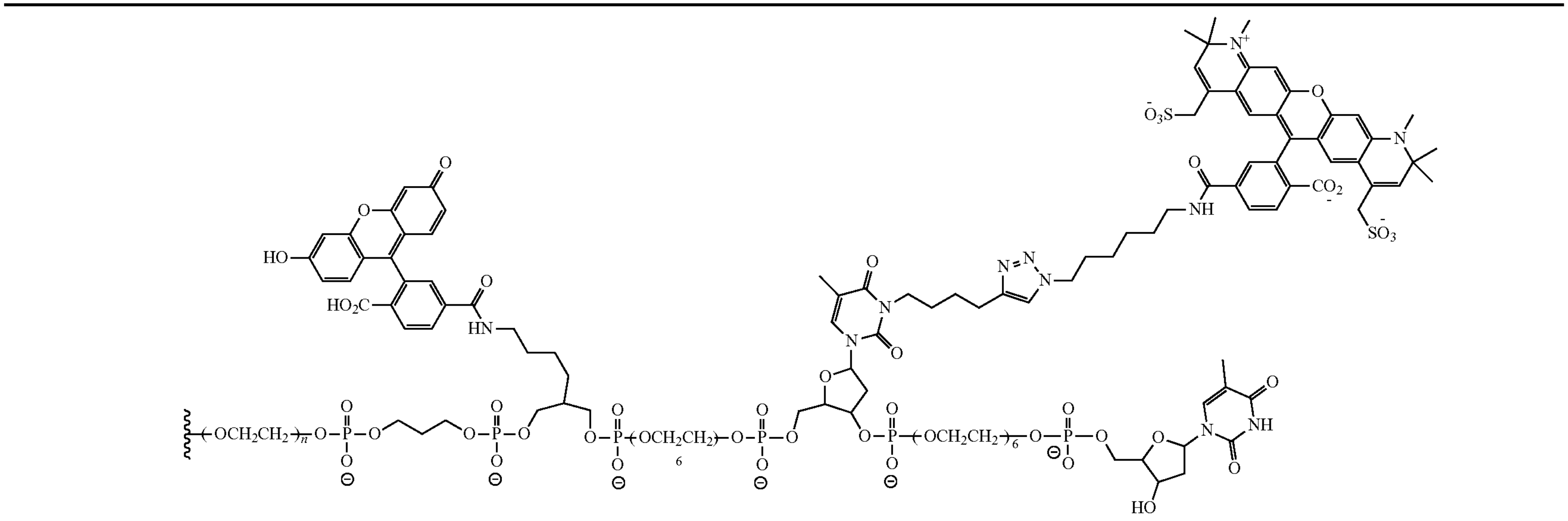<br>n = 15-30<br>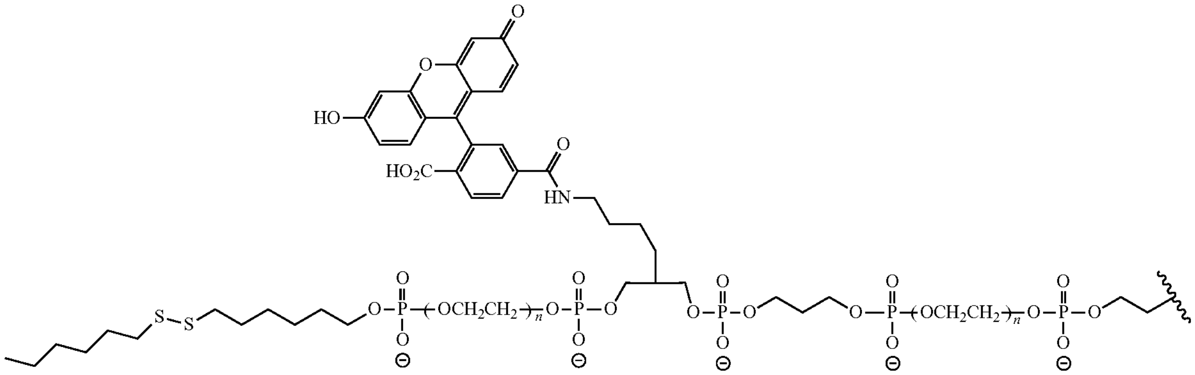<br>n = 15-30 |

TABLE 2-continued
| Exemplary Compounds of Structure (A), (I), or (II) | |
|---|---|
| No. | Structure |
| A-3 | 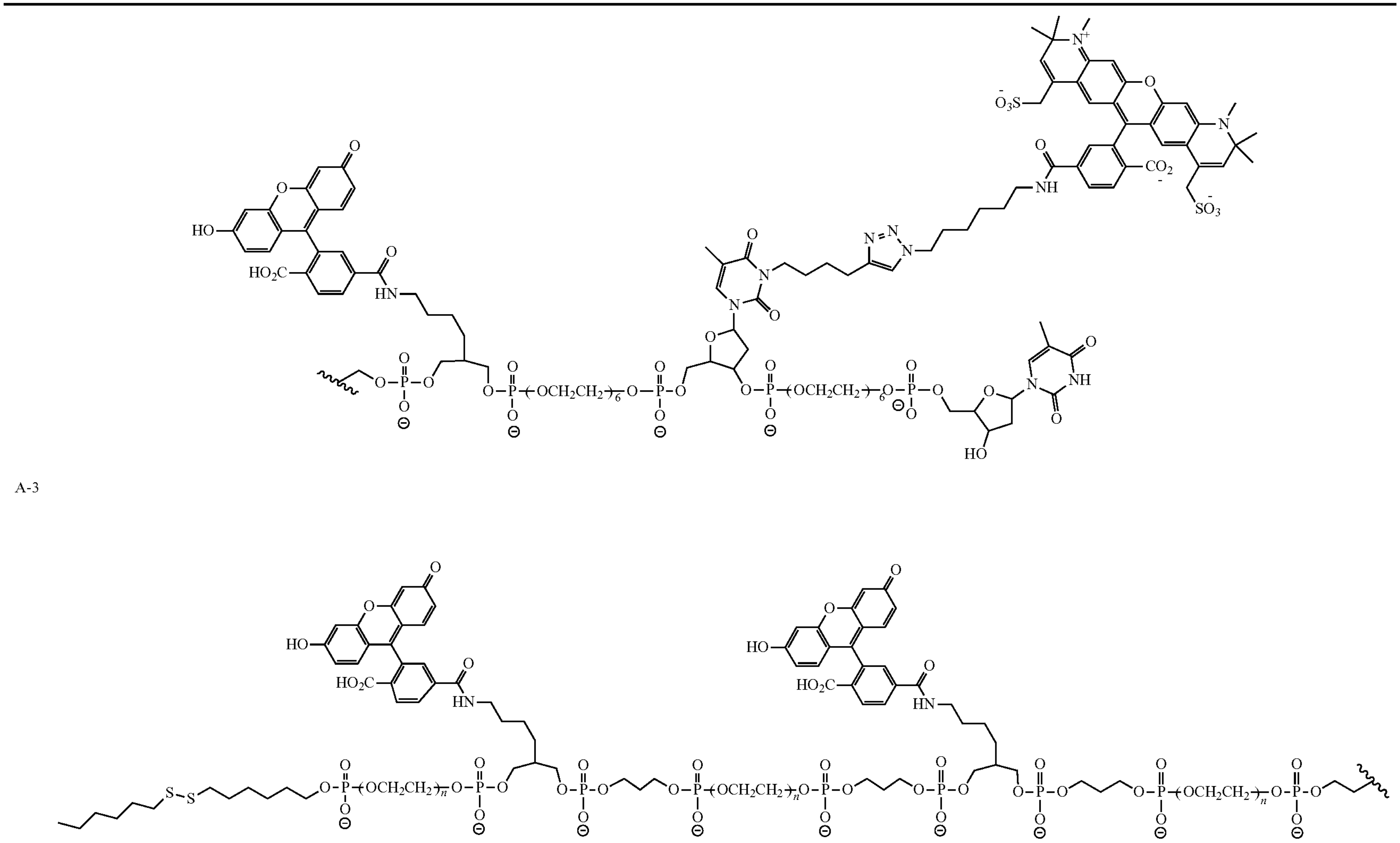 |

TABLE 2-continued
| Exemplary Compounds of Structure (A), (I), or (II) | |
|---|---|
| No. | Structure |
| A-4 | 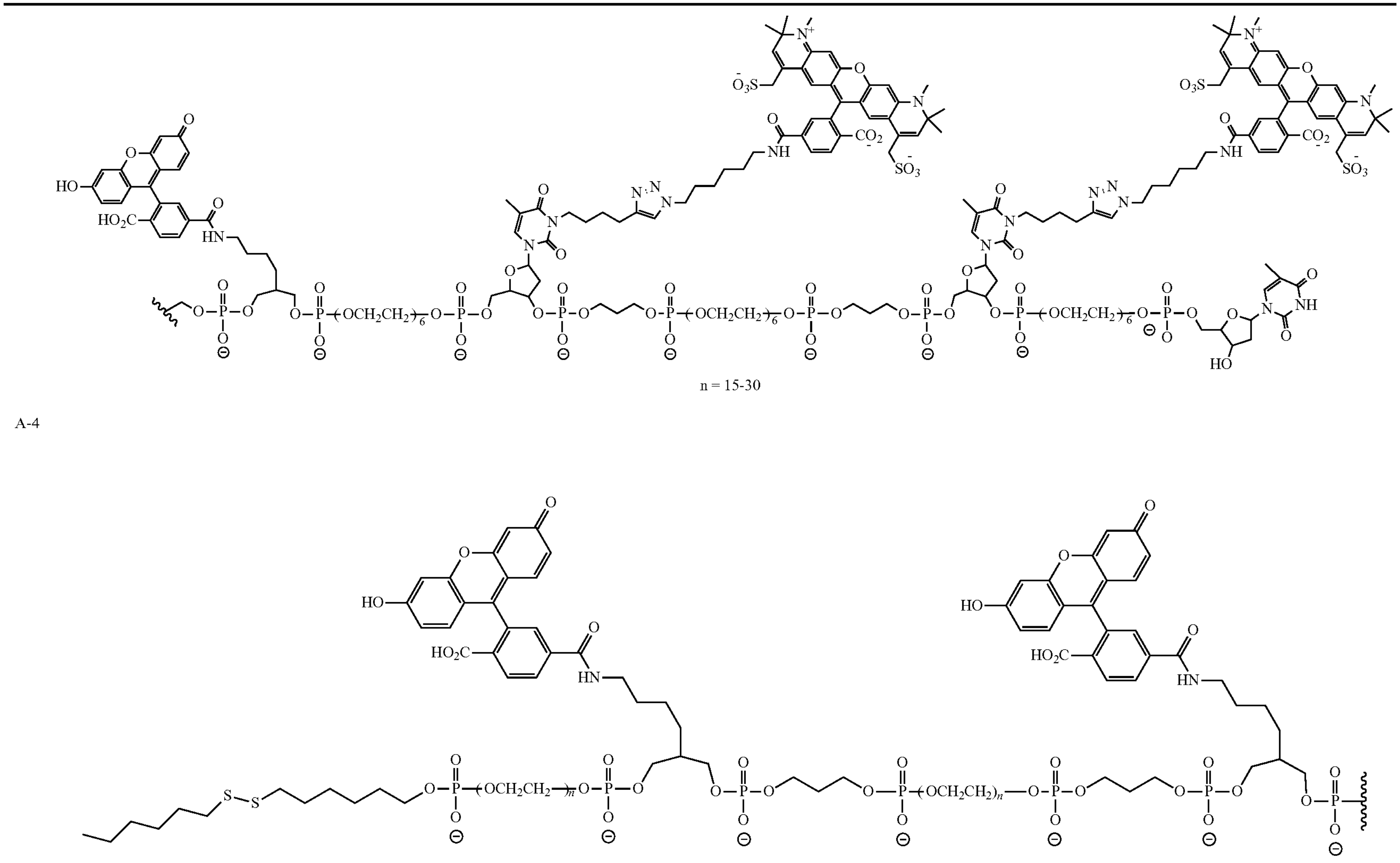 n = 15-30 |

TABLE 2-continued
| Exemplary Compounds of Structure (A), (I), or (II) | |
|---|---|
| No. | Structure |
| | 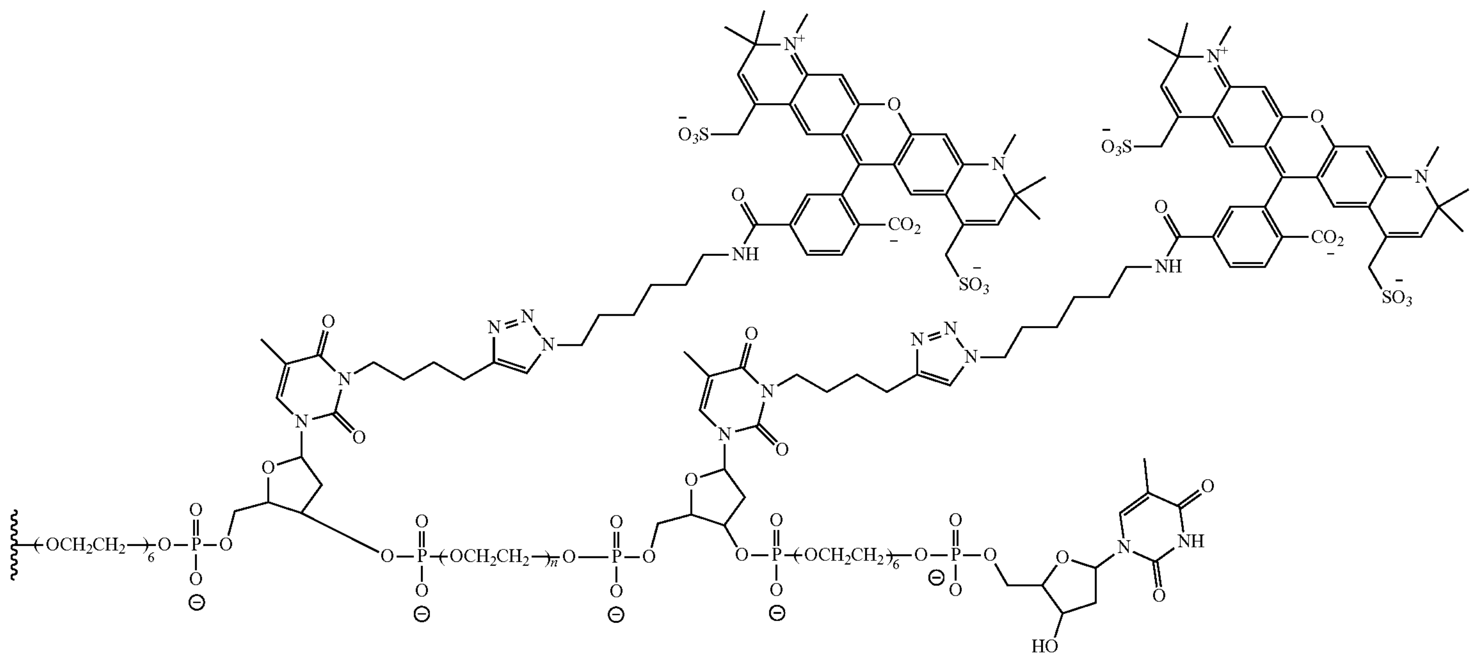 |
n = 15-30

TABLE 2-continued
| Exemplary Compounds of Structure (A), (I), or (II) | |
|---|---|
| No. | Structure |
| A-5 | 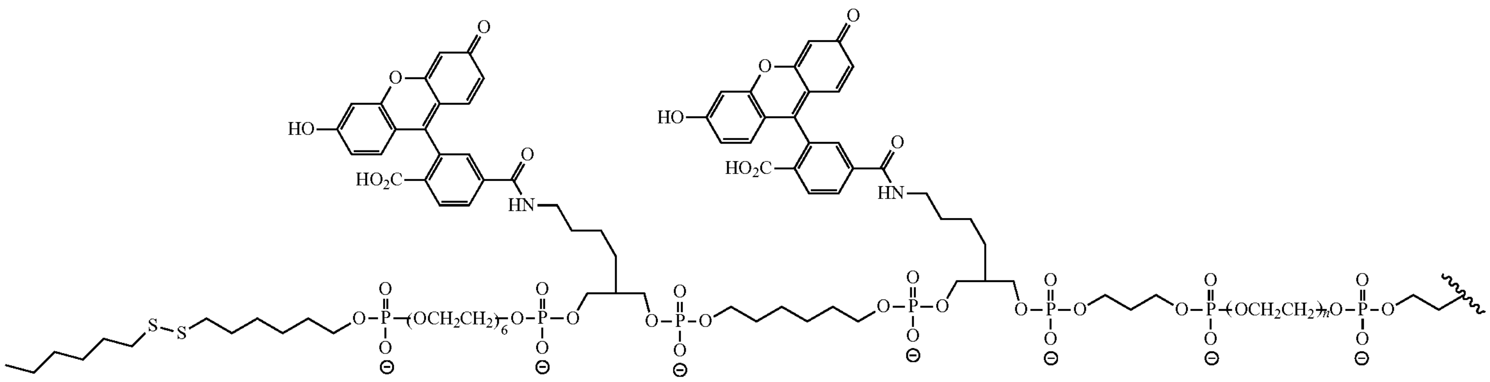 |

TABLE 2-continued
| Exemplary Compounds of Structure (A), (I), or (II) | |
|---|---|
| No. | Structure |
| | 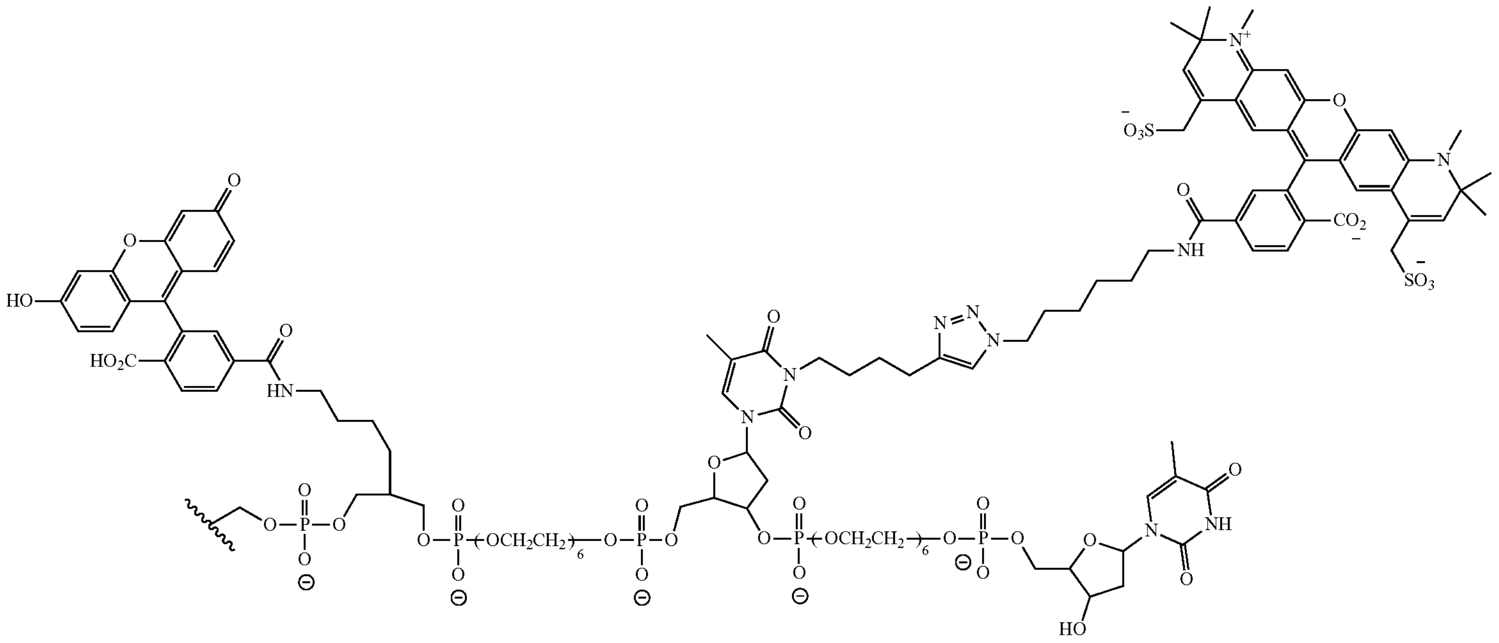 n = 15-30 |

TABLE 2-continued
| Exemplary Compounds of Structure (A), (I), or (II) | |
|---|---|
| No. | Structure |
| A-6 | 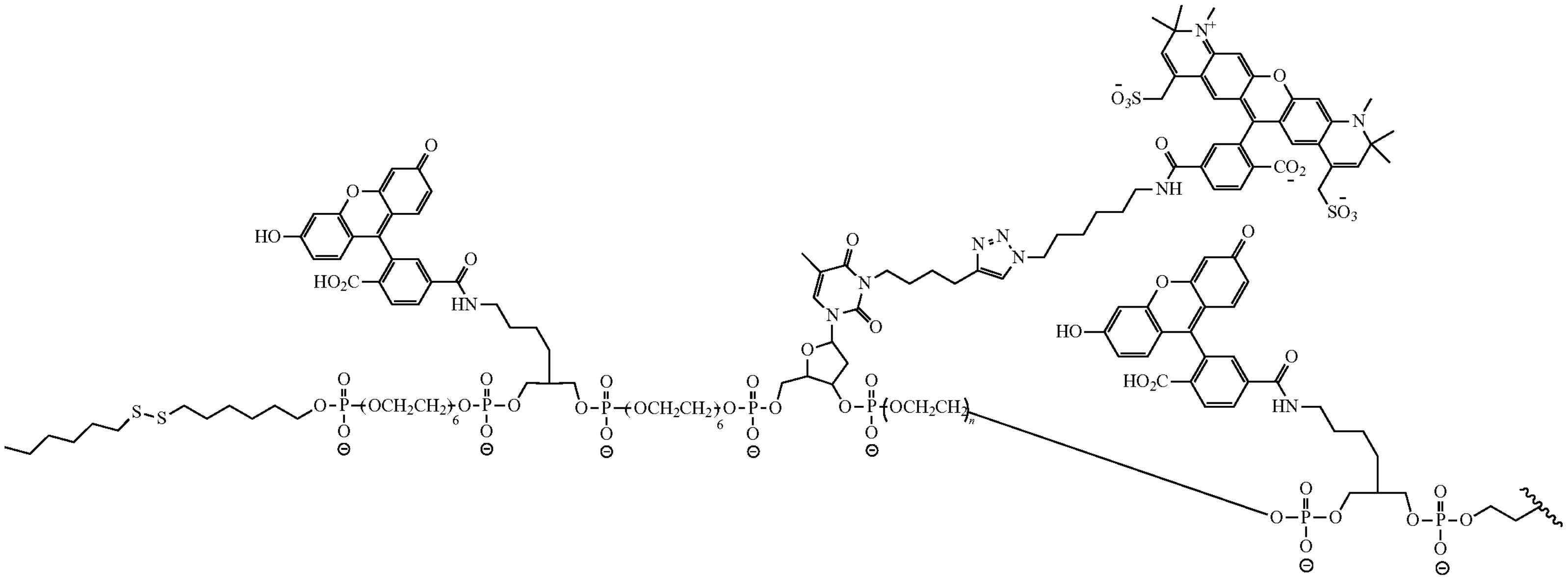 |

TABLE 2-continued
| Exemplary Compounds of Structure (A), (I), or (II) | |
|---|---|
| No. | Structure |
| | 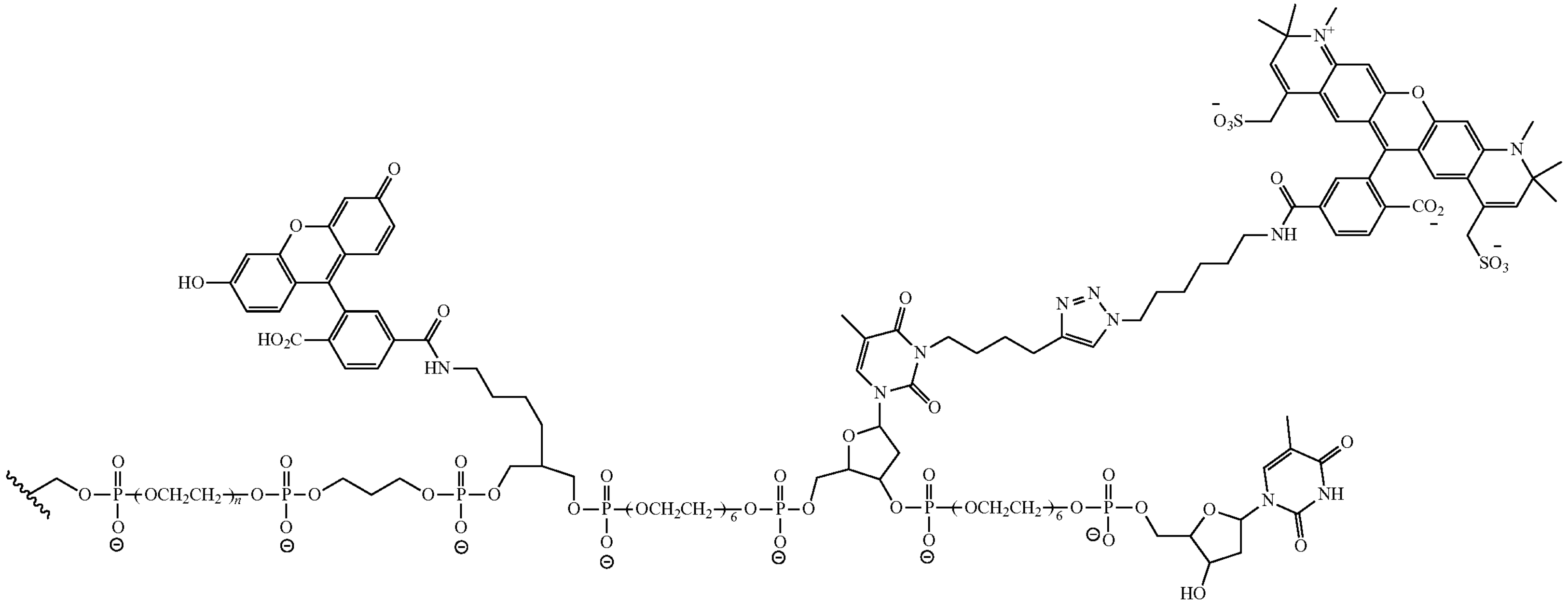 n = 15-30 |

TABLE 2-continued
| Exemplary Compounds of Structure (A), (I), or (II) | |
|---|---|
| No. | Structure |
| A-7 | 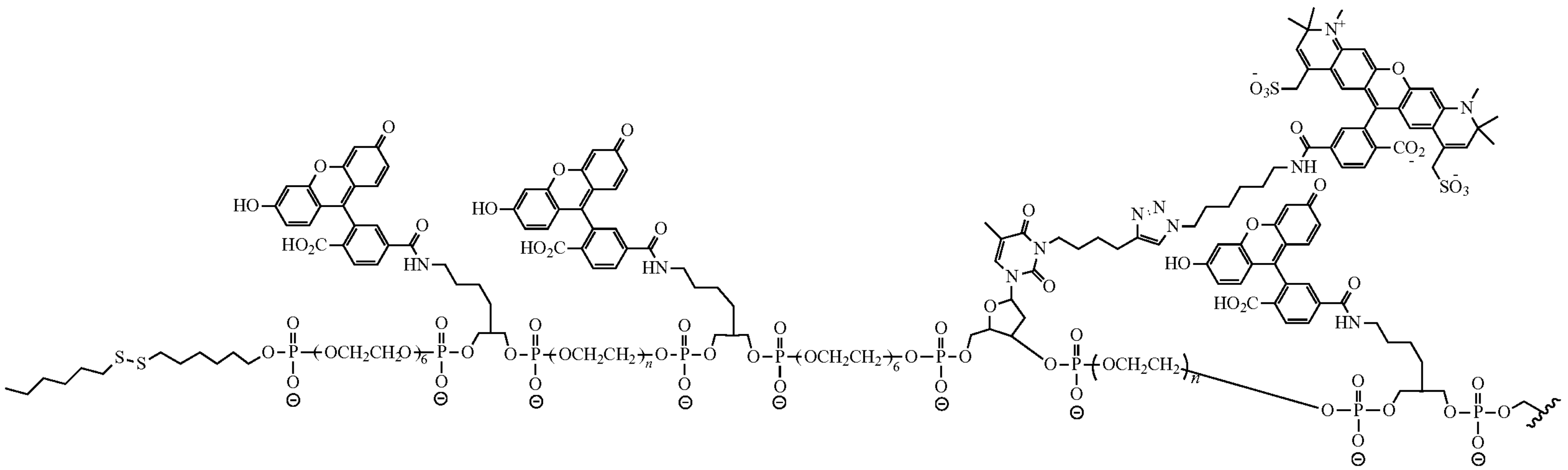 |

TABLE 2-continued
| Exemplary Compounds of Structure (A), (I), or (II) | |
| --- | --- |
| No. | Structure |
| | 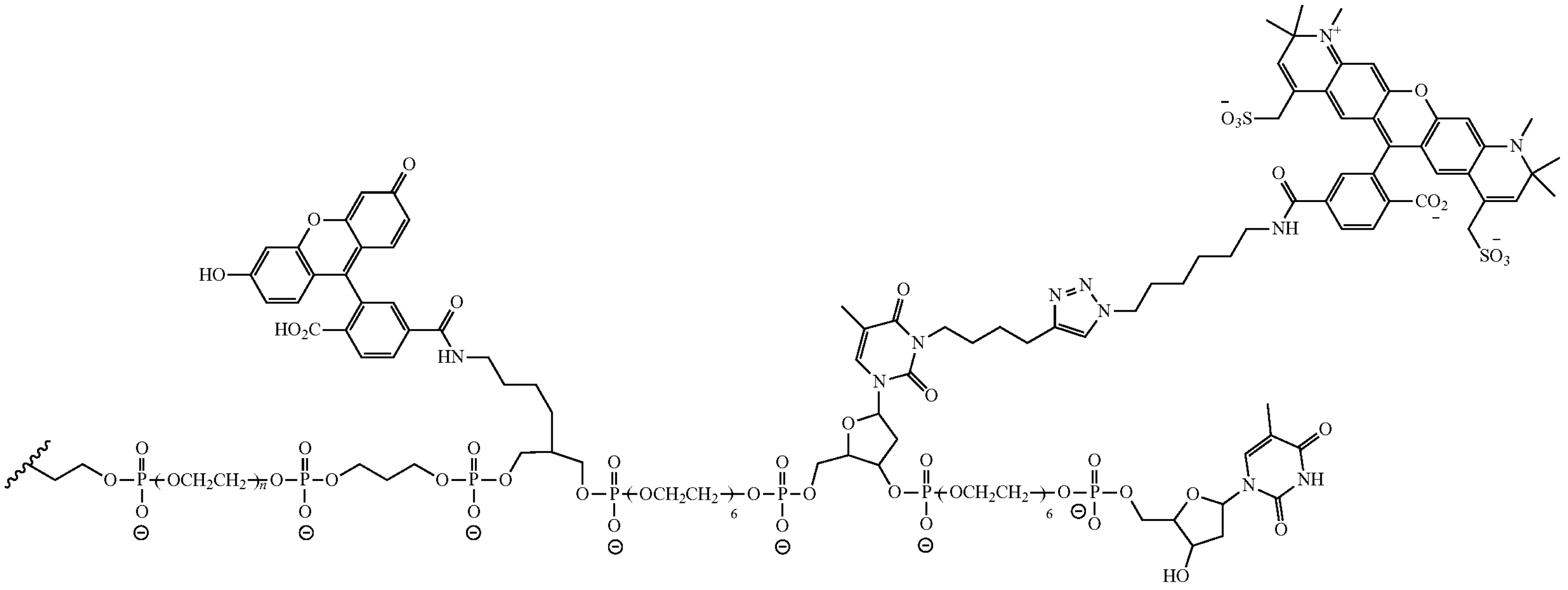 n = 15-30 |

TABLE 2-continued
| Exemplary Compounds of Structure (A), (I), or (II) | |
|---|---|
| No. | Structure |
| A-8 | 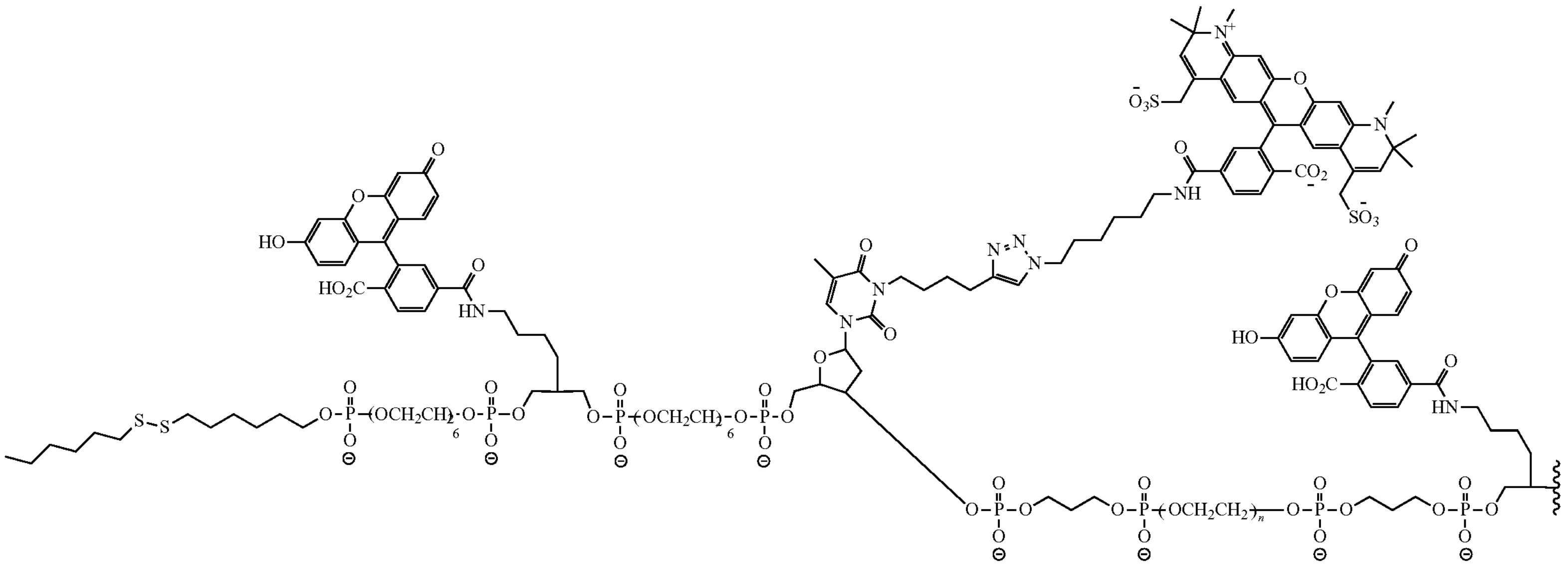 |
n = 15-30

TABLE 2-continued
| Exemplary Compounds of Structure (A), (I), or (II) | |
|---|---|
| No. | Structure |
| | 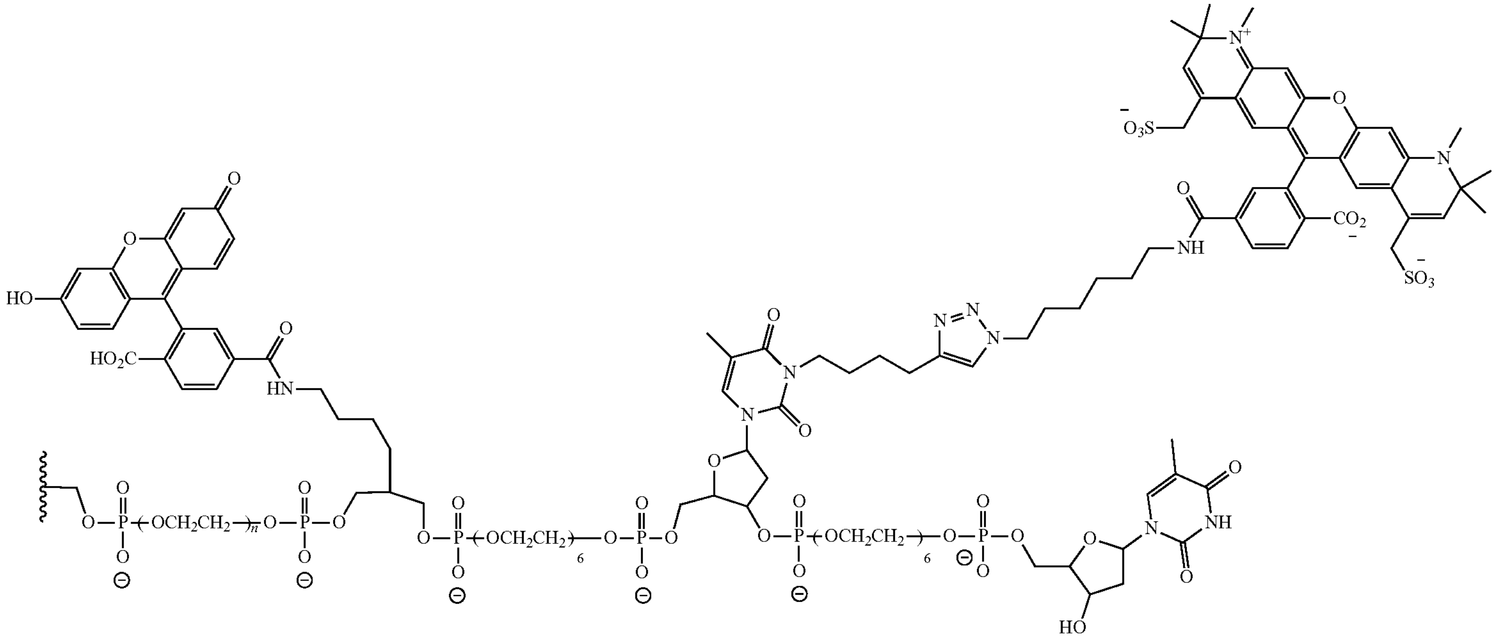 |
| | n = 15-30 |
* TBD = to be determined As used in Table 2 and throughout this disclosure, $R^2$, $R^3$, z and n have the definitions provided for compounds of structure (A), (I), or (II) unless otherwise indicated.

As used in Table 2 and throughout this disclosure, Fx, at each occurrence, independently refers to a fluorescent or colored moiety having one of the following structures:

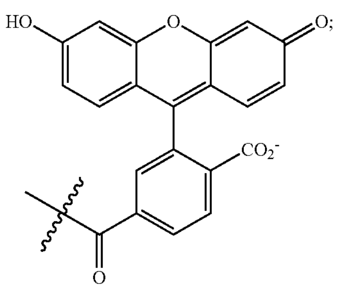

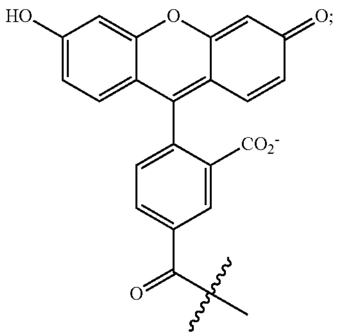

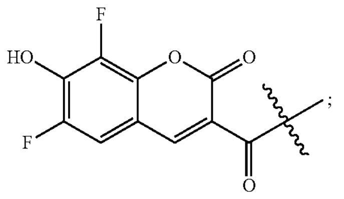

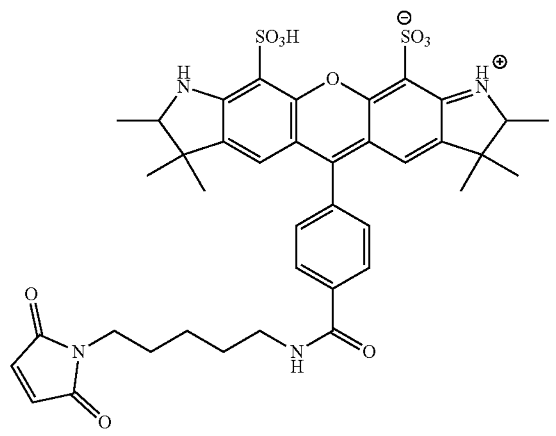

or

-continued

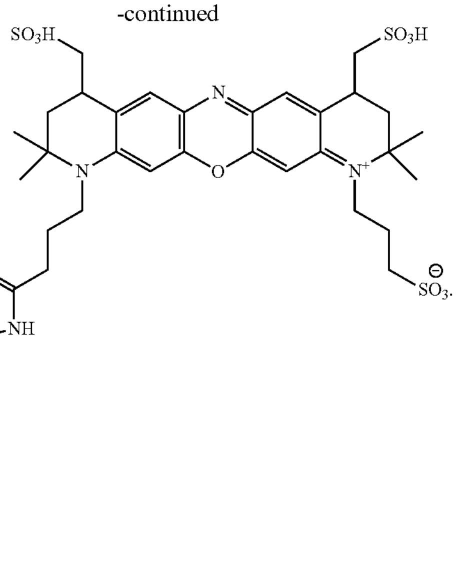

In some embodiments, Fx is fluorescein. It is well known in the art that fluorescein moieties tautomerize between quinoid, zwitterionic, and lactoid forms. One of skill in the art will readily understand that the form is dependent on pH and each form (e.g., quinoid, zwitterionic, and lactoid) are also included in the scope of embodiments of the disclosure.

As used in Table 2 above and throughout this disclosure, $M^1$ and $M^2$ are, at each occurrence, independently a fluorescent or colored moiety as described above for M. One of $M^1$ and $M^2$ is a FRET donor, and another one of $M^1$ and $M^2$ is a FRET acceptor. In some embodiments, $M^1$ is FAM and $M^2$ is AF594. In some embodiments, $M^1$ is CY3® and $M^2$ is AF680.

FAM refers to a moiety having one of the following structures:

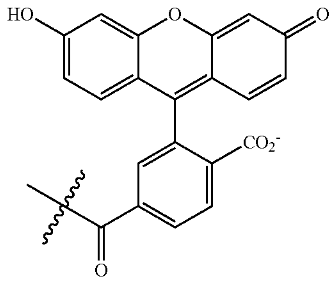

or

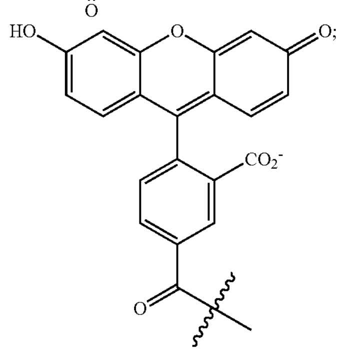

AF594 refers to a moiety having the following structure:

AF594

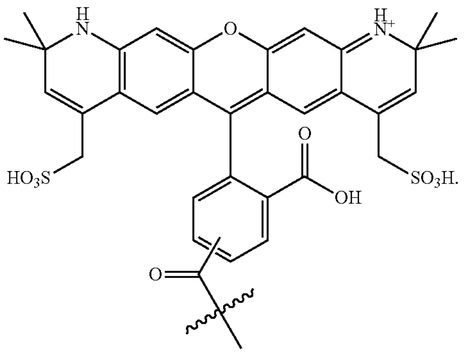

CY3® refers to a moiety having one of the following structures:

Cy3 ®

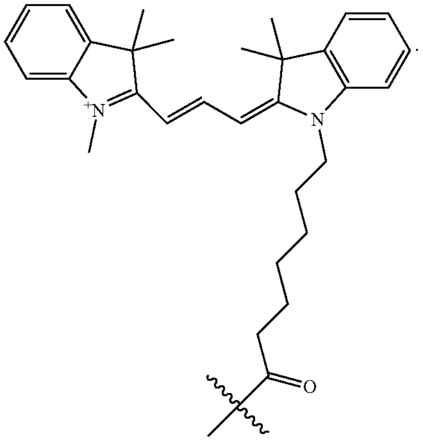

AF680 refers to a moiety having the following structure:

AF680

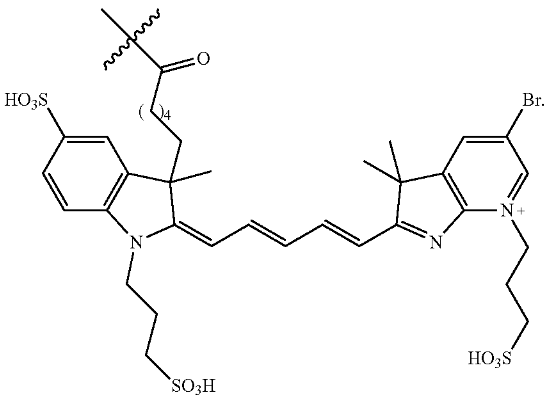

As used in Table 2 above and throughout this disclosure, dT refers to the following structure:

dT

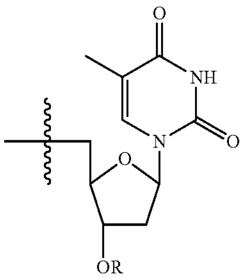

wherein:

R is H or a direct bond.

Some embodiments include any of the foregoing compounds, including the specific compounds provided in Table 2, conjugated to a targeting moiety, such as an antibody. In some embodiments, the antibody includes CD3, CD4, FoxP3, TNF-α, IFN-γ, clone 4S.B3, clone 206D, CD8a (D8A8Y) Rabbit mAb, Vimentin (D21H3) XP® Rabbit mAb, phospho-RB-Ser608, phospho-RB-Ser612, phospho-RB-Ser780, phospho-RB-Ser795, phospho-RB-Ser807, or phospho-RB-Ser811, anti-human IL17A, integrin alpha E/CD103, CCR9, or MOPC-21.

The present disclosure generally provides compounds having increased fluorescence emission relative to earlier known compounds. Accordingly, certain embodiments are directed to a fluorescent compound comprising Y fluorescent moieties M, wherein the fluorescent compound has a peak fluorescence emission upon excitation with a predetermined wavelength of ultraviolet light of at least 85% of Y times greater than the peak fluorescence emission of a single M moiety upon excitation with the same wavelength of ultraviolet light, and wherein Y is an integer of 2 or more. Fluorescent compounds include compounds which emit a fluorescent signal upon excitation with light, such as ultraviolet light.

In some embodiments, the fluorescent compound has a peak fluorescence emission of at least 90% of Y times greater, 95% of Y times greater, 97% of Y times greater or 99% of Y times greater than the peak fluorescence emission of a single M moiety.

In some embodiments, Y is an integer from 2 to 100, for example, from 2 to 10.

In some embodiments, the Y M moiety have, independently, one of the following structures:

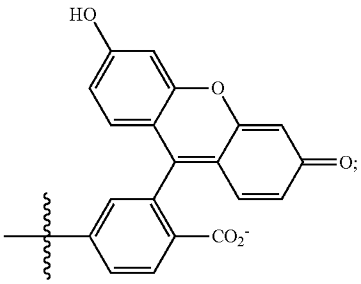

-continued
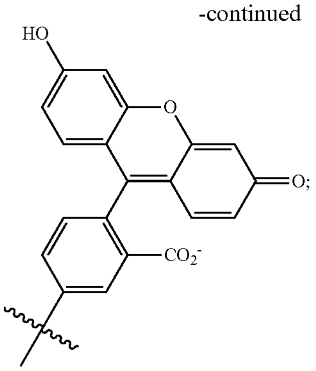
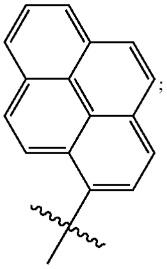
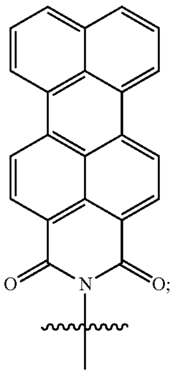
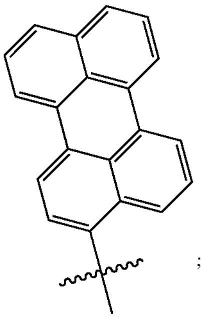
;
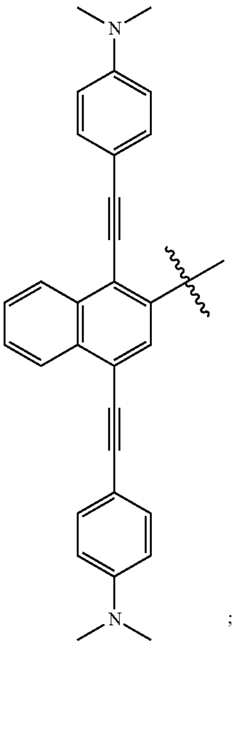
;
-continued
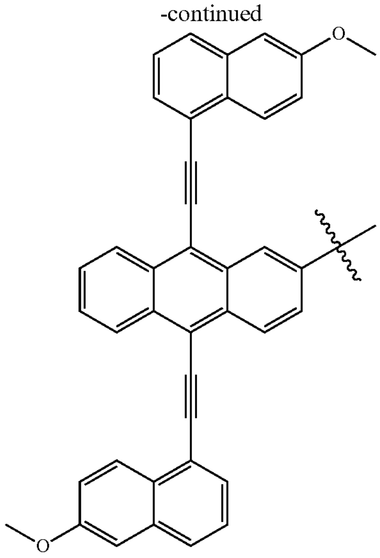
or
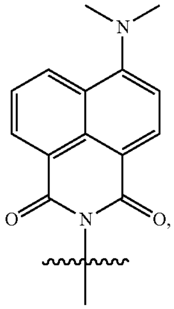
wherein indicates a point of attachment to the fluorescent compound.
In other embodiments, the single M moiety has, independently, one of the following structures:
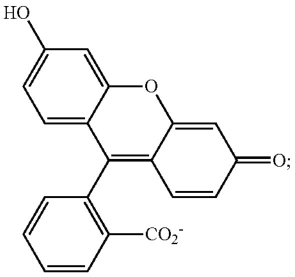
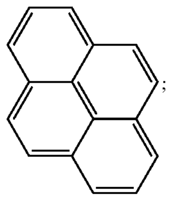
;

-continued
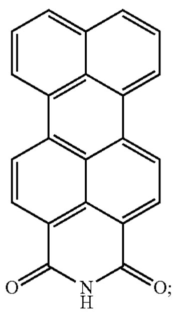
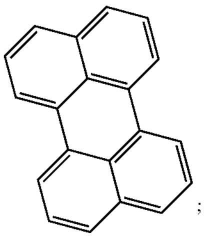
;
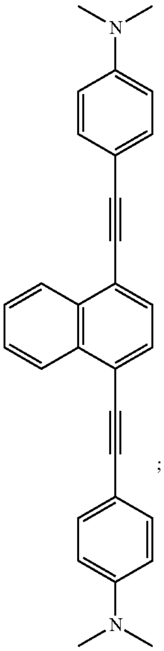
;
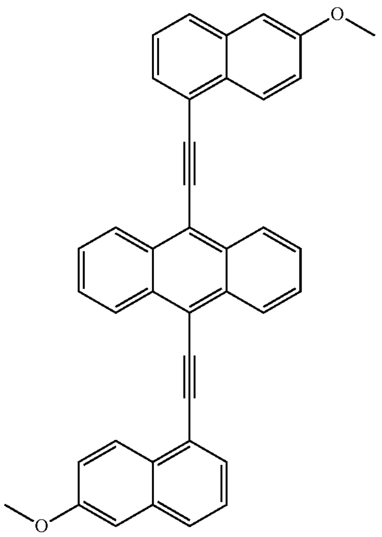
or
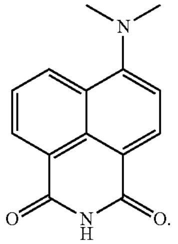
In more specific embodiments, the fluorescent compound comprises Y M moieties, independently having one of the following structures:
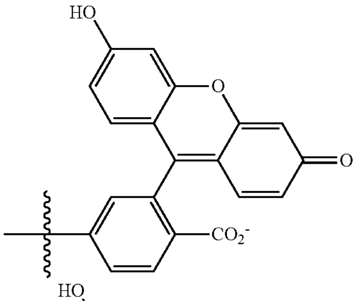
or
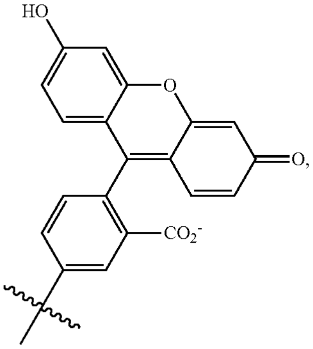
wherein ~ indicates a point of attachment to the fluorescent compound, and the single M moiety has the following structure:
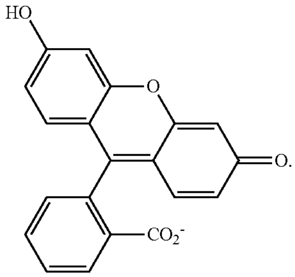
In some embodiments, the Y M moiety have, independently, one of the following structures:
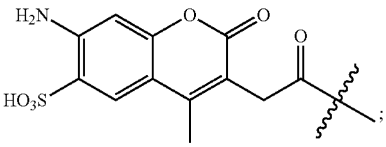
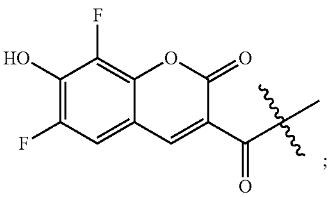

-continued
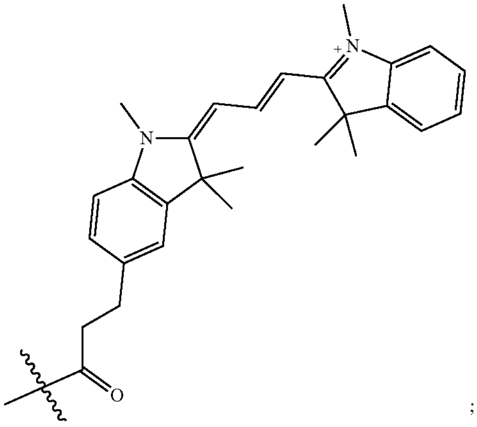
;
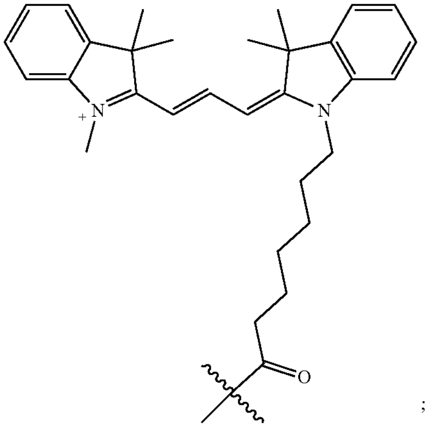
;
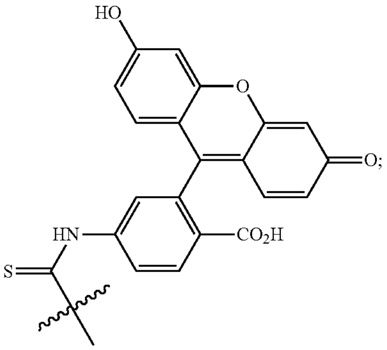
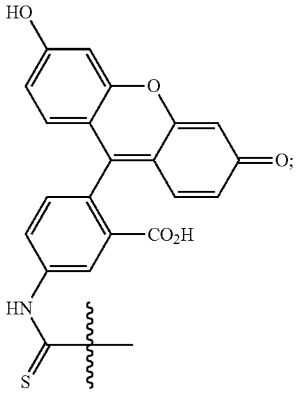
-continued
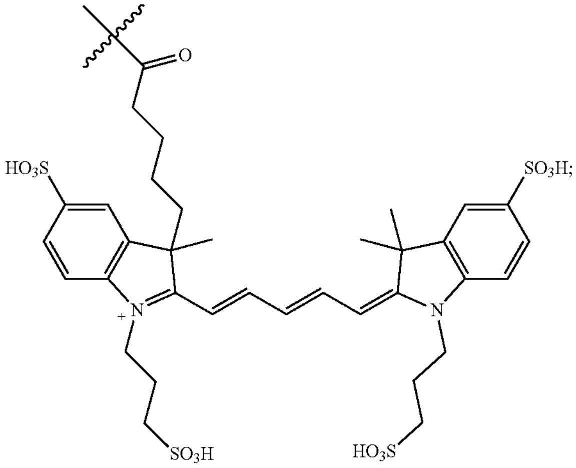
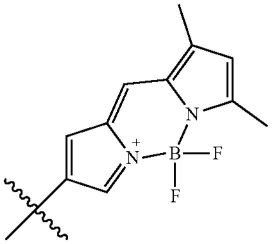
;
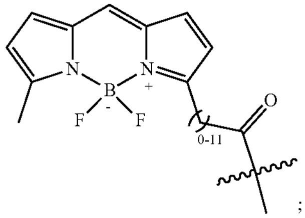
;
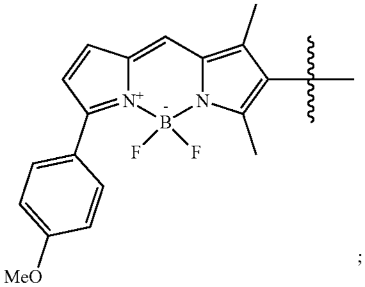
;
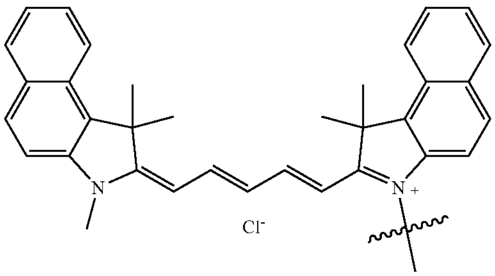
;

-continued
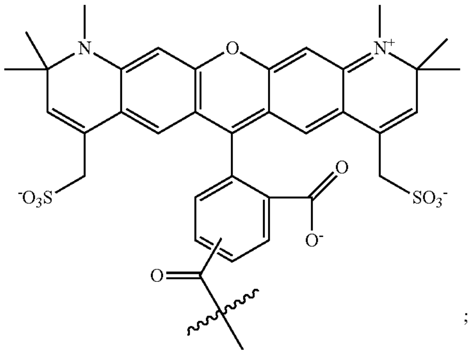
;
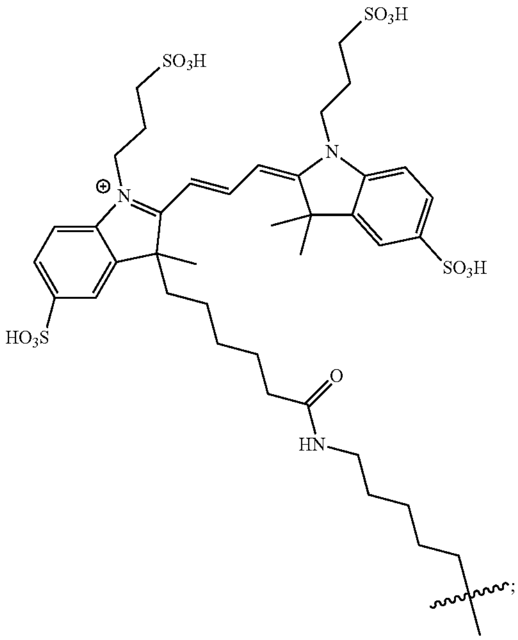
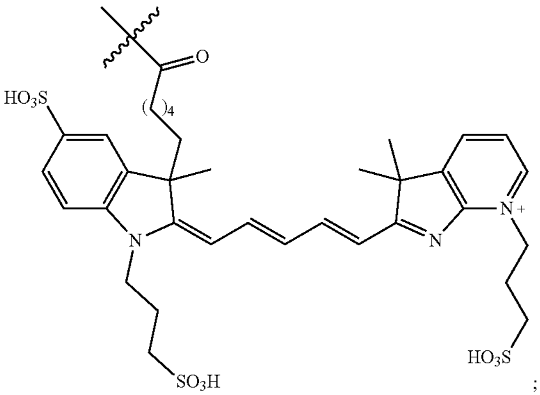
;
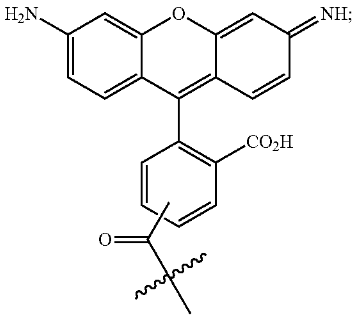
-continued
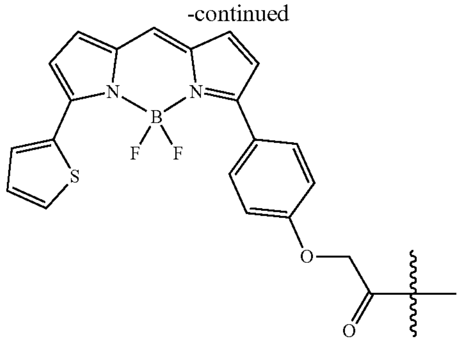
;
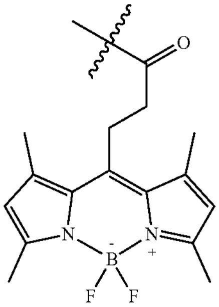
;
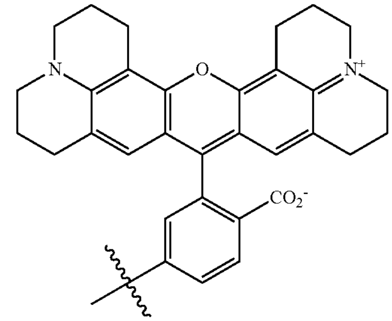
;
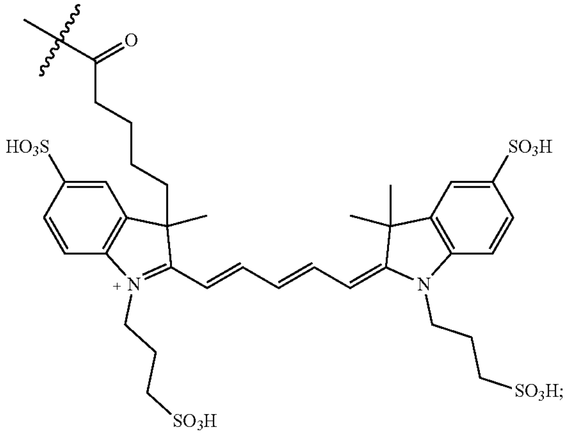

-continued
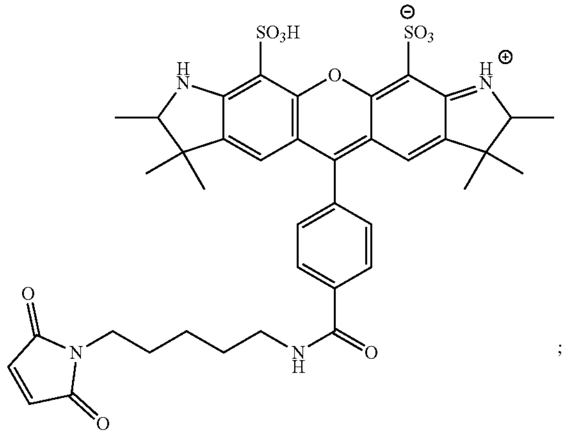
;
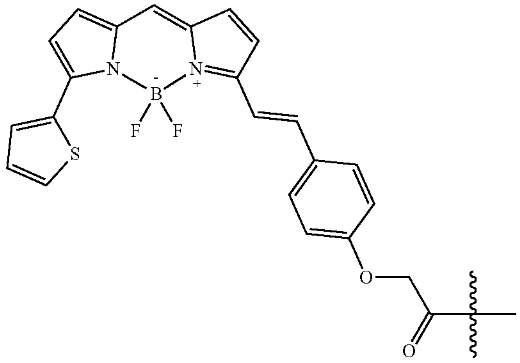
;
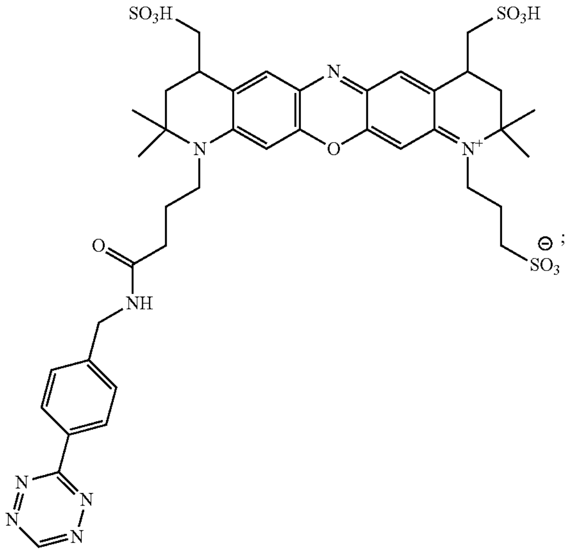
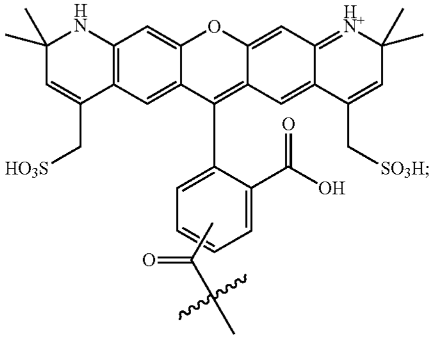
-continued
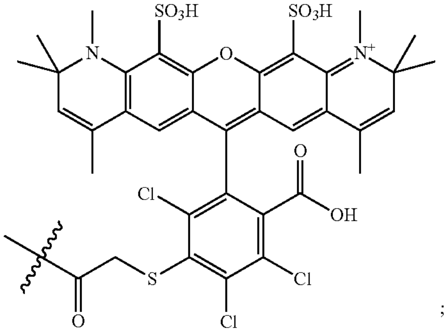
;
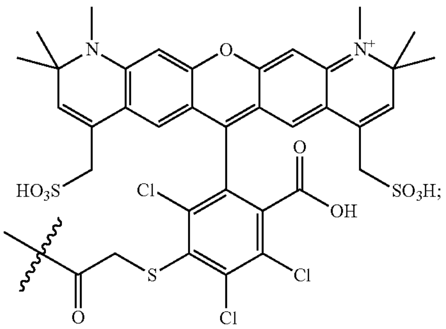
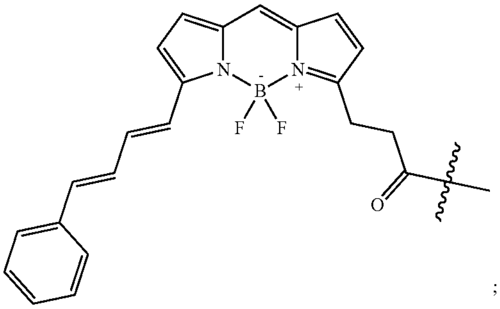
;
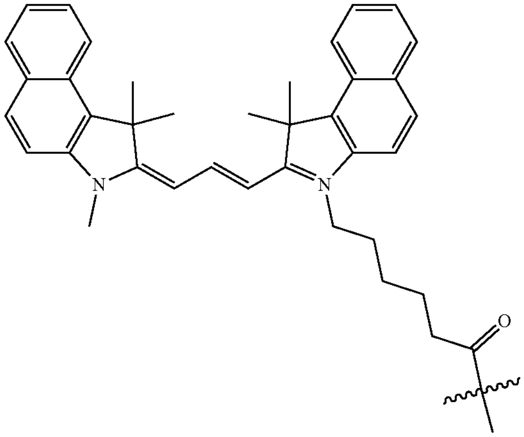
or -continued

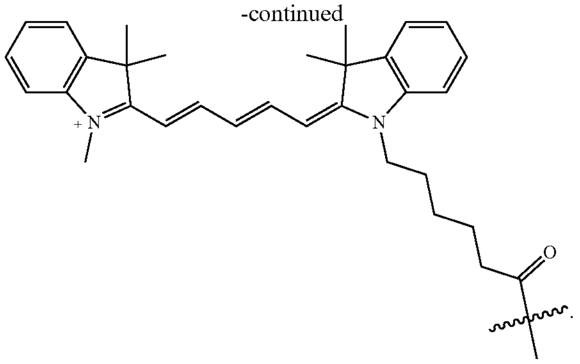

In other embodiments, the peak fluorescence emission is at a wavelength ranging from about 500 to about 550 nm.

In still more embodiments, the fluorescent compound comprises at least one ethylene oxide moiety.

Compositions comprising the fluorescent compound of any one of structure (A), (I), or (II) and an analyte are also provided.

The presently disclosed compounds are “tunable,” meaning that by proper selection of the variables in any of the foregoing compounds, one of skill in the art can arrive at a compound having a desired and/or predetermined molar fluorescence (molar brightness). The tunability of the compounds allows the user to easily arrive at compounds having the desired fluorescence and/or color for use in a particular assay or for identifying a specific analyte of interest. Although all variables may have an effect on the molar fluorescence of the compounds, proper selection of M, $L^4$, $L^5$, $L^6$, m, n and z is believed to play an important role in the molar fluorescence of the compounds. Accordingly, in one embodiment is provided a method for obtaining a compound having a desired molar fluorescence, the method comprising selecting an M moiety having a known fluorescence, preparing a compound of structure (A), (I), or (II) comprising the M moiety, and selecting the appropriate variables for $L^4$, $L^5$, $L^6$, m, n and z to arrive at the desired molar fluorescence.

Molar fluorescence in certain embodiments can be expressed in terms of the fold increase or decrease relative to the fluorescence emission of the parent fluorophore (e.g., monomer). In some embodiments the molar fluorescence of the present compounds is 1.1×, 1.5×, 2×, 3×, 4×, 5×, 6×, 7×, 8×, 9× 10× or even higher relative to the parent fluorophore. Various embodiments include preparing compounds having the desired fold increase in fluorescence relative to the parent fluorophore by proper selection of $L^4$, $L^5$, $L^6$, m, n and z.

For ease of illustration, various compounds comprising phosphorous moieties (e.g., phosphate and the like) are depicted in the anionic state (e.g., —OPO(OH)O—, $—OPO_3^{2-}$). One of skill in the art will readily understand that the charge is dependent on pH and the uncharged (e.g., protonated or salt, such as sodium or other cation) forms are also included in the scope of embodiments of the disclosure.

Compositions comprising any of the foregoing compounds and one or more analyte molecules (e.g., biomolecules) are provided in various other embodiments. In some embodiments, use of such compositions in analytical methods for detection of the one or more analyte molecules are also provided.

In still other embodiments, the compounds are useful in various analytical methods. For example, in certain embodiments the disclosure provides a method of staining a sample, the method comprising adding to said sample a compound of structure (A), (I), or (II), for example wherein one of $R^2$ or $R^3$ is a linker comprising a covalent bond to an analyte molecule (e.g., biomolecule) or microparticle, and the other of $R^2$ or $R^3$ is H, OH, alkyl, alkoxy, alkylether or $—OP(=R_a)(R_b)R_c$, in an amount sufficient to produce an optical response when said sample is illuminated at an appropriate wavelength.

In some embodiments of the foregoing methods, $R^2$ is a linker comprising a covalent linkage to an analyte molecule, such as a biomolecule. For example, a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In yet other embodiments of the foregoing method, $R^2$ is a linker comprising a covalent linkage to a solid support such as a microparticle. For example, in some embodiments the microparticle is a polymeric bead or nonpolymeric bead.

In even more embodiments, said optical response is a fluorescent response.

In other embodiments, said sample comprises cells, and some embodiments further comprise observing said cells by flow cytometry.

In still more embodiments, the method further comprises distinguishing the fluorescence response from that of a second fluorophore having detectably different optical properties.

In other embodiments, the disclosure provides a method for visually detecting an analyte molecule, such as a biomolecule, comprising:

(a) providing a compound of structure (A), (I), or (II), for example, wherein one of $R^2$ or $R^3$ is a linker comprising a covalent bond to the analyte molecule, and the other of $R^2$ or $R^3$ is H, OH, alkyl, alkoxy, alkylether or $—OP(=R_a)(R_b)R_c$; and (b) detecting the compound by its visible properties.

In some embodiments the analyte molecule is a nucleic acid, amino acid or a polymer thereof (e.g., polynucleotide or polypeptide). In still more embodiments, the analyte molecule is an enzyme, receptor, receptor ligand, antibody, glycoprotein, aptamer or prion.

In other embodiments, a method for visually detecting an analyte molecule, such as a biomolecule is provided, the method comprising:

(a) admixing any of the foregoing compounds with one or more analyte molecules; and (b) detecting the compound by its visible properties.

In other embodiments is provided a method for visually detecting an analyte molecule, the method comprising:

(a) admixing the compound of structure (A), (I), or (II), wherein $R^2$ or $R^3$ is Q or a linker comprising a covalent bond to Q, with the analyte molecule;

(b) forming a conjugate of the compound and the analyte molecule; and (c) detecting the conjugate by its visible properties.

Other exemplary methods include a method for detecting an analyte, the method comprising:

(a) providing a compound of structure (A), (I), or (II), wherein $R^2$ or $R^3$ comprises a linker comprising a covalent bond to a targeting moiety having specificity for the analyte;

(b) admixing the compound and the analyte, thereby associating the targeting moiety and the analyte; and (c) detecting the compound, for example by its visible or fluorescent properties.

In certain embodiments of the foregoing method, the analyte is a particle, such as a cell, and the method includes use of flow cytometry. For example, the compound may be provided with a targeting moiety, such as an antibody, for selectively associating with the desired cell, thus rendering the cell detectable by any number of techniques, such as visible or fluorescence detection. In some embodiments, the antibody is a polyclonal antibody. In other embodiments, the antibody is a monoclonal antibody. Appropriate antibodies can be selected by one of ordinary skill in the art depending on the desired end use. Exemplary antibodies for use in certain embodiments include CD3 (clone UCHT1), CD4 (clone OKT4), FoxP3, TNF-α, IFN-γ, clone 4S.B3, clone 206D, CD8a (D8A8Y) Rabbit mAb, Vimentin (D21H3) XP® Rabbit mAb, phospho-RB antibody such as phospho-RB-Ser608, phospho-RB-Ser612, phospho-RB-Ser780, phospho-RB-Ser795, phospho-RB-Ser807, or phospho-RB-Ser811, anti-human IL17A, integrin alpha E/CD103, CCR9, and MOPC-21.

In certain embodiments, the conjugating efficiency of forming a conjugate comprising a compound of structure (A), (I), or (II) and an analyte is greater than about 80%, 85%, 90%, 92%, 95%, 96%, 97%, 98%, 98.5%, or 99%.

In still other embodiments, the disclosure provides a method for increasing the brightness of a dye, the method comprising:

(a) providing a dye solution comprising a compound of structure (A), (I), or (II); and (b) aging the dye solution for a period of time.

In some embodiments, the dye solution is aged for at least one week. For example, in some embodiments, the dye solution is aged for about three weeks before use.

The dye solution may include various buffers. In some embodiments, the dye comprises ETOH. In some embodiments, the dye solution comprises a BD brilliant. In some embodiments, the dye solution comprises sodium chloride or potassium chloride.

Embodiments of the present compounds thus find utility in any number of methods, including, but not limited: cell counting; cell sorting; biomarker detection; quantifying apoptosis; determining cell viability; identifying cell surface antigens; determining total DNA and/or RNA content; identifying specific nucleic acid sequences (e.g., as a nucleic acid probe); and diagnosing diseases, such as blood cancers.

In addition to the above methods, embodiments of the compounds of structure (A), (I), or (II) find utility in various disciplines and methods, including but not limited to: imaging in endoscopy procedures for identification of cancerous and other tissues; single-cell and/or single molecule analytical methods, for example detection of polynucleotides with little or no amplification; cancer imaging, for example by including a targeting moiety, such as an antibody or sugar or other moiety that preferentially binds cancer cells, in a compound of structure (A), (I), or (II) to; imaging in surgical procedures; binding of histones for identification of various diseases; drug delivery, for example by replacing the M moiety in a compound of structure (A), (I), or (II) with an active drug moiety; and/or contrast agents in dental work and other procedures, for example by preferential binding of the compound of structure (I) to various flora and/or organisms.

It is understood that any embodiment of the compounds of structure (I), as set forth above, and any specific choice set forth herein for a $R^1$, $R^2$, $R^3$, $R^4$, $R^5$, L', $L^1$, $L^2$, $L^3$, $L^4$, $L^5$, $L^6$, M, m, n and/or z variable in the compounds of structure (I), as set forth above, may be independently combined with other embodiments and/or variables of the compounds of structure (I) to form embodiments of the disclosure not specifically set forth above. In addition, in the event that a list of choices is listed for any particular $R^1$, $R^2$, $R^3$, $R^4$, $R^5$, L', $L^1$, $L^2$, $L^3$, $L^4$, $L^5$, $L^6$, M, m, n and/or z variable in a particular embodiment and/or claim, it is understood that each individual choice may be deleted from the particular embodiment and/or claim and that the remaining list of choices will be considered to be within the scope of the disclosure.

It is also understood that any embodiment of the compounds of structure (II), as set forth above, and any specific choice set forth herein for a $R^1$, $R^2$, $R^3$, $R^4$, $R^5$, L', $L^{1c}$, $L^{1d}$, $L^2$, $L^3$, $L^4$, $L^5$, $L^6$, M, m, n and/or z variable in the compounds of structure (II), as set forth above, may be independently combined with other embodiments and/or variables of the compounds of structure (II) to form embodiments of the disclosure not specifically set forth above. In addition, in the event that a list of choices is listed for any particular $R^1$, $R^2$, $R^3$, $R^4$, $R^5$, L', $L^{1a}$, $L^{1d}$, $L^2$, $L^3$, $L^4$, $L^5$, $L^6$, M, m, n and/or z variable in a particular embodiment and/or claim, it is understood that each individual choice may be deleted from the particular embodiment and/or claim and that the remaining list of choices will be considered to be within the scope of the disclosure It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin or a 2-chlorotrityl-chloride resin.

Furthermore, all compounds of the disclosure which exist in free base or acid form can be converted to their salts by treatment with the appropriate inorganic or organic base or acid by methods known to one skilled in the art. Salts of the compounds of the disclosure can be converted to their free base or acid form by standard techniques.

The following Reaction Schemes illustrate exemplary methods of making compounds of structure (A), (I), or (II) of this disclosure. It is understood that one skilled in the art may be able to make these compounds by similar methods or by combining other methods known to one skilled in the art. It is also understood that one skilled in the art would be able to make, in a similar manner as described below, other compounds of structure (A), (I), or (II) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this disclosure.

Reaction Scheme I

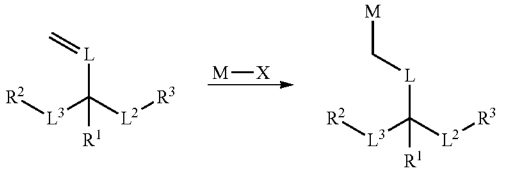

a b

Reaction Scheme I illustrates an exemplary method for preparing an intermediate useful for preparation of compounds of structure (I), where $R^1$, $L^2$, $L^3$ and M are as defined above, $R^2$ and $R^3$ are as defined above or are protected variants thereof and L is an optional linker. Referring to Reaction Scheme 1, compounds of structure a can be purchased or prepared by methods well-known to those of ordinary skill in the art. Reaction of a with M-X, where x is a halogen such as bromo, under Suzuki coupling conditions known in the art results in compounds of structure b. Compounds of structure b can be used for preparation of compounds of structure (I) as described below.

Reaction Scheme II

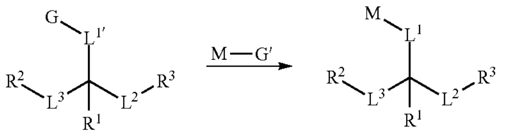

c d

Reaction Scheme II illustrates an alternative method for preparation of intermediates useful for preparation of compounds of structure (I). Referring to reaction Scheme II, where $R^1$, $L^1$, $L^2$, $L^3$, G and M are as defined above, and $R^2$ and $R^3$ are as defined above, or are protected variants thereof, a compound of structure c, which can be purchased or prepared by well-known techniques, is reacted with M-G' to yield compounds of structure d. Here, G and G' represent functional groups having complementary reactivity (i.e., functional groups which react to form a covalent bond). G' may be pendant to M or a part of the structural backbone of M. G and G' may be any number of functional groups described herein, such as alkyne and azide, respectively, amine and activated ester, respectively or amine and isothiocyanate, respectively, and the like.

The compound of structure (I) may be prepared from one of structures b or d by reaction under well-known automated DNA synthesis conditions with a phosphoramidite compound having the following structure (e):

(e)

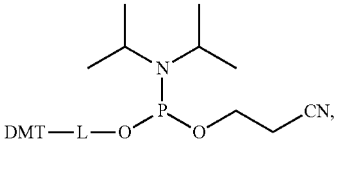

wherein L is an optional linker.

DNA synthesis methods are well-known in the art. Briefly, two alcohol groups, for example $R^2$ and $R^3$ in intermediates b or d above, are functionalized with a dimethoxytrityl (DMT) group and a 2-cyanoethyl-N,N-diisopropylamino phosphoramidite group, respectively. The phosphoramidite group is coupled to an alcohol group, typically in the presence of an activator such as tetrazole, followed by oxidation of the phosphorous atom with iodine. The dimethoxytrityl group can be removed with acid (e.g., chloroacetic acid) to expose the free alcohol, which can be reacted with a phosphoramidite group. The 2-cyanoethyl group can be removed after oligomerization by treatment with aqueous ammonia.

Preparation of the phosphoramidites used in the oligomerization methods is also well-known in the art. For example, a primary alcohol (e.g., $R^3$) can be protected as a DMT group by reaction with DMT-Cl. A secondary alcohol (e.g., $R^2$) is then functionalized as a phosphoramidite by reaction with an appropriate reagent such as 2-cyanoethyl N,N-dissopropylchlorophosphoramidite. Methods for preparation of phosphoramidites and their oligomerization are well-known in the art and described in more detail in the examples.

Compounds of structure (I) are prepared by oligomerization of intermediates b or d and e according to the well-known phophoramidite chemistry described above. The desired number of m and n repeating units is incorporated into the molecule by repeating the phosphoramidite coupling the desired number of times. It will be appreciated that compounds of structure (III) as, described below, can be prepared by analogous methods.

Additionally, compounds of the present disclosure can be prepared according to the methods described in PCT Pub. Nos. WO 2016/183185; WO 2017/173355; and WO 2017/177065, each of which are hereby incorporated by reference.

In various other embodiments, compounds useful for preparation of the compound of structure (I) are provided. The compounds can be prepared as described above in monomer, dimer and/or oligomeric form and then the M moiety covalently attached to the compound via any number of synthetic methodologies (e.g., the "click" reactions described above) to form a compound of structure (I). Accordingly, in various embodiments compounds are provided having the following structure (III):

(III)

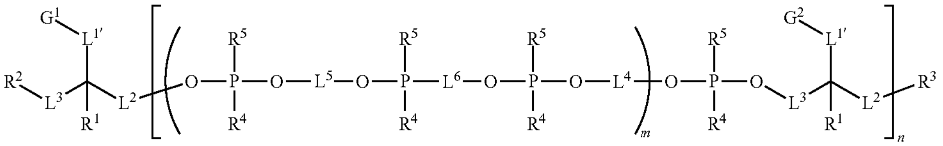

or a stereoisomer, salt or tautomer thereof, wherein:

$G^1$ and $G^2$, at each occurrence, independently a moiety comprising a reactive group, or protected analogue thereof, capable of forming a covalent bond with a complementary reactive group;

$L^{1'}$, $L^2$ and $L^3$ are, at each occurrence, independently optional alkylene, alkenylene, alkynylene, heteroalkylene, heteroalkenylene, heteroalkynylene, heteroarylene or heteroatomic linkers;

$L^4$ and $L^5$ are, at each occurrence, independently alkylene, alkenylene, alkynylene, heteroalkylene, heteroalkenylene or heteroalkynylene linkers;

$L^6$ is, at each occurrence, independently a heteroalkylene, heteroalkenylene or heteroalkynylene linker, provided at least one occurrence, $L^6$ is different from each of $L^4$ and $L^5$;

$R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q or a protected form thereof, or L';

$R^4$ is, at each occurrence, independently OH, SH, $O^-$, $S^-$, $OR_d$ or $SR_d$;

$R_5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (III);

m is, at each occurrence, independently an integer of zero or greater, provided at least one occurrence of m is an integer of one or greater; and n is an integer of one or greater.

In some embodiments, $L^6$ is, at each occurrence, independently an alkylene oxide linker.

In some embodiments, $L^4$ and $L^5$ are, at each occurrence, independently an alkylene linker. In some embodiments, $L^4$ and $L^5$ are, at each occurrence, independently $C_3$-$C_6$ alkylene. In some embodiments, at least one occurrence $L^4$ and $L^5$ are the same.

In some embodiments, $L^6$ is at each occurrence, independently a heteroalkylene linker. In other more specific embodiments, $L^6$ is at each occurrence, independently an alkylene oxide linker. In some embodiments, $L^6$ is polyethylene oxide. In some related embodiments, the compounds have the following structure (IIIa):

(IIIa)

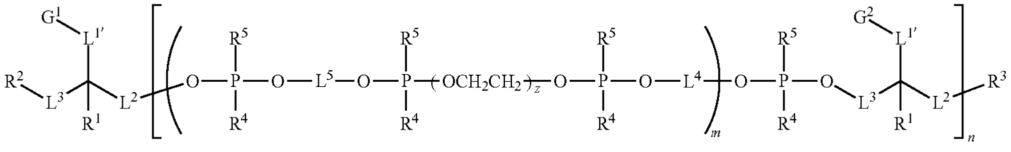

wherein:

$L^4$ and $L^5$ are, at each occurrence, independently an alkylene, alkenylene, alkynylene, heteroalkylene, heteroalkenylene, heteroalkynylene or heteroatomic linker, provided $L^4$ and $L^5$ are not polyethylene oxide; and z is an integer from 1 to 100.

In some embodiments, $L^4$ and $L^5$ are, at each occurrence, independently an alkylene. In some related embodiments, the compounds have the following structure (IIIb):

(IIIb)

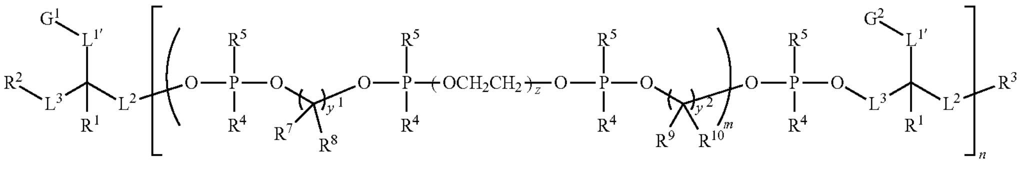

wherein:

$R^7$, $R^8$, $R^9$ and $R^{10}$ are, at each occurrence, independently H or alkyl; and $y^1$ and $y^2$ are, at each occurrence, independently an integer from 1 to 6; and z is an integer from 1 to 100.

In some embodiments, $R^7$, $R^8$, $R^9$ and $R^{10}$ are, at each occurrence, independently H.

In some embodiments, $L^2$ and $L^3$ are, at each occurrence, independently $C_1$-$C_6$ alkylene, $C_2$-$C_6$ alkenylene or $C_2$-$C_6$ alkynylene. For example, in some embodiments $L^2$ and $L^3$ are, at each occurrence, independently $C_1$-$C_6$ alkylene, and $R^7$, $R^8$, $R^9$ and $R^{10}$ are, at each occurrence, independently H. In some related embodiments, the compounds have the following structure (IIIc):

(IIIc)

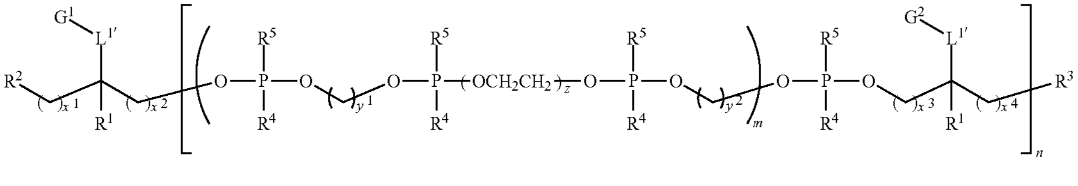

wherein:

$x^1$, $x^2$, $x^3$ and $x^4$ are, at each occurrence, independently an integer from 0 to 6;

$y^1$ and $y^2$ are, at each occurrence, independently an integer from 1 to 6; and z is an integer from 1 to 100.

In some embodiments, $x^1$ and $x^3$ are each 0 at each occurrence, and $x^2$ and $x^4$ are each 1 at each occurrence.

In some embodiments, $x^1$, $x^2$, $x^3$ and $x^4$ are each 1 at each occurrence.

In some embodiments, $y^1$ and $y^2$ are each 3 at each occurrence. In some embodiments, $y^1$ and $y^2$ are each 4 at each occurrence. In some embodiments, $y^1$ and $y^2$ are each 6 at each occurrence.

In some embodiments, z is an integer from 15 to 30. In other embodiments, z is an integer from 22 to 25.

In some embodiments, L" has one of the following structures:

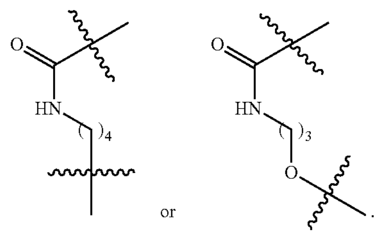

In some embodiments, $R^1$ is, at each occurrence, H.

In some embodiments, $L^2$ and $L^3$ are, at each occurrence, independently $C_1$-$C_6$ alkylene, $C_2$-$C_6$ alkenylene or $C_2$-$C_6$ alkynylene.

Reaction Scheme III

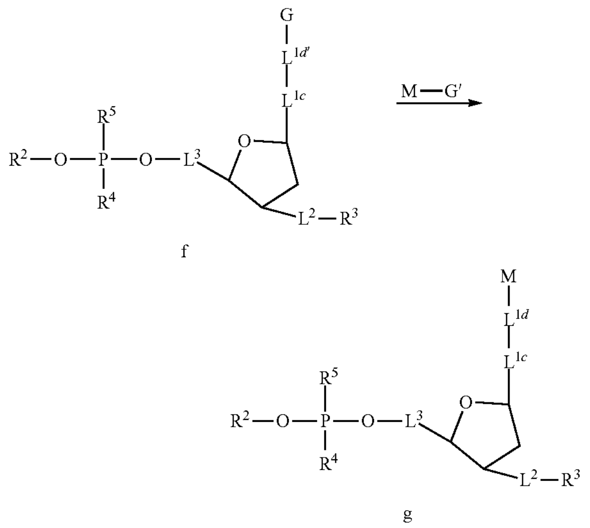

f g

Reaction Scheme III illustrates a method for preparation of intermediates useful for preparation of compounds of structure (II). Referring to reaction Scheme III, wherein $L^{1c}$, $L^{1d'}$, $L^2$, $L^3$, G and M are as defined above, and $R^2$ and $R^3$ are as defined above, or are protected variants thereof, a compound of structure f, which can be purchased or prepared by well-known techniques, is reacted with M-G' to yield compounds of structure g. Here, G and G' represent functional groups having complementary reactivity (i.e., functional groups which react to form a covalent bond). G' may be pendant to M or a part of the structural backbone of M. G and G' may be any number of functional groups described herein, such as alkyne and azide, respectively, amine and activated ester, respectively or amine and isothiocyanate, respectively, and the like.

Compounds of structure f can be prepared by oligomerization using well known phosphoramidite chemistry. Applicants have discovered intermediate compounds useful for synthesis of compounds of structures f. Accordingly, one embodiment provides a compound having the following structure h:

(h)

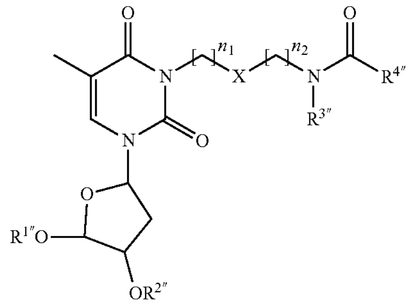

wherein:

$n_1$ is an integer from 1 to 6;

$n_2$ is an integer from 1 to 3;

X is O or a direct bond;

$R^{1}$" and $R^{2}$" are, at each occurrence, independently H, a protecting group, or an activated phosphorus moiety;

$R^{3}$" is H, or alkyl;

$R^{4}$" is alkoxy, haloalkyl, alkyl, an optionally substituted aryl or an optionally substituted aralkyl.

In some embodiments of compound (h), $n_1$ is 2. In some embodiments, n is 4. In some related embodiments, $n_2$ is 1. In certain embodiments, $n_1$ is 2 and $n_2$ is 1. In other embodiments, $n_1$ is 4 and $n_2$ is 1. In some of the foregoing embodiments, X is a direct bond.

In some embodiments of compound (h), $n_1$ is 2. In certain related embodiments, $n_2$ is 2. In some of the foregoing embodiments, X is O.

In some embodiments of compound (h), X is a direct bond. In some embodiments, X is O.

In some embodiments of compound (h), $R^{1}$" is H. In certain embodiments, is a protecting group, for example, a trityl protecting group. In some embodiments, $R^{1}$" is trityl. In some embodiments, $R^{1}$" is 4-methoxytrityl. In more specific embodiments, $R^{1}$" is 4,4'-dimethoxytrityl.

In some embodiments, $R^{2}$" is H. In some embodiments, $R^{2}$" is an activated phosphorus moiety. For example, in some embodiments $R^{2}$" comprises the following structure:

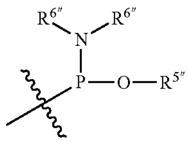

wherein:

$R_5$" is H or cyano alkyl; and $R^{6}$" is, at each occurrence, independently $C_1$-$C_6$ alkyl.

In some embodiments of compound (h), $R_5$" is H. In other embodiments, $R_5$" is 2-cyanoethyl.

In some embodiments, at least one occurrence of $R^{6}$" is isopropyl. In some embodiments, each occurrence of $R^{6}$" is isopropyl.

In certain specific embodiments, $R^{2}$" has the following structure:

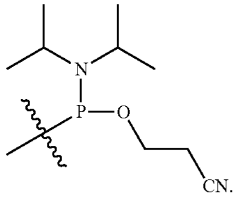 [SMILES: *P(OCCC#N)N(C(C)C)C(C)C]

In some embodiments of compound (h), $R^{3}$" is H.

In some embodiments of compound (h), $R^{4}$" is an aryl comprising 1, 2, or 3 aromatic rings, e.g., $R^{4}$" comprises 1 or 2 aromatic rings. In some embodiments, $R^{4}$" does not comprise silicon. In some embodiments, $R^{4}$" is $C_1$-$C_4$ haloalkyl. In more specific embodiments, $R^{4}$" is —$CF_3$. In some embodiments, $R^{4}$" is $C_1$-$C_4$ alkoxy. In more specific embodiments, $R^{4}$" is tert-butoxy.

In various other embodiments, compounds useful for preparation of the compound of structure (II) are provided. The compounds can be prepared as described above in monomer, dimer and/or oligomeric form and then the M moiety covalently attached to the compound via any number of synthetic methodologies (e.g., the "click" reactions described above) to form a compound of structure (II).

Accordingly, in various embodiments compounds are provided having the following structure (IV):

(IV)

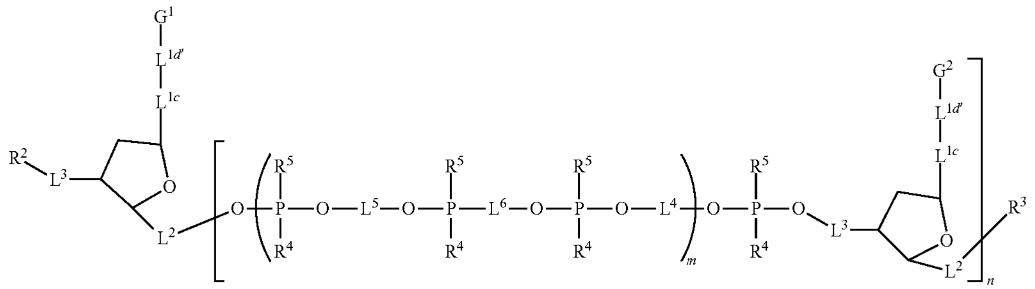

wherein:

$G^1$ and $G^2$ are, at each occurrence, independently a moiety comprising a reactive group, or protected analogue thereof, capable of forming a covalent bond with a complementary reactive group;

$L^{1c}$ is, at each occurrence, independently a heteroarylene linker;

$L^{1d'}$, $L^2$ and $L^3$ are, at each occurrence, independently optional alkylene, alkenylene, alkynylene, heteroalkylene, heteroalkenylene, heteroalkynylene or heteroatomic linkers;

$L^4$ and $L^5$ are, at each occurrence, independently alkylene, alkenylene, alkynylene, heteroalkylene, heteroalkenylene or heteroalkynylene linkers;

$L^6$ is, at each occurrence, independently a heteroalkylene, heteroalkenylene or heteroalkynylene linker, provided at least one occurrence, $L^6$ is different from each of $L^4$ and $L^5$;

$R^2$ and $R^3$ are each independently H, OH, SH, alkyl, alkoxy, alkylether, heteroalkyl, —OP(=$R_a$)($R_b$)$R_c$, Q or a protected form thereof, or L';

$R^4$ is, at each occurrence, independently OH, SH, $O^-$, $S^-$, $OR_d$ or $SR_d$;

$R_5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (IV);

m is, at each occurrence, independently an integer of zero or greater, provided at least one occurrence of m is an integer of one or greater; and n is an integer of one or greater.

In some embodiments, at least one occurrence of $L^{1c}$ is an optionally substituted 5-7 membered heteroarylene linker. In some embodiments, $L^{1c}$ is, at each occurrence independently an optionally substituted 5-7 membered heteroarylene linker. In some embodiments, $L^{1c}$ is, at each occurrence, substituted. For example, in some embodiments, $L^{1b}$ is, at each occurrence, substituted with at least one oxo. In some embodiments, $L^{1b}$ has one of the following structures:

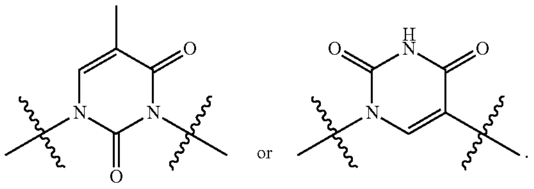 [SMILES: *n1cc(C)c(=O)n(*)c1=O ; *c1cn(*)c(=O)[nH]c1=O]

In some embodiments, at least one occurrence of $L^{1d'}$ is substituted. For example, in some embodiments, $L^{1d'}$ is substituted with oxo.

In some embodiments, at least one occurrence of $L^2$ is an alkylene linker. In some embodiments, $L^2$ is an alkylene linker at each occurrence.

In some embodiments, at least one occurrence of $L^3$ is absent. In some embodiments, $L^3$ is absent at each occurrence.

In some embodiments, $L^4$ and $L^5$ are, at each occurrence, independently an alkylene linker. In some embodiments, $L^4$ and $L^5$ are, at each occurrence, independently $C_3$-$C_6$ alkylene. In some embodiments, at least one occurrence $L^4$ and $L^5$ are the same.

In some embodiments, $L^6$ is, at each occurrence, independently a heteroalkylene linker. In some embodiments, $L^6$ is, at each occurrence, independently an alkylene oxide linker. In some embodiments, $L^6$ is, at each occurrence, independently polyethylene oxide. In some related embodiments, the compounds have the following structure (IVa):

(IVa)

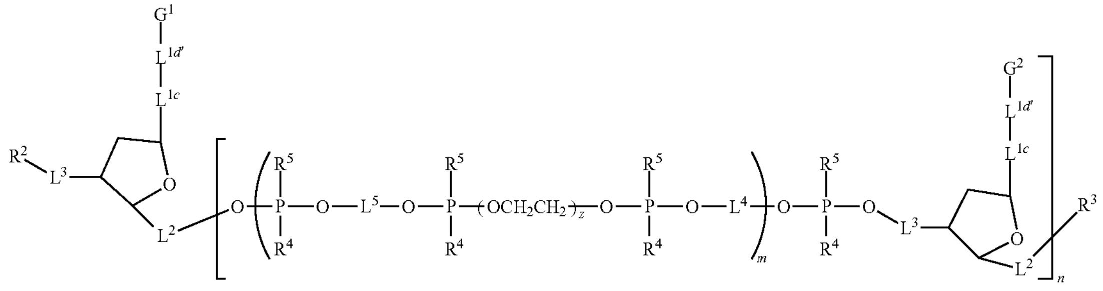

wherein:

$L^4$ and $L^5$ are, at each occurrence, independently an alkylene, alkenylene, alkynylene, heteroalkylene, heteroalkenylene, heteroalkynylene or heteroatomic linker, provided $L^4$ and $L^5$ are not polyethylene oxide; and z is an integer from 1 to 100.

In some embodiments, $L^4$ and $L^5$ are, at each occurrence, independently an alkylene linker. In some more specific embodiments, $L^4$ and $L^5$ are, at each occurrence, independently $C_3$-$C_6$ alkylene. In some embodiments, $L^4$ and $L^5$ are, at each occurrence, independently $C_3$ alkylene, $C_4$ alkylene, or $C_6$ alkylene. In some related embodiments, the compounds have the following structure (IVb):

(IVb)

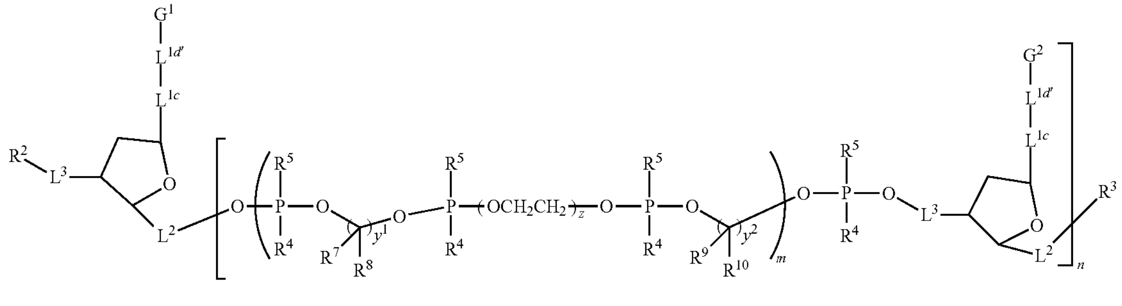

wherein:

$R^7$, $R^8$, $R^9$ and $R^{10}$ are, at each occurrence, independently H or alkyl; and $y^1$ and $y^2$ are, at each occurrence, independently an integer from 1 to 6; and z is an integer from 1 to 100.

In some embodiments, $R^7$, $R^8$, $R^9$ and $R^{10}$ are, at each occurrence, independently H. In some related embodiments, the compound has one of the following structures (IVc), (IVd), (IVe), or (IVf):

(IVc)

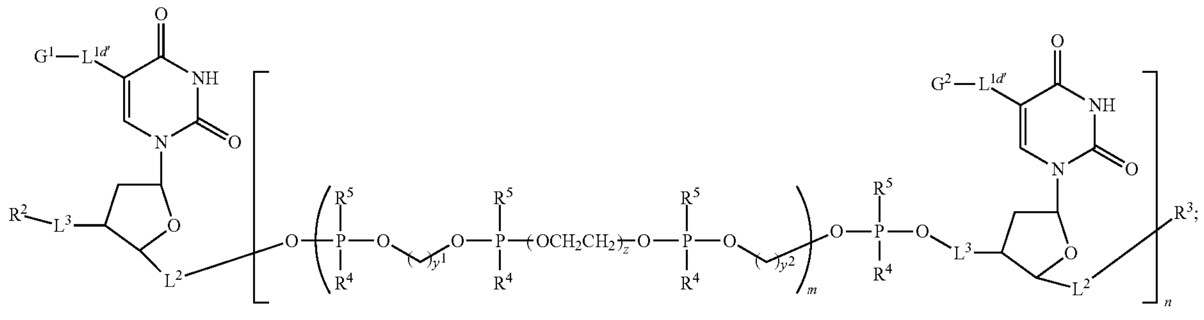

-continued
(IVd)
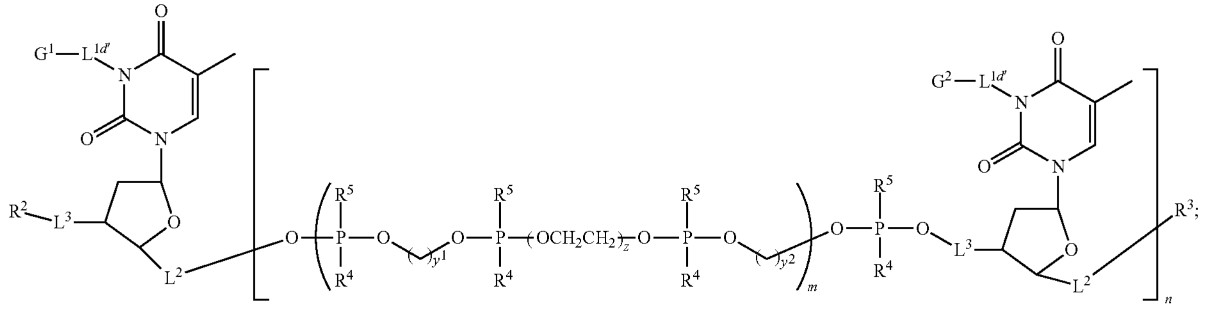
(IVe)
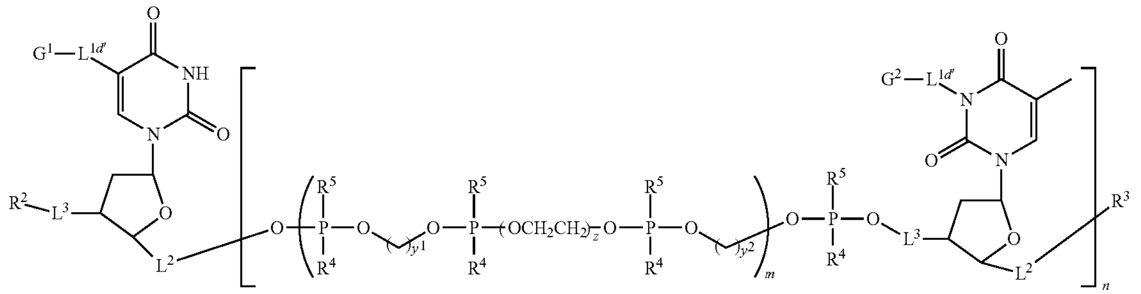
or
(IVf)
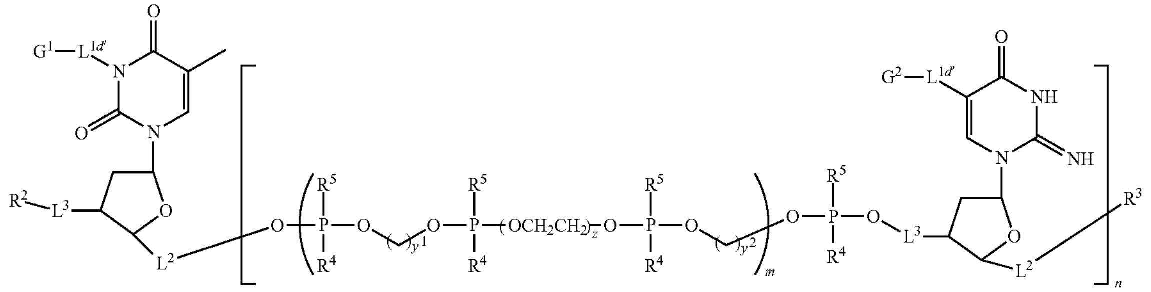

wherein:

$L^{1d'}$ is, at each occurrence, independently comprises an amide functional group or a triazolyl functional group;

$y^1$ and $y^2$ are, at each occurrence, independently an integer from 1 to 6; and z is an integer from 1 to 100.

In some embodiments, z is an integer from 15 to 30. In other embodiments, z is an integer from 22 to 25.

In some embodiments, $L^{1d'}$ comprises one of the following structures:

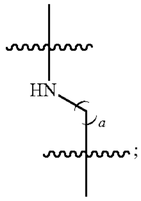
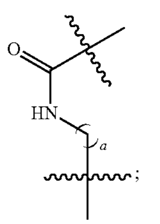
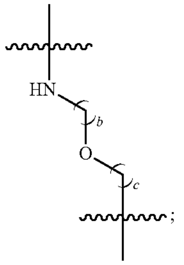
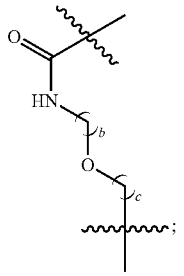
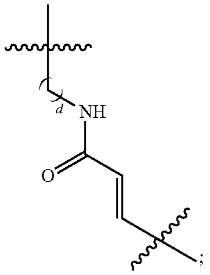
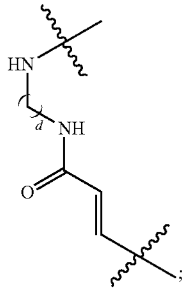
or
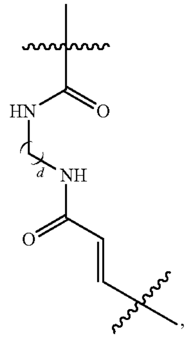

wherein a, b, c, and d are each independently an integer ranging from 1-6.

For example, in certain embodiments, $L^{1d'}$ has one of the following structures:

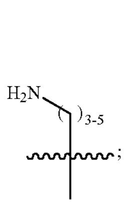
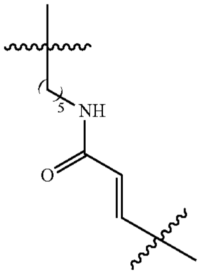
or

-continued

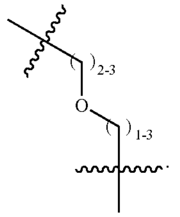

In some specific embodiments, $L^{1d'}$ is an alkylene, for example, ethylene, propylene, butylene or pentylene.

In some embodiments, $L^2$ is an alkylene linker (e.g., methylene) at each occurrence. In some specific embodiments of compound (II), $L^3$ is absent at each occurrence.

In other embodiments of structure (III) or (IV), G are, at each occurrence, independently a moiety comprising a reactive group capable of forming a covalent bond with a complementary reactive group.

The $G^1$ or $G^2$ moiety in the compound of structure (III) or (IV) can be selected from any moiety comprising a group having the appropriate reactivity group for forming a covalent bond with a complementary group on an M moiety. In exemplary embodiments, the $G^1$ or $G^2$ moiety can be selected from any of the Q moieties described herein, including those specific examples provided in Table 1. In some embodiments, $G^1$ or $G^2$ comprises, at each occurrence, independently a moiety suitable for reactions including: the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse-demand Diels-Alder, alkene and tetrazole photoreaction and various displacement reactions, such as displacement of a leaving group by nucleophilic attack on an electrophilic atom.

In some embodiments, $G^1$ or $G^2$ is, at each occurrence, independently a moiety comprising an aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin or thiirane functional group.

In other embodiments, $G^1$ or $G^2$ comprises, at each occurrence, independently an alkyne or an azide group. In other embodiments, $G^1$ or $G^2$ comprises, at each occurrence, independently an amino, isothiocyanate or activated ester group. In different embodiments, $G^1$ or $G^2$ comprises, at each occurrence, independently a reactive group capable of forming a functional group comprising an alkene, ester, amide, thioester, disulfide, carbocyclic, heterocyclic or heteroaryl group, upon reaction with the complementary reactive group. For example, in some embodiment the heteroaryl is triazolyl.

In any of the foregoing embodiments of compound (III) or (IV), $G^1$ or $G^2$, at each occurrence, independently has one of the following structures:

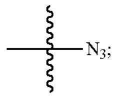
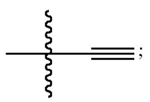
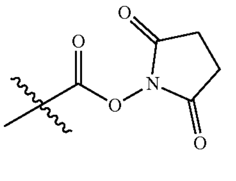
or

-continued

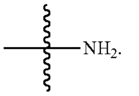

In some embodiments of compound (III) or (IV), $G^1$ or $G^2$ is, at each occurrence, independently

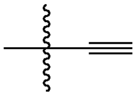 or 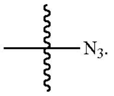

In some embodiments of compound (III) or (IV), at least one occurrence of $G^1$ or $G^2$ is a protected form of an amine. In some embodiments, $G^1$ or $G^2$ is, at a plurality of occurrences, independently a protected form of an amine. In certain embodiments, $G^1$ or $G^2$ is, at each occurrence, independently a protected form of an amine.

In some embodiments, at least one occurrence of $G^1$ is

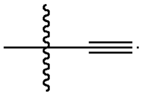 [SMILES: *C#C]

In some embodiments, $G^1$ is, at each occurrence, independently

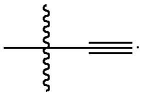

In some embodiments, at least one occurrence of $G^2$ is

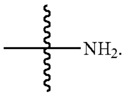 [SMILES: *N]

In some embodiments, $G^2$ is, at each occurrence, independently

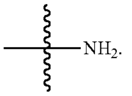 [SMILES: *N]

In some embodiments, $G^1$ is, at each occurrence,

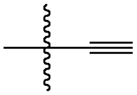

and $G^2$ is, at each occurrence,

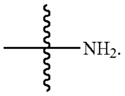

In some of the foregoing embodiments, the protected form of the amine is a trifluoroacetate protected amine. In some embodiments, the protected form of the amine is a BOC protected amine. In some embodiments, the protected form of the amine is an Fmoc protected amine. For example, in certain embodiments, at least one occurrence of $G^1$ or $G^2$ has one of the following structures:

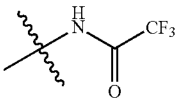 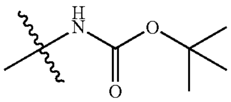

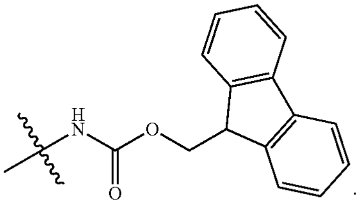

In more specific embodiments, G, at each occurrence, independently has one of the following structures:

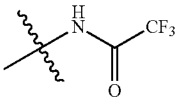 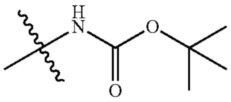

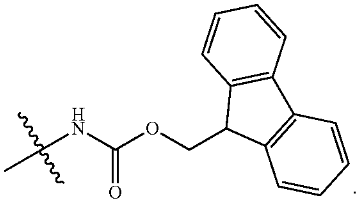

In some embodiments, $R^2$, $R^3$, $R^4$, $R^5$, $L^2$, $L^3$, $L^4$, $L^5$, or $L^6$ are as defined in any one of the foregoing embodiments. For example, in some embodiments of compound (III) or (IV), $R^4$ is at each occurrence independently OH, $O^-$ or $OR_d$. In some embodiments of compound (II) or (IV), $R^5$ is at each occurrence oxo.

In other various embodiments of the compounds of structure (III) or (IV), $R^2$ and $R^3$ are each independently OH or $—OP(=R_a)(R_b)R_c$. In some different embodiments, $R^2$ or $R^3$ is OH or $—OP(=R_a)(R_b)R_c$, and the other of $R^2$ or $R^3$ is Q or a linker comprising a covalent bond to Q.

In still more different embodiments of any of the foregoing compounds of structure (III) or (IV), $R^2$ and $R^3$ are each independently $—OP(=R_a)(R_b)R_c$. In some of these embodiments, $R_c$ is OL'.

In other embodiments of structure (III) or (IV), $R^2$ and $R^3$ are each independently $—OP(=R_a)(R_b)OL'$, and L' is a heteroalkylene linker to: Q, a targeting moiety, an analyte (e.g., analyte molecule), a solid support, a solid support residue, a nucleoside or a further compound of structure (III) or (IV).

The linker L' can be any linker suitable for attaching Q, a targeting moiety, an analyte (e.g., analyte molecule), a solid support, a solid support residue, a nucleoside or a further compound of structure (III) or (IV) to the compound of structure (III) or (IV). Advantageously certain embodiments include use of L' moieties selected to increase or optimize water solubility of the compound. In some certain embodiments, L' comprises an alkylene oxide or phosphodiester moiety, or combinations thereof.

In certain embodiments, L' has the following structure:

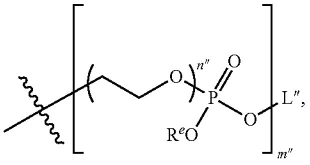

wherein:

- m" and n" are independently an integer from 1 to 10;
- $R^e$ is H, an electron pair or a counter ion;
- L" is $R_e$ or a direct bond or linkage to: Q, a targeting moiety, an analyte (e.g., analyte molecule), a solid support, a solid support residue, a nucleoside or a further compound of structure (III) or (IV).

In certain of the foregoing embodiments, the targeting moiety is an antibody or cell surface receptor antagonist. In some embodiments, the antibody includes CD3, CD4, FoxP3, TNF-α, IFN-γ, clone 4S.B3, clone 206D, CD8a (D8A8Y) Rabbit mAb, Vimentin (D21H3) XP® Rabbit mAb, phospho-RB-Ser608, phospho-RB-Ser612, phospho-RB-Ser780, phospho-RB-Ser795, phospho-RB-Ser807, or phospho-RB-Ser811, anti-human IL17A, integrin alpha E/CD103, CCR9, or MOPC-21.

In other more specific embodiments f any of the foregoing compounds of structure (III) or (IV), $R^2$ or $R^3$ has one of the following structures:

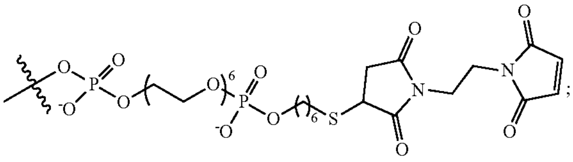
;

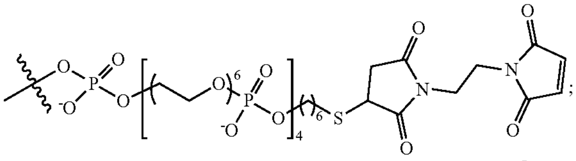
;

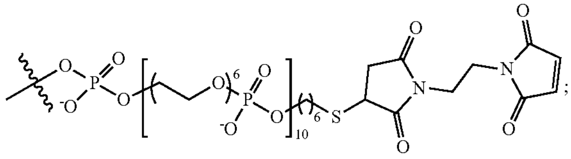
;

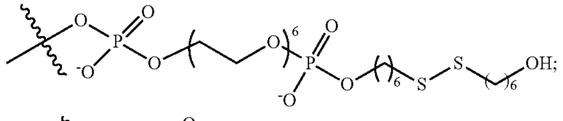

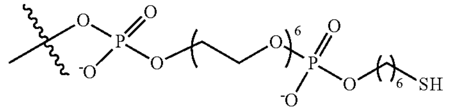
or

-continued

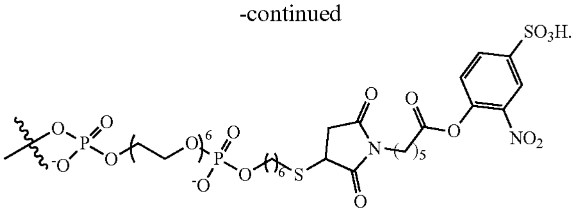

Certain embodiments of compounds of structure (III) or (IV) can be prepared according to solid-phase synthetic methods analogous to those known in the art for preparation of oligonucleotides. Accordingly, in some embodiments, L' is a linkage to a solid support, a solid support residue or a nucleoside. Solid supports comprising an activated deoxythymidine (dT) group are readily available, and in some embodiments can be employed as starting material for preparation of compounds of structure (III) or (IV). Accordingly, in some embodiments $R^2$ or $R^3$ has the following structure:

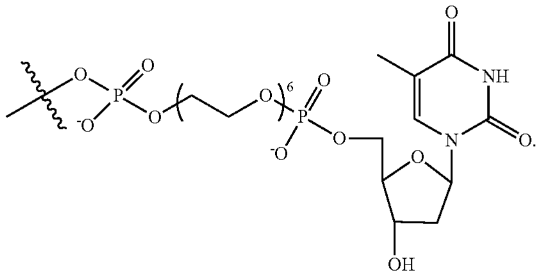

In still other embodiments of compounds of structure (III) or (IV), Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'. For example, in some embodiments, Q' is present on a further compound of structure (III) or (IV) (e.g., in the $R^2$ or $R^3$ position), and Q and Q' comprise complementary reactive groups such that reaction of the compound of structure (III) or (IV) and the further compound of structure (III) or (IV) results in covalently bound dimer of the compound of structure (III) or (IV). Multimer compounds of structure (III) or (IV) can also be prepared in an analogous manner and are included within the scope of embodiments of the disclosure.

The type of Q group and connectivity of the Q group to the remainder of the compound of structure (III) or (IV) is not limited, provided that Q comprises a moiety having appropriate reactivity for forming the desired bond.

In certain embodiments of compounds of structure (III) or (IV), the Q is a moiety which is not susceptible to hydrolysis under aqueous conditions, but is sufficiently reactive to form a bond with a corresponding group on an analyte molecule or solid support (e.g., an amine, azide or alkyne).

Certain embodiments of compounds of structure (III) or (IV) comprises Q groups commonly employed in the field of bioconjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group. In some embodiments, the activated ester is an N-succinimide ester, imidoester or polyflourophenyl ester. In other embodiments, the alkyne is an alkyl azide or acyl azide.

Exemplary Q moieties for compounds of structure (III) or (IV) are provided in Table I above.

As with compounds of structure (A), (I), or (II), in some embodiments of compounds of structure (III) or (IV), wherein Q is SH, the SH moiety will tend to form disulfide bonds with another sulfhydryl group on another compound of structure (III) or (IV). Accordingly, some embodiments include compounds of structure (III) or (IV), which are in the form of disulfide dimers, the disulfide bond being derived from SH Q groups.

In some other embodiments of compounds of structure (III) or (IV), one of $R^2$ or $R^3$ is OH or —OP(═$R_a$)($R_b$)$R_c$, and the other of $R^2$ or $R^3$ is a linker comprising a covalent bond to an analyte molecule, a linker comprising a covalent bond to a targeting moiety or a linker comprising a covalent bond to a solid support. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In some embodiments, the targeting moiety is an antibody or cell surface receptor antagonist. In still different embodiments, the solid support is a polymeric bead or nonpolymeric bead.

In other embodiments of compounds of structure (III) or (IV), m is, at each occurrence, independently an integer from 0 to 10. For example, in some embodiments m is, at each occurrence, independently an integer from 1 to 5, such as 1, 2, 3, 4 or 5. In some embodiments, m is 0. In some embodiments, m is 1. In some embodiments, m is 2. In some embodiments, m is 3. In some embodiments, m is 4. In some embodiments, m is 5.

In yet different embodiments of compounds of structure (III) or (IV), n is an integer from 1 to 100. For example, in some embodiments, n is an integer from 1 to 10. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some specific embodiments of compounds of structure (III) or (IV), n is 3 and for each n value m values are 1, 1, and 0 (e.g., compound IV-7). In other embodiments of compounds of structure (III) or (IV), n is 2 and for each n value m values are 1 and 0 (e.g., compound IV-8).

In yet different embodiments of compounds of structure (III) or (IV), z is an integer from 1-30, for example from 15 to 30 or from 22 to 25. In some embodiments, z is 23. In some embodiments, z is 21, 22, 23, 24 or 25. In some embodiments, z is an integer from 1 to 10, for example from 3 to 6. In some embodiments, z is 3, 4, 5, or 6.

In other different embodiments, the compound of structure (III) or (IV) is selected from Table 3.

TABLE 3
| Exemplary Compounds of Structure (III) or (IV) | |
|---|---|
| No. | Structure |
| III-1 | 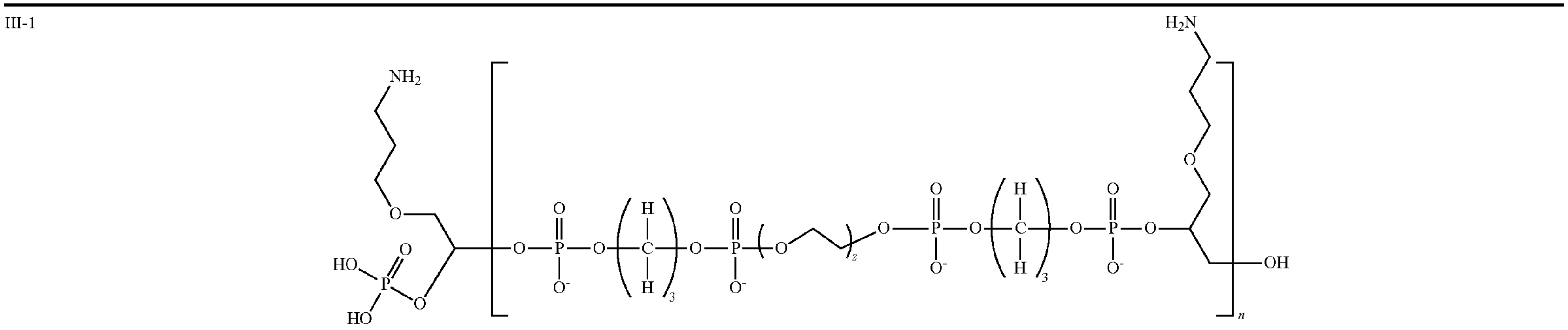 z = 22-25 and PEG MW = about 1,000<br>n = 1-9 |
| III-2 | 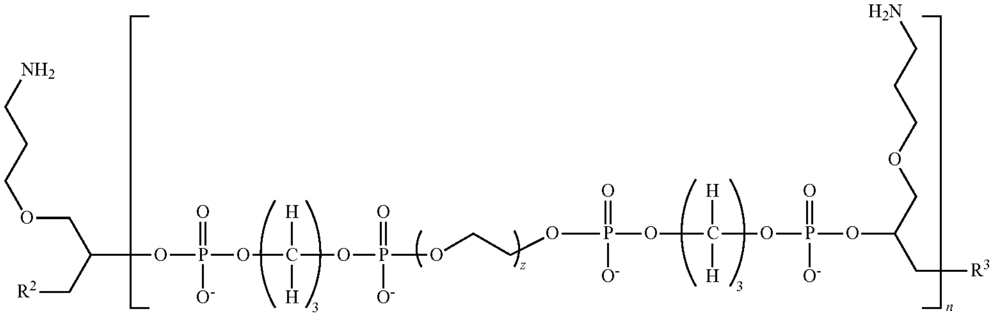 $R^2$ = 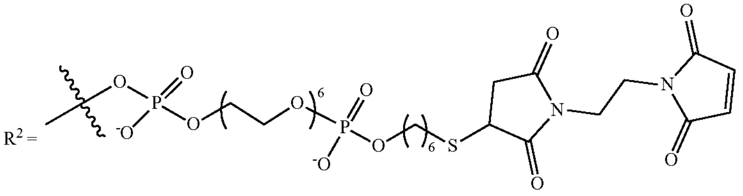 |

TABLE 3-continued
Exemplary Compounds of Structure (III) or (IV)
| No. | Structure |
|---|---|
| | 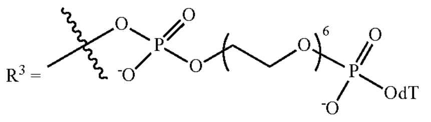 z = 22-25 and PEG MW = about 1,000<br>n = 1-10 |
| III-3 | 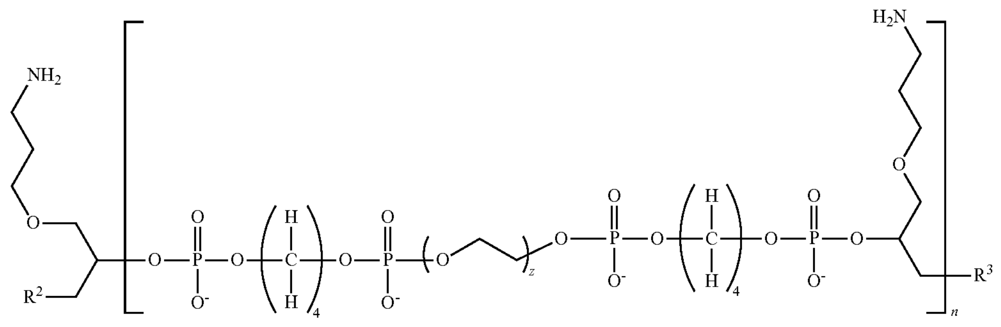 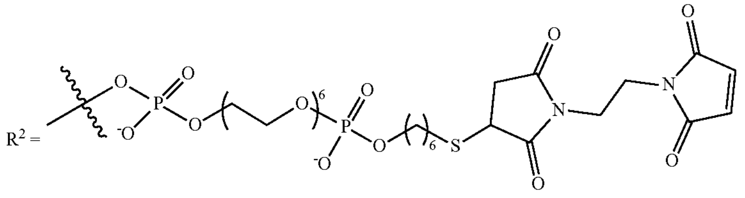 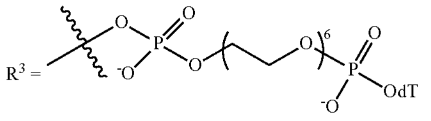 z = 22-25 and PEG MW = about 1,000<br>n = 1-10 |

TABLE 3-continued
| Exemplary Compounds of Structure (III) or (IV) | |
|---|---|
| No. | Structure |
| III-4 | 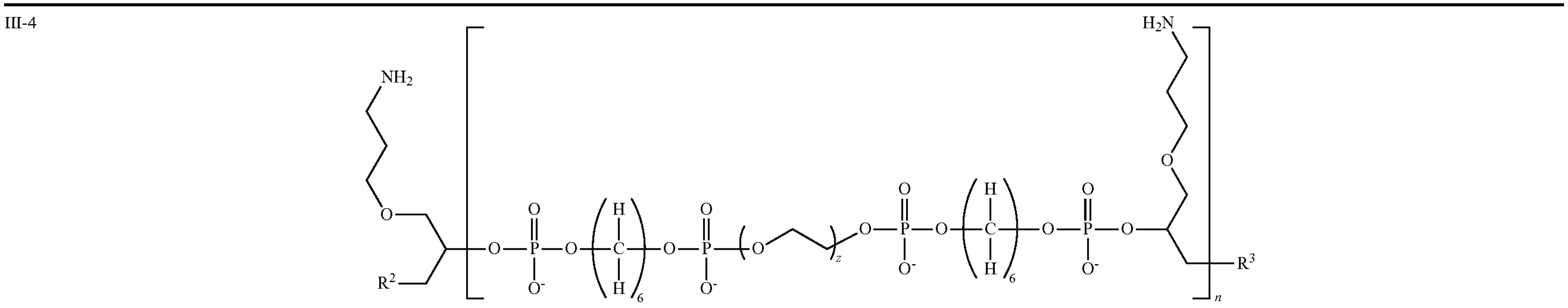 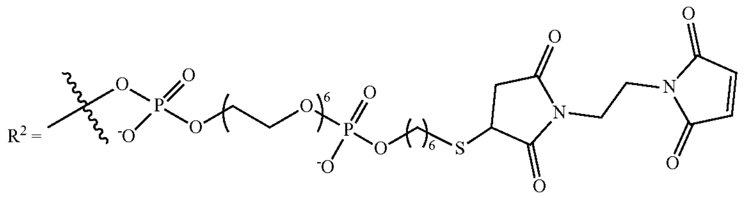 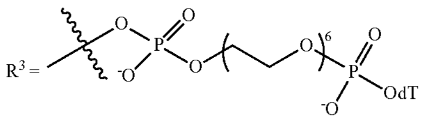 z = 22-25 and PEG MW = about 1,000 n = 1-10 |
| III-5 | 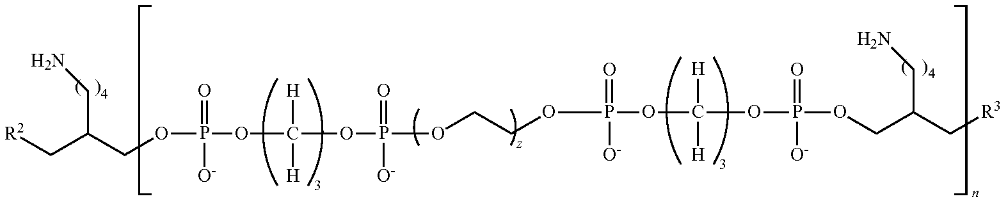 |

TABLE 3-continued
| Exemplary Compounds of Structure (III) or (IV) | |
|---|---|
| No. | Structure |
| | 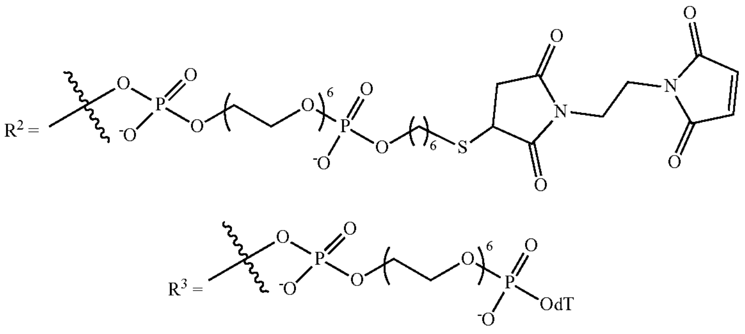 |
| | z = 22-25 and PEG MW = about 1,000<br>n = 1-10 |
| III-6 | 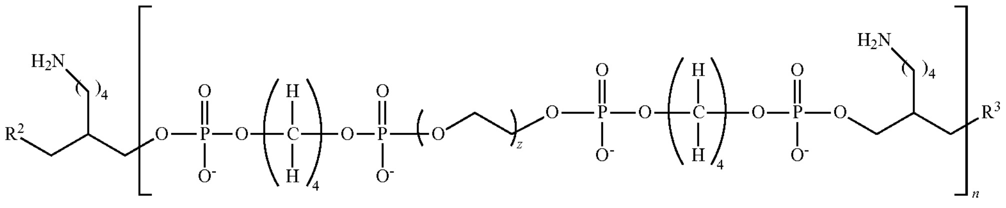 |
| | 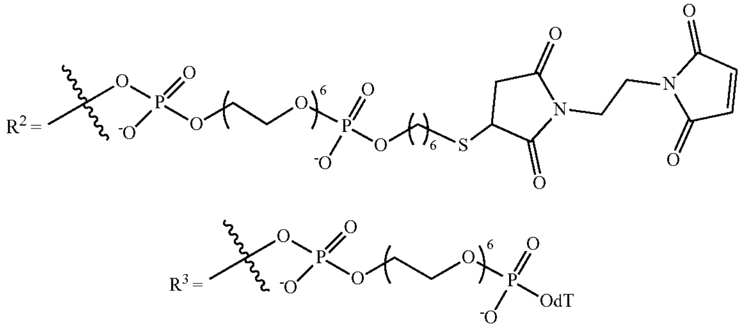 |

TABLE 3-continued
| Exemplary Compounds of Structure (III) or (IV) | |
| --- | --- |
| No. | Structure |
| III-7 | 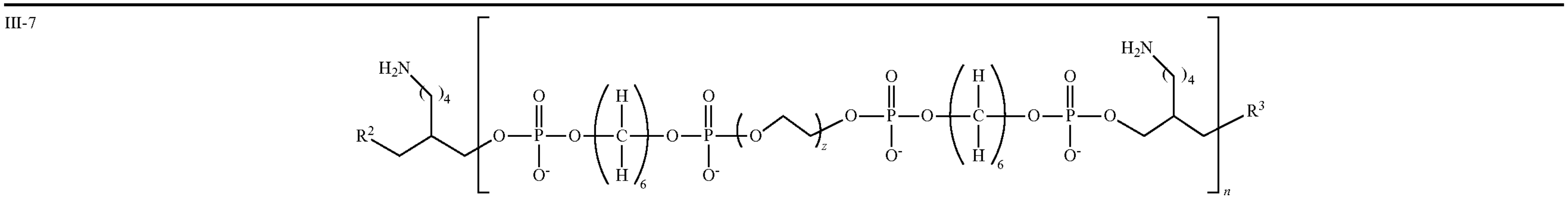 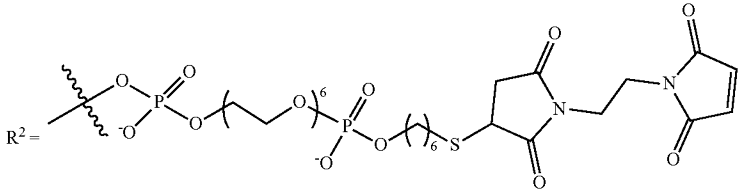 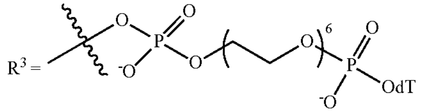 z = 22-25 and PEG MW = about 1,000<br>n = 1-10 |

TABLE 3-continued
| Exemplary Compounds of Structure (III) or (IV) | |
|---|---|
| No. | Structure |
| IV-1 | 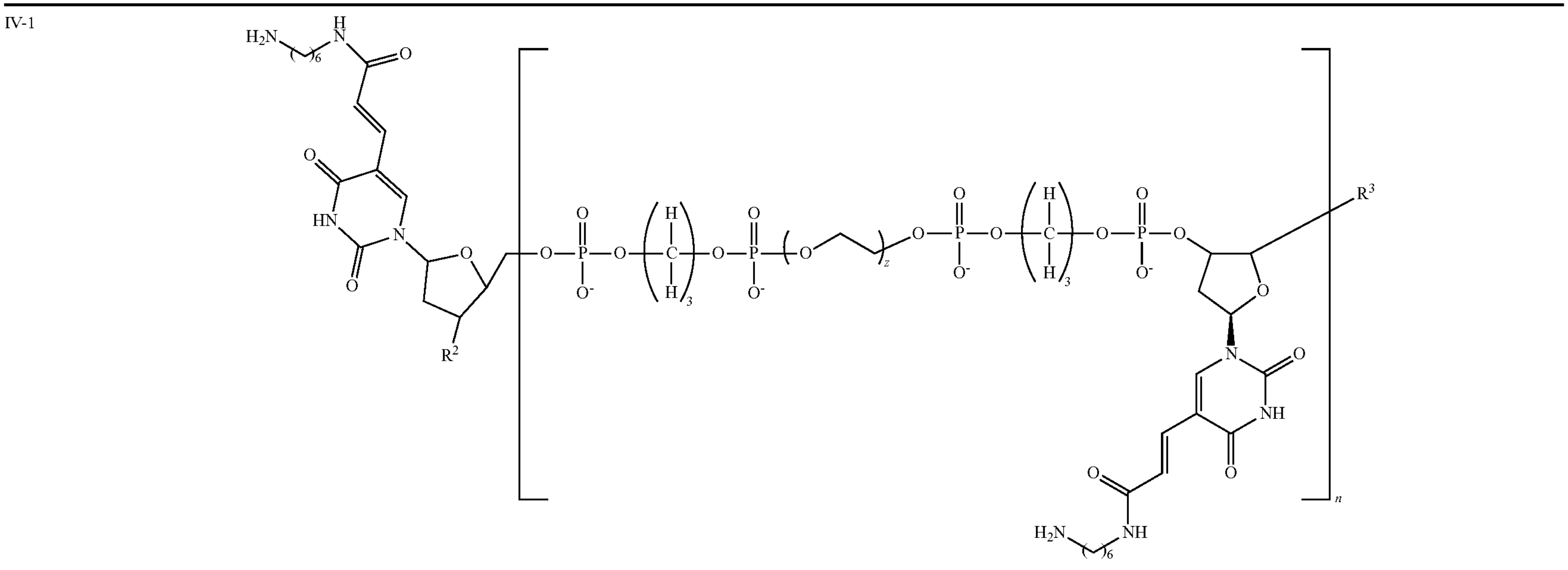 $R^2$ = 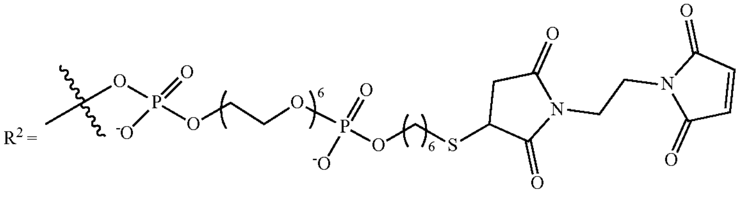 $R^3$ = 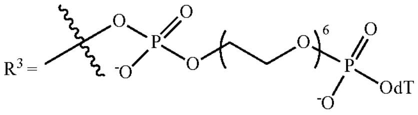 z = 22-25 and PEG MW = about 1,000<br>n = 1-10 |

TABLE 3-continued
| Exemplary Compounds of Structure (III) or (IV) | |
|---|---|
| No. | Structure |
| IV-2 | 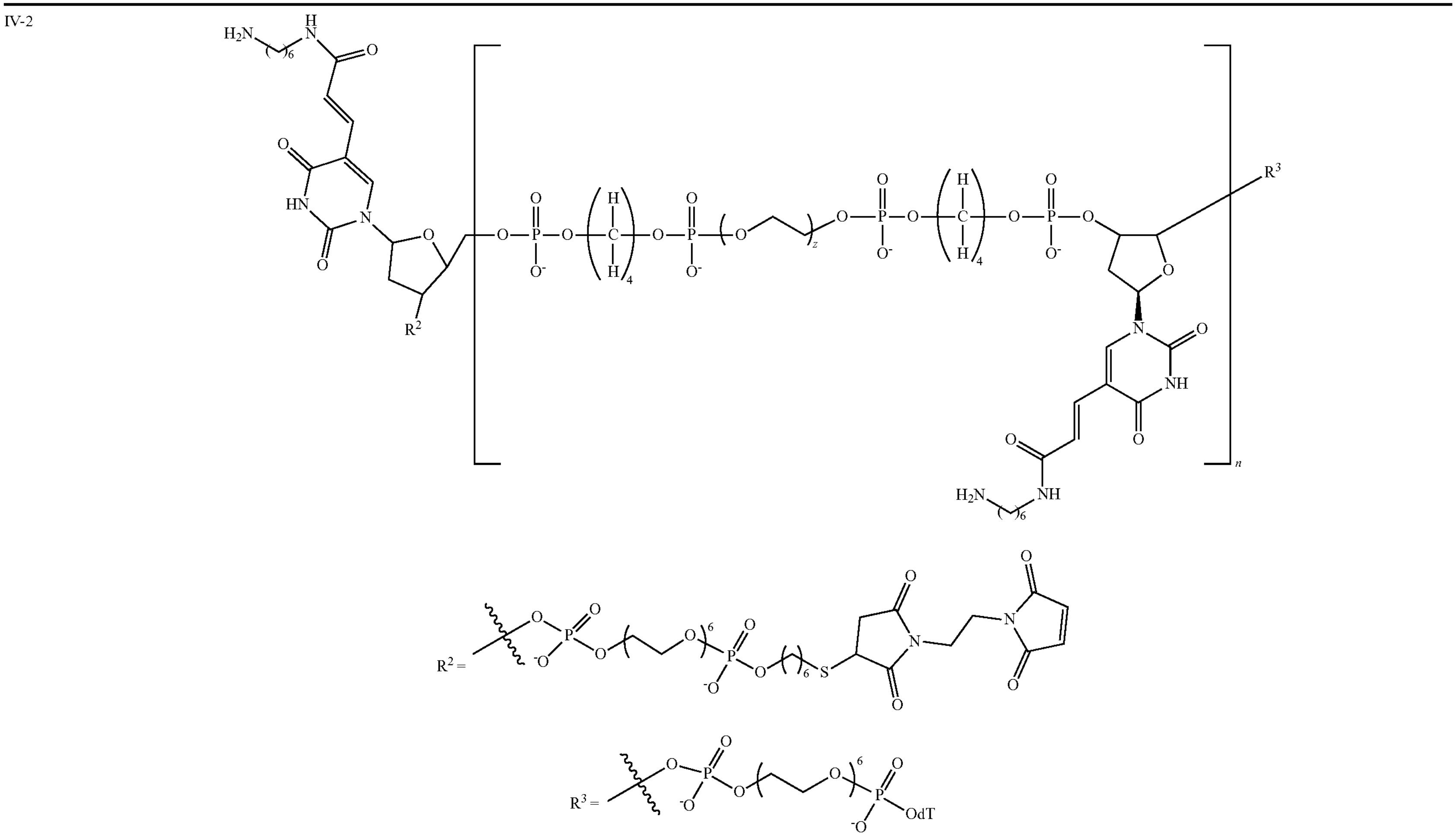 z = 22–25 and PEG MW = about 1,000<br>n = 1–10 |

TABLE 3-continued
| Exemplary Compounds of Structure (III) or (IV) | |
|---|---|
| No. | Structure |
| IV-3 | 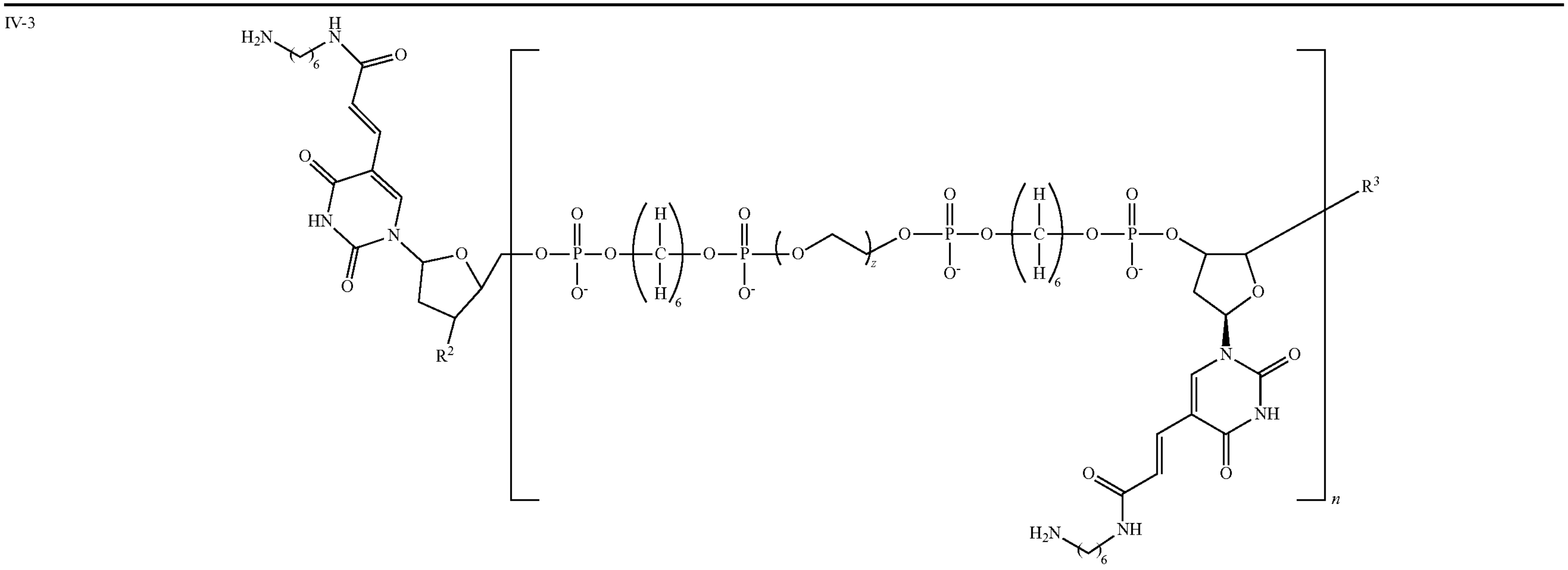<br>$R^2$ = 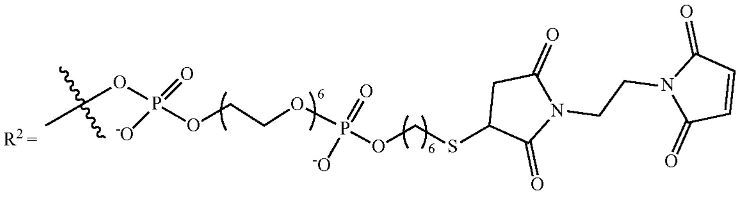<br>$R^3$ = 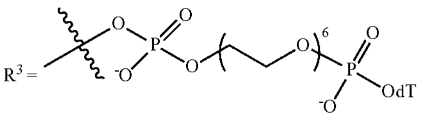<br>z = 22-25 and PEG MW = about 1,000<br>n = 1-10 |

TABLE 3-continued
| Exemplary Compounds of Structure (III) or (IV) | |
| --- | --- |
| No. | Structure |
| IV-4 | 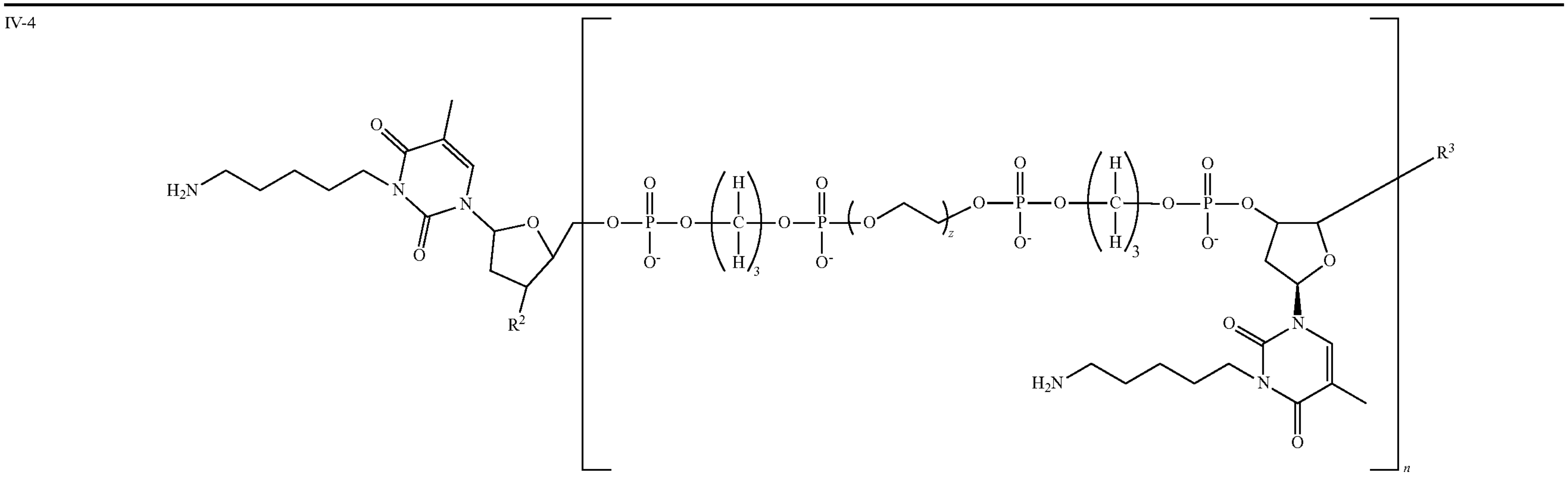 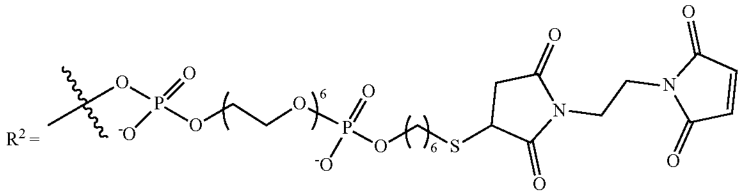 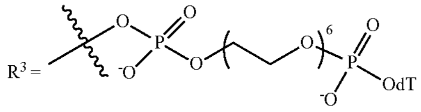 z = 22-25 and PEG MW = about 1,000<br>n = 1-10 |

TABLE 3-continued
| Exemplary Compounds of Structure (III) or (IV) | |
|---|---|
| No. | Structure |
| IV-5 | 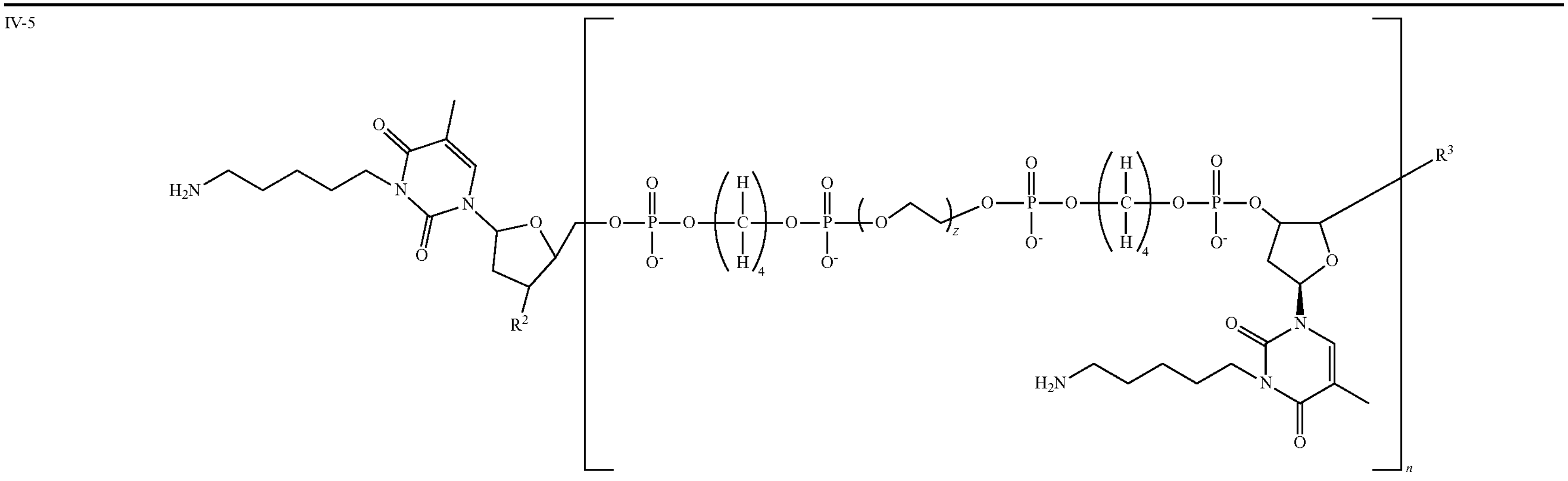 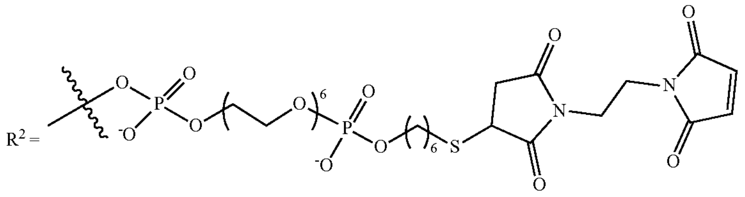 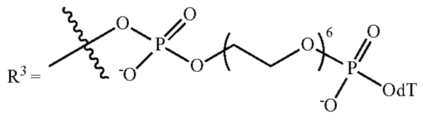 z = 22-25 and PEG MW = about 1,000 n = 1-10 |

TABLE 3-continued
| Exemplary Compounds of Structure (III) or (IV) | |
|---|---|
| No. | Structure |
| IV-6 | 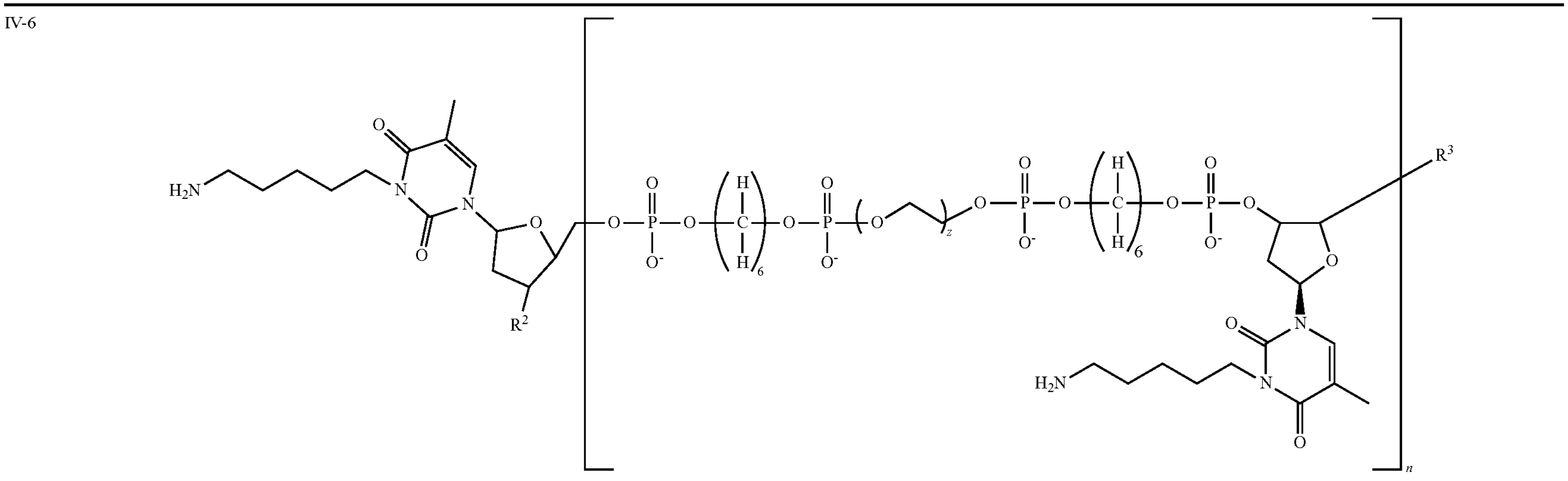 $R^2$ = 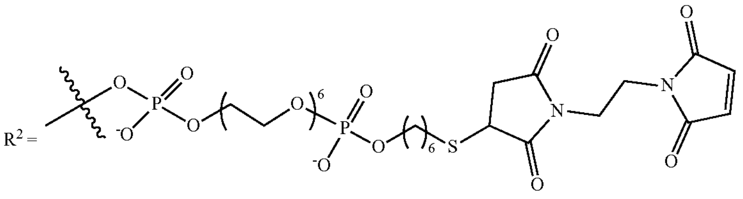 $R^3$ = 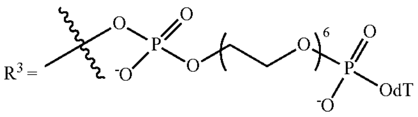 z = 22–25 and PEG MW = about 1,000<br>n = 1–10 |

TABLE 3-continued
Exemplary Compounds of Structure (III) or (IV)
| No. | Structure |
|---|---|
| A-1 | 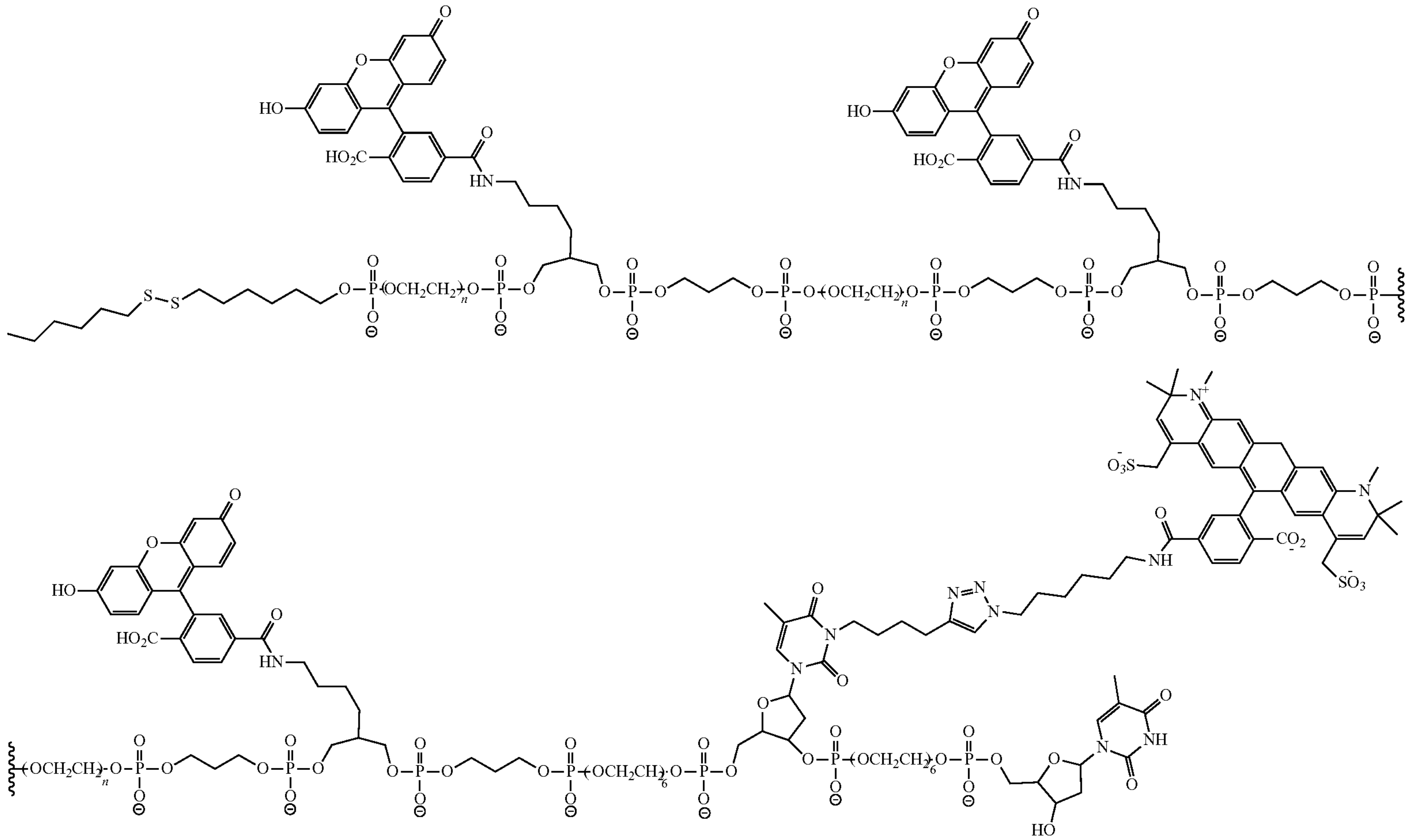 n = 15-30 |

TABLE 3-continued
| Exemplary Compounds of Structure (III) or (IV) | |
|---|---|
| No. | Structure |
| A-2 | 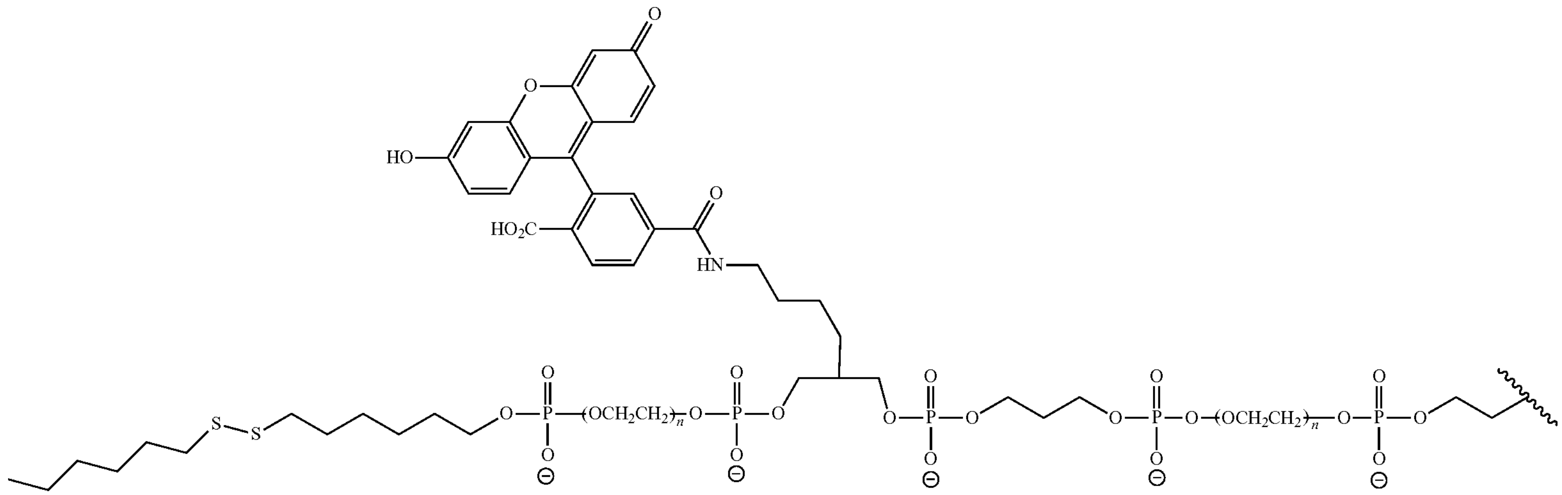 |
n = 15-30

TABLE 3-continued
| Exemplary Compounds of Structure (III) or (IV) | |
|---|---|
| No. | Structure |
| A-3 | 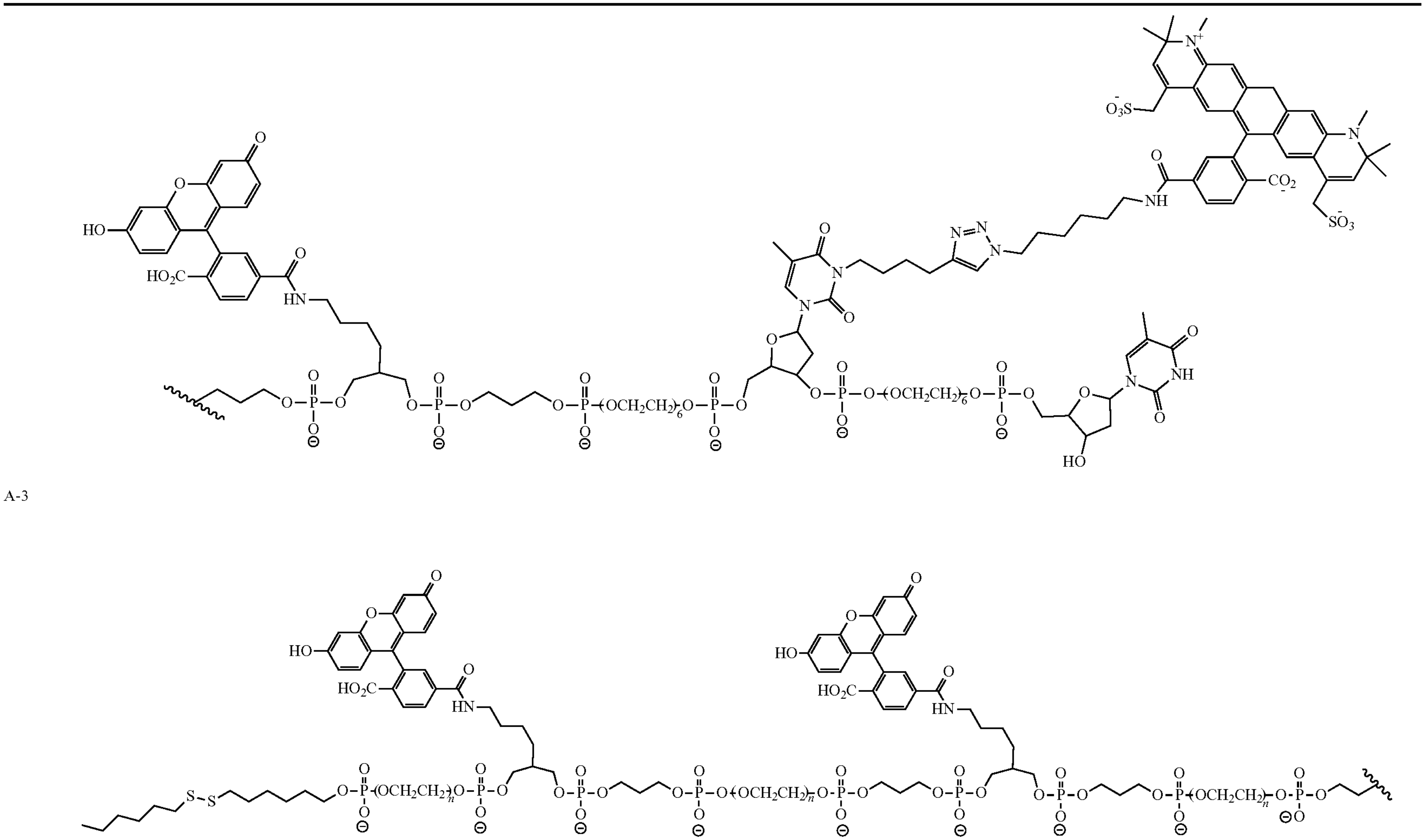 |

TABLE 3-continued
| Exemplary Compounds of Structure (III) or (IV) | |
|---|---|
| No. | Structure |
| A-4 | 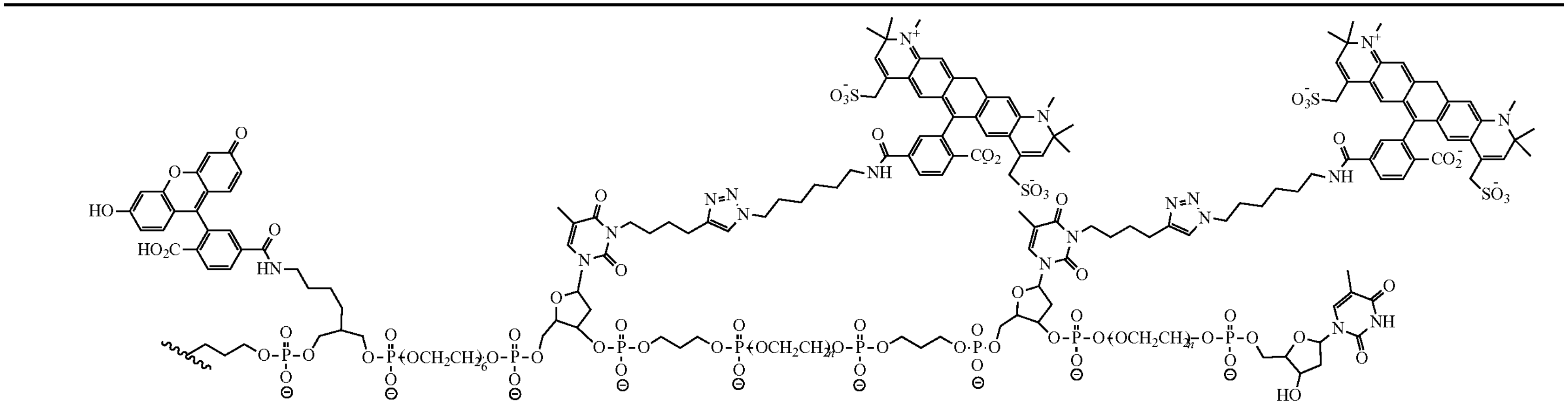 n = 15-30 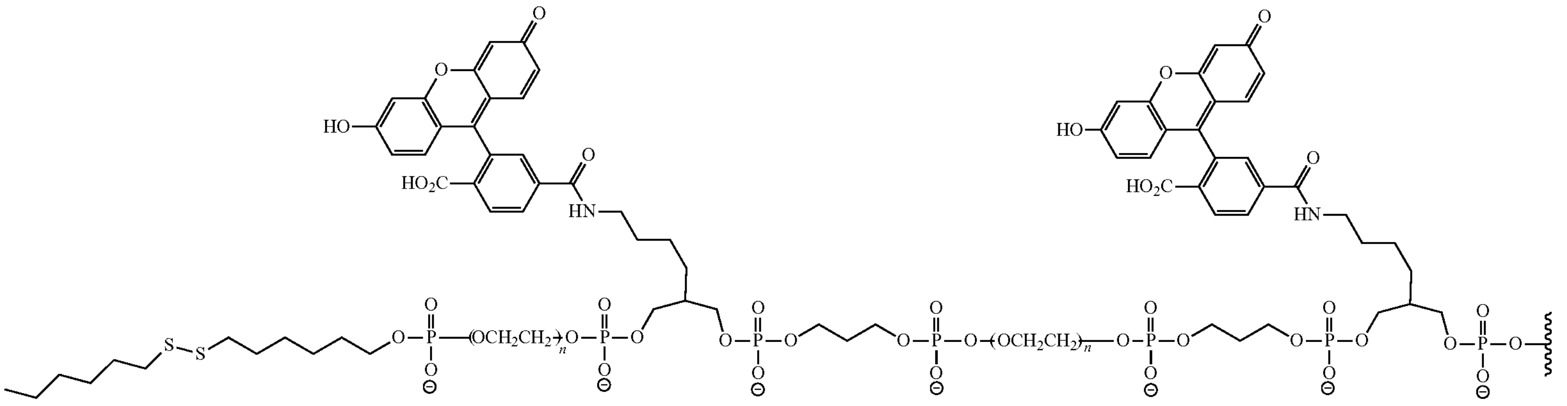 |

TABLE 3-continued
Exemplary Compounds of Structure (III) or (IV)
| No. | Structure |
|---|---|
| A-5 | 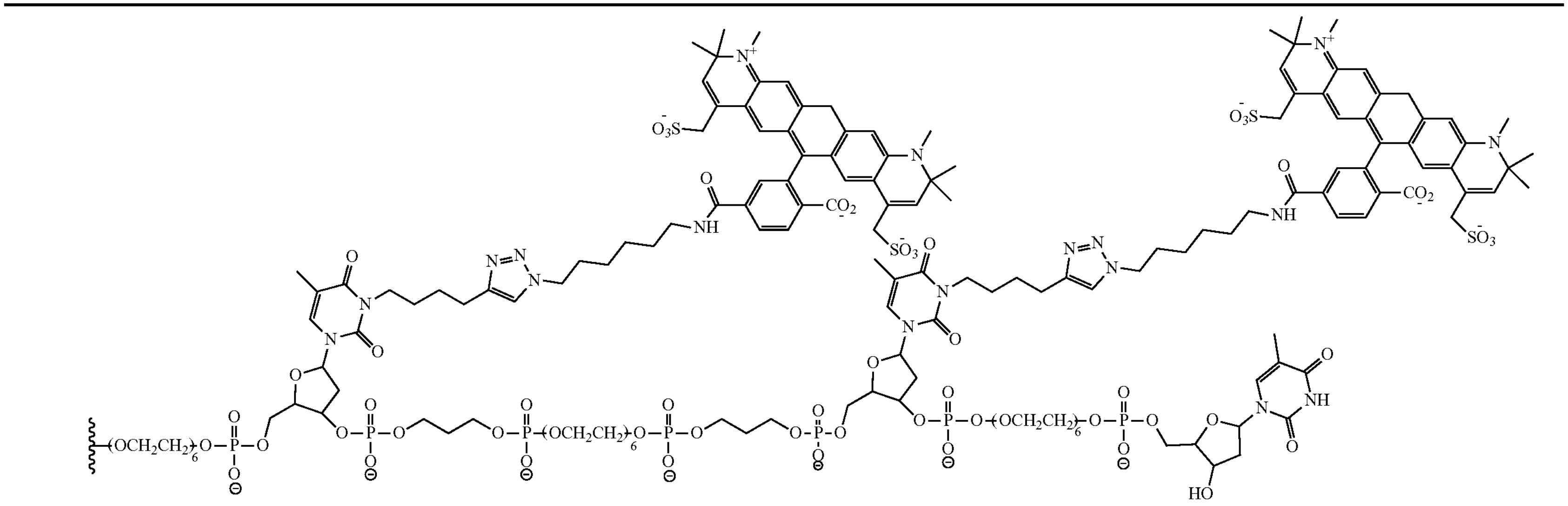 n = 15–30 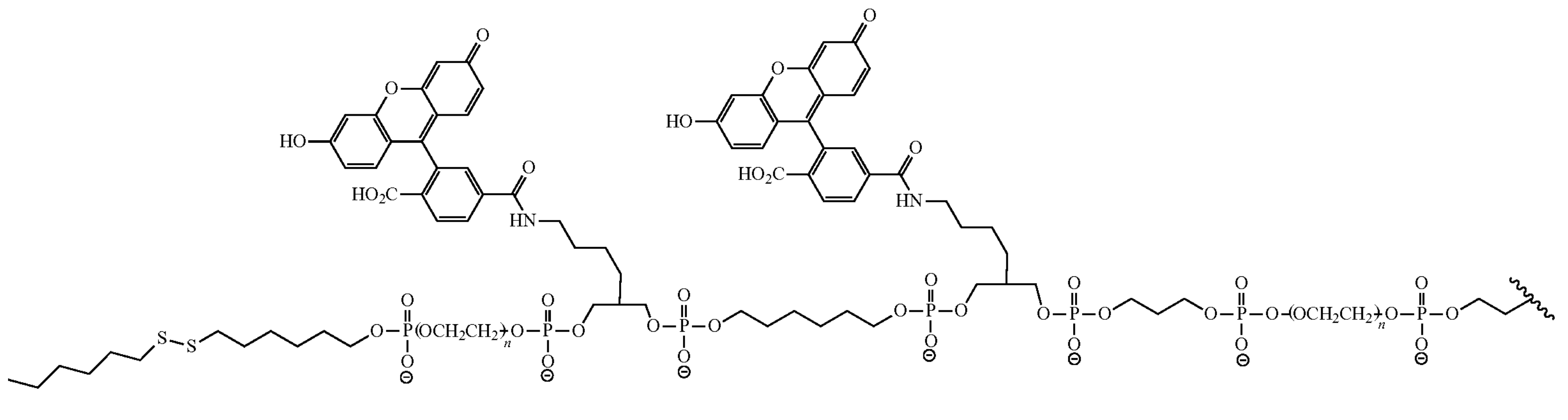 |

TABLE 3-continued
| Exemplary Compounds of Structure (III) or (IV) | |
|---|---|
| No. | Structure |
| | 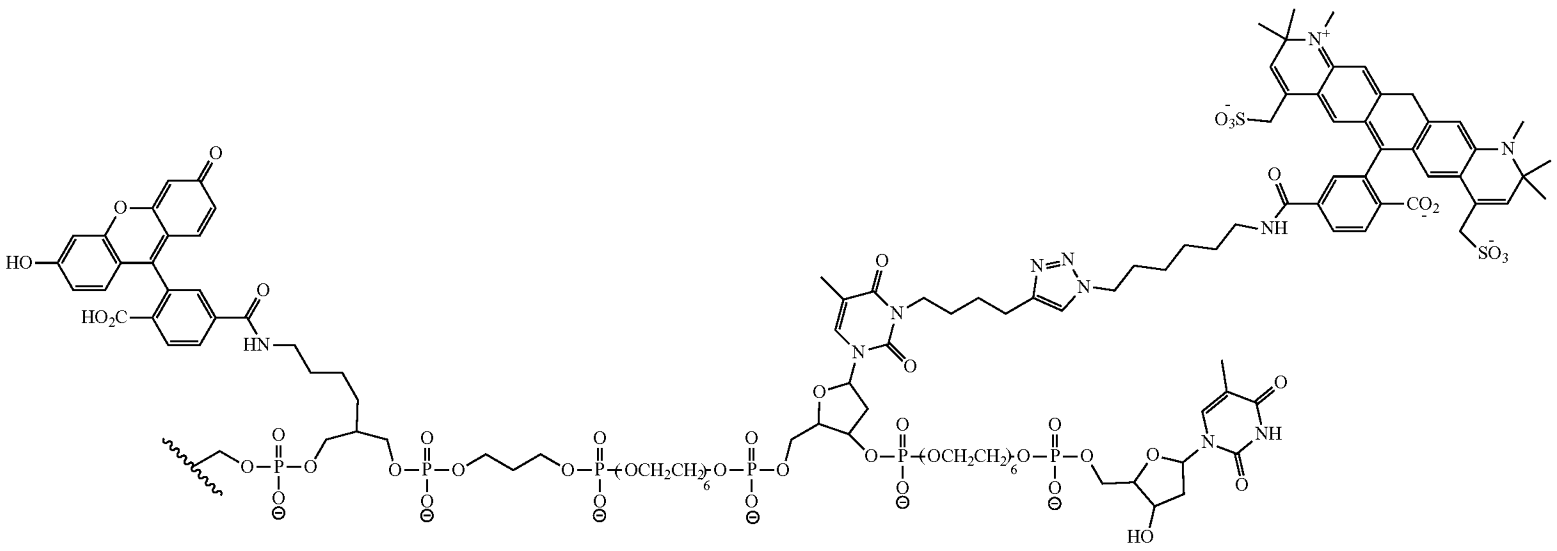 n = 15-30 |

TABLE 3-continued
Exemplary Compounds of Structure (III) or (IV)
| No. | Structure |
|---|---|
| A-6 | 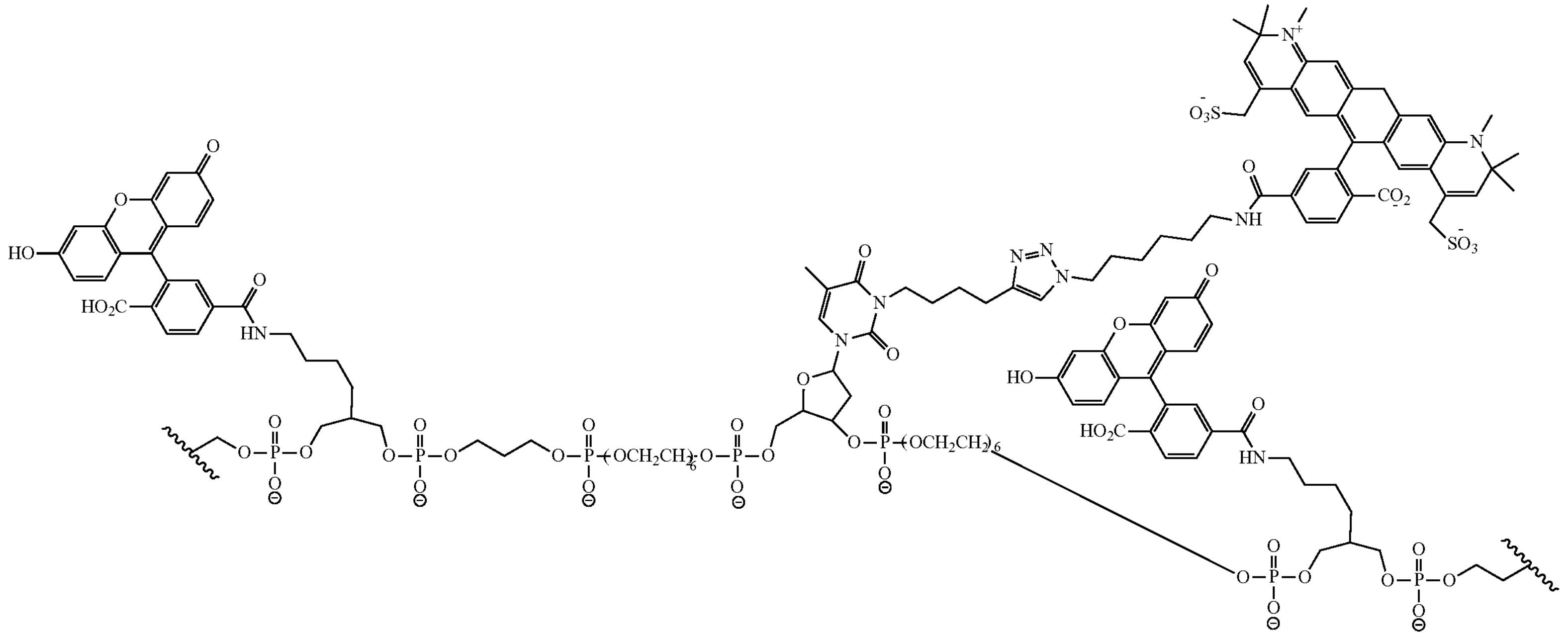 |

TABLE 3-continued
| Exemplary Compounds of Structure (III) or (IV) | |
|---|---|
| No. | Structure |
| | 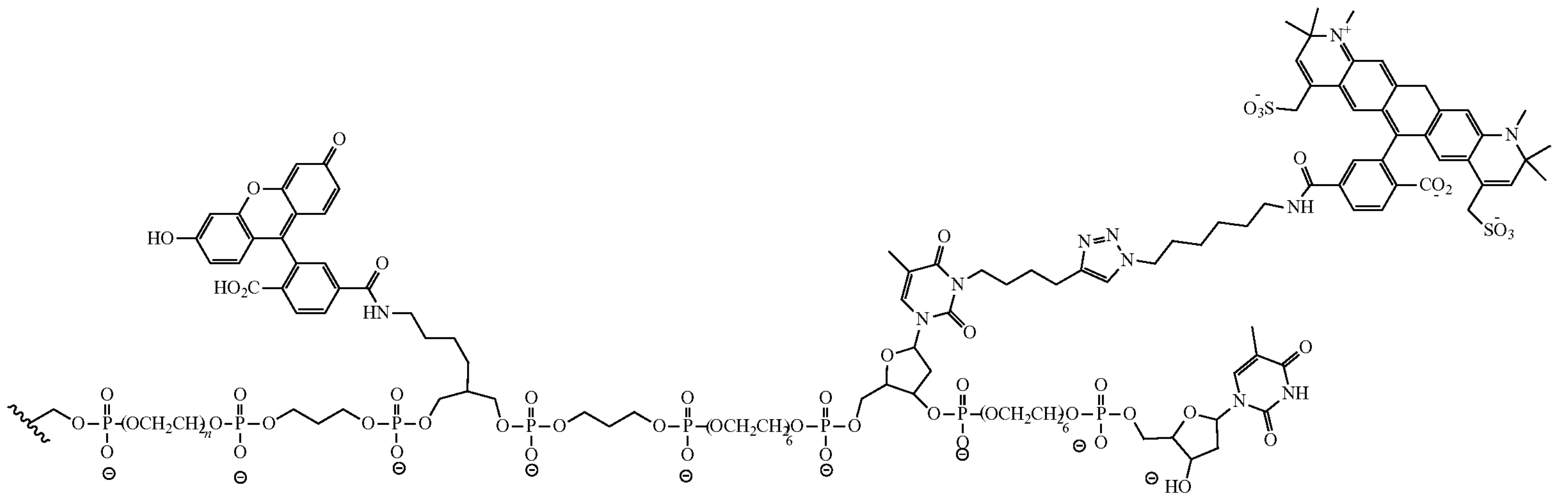 |
n = 15-30

TABLE 3-continued
| Exemplary Compounds of Structure (III) or (IV) | |
|---|---|
| No. | Structure |
| A-7 | 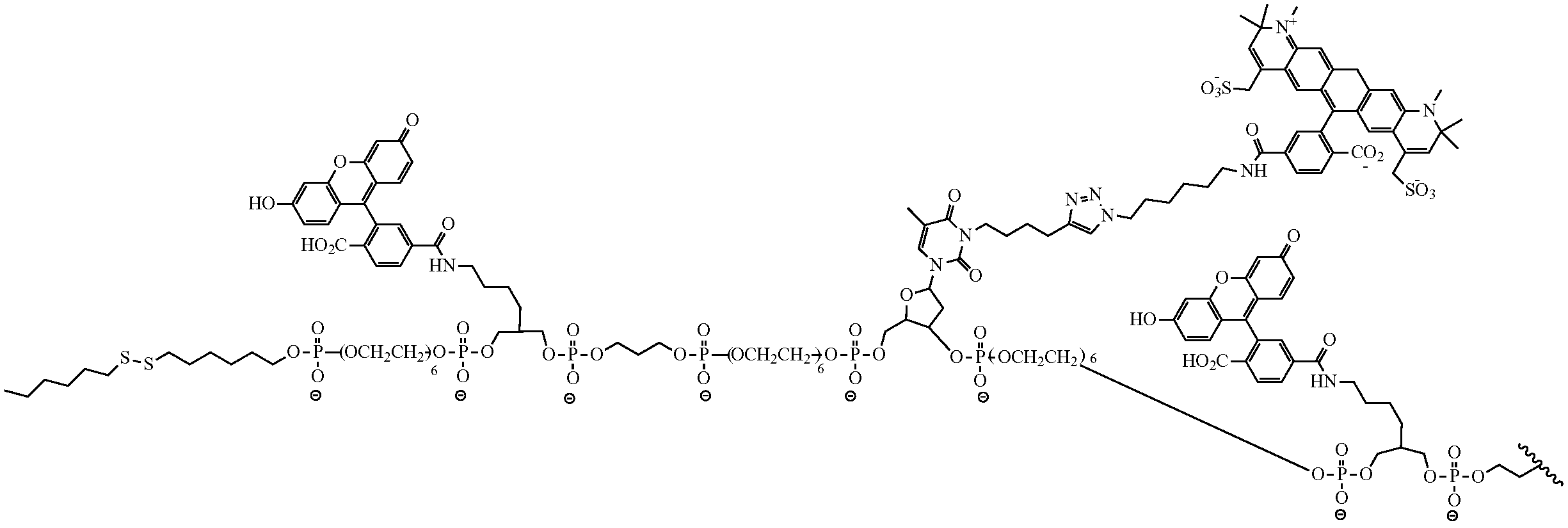 |

TABLE 3-continued
| Exemplary Compounds of Structure (III) or (IV) | |
|---|---|
| No. | Structure |
| | 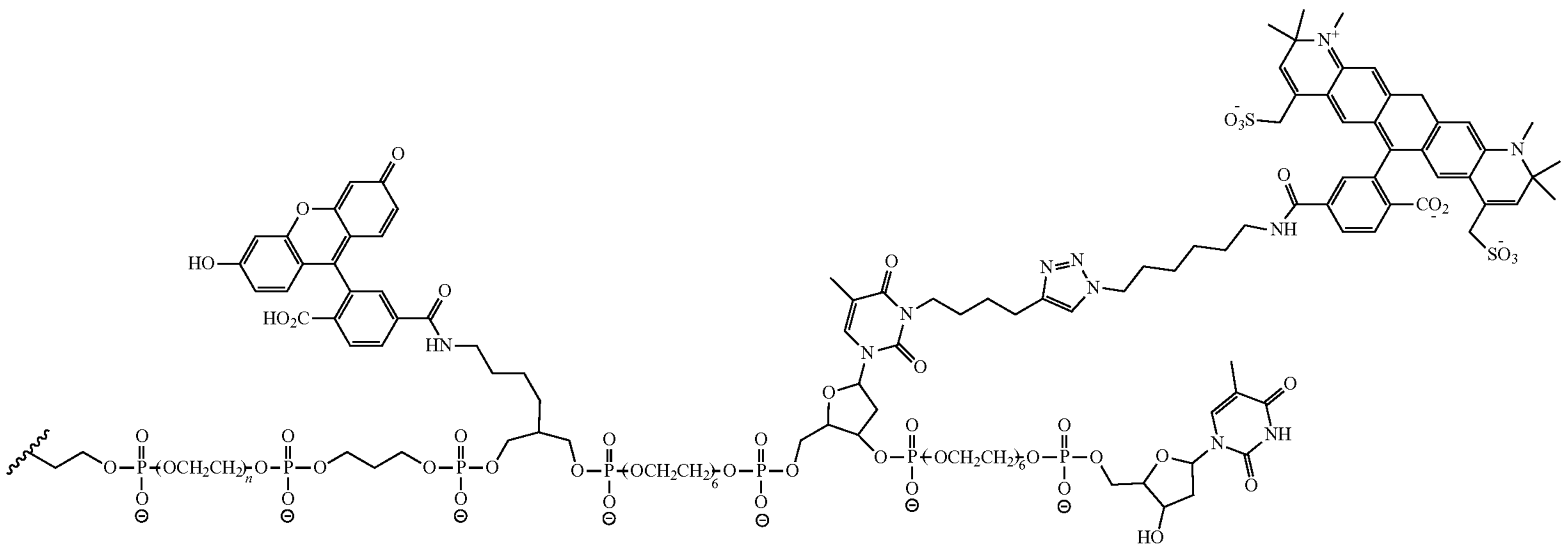 n = 15-30 |

TABLE 3-continued
| Exemplary Compounds of Structure (III) or (IV) | |
|---|---|
| No. | Structure |
| A-8 | 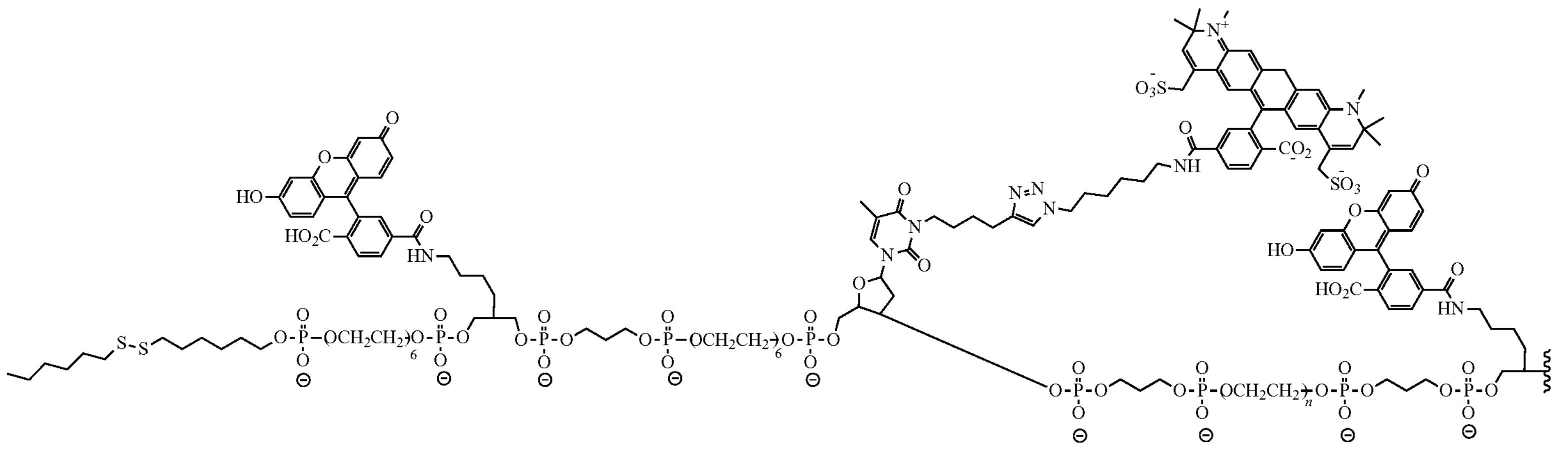 |
n = 15-30

TABLE 3-continued
| Exemplary Compounds of Structure (III) or (IV) | |
|---|---|
| No. | Structure |
| | 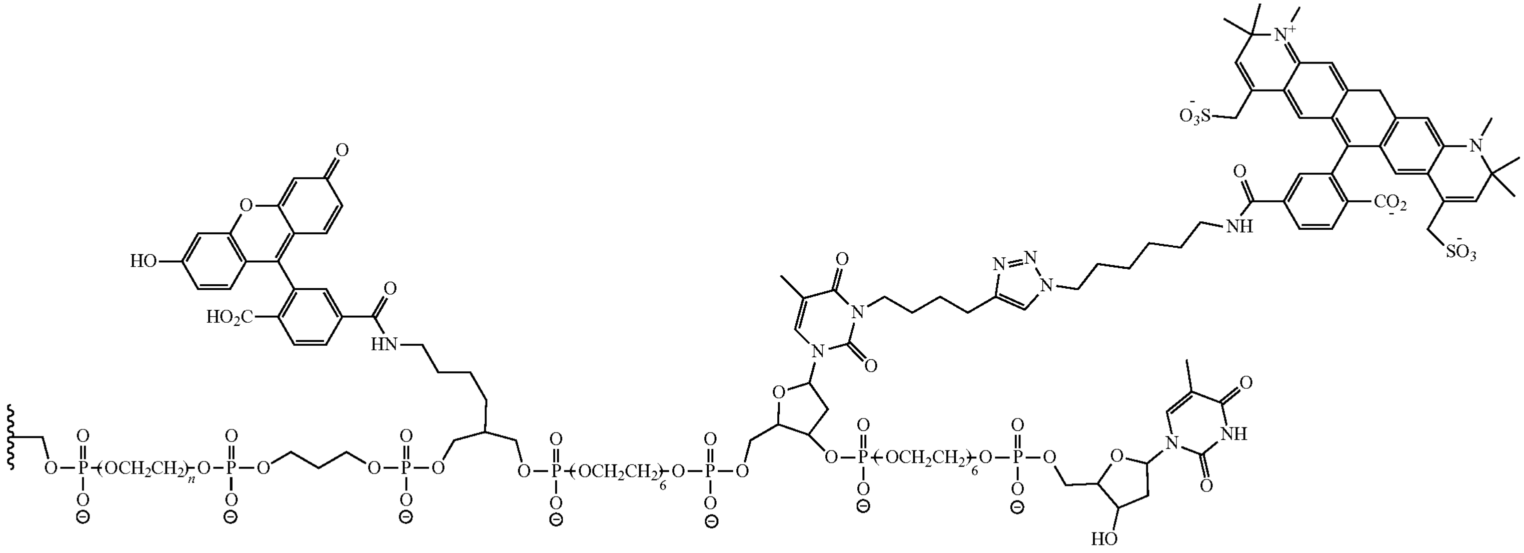 n = 15-30 |

In various embodiments, $G^1$ or $G^2$ in the compounds of Table 3 is alkynyl, such as ethynyl. In other embodiments, $G^1$ or $G^2$ in the compounds of Table 3 is an azide. In other embodiments, $G^1$ or $G^2$ in the compounds of Table 3 is amino ($NH_2$). In other embodiments, $G^1$ or $G^2$ in the compounds of Table 3 is an isothiocyanate. In other embodiments, $G^1$ or $G^2$ in the compounds of Table 3 is an activated ester, such as an ester of N-hydroxysuccinimide.

The compounds of structure (III) or (IV) can be used in various methods, for example in embodiments is provided a method for labeling an analyte, such as an analyte molecule, or targeting moiety, the method comprising:

(a) admixing any of the described compounds of structure (III) or (IV), wherein $R^2$ or $R^3$ is Q or a linker comprising a covalent bond to Q, with the analyte molecule or targeting moiety;

(b) forming a conjugate of the compound and the analyte molecule or targeting moiety; and (c) reacting the conjugate with a compound of formula M-$L^{1b}$-$G^{1'}$ or $G^{2'}$, thereby forming at least one covalent bond by reaction of at least one $G^1$ or $G^2$ and at least one $G^{1'}$ or $G^{2'}$, wherein:

$M^1$ and $M^2$ are a moiety comprising two or more carbon-carbon double bonds and at least one degree of conjugation;

$L^{1b}$ is an optional alkylene, heteroalkylene or heteroatomic linker; and $G^{1'}$ or $G^{2'}$ is a reactive group complementary to $G^1$ or $G^2$, respectively.

A different embodiment is a method for labeling an analyte, such as an analyte molecule or targeting moiety, the method comprising:

(a) admixing any of the compounds of structure (III) or (IV) disclosed herein, wherein $R^2$ or $R^3$ is Q or a linker comprising a covalent bond to Q, with a compound of formula M-$L^{1b}$-G', thereby forming at least one covalent bond by reaction of G and G'; and (b) reacting the product of step (A) with the analyte molecule or targeting moiety, thereby forming a conjugate of the product of step (A) and the analyte molecule or targeting moiety, wherein:

$M^1$ and $M^2$ are a moiety comprising two or more carbon-carbon double bonds and at least one degree of conjugation;

$L^{1b}$ is an optional alkylene, heteroalkylene or heteroatomic linker; and $G^{1'}$ or $G^{2'}$ is a reactive group complementary to $G^1$ or $G^2$, respectively.

Further, as noted above, the compounds of structure (III) are useful for preparation of compounds of structure (I), and the compounds of structure (IV) are useful for preparation of compounds of structure (II). Accordingly, in one embodiment is provided a method for preparing a compound of structure (I), the method comprising admixing a compound of structure (III) with a compound of formula M-$L^{1b}$-G', thereby forming at least one covalent bond by reaction of G and G'. In another embodiment is provided a method for preparing a compound of structure (II), the method comprising admixing a compound of structure (IV) with a compound of formula M-$L^{1b}$-G', thereby forming at least one covalent bond by reaction of G and G', wherein:

$M^1$ and $M^2$ are a moiety comprising two or more carbon-carbon double bonds and at least one degree of conjugation or $M^1$ and $M^2$ are, at each occurrence, independently a chromophore, provided that at least one of $M^1$ and $M^2$ is a FRET donor, and another one of $M^1$ and $M^2$ is a corresponding FRET acceptor;

$L^{1b}$ is an optional alkylene, heteroalkylene or heteroatomic linker; and

G' is a reactive group complementary to G.

The following examples are provided for purposes of illustration, not limitation.

EXAMPLES

General Methods

Mass spectral analysis was performed on a Waters/Micromass Quattro micro MS/MS system (in MS only mode) using MassLynx 4.1 acquisition software. Mobile phase used for LC/MS on dyes was 100 mM 1,1,1,3,3,3-hexafluoro-2-propanol (HFIP), 8.6 mM triethylamine (TEA), pH 8. Phosphoramidites and precursor molecules were also analyzed using a Waters Acquity UHPLC system with a 2.1 mm×50 mm Acquity BEH-C18 column held at 45° C., employing an acetonitrile/water mobile phase gradient. Molecular weights for monomer intermediates were obtained using tropylium cation infusion enhanced ionization on a Waters/Micromass Quattro micro MS/MS system (in MS only mode). Excitation and emission profiles experiments were recorded on a Cary Eclipse spectra photometer.

All reactions were carried out in oven dried glassware under a nitrogen atmosphere unless otherwise stated. Commercially available DNA synthesis reagents were purchased from Glen Research (Sterling, VA). Anhydrous pyridine, toluene, dichloromethane, diisopropylethyl amine, triethylamine, acetic acid, pyridine, and THF were purchased from Aldrich. All other chemicals were purchase from Aldrich or TCI and were used as is with no additional purification.

Example 1

Synthesis of Dyes with Alkylene-Polyethylene Glycol-Alkylene Spacer

Compounds with alkylene-polyethylene oxide-alkylene linkers were prepared as followed:

The oligofluoroside constructs (i.e., compounds of structure (I) or (II)) were synthesized on an Applied Biosystems 394 DNA/RNA synthesizer on 1 μmol scale and possessed a 3'-phosphate group or 3'-$S_2$—$(CH_2)_6$—OH group or any of the other groups described herein. Synthesis was performed directly on CPG beads or on Polystyrene solid support using standard phopshoporamadite chemistry. The oligofluorosides were synthesized in the 3' to 5' direction using standard solid phase DNA methods, and coupling employed standard β-cyanoethyl phosphoramidite chemistry. Fluoroside phosphoramidite and spacers (e.g., polyethylene glycol phosphoramidite, propane-diol phosphoramidite, butane-diol ohosphoramidite, and hexane-diol phosphoramidite) and linker (e.g., 5'-amino-modifier phosphoramidite and thiol-modifiers S2 phosphoramidite) were dissolved in acetonitrile to make 0.1 M solutions, and were added in successive order using the following synthesis cycle: 1) removal of the 5'-dimethoxytrityl protecting group with dichloroacetic acid in dichloromethane, 2) coupling of the next phosphoramidite with activator reagent in acetonitrile, 3) oxidation of P(III) to form stable P(v) with iodine/pyridine/water, and 4) capping of any unreacted 5'-hydroxyl groups with acetic anhydride/1-methylimidizole/acetonitrile. The synthesis cycle was repeated until the full length oligofluoroside construct was assembled. At the end of the chain assembly, the monomethoxytrityl (MMT) group or dimethoxytrityl (DMT) group was removed with dichloroacetic acid in dichloromethane.

The compounds were provided on controlled-pore glass (CPG) support at 0.2 umol scale in a labeled Eppendorf tube. 400 μL of 20-30% $NH_4OH$ was added and mixed gently. Open tubes were placed at 55° C. for −5 minutes or until excess gases had been liberated, and then were closed tightly and incubated for 2 hrs (+/−15 min.). Tubes were removed from the heat block and allowed to reach room temperature, followed by centrifugation at 13,400 RPM for 30 seconds to consolidate the supernatant and solids. Supernatant was carefully removed and placed into a labeled tube, and then 150 μL acetonitrile was added to wash the support. After the wash was added to the tubes they were placed into a CentriVap apparatus at 40° C. until dried.

The products were characterized by ESI-MS, UV-absorbance, and fluorescence spectroscopy.

Example 2

Comparative Stain Index from Flow Cytomeyry Measurements

Representative compounds of structure (I) comprising propylene/phosphate/polyethylene glycol/phosphate/propylene spacers (C3-PEG-C3) and 3, 5, 7 or 10 fluorophore moieties (referred to as C3-3xFAM, C3-5xFAM, C3-7xFAM, and C3-10xFAM, respectively) were prepared according to Example 1. Flow cytometry measurements for representative compounds of structure (I), control compound PEG-5xFAM, fluorescein (FITC) and Alexa Fluor® 488 dye (AF488), were conducted. Results are presented in FIG. 1. Representative compounds of structure (I) (C3-3xFAM, C3-5xFAM, C3-7xFAM and C3-10xFAM), control compound (PEG-5xFAM), FITC and AF488 are provided in Table 4.

TABLE 4

| Compound | Spacer | Strucutre |
| --- | --- | --- |
| C3-3xFAM | C3-PEG-C3 | 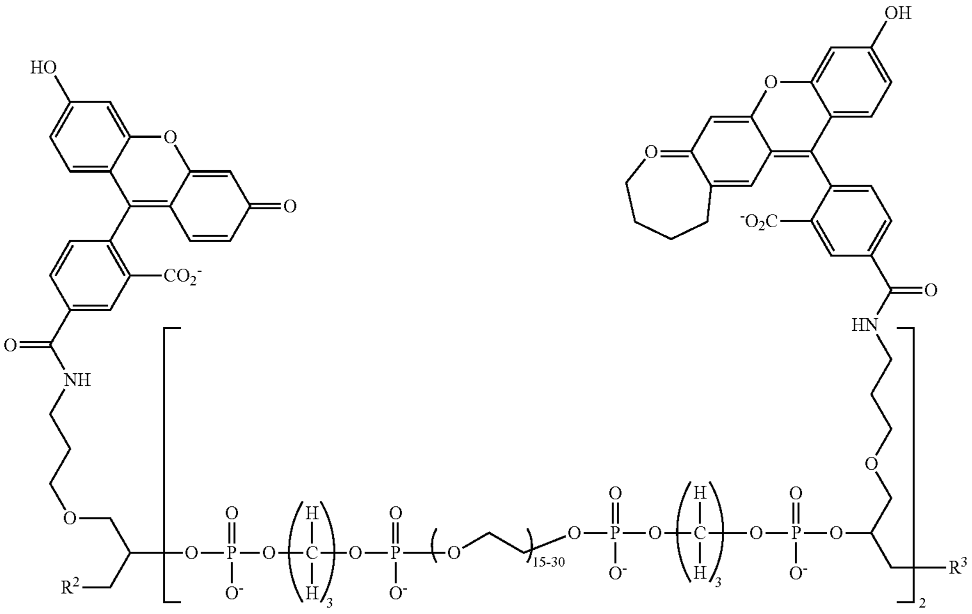 |

TABLE 4-continued
| Compound | Spacer | Strucutre |
| --- | --- | --- |
| C3-5xFAM | C3-PEG-C3 | 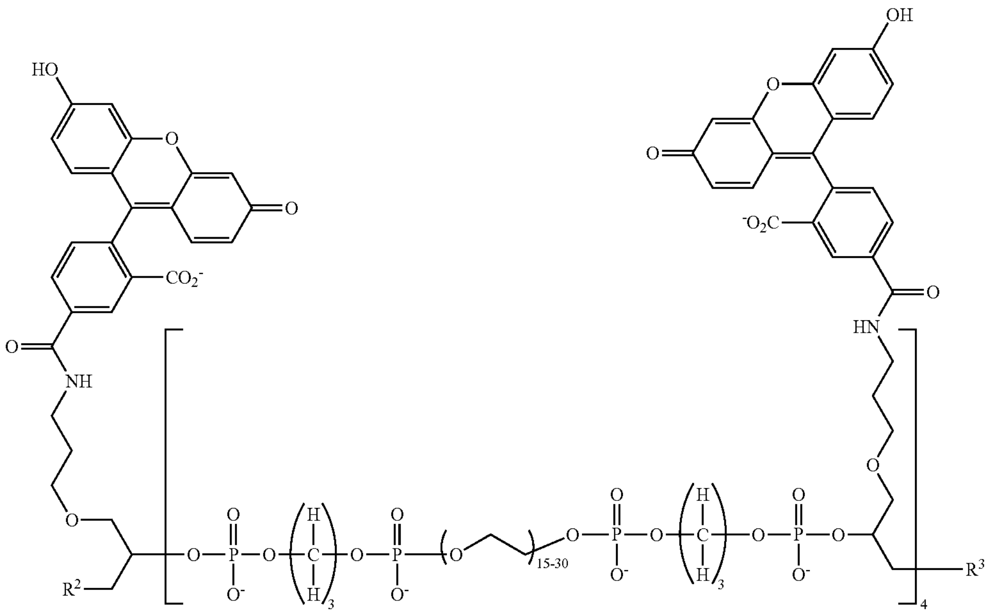 |
| C3-7xFAM | C3-PEG-C3 | 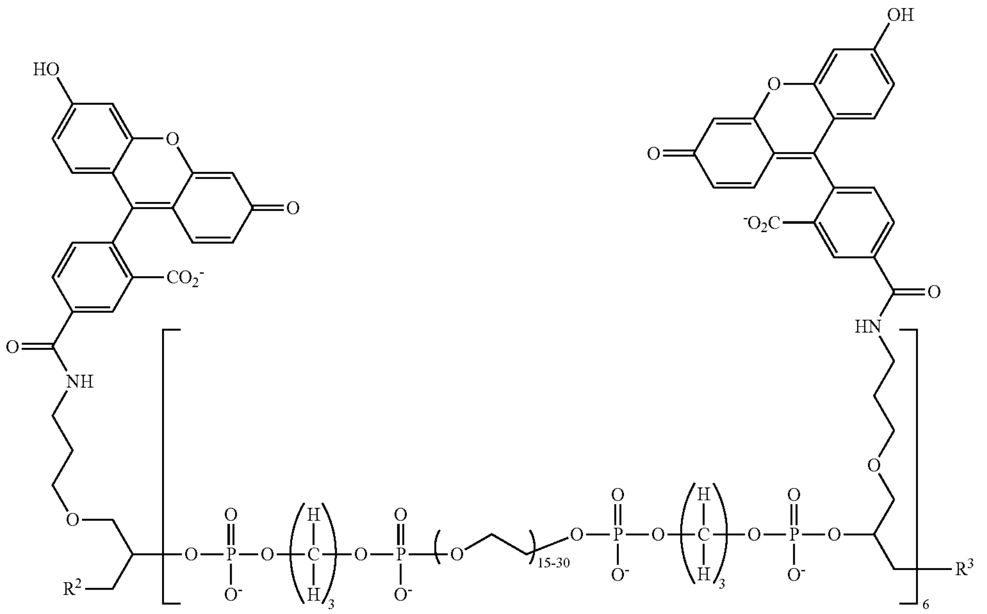 |

TABLE 4-continued
| Compound | Spacer | Strucutre |
| --- | --- | --- |
| C3-10xFAM | C3-PEG-C3 | 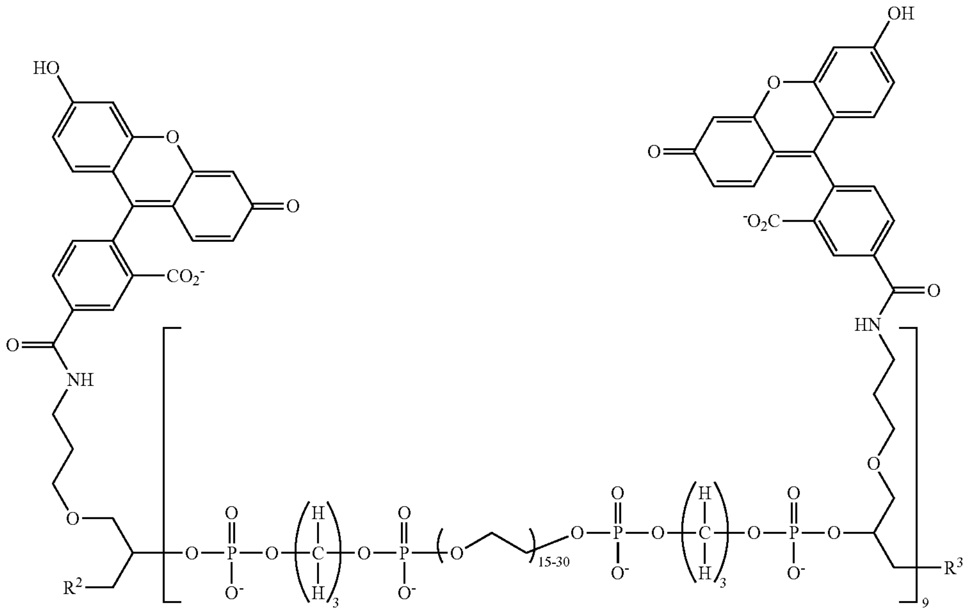 |
| PEG-5xFAM | C3-PEG-C3 | 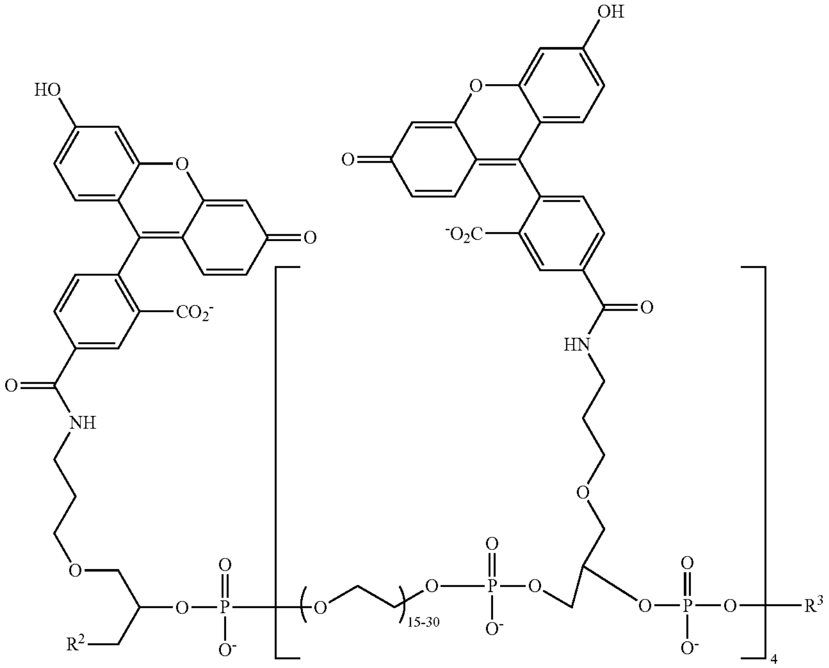 |
| FITC | | 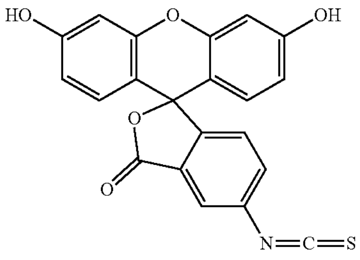 [SMILES: O=C1OC2(c3ccc(O)cc3Oc3cc(O)ccc32)c2ccc(N=C=S)cc21] |

TABLE 4-continued

| Compound | Spacer | Strucutre |
|---|---|---|
| AF488 | | 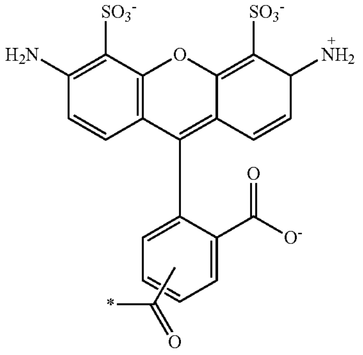 |

As used in Table 4, $R^2$ and $R^3$ refer to moieties having the following structures, respectively:

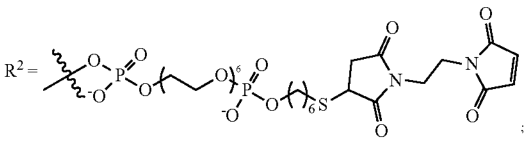

; and

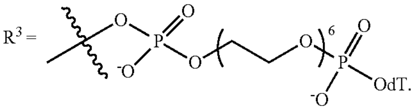

The data for the stain index show that by introducing a linker including propylene (C3) linker groups around a PEG linker group, compounds according to embodiments of the present disclosure have brightnesses about 4-7 times higher than that that of FITC and AF488. Compounds according to embodiments of the present disclosure also shown higher brightnesses than corresponding control compound (PEG-5×FAM) containing the same amount of fluorophores (i.e., dyes). The increased brightnesses may be due to the more spatial separation between the fluorophore moieties by introducing propylene linker groups around PEG.

Example 3

Comparative Fluorescence Emission Response Over Time

Figure 2:
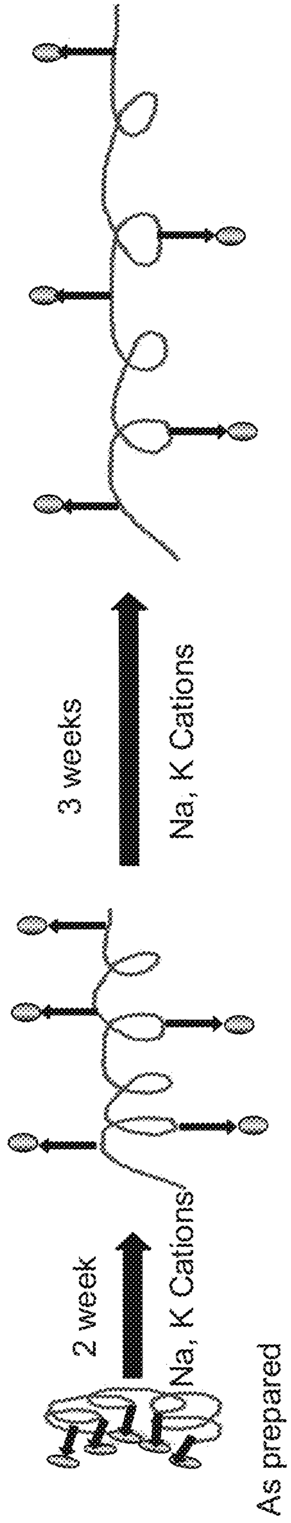
FIG. 2 shows a schematic representation of increased separation efficiencies of a representative compound in a NaCl and KCl solution over time.

The fluorescence emission stability of compounds of structure (I) comprising C3-PEG-C3 spacers and 3, 5, 7 or 10 fluorophore moieties (i.e., compounds C3-3×FAM, C3-5×FAM, C3-7×FAM, and C3-10×FAM provided in Table 4) were compared with corresponding control compounds FITC, AF488. Results are summarized in Table 5. The data show that compounds according to embodiments of the present disclosure have increased fluorescence emission over time. After three weeks, the brightnesses of all the compounds according to embodiments of the present disclosure are increased, while the brightnesses of the control compounds, FITC and AF488 remain the same. The increased brightness over time may be due to the increased separation efficiency as compounds of structure (I) "age" over time (FIG. 2).

TABLE 5

| | Week 1 | | Week 3 | |
|---|---|---|---|---|
| Compound | vs FITC | vs AF488 | vs FITC | vs AF488 |
| C3-3xFAM | 1.7 | 1.3 | 3.0 | 1.7 |
| C3-5xFAM | 1.2 | 0.9 | 5.2 | 2.9 |
| C3-7xFAM | 1.1 | 0.8 | 5.9 | 3.3 |
| C3-10xFAM | 1.1 | 0.8 | 7.4 | 4.1 |
| FITC | 1 | 1 | 1 | 1 |
| AF488 | 1 | 1 | 1 | 1 |

Example 4

General Flow Cytometry Methods

Unless otherwise noted, the following general procedures were used in throughout the following Examples:

Lysis of Whole Blood:

Buffered Ammonium Chloride Method. For staining of live cells, ethylenediaminetetraacetate (EDTA) anticoagulated normal human blood is bulk lysed with Ammonium Chloride solution (ACK), 15 mL blood to 35 mL lyse for 15 min at room temperature (RT). The cells were washed twice with 50% Hank's Balanced Salt Solution (HBSS) and 50% 1% Fetal Bovine Serum (FBS) 1× Dulbecco's Phosphate-Buffered Saline (PBS) with 0.02% sodium azide. The cells were then re-suspended to 100 μL/test/0.1-1×10e6 in donor plasma. Cells in plasma were added to pre-diluted antibodies for $V_f$ of 100 μL 1% Bovine Serum Albumin (BSA) and 1× DPBS with 0.02% sodium azide in polypropylene 96 well HTS plates. After incubating for 45 min. at RT, the cells were washed twice with 50% HBSS and 50%-1% FBS 1× DPBS with 0.02% sodium azide.

Lyse/Fixation Method. Blood was lysed with 1.0 mL RBC lysing solution (ammonium chloride), 100-15 mL blood to 35 mL lyse for 15 min at RT. The cells were then washed twice with 50% HBSS and 50%-1% FBS 1× DPBS with 0.02% sodium azide. Cells were then re-suspended to 100 μL/test/1×10e6 in donor plasma. Pre-diluted antibodies were added in 100 μL 1% BSA and 1× DPBS with 0.02% sodium azide. 100 μL cells were added to 96 well polypropylene HTS plates (total 200 μL test size). After incubation for 45 min. at RT the cells were washed twice with 50% HBSS and 50% 1% FBS 1× DPBS with 0.02% sodium azide.

Preparation of Antibody Conjugates:

Antibody conjugates were prepared by reacting a compound of structure (I) or (II) comprising a Q moiety having the following structure:

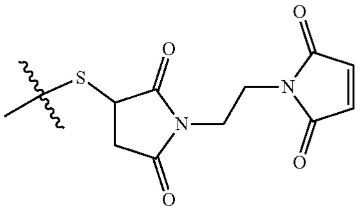 [SMILES: *SC1CC(=O)N(CCN2C(=O)C=CC2=O)C1=O]

with the desired antibody. The compound and antibody are thus conjugated by reaction of an S on the antibody with the Q moiety to form the following linking structure:

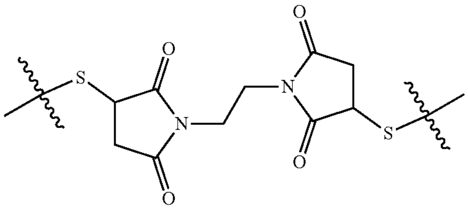 [SMILES: *SC1CC(=O)N(CCN2C(=O)CC(S*)C2=O)C1=O]

Antibody conjugates are indicated by the antibody name following by the compound number. For example, UCHT1-C3-3xFx indicates a conjugate formed between a UCHT1 antibody and a compound of structure (I) comprising $C_3$ linkers and three (3) fluorophores (Fx). If a referenced compound number does not include the above Q moiety in Table 1, it is understood that the Q moiety was installed and the conjugate prepared from the resulting compound having the Q moiety.

Dilution of Conjugates:

Antibodies were brought to RT. The antibody conjugates were diluted to concentrations in a range of 0.1-540 nM (8.0 micrograms or less per test) in a cell staining buffer (1× DPBS, 1% BSA, 0.02% sodium azide). In some examples, serial dilutions for each sample started at 269 nM antibody in cell staining buffer, and the antibody dilutions were kept protected from light until use. In other experiments, dilutions started at 4.0 μg antibody/test size, with the test size ranging from 100-200 μL. Titers were performed in two fold or four fold dilutions to generate binding curves. In some cases, 8.0 or 2.0 μg/test size were used in first well in a dilution series.

Flow Cytometry with Conjugate:

After physical characterization, the conjugates were tested for activity and functionality (antibody binding affinity and brightness of dye) and compared to reference antibody staining. Then the quality of resolution was determined by reviewing the brightness in comparison to auto-fluorescent negative controls, and other non-specific binding using the flow cytometer. Whole blood screening was the most routine for testing the conjugates. Bridging studies were implemented as new constructs were formed.

Perform Free Dye Flow Cytometry:

After molecular and physical characterization, the dyes were also tested for potential affinity to cells compared to a reference dye stain. Because dyes have the potential to also function as cellular probes and bind to cellular material, dyes can be generally screened against blood at high concentrations (>100 nM-to-10,000 nM) to ascertain specific characteristics. Expected or unexpected off target binding was then qualified by evaluating brightness and linearity upon dilution in comparison to auto-fluorescent negative controls, and other dye controls using the flow cytometer.

Flow Cytometry Workflow:

Cells were cultured and observed for visual signs of metabolic stress for dye screening or off target binding (data not shown), or fresh healthy cells were used for conjugate screening. Cells were counted periodically to check cell density (1x10e5 and 1x10e6 viable cells/mL). Antibody conjugates were diluted (preferably in plate or tubes) before harvesting cells in stain buffer (DPBS, 0.1% BSA, 0.02% sodium azide). Cells with a viability range of 80-85% were used. The cells were washed twice by centrifuging and washing cells with buffer to remove pH indicator, and to block cells with Ig and other proteins contained in FBS. The cell density was adjusted to test size in stain buffer. The cells were plated, one test per well, or dyes (pre-diluted) were applied to cells in plate. Then, the cells were incubated 45 min at 23° C. The cells were washed twice by centrifuging and washing cells with wash buffer, then aspirating the plate. The cells were re-suspended in acquisition buffer. 5000 intact cells were acquired by flow cytometry.

The fluorescence of the dyes was detected by 488 nM blue laser line by flow cytometry with peak emission (521 nM) detected using 525/50 bandpass filter. At least 1500 intact cells, with target acquisitions of 3000-5000 intact cells, were acquired by flow cytometry and analyzed to identify viable cells present in the cell preparation.

Data Analysis Methods:

Descriptive Statistics. The EC-800 software allows a user to collect numerous statistical data for each sample acquisition. Mean or Median Fluorescence Intensity (MFI) in the FL1-A channel was used to measure the brightness of an antibody-dye reagent when it was being interrogated by flow cytometry and when noise was reviewed. Other statistics were evaluated to determine dye characteristics and overall quality of the reagents including median Signal-to-Noise and absolute fluorescence (median or Geomean).

Histograms. The flow cytometry events were gated by size on forward versus side scatter (cell volume versus cell granularity). Those cells were then gated by fluorescent emission at 515 nm for Mean Fluorescence Intensity (MFI). The data collected are presented as dual parameter histograms plotted as number of events on the y-axis versus fluorescent intensity, which is represented on a log scale on the x-axis. The data may be summarized by affinity curves, or histograms of relative fluorescence intensity.

Binding Curves. MFI was chosen as it is the parameter that best measures the brightness of an antibody-dye reagent when it is being interrogated by FCM, this can be expressed as the geometric mean, median, or mean, and represent absolute fluorescence measurements. For comparison, where the noise can be highly characterized, a Signal-to-Noise ratio is reported as MFI, S/N.

Bi-Variate, Dual Parameter Histograms. In some cases, the FCM events were not gated in order to review qualitative outputs, and data are expressed by cell granularity (SSC) versus dye fluorescence. This method allows for the overall evaluation of all populations recovered in whole blood.

Example 5

Flow cytometry analysis of control compound (Spacer=PEG) and compound of structure (I) (Spacer=propylene/phosphate/PEG/phosphate/propylene (C3-PEG-C3)) sequence constructs on various dyes were conjugated to CD4 (clone OKT4) antibody and eluted in 1× d-PBS (phosphate buffered saline). The dyes used include FAM, pacific blue (PB), Alexa Fluor® 532 (AF532), and Alexa Fluor® 660 (AF660). Whole blood was stained using 0.5 ug of the antibody conjugates and screened on a spectral instrument.

Table 6 shows the difference in Stain Index (SI) between control compounds with PEG spacers and compounds of structure (I) with C3-PEG-C3 spacers. Compounds of structure (I) with C3-PEG-C3 spacers have higher SI values than the corresponding control compound with PEG spacers and existing compounds on the market. Compounds of structure (I) with C3-PEG-C3 spacers also show increase in the SI values as the number of the fluorophores on the backbone increases.

TABLE 6

| Compound (Spacer) | DOL | Signal to Noise Ratio | Stain Index |
|---|---|---|---|
| 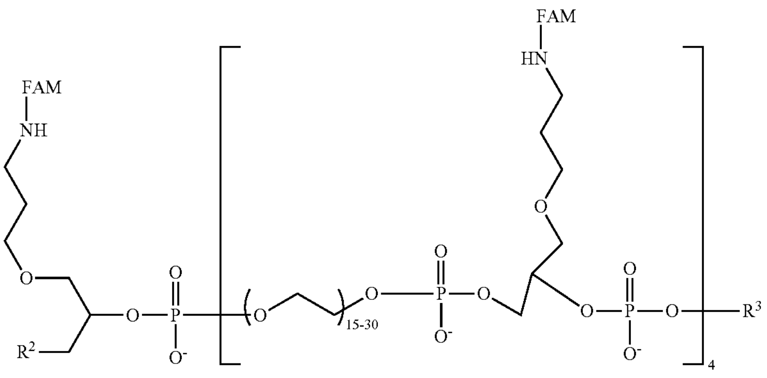 PEG-5xFAM (PEG) | 3.25 | 105.1 | 58.8 |
| 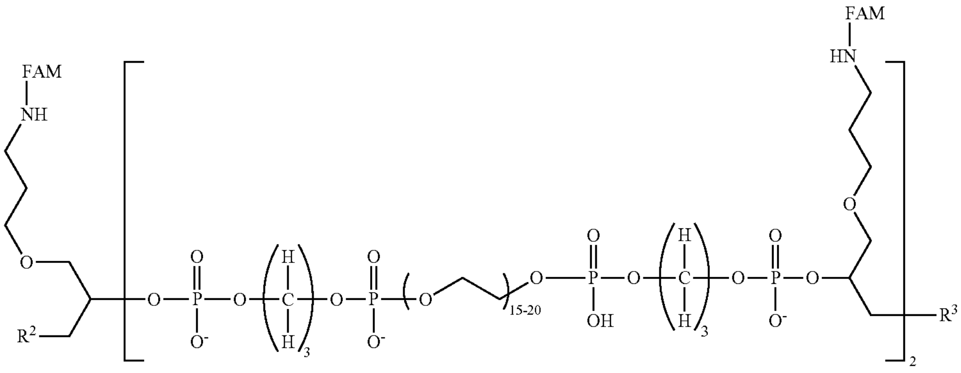 C3-3xFAM (C3-PEG-C3) | 5.07 | 125.6 | 75.3 |
| 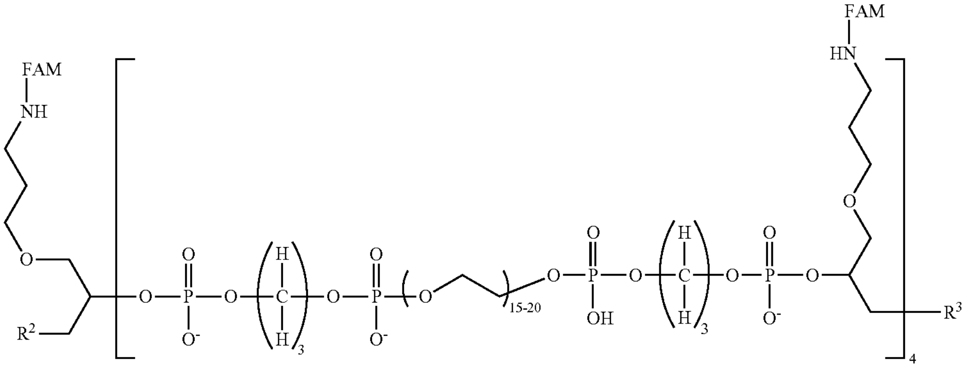 C3-5xFAM (C3-PEG-C3) | 4.35 | 280.6 | 103.4 |

TABLE 6-continued
| Compound (Spacer) | DOL | Signal to Noise Ratio | Stain Index |
|---|---|---|---|
| 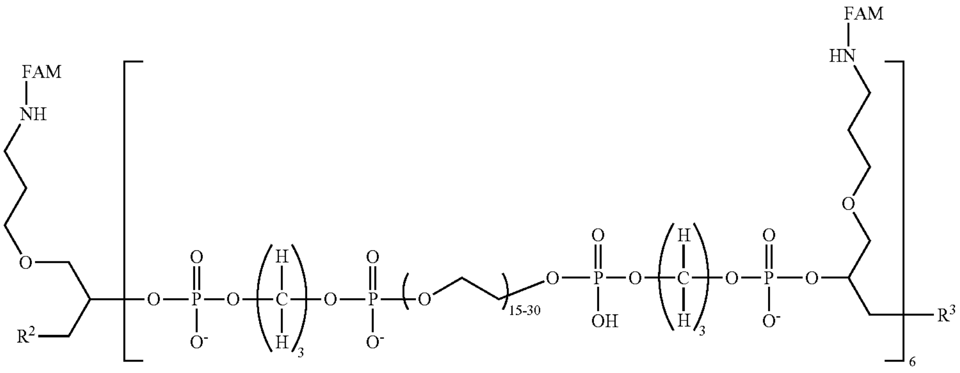 C3-7xFAM (C3-PEG-C3) | 3.70 | 351.1 | 148.8 |
| 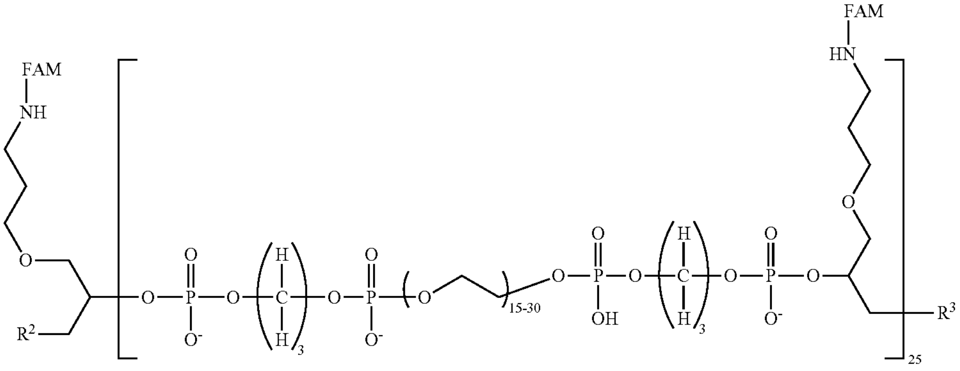 C3-10xFAM (C3-PEG-C3) | 2.91 | 291.5 | 153.3 |
| 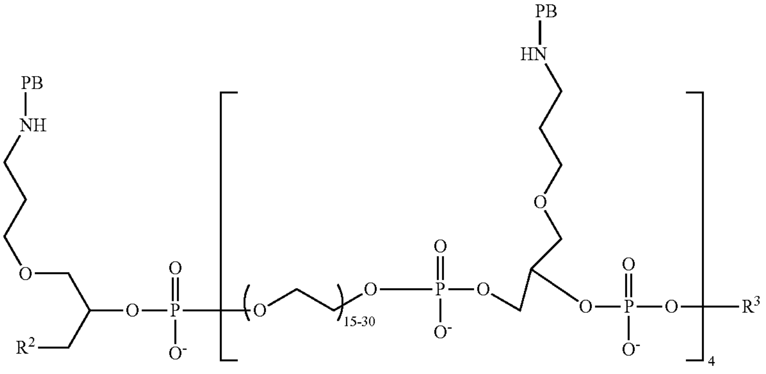 PEG-5xPB (PEG) | 3.25 | 122.3 | 71.6 |

TABLE 6-continued
| Compound (Spacer) | DOL | Signal to Noise Ratio | Stain Index |
|---|---|---|---|
| 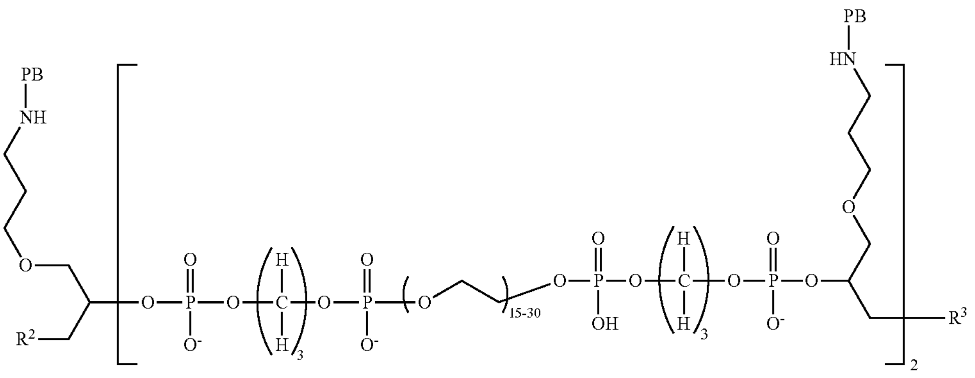 C3-3xPB (C3-PEG-C3) | 5.07 | 124.3 | 95.5 |
| 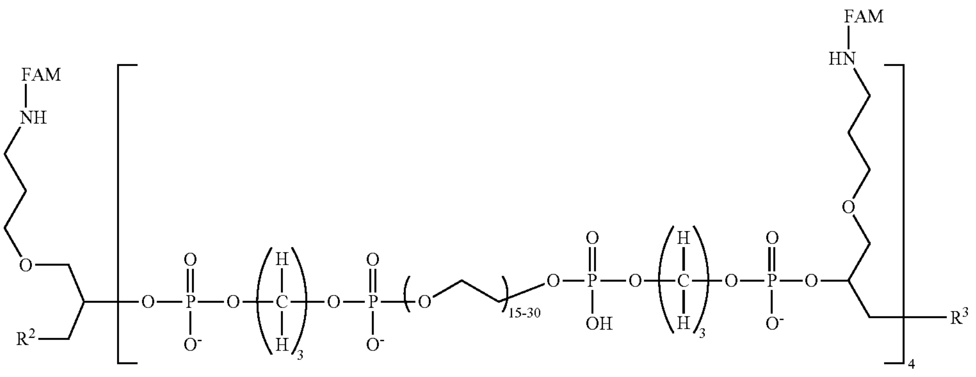 C3-5xPB (C3-PEG-C3) | 4.35 | 284.4 | 143.3 |
| 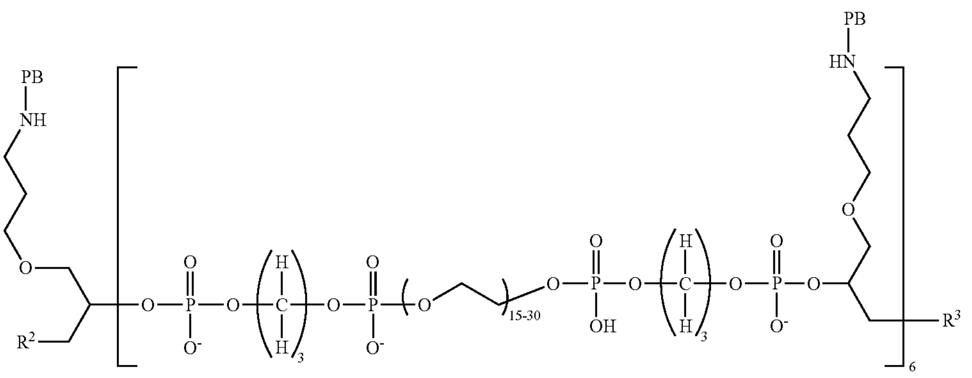 C3-7xPB (C3-PEG-C3) | 3.70 | 694.5 | 342.2 |

TABLE 6-continued
| Compound (Spacer) | DOL | Signal to Noise Ratio | Stain Index |
|---|---|---|---|
| 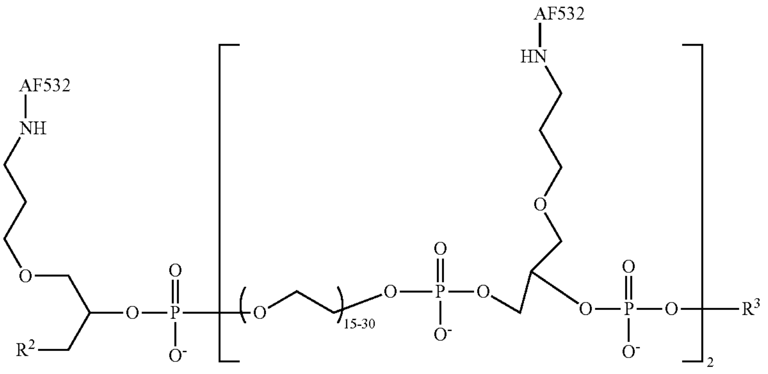 PEG-5xAF532 (PEG) | 5.60 | 29.0 | 24.3 |
| 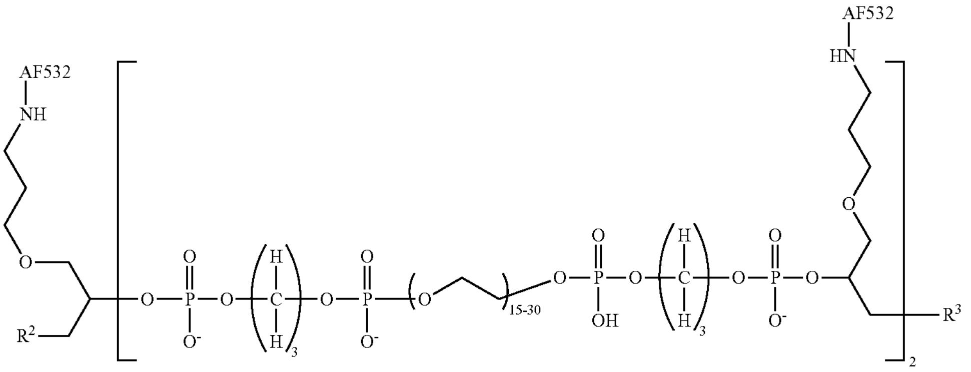 C3-3xAF532 (C3-PEG-C3) | 5.40 | 57.9 | 49.4 |
| 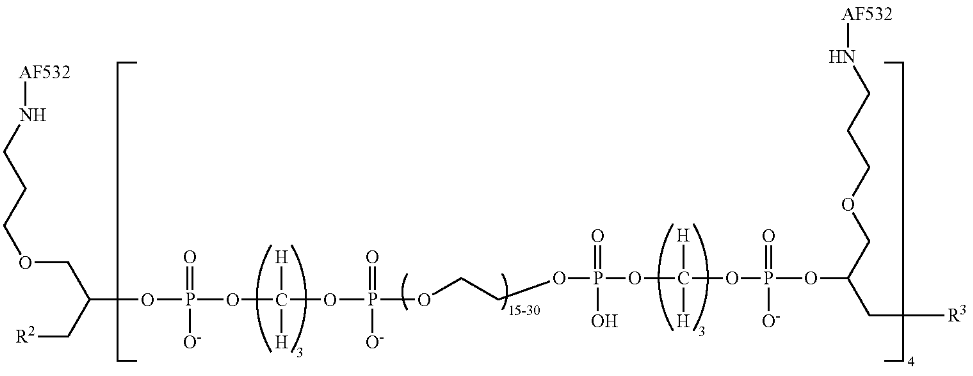 C3-5xAF532 (C3-PEG-C3) | 4.19 | 59.2 | 47.5 |

TABLE 6-continued
| Compound (Spacer) | DOL | Signal to Noise Ratio | Stain Index |
|---|---|---|---|
| 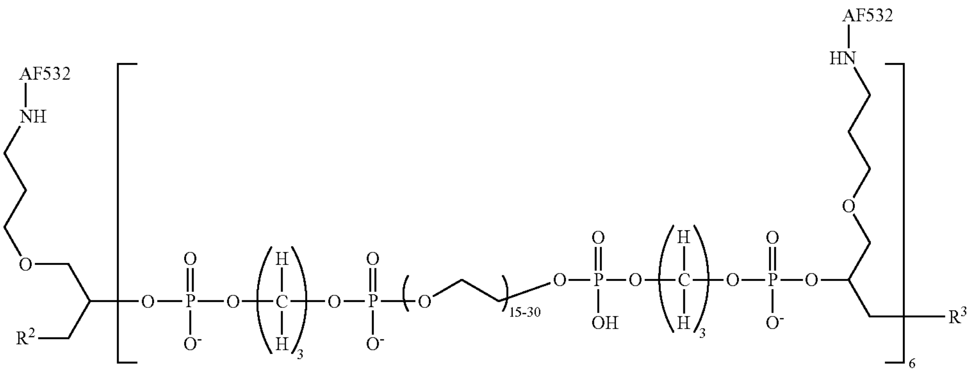 C3-7xAF532 (C3-PEG-C3) | 3.75 | 54.6 | 46.7 |
| 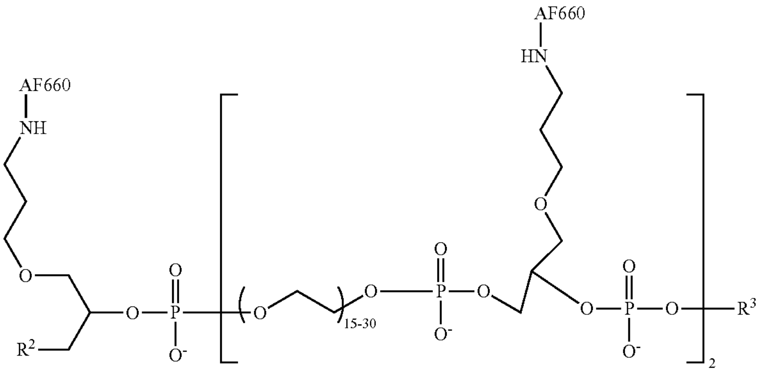 PEG-5xAF660 (PEG) | 3.57 | 308.5 | 25.3 |
| 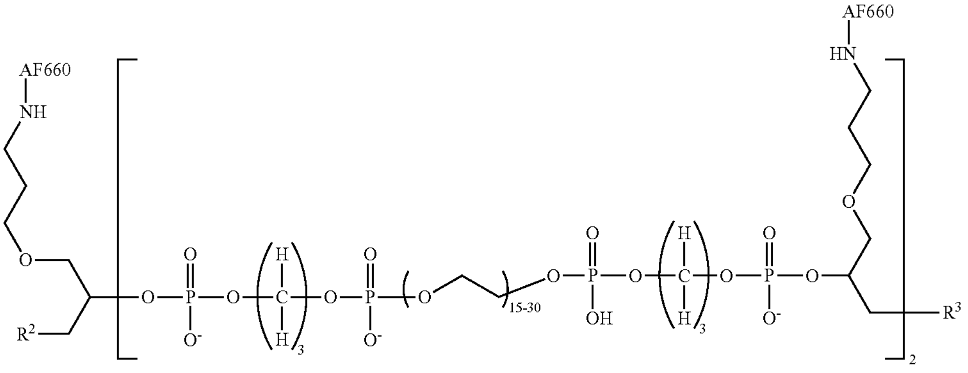 C3-3xAF660 (C3-PEG-C3) | 3.26 | 390.9 | 32.4 |

TABLE 6-continued
| Compound (Spacer) | DOL | Signal to Noise Ratio | Stain Index |
|---|---|---|---|
| 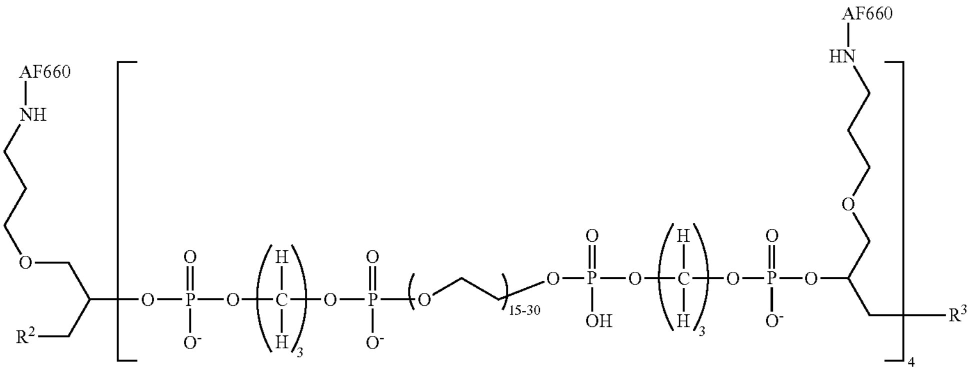 C3-5xAF660 (C3-PEG-C3) | 3.67 | 649.1 | 60.4 |
| 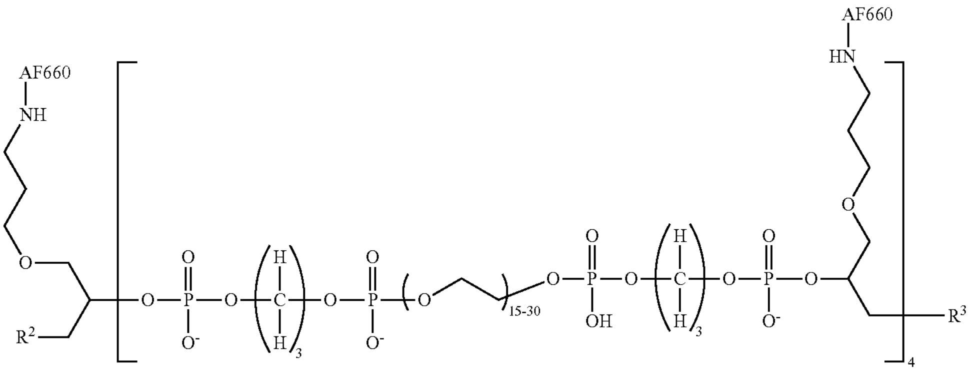 C3-7xAF660 (C3-PEG-C3) | 4.30 | 868.0 | 98.9 |

As used in Table 6, $R^2$ and $R^3$ refer to moieties having the following structures, respectively:

$R^2$ =
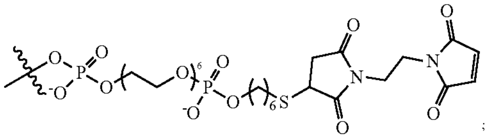
; and $R^3$ =
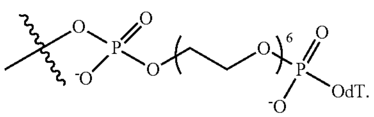

FAM refers to a moiety having one of the following structures:

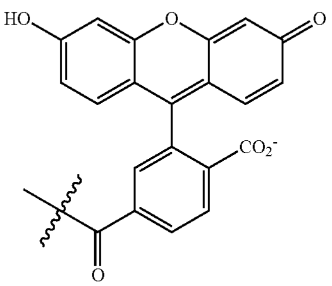
or

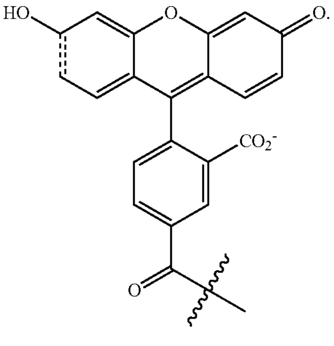

PB refers to a moiety having the following structure:

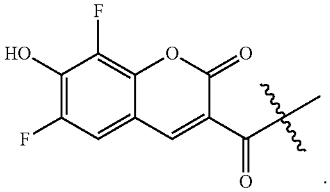 [SMILES: *C(=O)c1cc2cc(F)c(O)c(F)c2oc1=O]

AF532 refers to a moiety having the following structure:

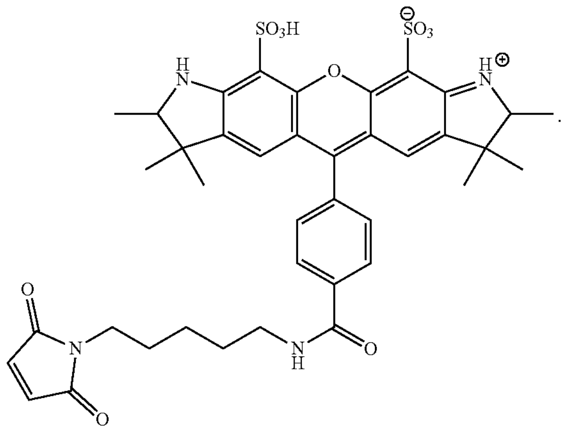

AF660 refers to a moiety having the following structure:

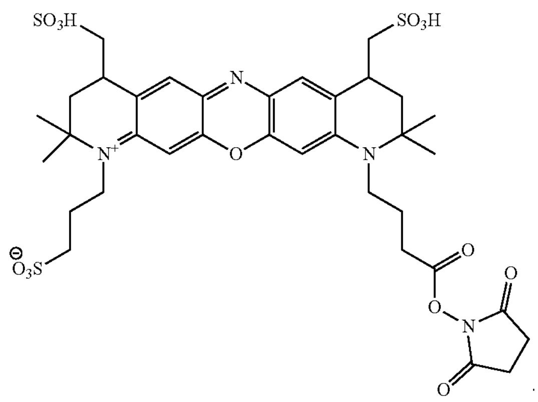

Example 6

Figure 3:
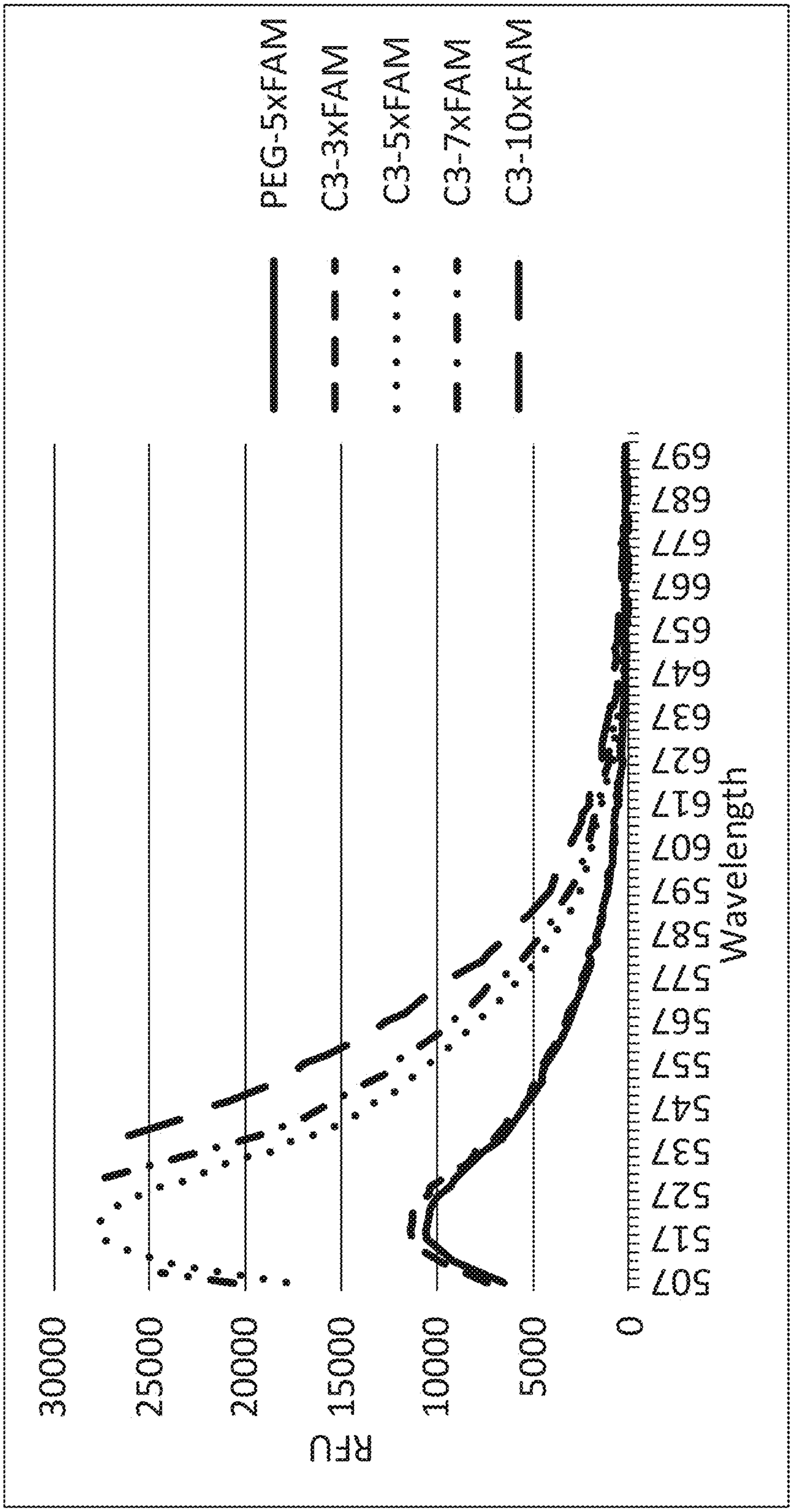
FIG. 3 provides in vitro analysis of control compound construct and representative compound of structures (I) constructs.

CD3 (clone UCHT1) antibody was conjugated to either control compound (PEG-5x-FAM) or compound of structure (I) (C3-3x-FAM, C3-5x-FAM, C3-7x-FAM, or C3-10x-FAM) constructs. 0.5 ug of antibody conjugates were diluted in Dulbecco 1× PBS and mixed using reverse pipetting and analyzed on Synergy plate reader at emission of 488 nm. The degree of labeling (DOL) was accounted for by taking the signal intensity and dividing by DOL and then graphed. The results of in vitro analysis of control compound (PEG-5× FAM) and compound of structure (I) (C3-3×FAM, C3-5× FAM, C3-7×FAM, or C3-10×FAM) are summarized in FIG. 3. As shown in FIG. 3, C3-10×FAM construct is as bright as PEG-5×FAM construct. As the number of fluorophores on the backbone of compounds of structure (I) increases, the signal intensity of the corresponding compounds is increased. The C3-7×FAM and C3-10×FAM constructs are so bright the signal is off scale at 0.5 ug.

Example 7

Dye constructs were conjugated to CD3 (clone UCHT1) antibody and eluted in 1× d-PBS. Whole blood was stained using 0.5 ug of the antibody conjugates and screened on a spectral instrument. Previously, cyclodextrin (CD) has been shown to increase the brightness of FAM when analyzed in aqueous solution. Compound of structure (I) constructs (C3-5xFAM & C3-7xFAM) are brighter than control compound construct (PEG-5x-FAM), even with the addition of cyclodextrin (CD) to the maleimide of control compound construct (PEG-5x-FAM). Effects of buffers on stain index of control compound and compound of Structure (I) constructs are summarized in Table 7. Structures of compounds PEG-5xFAM, C3-5xFAM, and C3-7xFAM are provided in Table 6.

TABLE 7

| Compound (Spacer) | Buffer | DOL | Stain Index |
|---|---|---|---|
| PEG-5xFAM | 2 mM $NaPO_4$ | 2.76 | 145.1 |
| (PEG) | 2 mM $NaPO_4$ + CD | 2.65 | 181.4 |
| C3-5xFAM | 2 mM $NaPO_4$ | 3.59 | 242.2 |
| (C3-PEG-C3) | 2 mM $NaPO_4$ + CD | 2.91 | 275.3 |
| C3-7xFAM | 2 mM $NaPO_4$ | 3.62 | 279.1 |
| (C3-PEG-C3) | 2 mM $NaPO_4$ + CD | 2.32 | 325.3 |

Figure 4:
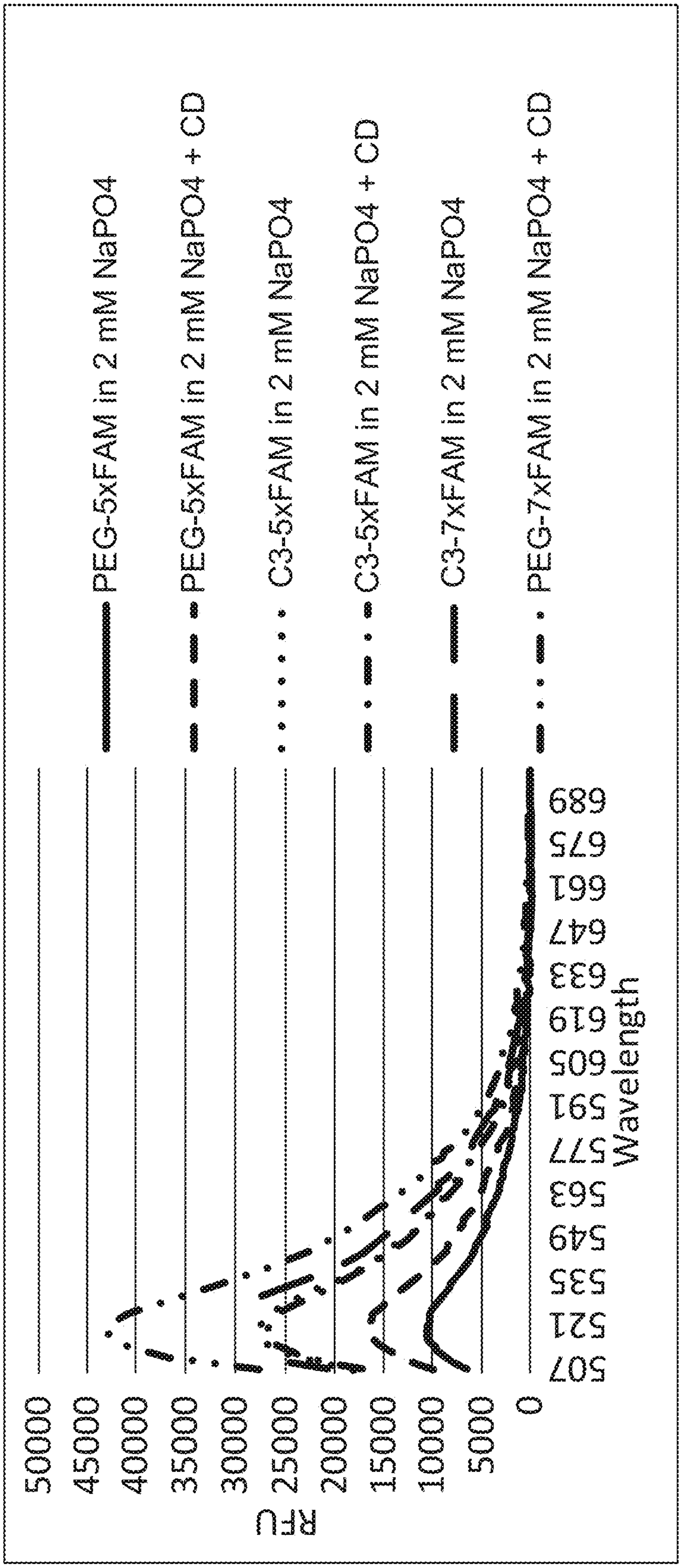
FIG. 4 shows effects of buffers on brightness of control compound construct and representative compound of structures (I) constructs.

2 mM $NaPO_4$ buffer or 2 mM $NaPO_4$ buffer+5 mM cyclodextrin (CD) and then lyophilized. The maleimide samples were then re-suspended in water and conjugated to CD3 antibody and eluted in 1× d-PBS 0.5 ug of antibody conjugates were diluted in Dulbecco 1× PBS and mixed using reverse pipetting and analyzed on Synergy plate reader at emission of 488 nm. The degree of labeling (DOL) was accounted for by taking the signal intensity and dividing by DOL and then graphed. The effects of buffers on control compound construct PEG-5xFAM and compound of structure (I) constructs C3-5xFAM and C3-7xFAM are illustrated in FIG. 4. As shown in FIG. 4, compound of structure (I) constructs C3-5xFAM and C3-7xFAM are brighter than control compound construct PEG-5xFAM, even with the addition of CD.

Example 8

Preparation of Phosphoramidites and Compounds

Exemplary compounds were prepared using standard solid-phase oligonucleotide synthesis protocols and a fluorescein-containing phosphoramidite having the following structure:

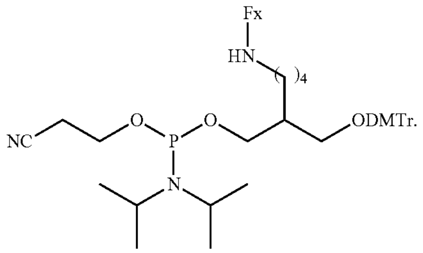

which was purchased from ChemGenes (Cat. #CLP-9780).

Exemplary linkers ($L^6$) were included in the compounds by coupling with a phosphoramidite having the following structure:

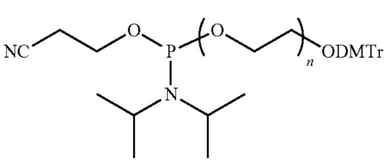

which is also commercially available.

Exemplary linkers ($L^4$/$L^5$) were included in the compounds by coupling with a phosphoramidite having one of the following structures:

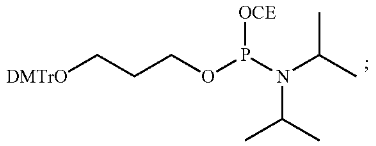

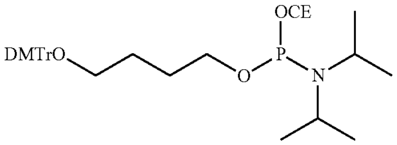

or

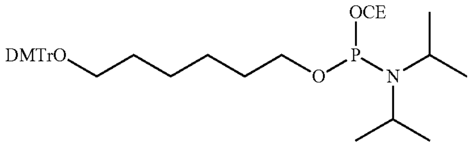

which are also commercially available.

Other exemplary compounds were prepared using a phosphoramidite prepared according to the following scheme:

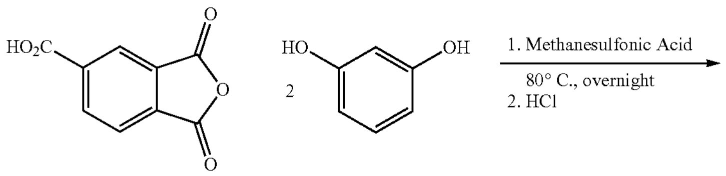

-continued
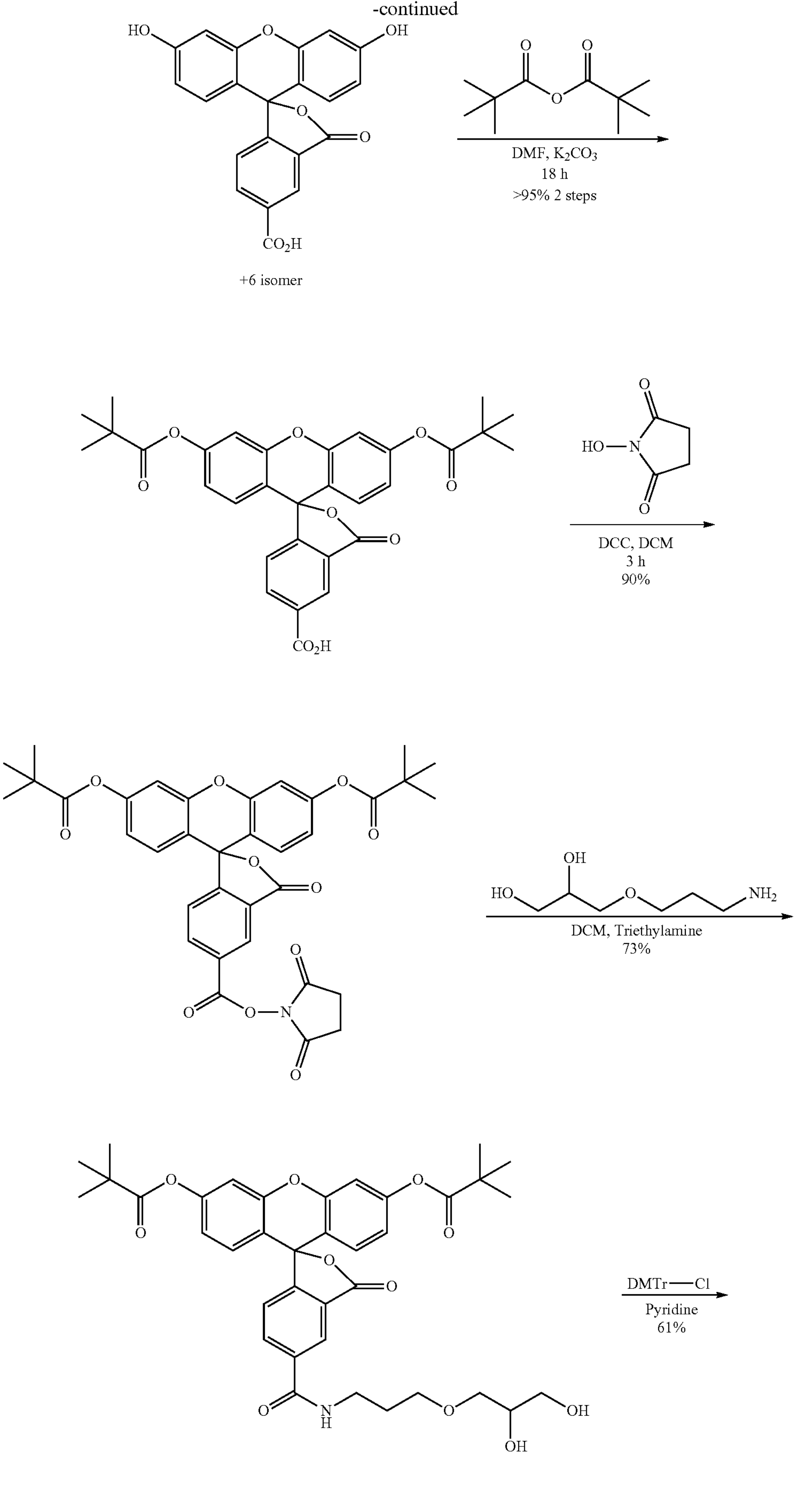

-continued

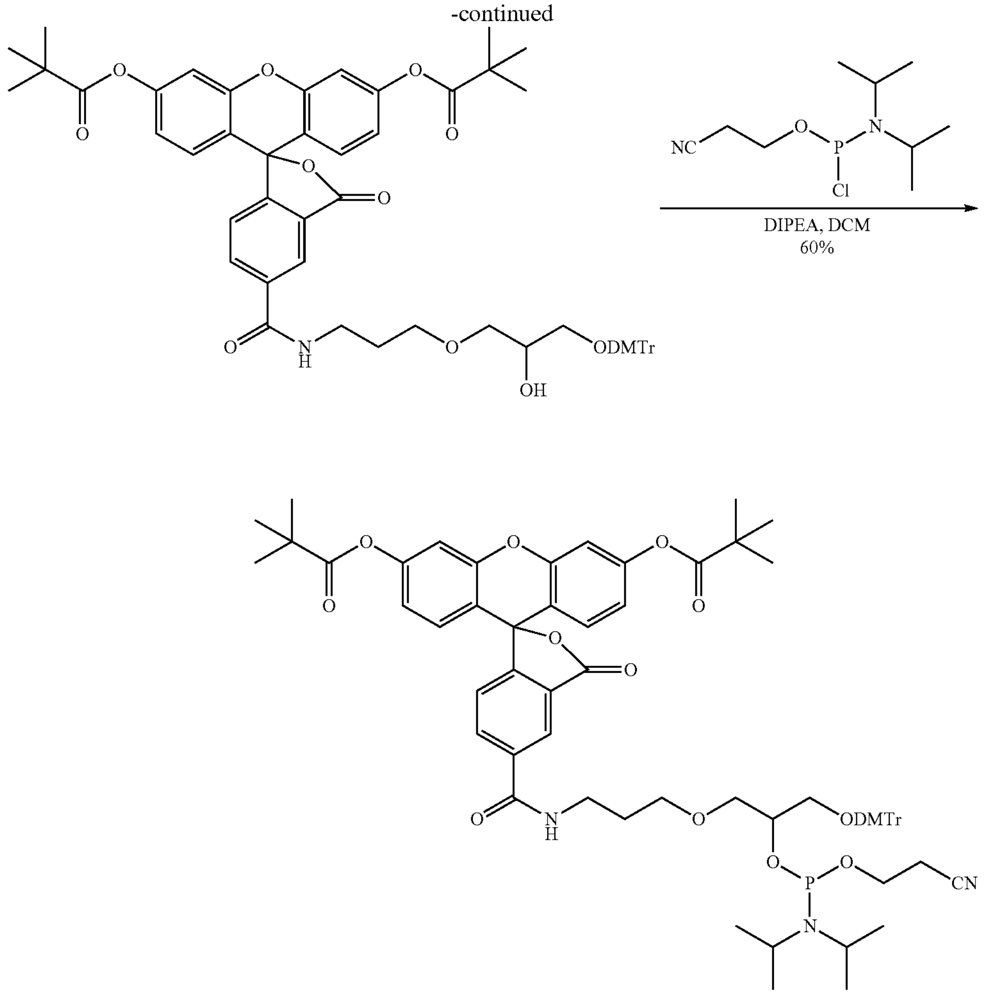

Final deprotection produces the desired Fx moiety. Other commercially available phosphoramidite reagents were employed as appropriate to install the various portions of the compounds. Q moieties having the following structure:

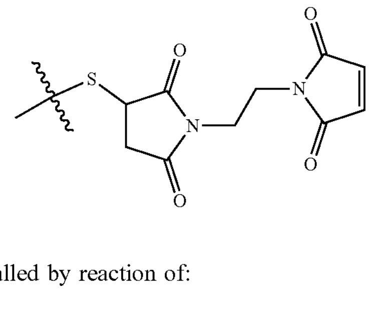

were installed by reaction of:

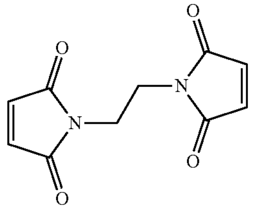 [SMILES: O=C1C=CC(=O)N1CCN1C(=O)C=CC1=O]

with a free sulfhydryl. Other Q moieties are installed in an analogous manner according to knowledge of one of ordinary skill in the art.

The various embodiments described above can be combined to provide further embodiments. All of the U.S. patents, U.S. patent application publications, U.S. patent applications, foreign patents, foreign patent applications and non-patent publications referred to in this specification including U.S. Provisional Patent Application Ser. No. 63/122,285, filed Dec. 7, 2020, and 63/219,706, filed Jul. 8, 2021, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A compound having the following structure (Ib):

(Ib)

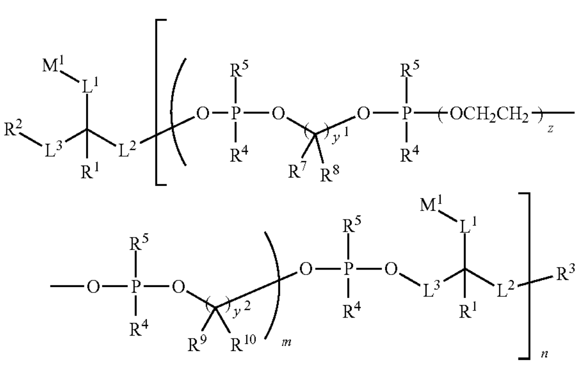

or a stereoisomer, salt or tautomer thereof, wherein:

$M^1$ is a FRET acceptor;

$M^2$ is a FRET donor;

$L^1$ is at each occurrence, independently either i) an alkylene linker; or ii) a, heteroalkylene, heteroalkenylene, heteroalkynylene or heteroatomic linker including at least one nitrogen atom;

$L^2$ and $L^3$ are, at each occurrence, independently an alkylene or heteroalkylene linker;

$R^1$ is, at each occurrence, H;

$R^2$ and $R^3$, each independently, comprises a deoxythymidine (dT) group or are Q, or a protected form thereof, or L';

$R^4$ is, at each occurrence, independently OH, $O^-$, or $OR_d$;

$R^5$ is, at each occurrence, oxo;

$R_d$ is a counter ion;

Q is, at each occurrence, independently a moiety comprising a reactive group, or protected form thereof, capable of forming a covalent bond with an analyte molecule, a targeting moiety, or a complementary reactive group Q';

$L^1$ is a linker comprising a covalent bond to Q;

m is, at each occurrence, independently an integer of one or greater;

n is an integer of one or greater;

z is an integer from 15 to 30;

$R^7$, $R^8$, $R^9$ and $R^{10}$ are, at each occurrence, H; and $y^1$ and $y^2$ are, at each occurrence, independently an integer from 3 to 6.

2. The compound of claim 1, wherein for at least one occurrence of $L^1$, $L^1$ is a linker comprising a triazolyl functional group.

3. The compound of claim 1, wherein $L^1$ has one of the following structures:

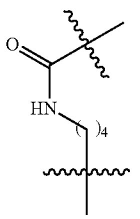

or

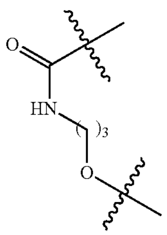

.

4. The compound of claim 1, wherein for at least one occurrence of $L^1$, $L^1$-$M^1$ or $L^1$-$M^2$ has one of the following structures:

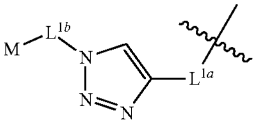

or

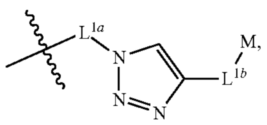

wherein $L^{1a}$ and $L^{1b}$ are each independently optional linkers and wherein M is $M^1$ or $M^2$.

5. The compound of claim 4, wherein $L^{1a}$ or $L^{1b}$, or both, is absent.

6. The compound of claim 4, wherein La and $L^1$b, when present, are each independently alkylene or heteroalkylene.

7. The compound of claim 4, wherein $L^{1a}$ and $L^{1b}$, when present, independently have one of the following structures:

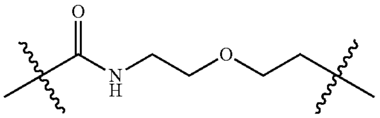

;

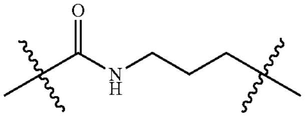

or

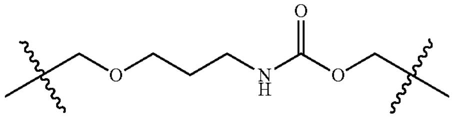

.

8. The compound of claim 1, wherein $M^2$-$L^1$ has the following structure:

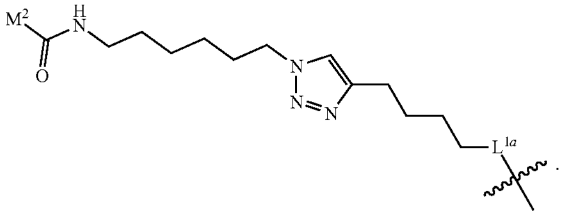

and wherein $L^{1a}$ is an optional linker.

9. The compound of claim 1, wherein $L^1$ comprises an alkylene oxide or phosphodiester moiety, or combinations thereof.

10. The compound of claim 1, wherein $L^1$ has the following structure:

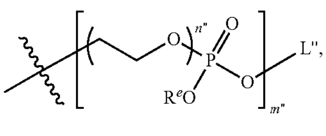

wherein:

m" and n" are independently an integer from 1 to 10;

$R^e$ is H, an electron pair or a counter ion; and

L" is a direct bond or linkage to Q.

11. The compound of claim 1, wherein $R^3$ has one of the following structures:

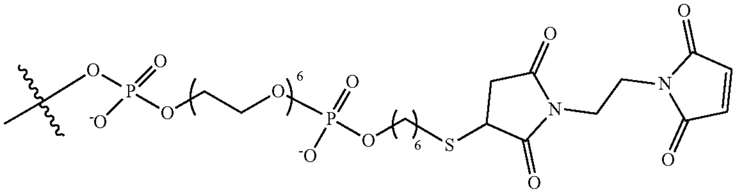
;
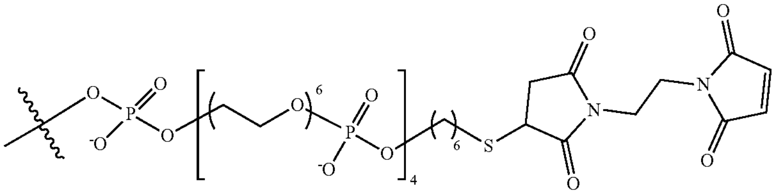
;
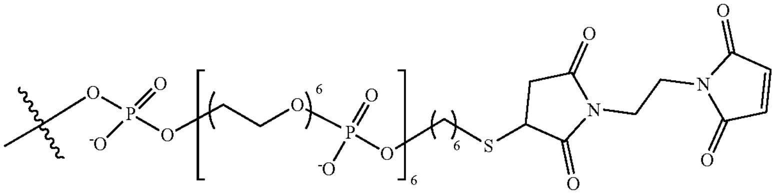
;
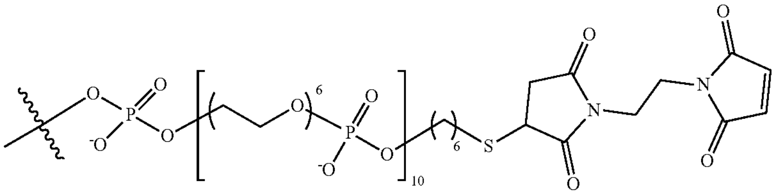
;
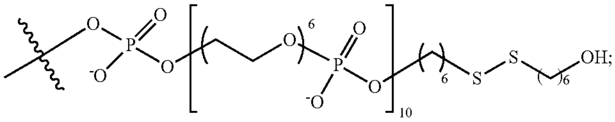
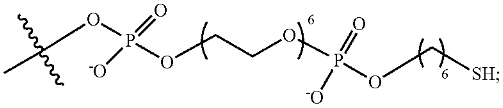
or
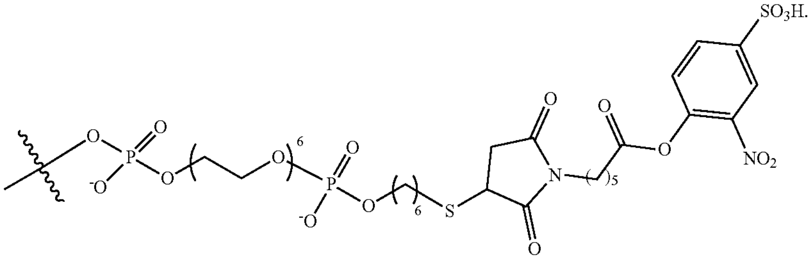

12. The compound of claim 1, wherein Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group, wherein the activated ester is an N-succinimide ester, imidoester or polyflourophenyl ester, and wherein the azide is an alkyl azide or acyl azide.

13. The compound of claim 1, wherein Q has one of the following structures:

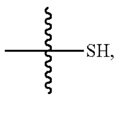
,
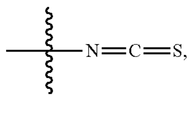
,
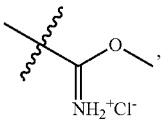
,

-continued

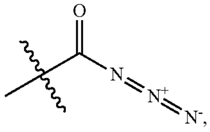
,
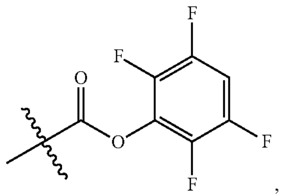
,
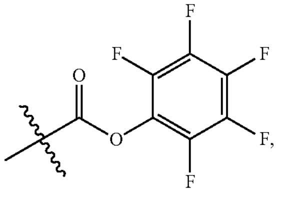
,

-continued

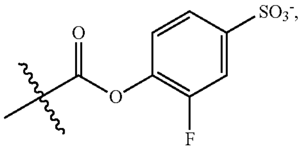

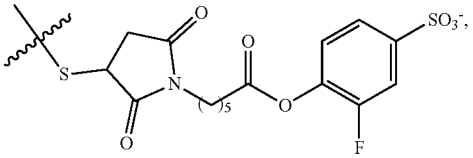

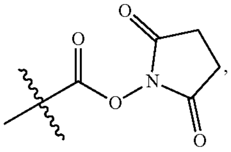,

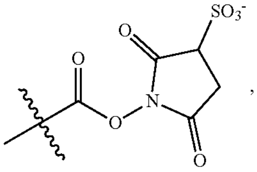,

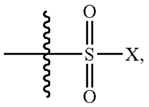

X = halo

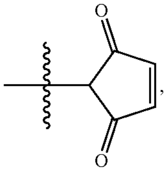,

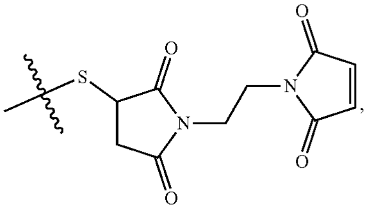,

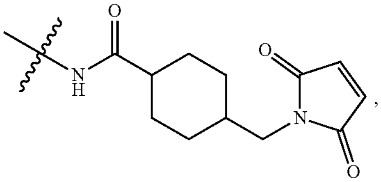,

-continued

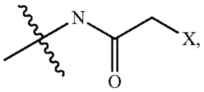

X = halo

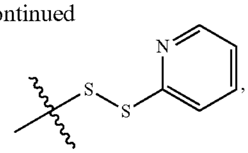,

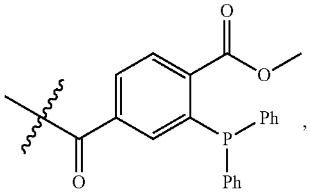,

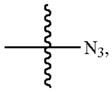

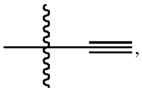

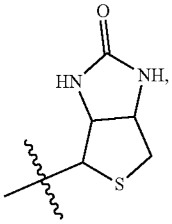

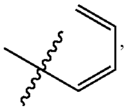,

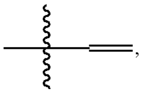,

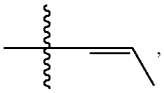, and —$NH_2$.

EWG = eletron withdrawing group

14. The compound of claim 1, wherein the analyte molecule is a nucleic acid, amino acid or a polymer thereof, an enzyme, receptor, receptor ligand, glycoprotein, aptamer or prion.

15. The compound of claim 1, wherein the targeting moiety: targets CD3, CD4, FoxP3, TNF-α, or IFN-γ andis an antibody or cell surface receptor antagonist, wherein the antibody comprises clone 4S.B3, clone 206D, CD8a (D8A8Y) Rabbit mAb, phospho-RB-Ser608, phospho-RB-Ser612, phospho-RB-Ser780, phospho-RB-Ser795, phospho-RB-Ser807, or phospho-RB-Ser811, anti-human IL17A, integrin alpha E/CD103, CCR9 or MOPC-21.

* * * * *